United States Patent
Xu et al.

(10) Patent No.: US 6,395,278 B1
(45) Date of Patent: May 28, 2002

(54) PROSTATE SPECIFIC FUSION PROTEIN COMPOSITIONS

(75) Inventors: Jiangchun Xu, Bellevue; Davin C. Dillon; Jennifer L. Mitcham, both of Redmond; Susan L. Harlocker, Seattle; Jiang Yuqiu, Kent, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/352,616

(22) Filed: Jul. 13, 1999

Related U.S. Application Data

(63) Continuation-in-part of application No. 09/288,946, filed on Apr. 9, 1999, which is a continuation-in-part of application No. 09/232,149, filed on Jan. 15, 1999, which is a continuation-in-part of application No. 09/159,812, filed on Sep. 23, 1998, which is a continuation-in-part of application No. 09/115,453, filed on Jul. 14, 1998, which is a continuation-in-part of application No. 09/030,607, filed on Feb. 25, 1998, now Pat. No. 6,262,245, which is a continuation-in-part of application No. 09/020,956, filed on Feb. 9, 1998, now Pat. No. 6,261,562, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.$^7$ .................. A61K 38/48; A61K 39/00; C12N 15/57; C12N 9/48; C07K 14/00

(52) U.S. Cl. ................ 424/192.1; 424/185.1; 424/94.64; 435/212; 530/403

(58) Field of Search .............. 424/94.64, 1.17, 424/1.21, 1.29, 185.1, 192.1; 549/408; 435/372.3, 212; 530/350, 403

(56) References Cited

U.S. PATENT DOCUMENTS

| | | | | |
|---|---|---|---|---|
| 5,643,756 A | * | 7/1997 | Kayman et al. | 435/69.7 |
| 5,786,148 A | | 7/1998 | Bandman et al. | 435/6 |
| 6,168,804 B1 | * | 1/2001 | Samuel et al. | 424/450 |

FOREIGN PATENT DOCUMENTS

| | | |
|---|---|---|
| DE | 19649207 | 11/1996 |
| EP | 317 141 A2 | 5/1989 |
| EP | 652 014 A1 | 5/1995 |
| EP | 936 270 A2 | 8/1999 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/14772 | 6/1995 |
| WO | WO 95/30758 | 11/1995 |
| WO | WO 96/21671 | 7/1996 |
| WO | WO 97/33909 | 9/1997 |
| WO | WO 98/12302 | 3/1998 |
| WO | WO 98/17687 | 4/1998 |
| WO | WO 98/20117 | 5/1998 |
| WO | WO 98/31799 | 7/1998 |
| WO | WO 98/37093 | 8/1998 |
| WO | WO 98/37418 | 8/1998 |
| WO | WO 98/38310 | 9/1998 |
| WO | WO 98/39446 | 9/1998 |
| WO | WO 98/45435 | 10/1998 |
| WO | WO 98/50567 | 11/1998 |
| WO | WO 99/06548 | 2/1999 |
| WO | WO 99/06552 | 2/1999 |
| WO | WO 99/25825 | 5/1999 |
| WO | WO 99/31236 | 6/1999 |

OTHER PUBLICATIONS

Anh and Kunkel, "The structural and functional diversity of dystrophin," *Nature Genetics* 3:283–291, Apr., 1993.

Alexeyev et al., "Improved antibiotic–resistance gene cassettes and omega elements for *Escherichia coli* vector construction and in vitro deletion/insertion mutagenesis," *Gene* 160:63–67, 1995.

Blok et al., "Isolation of cDNA that are differentially expressed between androgen–dependent and androgen–independent prostate carcinoma cells using differential display PCR," *The Prostate* 26:213–224, 1995.

Cawthon et al., "cDNA sequence and genomic structure of EV12B, a gene lying within an intron of the neurofibromatosis type 1 gene," *Genomics* 9:446–460, 1991.

Chu et al., "CpG oligodeoxynucleotides act as adjuvants that switch on T helper 1 (Th1) immunity," *J. Exp. Med.* 186(10):1623–1631, Nov. 17, 1997.

Coleman et al., *Fundamental Immunology*, Wm. C. Brown Publishers, Dubuque, Iowa, 1989, pp. 465–466.

Database EMBL Accession No. AA453562, Jun. 11, 1997, Hillier et al., "*Homo sapiens* cDNA clone 788180."

Derwent Geneseq Database, Accession No. V58522, Dec. 8, 1998.

Derwent Geneseq Database, Accession No. V61287, Jan. 6, 1999.

Duerst et al., "Nucleic acid characteristic of late or early passage cells immortalized by papilloma virus–and related polypeptide(s) and antibodies, used for diagnosis and treatment of cervical cancer and assessing potential for progression of cervical lesions," Derwent World Patent Index, Accession No. 1998–121623, 1998. See also German Patent DE 19649207 Ci.

(List continued on next page.)

*Primary Examiner*—Marianne P. Allen
*Assistant Examiner*—Marjorie A. Moran
(74) *Attorney, Agent, or Firm*—Seed Intellectual Property Law Group PLLC

(57) ABSTRACT

Compositions and methods for the therapy and diagnosis of cancer, such as prostate cancer, are disclosed. Compositions may comprise one or more prostate tumor proteins, immunogenic portions thereof, or polynucleotides that encode such portions. Alternatively, a therapeutic composition may comprise an antigen presenting cell that expresses a prostate tumor protein, or a T cell that is specific for cells expressing such a protein. Such compositions may be used, for example, for the prevention and treatment of diseases such as prostate cancer. Diagnostic methods based on detecting a prostate tumor protein, or mRNA encoding such a protein, in a sample are also provided.

10 Claims, 5 Drawing Sheets

OTHER PUBLICATIONS

El–Shirbiny, Prostatic Specific Antigen, *Advances In Clinical Chemistry 31*:99–133, 1994.

Ezzell, C., "Cancer vaccines: an idea whose time has come?" *The Journal of NIH Research 7*:46–49, Jan., 1995.

Harris et al., "Polycystic Kidney Disease 1: identification and analysis of the primary defect," *J. Am. Soc. of Nephrol. 6*:1125–1133, 1995.

Hillier et al., Genbank Accession No. AA100799, Dec. 23, 1997.

Hillier et al., Genbank Accession No. R20590, Apr. 18, 1995.

Hudson, T., Genbank Accession No. G22461, May 31, 1996.

Kroger, B. "New serine protease form human prostate, useful for identifying specific inhibitors, antibodies and probes," Derwent World Patent Index, Accession No. 99–432218, 1999. See also European Patent EP 936 270 A2.

National Cancer Institute, Cancer Genome Anatomy Project (NCI–CGAP), Genbank Accession No. AA551449, Sep. 5, 1997.

National Cancer Institute, Cancer Genome Anatomy Project (NCI–CGAP), Genbank Accession No. AA551759, Aug. 11, 1997.

National Cancer Institute, Cancer Genome Anatomy Project (NCI–CGAP), Genbank Accession No. AA631143, Oct. 31, 1997.

National Cancer Institute, Cancer Genome Anatomy Project (NCI–CGAP), Genbank Accesssion No. AA653016, Nov. 25, 1997.

Robson et al., "Identification of prostatic adrogen regulated genes using the differential display technique," *Proceedings of the American Association for Cancer Research Meeting 86*, 36: p. 266, Abstract No. 1589, 1995.

Short et al., "λZAP: a bacteriophage λ expression vector with in vivo excision properties," *Nucleic Acids Research 16*(15):7583–7600, 1988.

Sjögren, H., "Therapeutic Immunization Against Cancer Antigens Using Genetically Engineered Cells," *Immunotechnology 3*: 161–172, 1997.

Zitvogel et al., "Eradication of Established Murine Tumors Using a Novel Cell–Free Vaccine: Dendritic Cell–Derived Exosomers," *Nature Medicine 4*(5): 594–600, 1998.

Busselmakers et al., Genbank Accession No. AF103907, Aug. 14, 2000.

Busselmakers et al., Genbank Accession No. AF103908, Aug. 14, 2000.

Hara et al., "Characterization of cell phenotype by a novel cDNA library subtraction system: expression of $CD8\alpha$ in a mast cell–derived interleukin–4–dependent cell line," *Blood 84*(1):189–199, Jul. 1, 1994.

Lalvani et al., "Rapid effector function in $CD8^+$ memory cells," *J. Exp. Med. 186*(6):859–865, Sep. 15, 1997.

Nelson et al., Genbank Accession No. NP_004908, Mar. 18, 2000.

Schena et al., "Parallel human genome analysis: Microarray–based expression monitoring of 1000 genes," *Proc. Natl. Acad. Sci. USA 93*(19):10614–10619, Sep. 17, 1996.

Sherman et al., "Selecting T cell receptors with high affinity for self–MHC by decreasing the contribution of CD8," *Science 258*(5083):815–818, Oct. 30, 1992.

Smith et al., "Major susceptibility locus for prostate cancer on chromosome 1 suggested by genome–wide search," *Science 274*(5291):1371–1374, Nov. 22, 1996.

Theobald, et al., "Targeting p53 as a general tumor antigen," *Proc. Natl. Sci. USA 92*(25):11993–11997, Dec. 5, 1995.

Van Tsai et al., "In vitro immunization and expansion of antigen–specific cytotoxic T lymphocytes for adoptive immunotherapy using peptide–pulsed dendritic cells," *Critical Reviews in Immunology 18*:65–75, 1998.

Vasmatzis et al., "Discovery of three genes specifically expressed in human prostate by expressed sequence tag database analysis," *Proc. Natl. Acad. Sci. USA 95*(1):300–304, Jan. 6, 1998.

Yee et al., "Isolation of tyrosinase–specific $CD8^+$ T cell clones from the peripheral blood of melanoma patients following in vitro stimulation with recombinant vaccinia virus," *The Journal of Immunology 157*(9):4079–4086, Nov. 1, 1996.

Bandman et al. Sequence alignment for US 5922321.*

Bandman et al. Geneseq accession No. W60592. (Sep. 1998).*

* cited by examiner

PROSTATE SPECIFIC FUSION PROTEIN COMPOSITIONS

CROSS REFERENCE TO RELATED APPLICATIONS

This application is a continuation-in-part of U.S. patent application No. Ser. 09/288,946, filed Apr. 9, 1999, which is a continuation-in-part of U.S. patent application Ser. No. 09/232,149, filed Jan. 15, 1999, which is a continuation-in-part of U.S. patent application Ser. No. 09/159,812, filed Sep. 23, 1998, which is a continuation-in-part of U.S. patent application Ser. No. 09/115,453, filed Jul. 14 1998, which is a continuation-in-part of U.S. patent application Ser. No. 09/030,607, U.S. Pat. No. 6,262,245 filed Feb. 25, 1998, which is a continuation-in-part of U.S. patent application Ser. No. 09/020,956, U.S. Pat. No. 6,261,562 filed Feb. 9, 1998, which is a continuation-in-part of U.S. patent application Ser. No. 08/904,804, filed Aug. 1, 1997 now abandoned, which is a continuation-in-part of U.S. patent application Ser No. 08/806,099, filed Feb. 25, 1997 now abandoned.

TECHNICAL FIELD

The present invention relates generally to therapy and diagnosis of cancer, such as prostate cancer. The invention is more specifically related to polypeptides comprising at least a portion of a prostate tumor protein, and to polynucleotides encoding such polypeptides. Such polypeptides and polynucleotides may be used in vaccines and pharmaceutical compositions for prevention and treatment of prostate cancer, and for the diagnosis and monitoring of such cancers.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

In spite of considerable research into therapies for these and other cancers, prostate cancer remains difficult to diagnose and treat effectively. Accordingly, there is a need in the art for improved methods for detecting and treating such cancers. The present invention fulfills these needs and further provides other related advantages.

SUMMARY OF THE INVENTION

Briefly stated, the present invention provides compositions and methods for the diagnosis and therapy of cancer, such as prostate cancer. In one aspect, the present invention provides polypeptides comprising at least a portion of a prostate tumor protein, or a variant thereof. Certain portions and other variants are immunogenic, such that the ability of the variant to react with antigen-specific antisera is not substantially diminished. Within certain embodiments, the polypeptide comprises at least an immunogenic portion of a prostate tumor protein, or a variant thereof, wherein the tumor protein comprises an amino acid sequence that is encoded by a polynucleotide sequence selected from the group consisting of: (a) sequences recited in any one of SEQ ID NOs:1–111, 115–171, 173–175, 177, 179–305, 307–315, 326, 328, 330, 332–335, 340–375, 381, 382 or 384–472; (b) sequences that hybridize to any of the foregoing sequences under moderately stringent conditions; and (c) complements of any of the sequence of (a) or (b). In certain specific embodiments, such a polypeptide comprises at least a portion, or variant thereof, of a tumor protein that includes an amino acid sequence selected from the group consisting of sequences recited in any one of SEQ ID NO: 112–114, 172, 176, 178, 327, 329, 331, 336, 339, 376–380 and 383.

The present invention further provides polynucleotides that encode a polypeptide as described above, or a portion thereof (such as a portion encoding at least 15 amino acid residues of a prostate tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines are provided. Such vaccines comprise a polypeptide or polynucleotide as described above and a non-specific immune response enhancer.

The present invention further provides pharmaceutical compositions that comprise: (a) an antibody or antigen-binding fragment thereof that specifically binds to a prostate tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) a non-specific immune response enhancer.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a prostate tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a prostate tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a prostate tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be prostate cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a prostate tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a prostate tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 illustrates the ability of T cells to kill fibroblasts expressing the representative prostate tumor polypeptide P502S, as compared to control fibroblasts. The percentage lysis is shown as a series of effector:target ratios, as indicated.

FIGS. 2A and 2B illustrate the ability of T cells to recognize cells expressing the representative prostate tumor polypeptide P502S. In each case, the number of γ-interferon spots is shown for different numbers of responders. In FIG. 2A, data is presented for fibroblasts pulsed with the P2S-12 peptide, as compared to fibroblasts pulsed with a control E75 peptide. In FIG. 2B, data is presented for fibroblasts expressing P502S, as compared to fibroblasts expressing HER-2/neu.

FIG. 3 represents a peptide competition binding assay showing that the P1S#10 peptide, derived from P501S, binds HLA-A2. Peptide PIS#10 inhibits HLA-A2 restricted presentation of fluM58 peptide to CTL clone D150M58 in TNF release bioassay. D150M58 CTL is specific for the HLA-A2 binding influenza matrix peptide fluM58.

Figure 6A:
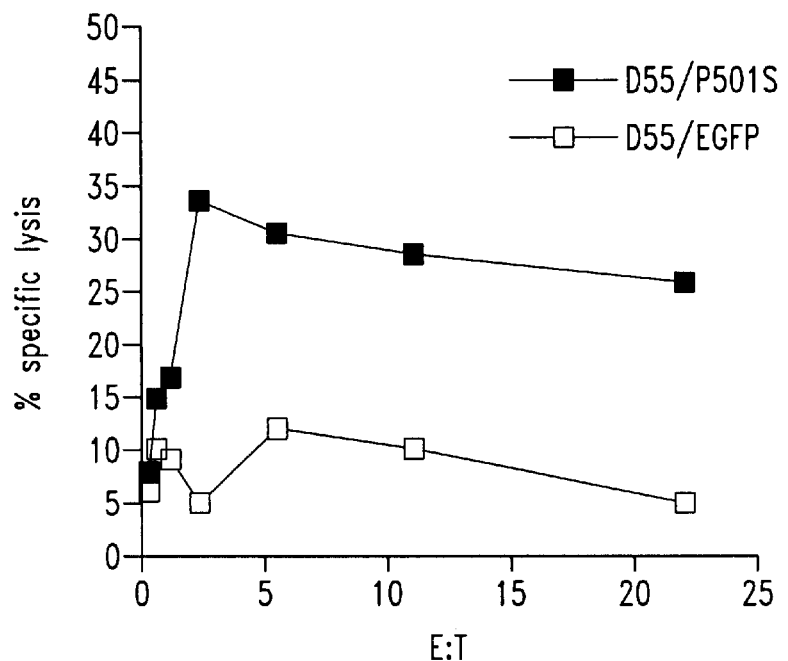
Figure 6B:
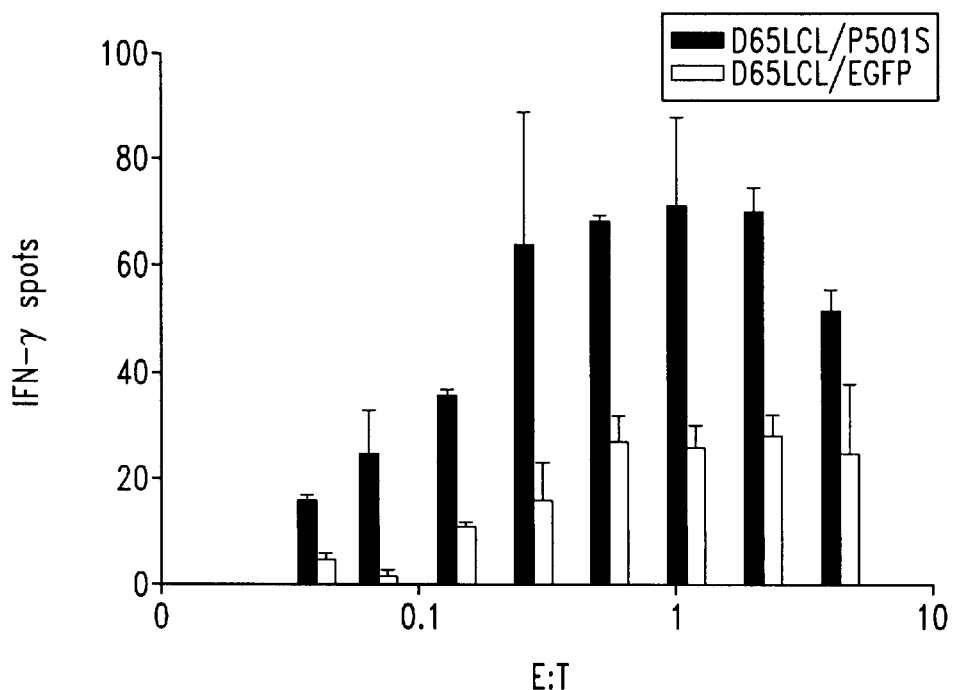

FIGS. 6A and 6B are graphs illustrating the specificity of a CD8+ cell line (3A-1) for a representative prostate tumor antigen (P501 S). FIG. 6A shows the results of a $^{51}$Cr release assay. The percent specific lysis is shown as a series of effector:target ratios, as indicated. FIG. 6B shows the production of interferon-gamma by 3A-1 cells stimulated with autologous B-LCL transduced with P501S, at varying effector:target rations as indicated.

SEQ ID NO: 1 is the determined cDNA sequence for F1-13

SEQ ID NO: 2 is the determined 3' cDNA sequence for F1-12

SEQ ID NO: 3 is the determined 5' cDNA sequence for F1-12

SEQ ID NO 4 is the determined 3' cDNA sequence for F1-16

SEQ ID NO: 5 is the determined 3' cDNA sequence for H1-16

SEQ ID NO: 6 is the determined 3' cDNA sequence for H1-9

SEQ ID NO: 7 is the determined 3' cDNA sequence for H1-4

SEQ ID NO: 8 is the determined 3' cDNA sequence for J1-17

SEQ ID NO: 9 is the determined 5' cDNA sequence for J1-17

SEQ ID NO: 10 is the determined 3' cDNA sequence for L1-12

SEQ ID NO: 11 is the determined 5' cDNA sequence for L1-12

SEQ ID NO: 12 is the determined 3' cDNA sequence for N1-1862

SEQ ID NO: 13 is the determined 5' cDNA sequence for N1-1862

SEQ ID NO: 14 is the determined 3' cDNA sequence for J1-13

SEQ ID NO: 15 is the determined 5' cDNA sequence for J1-13

SEQ ID NO: 16 is the determined 3' cDNA sequence for J1-19

SEQ ID NO: 17 is the determined 5' cDNA sequence for J1-19

SEQ ID NO: 18 is the determined 3' cDNA sequence for J1-25

SEQ ID NO: 19 is the determined 5' cDNA sequence for J1-25

SEQ ID NO: 20 is the determined 5' cDNA sequence for J1-24

SEQ ID NO: 21 is the determined 3' cDNA sequence for J1-24

SEQ ID NO: 22 is the determined 5' cDNA sequence for K1-58

SEQ ID NO: 23 is the determined 3' cDNA sequence for K1-58

SEQ ID NO: 24 is the determined 5' cDNA sequence for K1-63

SEQ ID NO: 25 is the determined 3' cDNA sequence for K1-63

SEQ ID NO: 26 is the determined 5' cDNA sequence for L1-4

SEQ ID NO: 27 is the determined 3' cDNA sequence for L1-4

SEQ ID NO: 28 is the determined 5' cDNA sequence for L1-14

SEQ ID NO: 29 is the determined 3' cDNA sequence for L1-14

SEQ ID NO: 30 is the determined 3' cDNA sequence for J1-12

SEQ ID NO: 31 is the determined 3' cDNA sequence for J1-16

SEQ ID NO: 32 is the determined 3' cDNA sequence for J1-21

SEQ ID NO: 33 is the determined 3' cDNA sequence for K1-48

SEQ ID NO: 34 is the determined 3' cDNA sequence for K1-55

SEQ ID NO: 35 is the determined 3' cDNA sequence for L1-2

SEQ I D NO: 36 is the determined 3' cDNA sequence for L1-6

SEQ ID NO: 37 is the determined 3' cDNA sequence for N1-1858

SEQ ID NO: 38 is the determined 3' cDNA sequence for N1-1860

SEQ ID NO: 39 is the determined 3' cDNA sequence for N1-1861

SEQ ID NO: 40 is the determined 3' cDNA sequence for N1-1864

SEQ ID NO: 41 is the determined cDNA sequence for P5

SEQ ID NO: 42 is the determined cDNA sequence for P8

SEQ ID NO: 43 is the determined cDNA sequence for P9

SEQ ID NO: 44 is the determined cDNA sequence for P18

SEQ ID NO: 45 is the determined cDNA sequence for P20

SEQ ID NO: 46 is the determined cDNA sequence for P29

SEQ ID NO: 47 is the determined cDNA sequence for P30

SEQ ID NO: 48 is the determined cDNA sequence for P34

SEQ ID NO: 49 is the determined cDNA sequence for P36

SEQ ID NO: 50 is the determined cDNA sequence for P38

SEQ ID NO: 51 is the determined cDNA sequence for P39

SEQ ID NO: 52 is the determined cDNA sequence for P42

SEQ ID NO: 53 is the determined cDNA sequence for P47

SEQ ID NO: 54 is the determined cDNA sequence for P49

SEQ ID NO: 55 is the determined cDNA sequence for P50

SEQ ID NO: 56 is the determined cDNA sequence for P53

SEQ ID NO: 57 is the determined cDNA sequence for P55

SEQ ID NO: 58 is the determined cDNA sequence for P60

SEQ ID NO: 59 is the determined cDNA sequence for P64

SEQ ID NO: 60 is the determined cDNA sequence for P65

SEQ ID NO: 61 is the determined cDNA sequence for P73

SEQ ID NO: 62 is the determined cDNA sequence for P75

SEQ ID NO: 63 is the determined cDNA sequence for P76

SEQ ID NO: 64 is the determined cDNA sequence for P79

SEQ ID NO: 65 is the determined cDNA sequence for P84

SEQ ID NO: 66 is the determined cDNA sequence for P68

SEQ ID NO: 67 is the determined cDNA sequence for P80

SEQ ID NO: 68 is the determined cDNA sequence for P82

SEQ ID NO: 69 is the determined cDNA sequence for U1-3064

SEQ ID NO: 70 is the determined cDNA sequence for U1-3065
SEQ ID NO: 71 is the determined cDNA sequence for V1-3692
SEQ ID NO: 72 is the determined cDNA sequence for 1A-3905
SEQ ID NO: 73 is the determined cDNA sequence for V1-3686
SEQ ID NO: 74 is the determined cDNA sequence for R1-2330
SEQ ID NO: 75 is the determined cDNA sequence for 1B-3976
SEQ ID NO: 76 is the determined cDNA sequence for V1-3679
SEQ ID NO: 77 is the determined cDNA sequence for 1G-4736
SEQ ID NO: 78 is the determined cDNA sequence for 1G-4738
SEQ ID NO: 79 is the determined cDNA sequence for 1G-4741
SEQ ID NO: 80 is the determined cDNA sequence for 1G-4744
SEQ ID NO: 81 is the determined cDNA sequence for 1G-4734
SEQ ID NO: 82 is the determined cDNA sequence for 1H-4774
SEQ ID NO: 83 is the determined CDNA sequence for 1H-4781
SEQ ID NO: 84 is the determined cDNA sequence for 1H-4785
SEQ ID NO: 85 is the determined cDNA sequence for 1H-4787
SEQ ID NO: 86 is the determined cDNA sequence for 1H-4796
SEQ ID NO: 87 is the determined cDNA sequence for 1I-4807
SEQ ID NO: 88 is the determined cDNA sequence for 1I-4810
SEQ ID NO: 89 is the determined cDNA sequence for 1-4811
SEQ ID NO: 90 is the determined cDNA sequence for 1J-4876
SEQ ID NO: 91 is the determined cDNA sequence for 1K-4884
SEQ ID NO: 92 is the determined cDNA sequence for 1K-4896
SEQ ID NO: 93 is the determined cDNA sequence for 1G-4761
SEQ ID NO: 94 is the determined cDNA sequence for 1G-4762
SEQ ID NO: 95 is the determined cDNA sequence for 1H-4766
SEQ ID NO: 96 is the determined cDNA sequence for 1H-4770
SEQ ID NO: 97 is the determined cDNA sequence for 1H-4771
SEQ ID NO: 98 is the determined cDNA sequence for 1H-4772
SEQ ID NO: 99 is the determined cDNA sequence for 1D-4297
SEQ ID NO: 100 is the determined cDNA sequence for 1D-4309
SEQ ID NO: 101 is the determined cDNA sequence for 1D-4278
SEQ ID NO: 102 is the determined cDNA sequence for 1D-4288
SEQ ID NO: 103 is the determined cDNA sequence for 1-D-4283
SEQ ID NO: 104 is the determined cDNA sequence for 1D-4304
SEQ ID NO: 105 is the determined cDNA sequence for 1D-4296
SEQ ID NO: 106 is the determined cDNA sequence for 1D-4280
SEQ ID NO: 107 is the determined full length cDNA sequence for F1-12 (also referred to as P504S)
SEQ ID NO: 108 is the predicted amino acid sequence for F1-12
SEQ ID NO: 109 is the determined full length cDNA sequence for J1-17
SEQ ID NO: 110 is the determined full length cDNA sequence for L1-12
SEQ ID NO: 111 is the determined full length cDNA sequence for N1-1862
SEQ ID NO: 112 is the predicted amino acid sequence for J1-17
SEQ ID NO: 113 is the predicted amino acid sequence for L1-12
SEQ ID NO: 114 is the predicted amino acid sequence for N1-1862
SEQ ID NO: 115 is the determined cDNA sequence for P89
SEQ ID NO: 116 is the determined cDNA sequence for P90
SEQ ID NO: 117 is the determined cDNA sequence for P92
SEQ ID NO: 118 is the determined cDNA sequence for P95
SEQ ID NO: 119 is the determined cDNA sequence for P98
SEQ ID NO: 120 is the determined cDNA sequence for P102
SEQ ID NO: 121 is the determined cDNA sequence for P110
SEQ ID NO: 122 is the determined cDNA sequence for P111
SEQ ID NO: 123 is the determined cDNA sequence for P114
SEQ ID NO: 124 is the determined cDNA sequence for P115
SEQ ID NO: 125 is the determined cDNA sequence for P116
SEQ ID NO: 126 is the determined cDNA sequence for P124
SEQ ID NO: 127 is the determined cDNA sequence for P126
SEQ ID NO: 128 is the determined CDNA sequence for P130
SEQ ID NO: 129 is the determined cDNA sequence for P133
SEQ ID NO: 130 is the determined cDNA sequence for P138
SEQ ID NO: 131 is the determined cDNA sequence for P143

SEQ ID NO: 132 is the determined cDNA sequence for P151

SEQ ID NO: 133 is the determined cDNA sequence for P156

SEQ ID NO: 134 is the determined cDNA sequence for P157

SEQ ID NO: 135 is the determined cDNA sequence for P166

SEQ ID NO: 136 is the determined cDNA sequence for P176

SEQ ID NO: 137 is the determined cDNA sequence for P178

SEQ ID NO: 138 is the determined cDNA sequence for P179

SEQ ID NO: 139 is the determined cDNA sequence for P185

SEQ ID NO: 140 is the determined cDNA sequence for P192

SEQ ID NO: 141 is the determined cDNA sequence for P201

SEQ ID NO: 142 is the determined cDNA sequence for P204

SEQ ID NO: 143 is the determined cDNA sequence for P208

SEQ ID NO: 144 is the determined cDNA sequence for P211

SEQ ID NO: 145 is the determined cDNA sequence for P213

SEQ ID NO: 146 is the determined cDNA sequence for P219

SEQ ID NO: 147 is the determined cDNA sequence for P237

SEQ ID NO: 148 is the determined cDNA sequence for P239

SEQ ID NO: 149 is the determined cDNA sequence for P248

SEQ ID NO: 150 is the determined cDNA sequence for P251

SEQ ID NO: 151 is the determined cDNA sequence for P255

SEQ ID NO: 152 is the determined cDNA sequence for P256

SEQ ID NO: 153 is the determined cDNA sequence for P259

SEQ ID NO: 154 is the determined cDNA sequence for P260

SEQ ID NO: 155 is the determined cDNA sequence for P263

SEQ ID NO: 156 is the determined cDNA sequence for P264

SEQ ID NO: 157 is the determined cDNA sequence for P266

SEQ ID NO: 158 is the determined cDNA sequence for P270

SEQ ID NO: 159 is the determined cDNA sequence for P272

SEQ ID NO: 160 is the determined cDNA sequence for P278

SEQ ID NO: 161 is the determined cDNA sequence for P105

SEQ ID NO: 162 is the determined cDNA sequence for P107

SEQ ID NO: 163 is the determined cDNA sequence for P137

SEQ ID NO: 164 is the determined cDNA sequence for P194

SEQ ID NO: 165 is the determined cDNA sequence for P195

SEQ ID NO: 166 is the determined cDNA sequence for P196

SEQ ID NO: 167 is the determined cDNA sequence for P220

SEQ ID NO: 168 is the determined cDNA sequence for P234

SEQ ID NO: 169 is the determined cDNA sequence for P235

SEQ ID NO: 170 is the determined cDNA sequence for P243

SEQ ID NO: 171 is the determined cDNA sequence for P703P-DE1

SEQ ID NO: 172 is the predicted amino acid sequence for P703P-DE1

SEQ ID NO: 173 is the determined cDNA sequence for P703P-DE2

SEQ ID NO: 174 is the determined cDNA sequence for P703P-DE6

SEQ ID NO: 175 is the determined cDNA sequence for P703P-DE13

SEQ ID NO: 176 is the predicted amino acid sequence for P703P-DE13

SEQ ID NO: 177 is the determined cDNA sequence for P703P-DE14

SEQ ID NO: 178 is the predicted amino acid sequence for P703P-DE14

SEQ ID NO: 179 is the determined extended cDNA sequence for 1G-4736

SEQ ID NO: 180 is the determined extended cDNA sequence for 1G-4738

SEQ ID NO: 181 is the determined extended cDNA sequence for1G-4741

SEQ ID NO: 182 is the determined extended cDNA sequence for1G-4744

SEQ ID NO: 183 is the determined extended cDNA sequence for1H-4774

SEQ ID NO: 184 is the determined extended cDNA sequence for 1H-4781

SEQ ID NO: 185 is the determined extended cDNA sequence for 1H-4785

SEQ ID NO: 186 is the determined extended cDNA sequence for 1H-4787

SEQ ID NO: 187 is the determined extended cDNA sequence for 1H-4796

SEQ ID NO: 188 is the determined extended cDNA sequence for 1I-4807

SEQ ID NO: 189 is the determined 3' cDNA sequence for 1I-4810

SEQ ID NO: 190 is the determined 3' cDNA sequence for 1-4811

SEQ ID NO: 191 is the determined extended cDNA sequence for 1J-4876

SEQ ID NO: 192 is the determined extended cDNA sequence for 1K-4884

SEQ ID NO: 193 is the determined extended cDNA sequence for 1K-4896

SEQ ID NO: 194 is the determined extended cDNA sequence for 1G-4761

SEQ ID NO: 195 is the determined extended cDNA sequence for 1G-4762

SEQ ID NO: 196 is the determined extended cDNA sequence for 1H-4766

SEQ ID NO: 197 is the determined 3' cDNA sequence for 1H-4770

SEQ ID NO: 198 is the determined 3' cDNA sequence for 1H-4771

SEQ ID NO: 199 is the determined extended cDNA sequence for 1H-4772

SEQ ID NO: 200 is the determined extended cDNA sequence for 1D-4309

SEQ ID NO: 201 is the determined extended cDNA sequence for 1D.14278

SEQ ID NO: 202 is the determined extended cDNA sequence for 1D-4288

SEQ ID NO: 203 is the determined extended cDNA sequence for 1D-4283

SEQ ID NO: 204 is the determined extended cDNA sequence for 1D-4304

SEQ ID NO: 205 is the determined extended cDNA sequence for 1-D14296

SEQ ID NO: 206 is the determined extended cDNA sequence for 1D-4280

SEQ ID NO: 207 is the determined cDNA sequence for 10-d8fwd

SEQ ID NO: 208 is the determined cDNA sequence for 10-H10con

SEQ ID NO: 209 is the determined cDNA sequence for 11-C8rev

SEQ ID NO: 210 is the determined cDNA sequence for 7.g6fwd

SEQ ID NO: 211 is the determined cDNA sequence for 7.g6rev

SEQ ID NO: 212 is the determined cDNA sequence for 8-b5fwd

SEQ ID NO: 213 is the determined cDNA sequence for 8-b5rev

SEQ ID NO: 214 is the determined cDNA sequence for 8-b6fwd

SEQ ID NO: 215 is the determined cDNA sequence for 8-b6 rev

SEQ ID NO: 216 is the determined cDNA sequence for 8-d4fwd

SEQ ID NO: 217 is the determined cDNA sequence for 8-d9rev

SEQ ID NO: 218 is the determined cDNA sequence for 8-g3fwd

SEQ ID NO: 219 is the determined cDNA sequence for 8-g3rev

SEQ ID NO: 220 is the determined cDNA sequence for 8-h11rev

SEQ ID NO: 221 is the determined cDNA sequence for g-f12fwd

SEQ ID NO: 222 is the determined cDNA sequence for g-f3rev

SEQ ID NO: 223 is the determined cDNA sequence for P509S

SEQ ID NO: 224 is the determined cDNA sequence for P510S

SEQ ID NO: 225 is the determined cDNA sequence for P703DE5

SEQ ID NO: 226 is the determined cDNA sequence for 9-A11

SEQ ID NO: 227 is the determined cDNA sequence for 8-C6

SEQ ID NO: 228 is the determined cDNA sequence for 8-H7

SEQ ID NO: 229 is the determined cDNA sequence for JPTPN13

SEQ ID NO: 230 is the determined cDNA sequence for JPTPN 14

SEQ ID NO: 231 is the determined cDNA sequence for JPTPN23

SEQ ID NO: 232 is the determined cDNA sequence for JPTPN24

SEQ ID NO: 233 is the determined cDNA sequence for JPTPN25

SEQ ID NO: 234 is the determined cDNA sequence for JPTPN30

SEQ ID NO: 235 is the determined cDNA sequence for JPTPN34

SEQ ID NO: 236 is the determined cDNA sequence for PTPN35

SEQ ID NO: 237 is the determined cDNA sequence for JPTPN36

SEQ ID NO: 238 is the determined cDNA sequence for JPTPN38

SEQ ID NO: 239 is the determined cDNA sequence for JPTPN39

SEQ ID NO: 240 is the determined cDNA sequence for JPTPN40

SEQ ID NO: 241 is the determined cDNA sequence for JPTPN41

SEQ ID NO: 242 is the determined cDNA sequence for JPTPN42

SEQ ID NO: 243 is the determined cDNA sequence for JPTPN45

SEQ ID NO: 244 is the determined cDNA sequence for JPTPN46

SEQ ID NO: 245 is the determined cDNA sequence for JPTPN51

SEQ ID NO: 246 is the determined cDNA sequence for JPTPN56

SEQ ID NO: 247 is the determined cDNA sequence for PTPN64

SEQ ID NO: 248 is the determined cDNA sequence for JPTPN65

SEQ ID NO: 249 is the determined cDNA sequence for JPTPN67

SEQ ID NO: 250 is the determined cDNA sequence for JPTPN76

SEQ ID NO: 251 is the determined cDNA sequence for JPTPN84

SEQ ID NO: 252 is the determined CDNA sequence for JPTPN85

SEQ ID NO: 253 is the determined cDNA sequence for JPTPN86

SEQ ID NO: 254 is the determined cDNA sequence for JPTPN87

SEQ ID NO: 255 is the determined cDNA sequence for JPTPN88

SEQ ID NO: 256 is the determined cDNA sequence for JP1F1
SEQ ID NO: 257 is the determined cDNA sequence for JP1F2
SEQ ID NO: 258 is the determined cDNA sequence for JP1C2
SEQ ID NO: 259 is the determined cDNA sequence for JP1B1
SEQ ID NO: 260 is the determined cDNA sequence for JP1B2
SEQ ID NO: 261 is the determined cDNA sequence for JP1D3
SEQ ID NO: 262 is the determined cDNA sequence for JP1A4
SEQ ID NO: 263 is the determined cDNA sequence for JP1F5
SEQ ID NO: 264 is the determined cDNA sequence for JP1E6
SEQ ID NO: 265 is the determined cDNA sequence for JP1D6
SEQ ID NO: 266 is the determined cDNA sequence for JP1B5
SEQ ID NO: 267 is the determined cDNA sequence for JP1A6
SEQ ID NO: 268 is the determined cDNA sequence for JP1E8
SEQ ID NO: 269 is the determined cDNA sequence for JP1D7
SEQ ID NO: 270 is the determined cDNA sequence for JP1D9
SEQ ID NO: 271 is the determined cDNA sequence for JP1C10
SEQ ID NO: 272 is the determined cDNA sequence for JP1A9
SEQ ID NO: 273 is the determined cDNA sequence for JP1F12
SEQ ID NO: 274 is the determined cDNA sequence for JP1E12
SEQ ID NO: 275 is the determined cDNA sequence for JP1D11
SEQ ID NO: 276 is the determined cDNA sequence for JP1C11
SEQ ID NO: 277 is the determined cDNA sequence for JP1C12
SEQ ID NO: 278 is the determined cDNA sequence for JP1B12
SEQ ID NO: 279 is the determined cDNA sequence for JP1-A12
SEQ ID NO: 280 is the determined cDNA sequence for JP8G2
SEQ ID NO: 281 is the determined cDNA sequence for JP8H1
SEQ ID NO: 282 is the determined cDNA sequence for JP8H2
SEQ ID NO: 283 is the determined cDNA sequence for JP8A3
SEQ ID NO: 284 is the determined cDNA sequence for JP8A4
SEQ ID NO: 285 is the determined cDNA sequence for JP8C3
SEQ ID NO: 286 is the determined cDNA sequence for JP8G4
SEQ ID NO: 287 is the determined cDNA sequence for JP8B6
SEQ ID NO: 288 is the determined cDNA sequence for JP8D6
SEQ ID NO: 289 is the determined cDNA sequence for JP8F5
SEQ ID NO: 290 is the determined cDNA sequence for JP8A8
SEQ ID NO: 291 is the determined cDNA sequence for JP8C7
SEQ ID NO: 292 is the determined cDNA sequence for JP8D7
SEQ ID NO: 293 is the determined cDNA sequence for P8D8
SEQ ID NO: 294 is the determined cDNA sequence for JP8E7
SEQ ID NO: 295 is the determined cDNA sequence for JP8F8
SEQ ID NO: 296 is the determined cDNA sequence for JP8G8
SEQ ID NO: 297 is the determined cDNA sequence for JP8B10
SEQ ID NO: 298 is the determined cDNA sequence for JP8C10
SEQ ID NO: 299 is the determined cDNA sequence for JP8E9
SEQ ID NO: 300 is the determined cDNA sequence for JP8E10
SEQ ID NO: 301 is the determined cDNA sequence for JP8F9
SEQ ID NO: 302 is the determined cDNA sequence for JP8H9
SEQ ID NO: 303 is the determined cDNA sequence for JP8C12
SEQ ID NO: 304 is the determined cDNA sequence for JP8E11
SEQ ID NO: 305 is the determined cDNA sequence for JP8E12
SEQ ID NO: 306 is the amino acid sequence for the peptide PS2#12
SEQ ID NO: 307 is the determined cDNA sequence for P711P
SEQ ID NO: 308 is the determined cDNA sequence for P712P
SEQ ID NO: 309 is the determined cDNA sequence for CLONE23
SEQ ID NO: 310 is the determined cDNA sequence for P774P
SEQ ID NO: 311 is the determined cDNA sequence for P775P
SEQ ID NO: 312 is the determined cDNA sequence for P715P
SEQ ID NO: 313 is the determined cDNA sequence for P710P
SEQ ID NO: 314 is the determined cDNA sequence for P767P
SEQ ID NO: 315 is the determined cDNA sequence for P768P
SEQ ID NO: 316–325 are the determined cDNA sequences of previously isolated genes
SEQ ID NO: 326 is the determined cDNA sequence for P703PDE5

SEQ ID NO: 327 is the predicted amino acid sequence for P703PDE5

SEQ ID NO: 328 is the determined cDNA sequence for P703P6.26

SEQ ID NO: 329 is the predicted amino acid sequence for P703P6.26

SEQ ID NO: 330 is the determined cDNA sequence for P703PX-23

SEQ ID NO: 331 is the predicted amino acid sequence for P703PX-23

SEQ ID NO: 332 is the determined full length cDNA sequence for P509S

SEQ ID NO: 333 is the determined extended cDNA sequence for P707P (also referred to as 11-C9)

SEQ ID NO: 334 is the determined cDNA sequence for P714P

SEQ ID NO: 335 is the determined cDNA sequence for P705P (also referred to as 9-F3)

SEQ ID NO: 336 is the predicted amino acid sequence for P705P

SEQ ID NO: 337 is the amino acid sequence of the peptide P1 S#10

SEQ ID NO: 338 is the amino acid sequence of the peptide p5

SEQ ID NO: 339 is the predicted amino acid sequence of P509S

SEQ ID NO: 340 is the determined cDNA sequence for P778P

SEQ ID NO: 341 is the determined cDNA sequence for P786P

SEQ ID NO: 342 is the determined cDNA sequence for P789P

SEQ ID NO: 343 is the determined cDNA sequence for a clone showing homology to Homo sapiens MM46 mRNA SEQ ID NO: 344 is the determined cDNA sequence for a clone showing homology to Homo sapiens TNF-alpha stimulated ABC protein (ABC50) mRNA SEQ ID NO: 345 is the determined cDNA sequence for a clone showing homology to Homo sapiens mRNA for E-cadherin SEQ ID NO: 346 is the determined cDNA sequence for a clone showing homology to Human nuclear-encoded mitochondrial serine hydroxymethyltransferase (SHMT)

SEQ ID NO: 347 is the determined cDNA sequence for a clone showing homology to Homo sapiens natural resistance-associated macrophage protein2 (NRAMP2)

SEQ ID NO: 348 is the determined cDNA sequence for a clone showing homology to Homo sapiens phosphoglucomutase-related protein (PGMRP)

SEQ ID NO: 349 is the determined cDNA sequence for a clone showing homology to Human mRNA for proteosome subunit p40

SEQ ID NO: 350 is the determined cDNA sequence for P777P

SEQ ID NO: 351 is the determined cDNA sequence for P779P

SEQ ID NO: 352 is the determined cDNA sequence for P790P

SEQ ID NO: 353 is the determined cDNA sequence for P784P

SEQ ID NO: 354 is the determined cDNA sequence for P776P

SEQ ID NO: 355 is the determined cDNA sequence for P780P

SEQ ID NO: 356 is the determined cDNA sequence for P544S

SEQ ID NO: 357 is the determined cDNA sequence for P745S

SEQ ID NO: 358 is the determined cDNA sequence for P782P

SEQ ID NO: 359 is the determined cDNA sequence for P783P

SEQ ID NO: 360 is the determined cDNA sequence for unknown 17984

SEQ ID NO: 361 is the determined cDNA sequence for P 787P

SEQ ID NO: 362 is the determined cDNA sequence for P788P

SEQ ID NO: 363 is the determined cDNA sequence for unknown 17994

SEQ ID NO: 364 is the determined cDNA sequence for P781P

SEQ ID NO: 365 is the determined cDNA sequence for P785P

SEQ ID NO: 366–375 are the determined cDNA sequences for splice variants of B305D.

SEQ ID NO: 376 is the predicted amino acid sequence encoded by the sequence of SEQ ID NO: 366.

SEQ ID NO: 377 is the predicted amino acid sequence encoded by the sequence of SEQ ID NO: 372.

SEQ ID NO: 378 is the predicted amino acid sequence encoded by the sequence of SEQ ID NO: 373.

SEQ ID NO: 379 is the predicted amino acid sequence encoded by the sequence of SEQ ID NO: 374.

SEQ ID NO: 380 is the predicted amino acid sequence encoded by the sequence of SEQ ID NO: 375.

SEQ ID NO: 381 is the determined cDNA sequence for B716P.

SEQ ID NO: 382 is the determined full-length cDNA sequence for P711P.

SEQ ID NO: 383 is the predicted amino acid sequence for P711P.

SEQ ID NO: 384 is the cDNA sequence for P1000C.

SEQ ID NO: 385 is the cDNA sequence for CGI-82.

SEQ ID NO:386 is the cDNA sequence for 23320.

SEQ ID NO:387 is the cDNA sequence for CGI-69.

SEQ ID NO:388 is the cDNA sequence for L-iditol-2-dehydrogenase.

SEQ ID NO:389 is the cDNA sequence for 23379.

SEQ ID NO:390 is the cDNA sequence for 23381.

SEQ ID NO:391 is the cDNA sequence for KIAA0122.

SEQ ID NO:392 is the cDNA sequence for 23399.

SEQ ID NO:393 is the cDNA sequence for a previously identified gene.

SEQ ID NO:394 is the cDNA sequence for HCLBP.

SEQ ID NO:395 is the cDNA sequence for transglutaminase.

SEQ ID NO:396 is the cDNA sequence for a previously identified gene.

SEQ ID NO:397 is the cDNA sequence for PAP.

SEQ ID NO:398 is the cDNA sequence for Ets transcription factor PDEF.

SEQ ID NO:399 is the cDNA sequence for hTGR.
SEQ ID NO:400 is the cDNA sequence for KIAA0295.
SEQ ID NO:401 is the cDNA sequence for 22545.
SEQ ID NO:402 is the cDNA sequence for 22547.
SEQ ID NO:403 is the cDNA sequence for 22548.
SEQ ID NO:404 is the cDNA sequence for 22550.
SEQ ID NO:405 is the cDNA sequence for 22551.
SEQ ID NO:406 is the cDNA sequence for 22552.
SEQ ID NO:407 is the cDNA sequence for 22553.
SEQ ID NO:408 is the cDNA sequence for 22558.
SEQ ID NO:409 is the cDNA sequence for 22562.
SEQ ID NO:410 is the cDNA sequence for 22565.
SEQ ID NO:411 is the cDNA sequence for 22567.
SEQ ID NO:412 is the cDNA sequence for 22568.
SEQ ID NO:413 is the cDNA sequence for 22570.
SEQ ID NO:414 is the cDNA sequence for 22571.
SEQ ID NO:415 is the cDNA sequence for 22572.
SEQ ID NO:416 is the cDNA sequence for 22573.
SEQ ID NO:417 is the cDNA sequence for 22573.
SEQ ID NO:418 is the cDNA sequence for 22575.
SEQ ID NO:419 is the cDNA sequence for 22580.
SEQ ID NO:420 is the cDNA sequence for 22581.
SEQ ID NO:421 is the cDNA sequence for 22582.
SEQ ID NO:422 is the cDNA sequence for 22583.
SEQ ID NO:423 is the cDNA sequence for 22584.
SEQ ID NO:424 is the cDNA sequence for 22585.
SEQ ID NO:425 is the cDNA sequence for 22586.
SEQ ID NO:426 is the cDNA sequence for 22587.
SEQ ID NO:427 is the cDNA sequence for 22588.
SEQ ID NO:428 is the cDNA sequence for 22589.
SEQ ID NO:429 is the cDNA sequence for 22590.
SEQ ID NO:430 is the cDNA sequence for 22591.
SEQ ID NO:431 is the cDNA sequence for 22592.
SEQ ID NO:432 is the cDNA sequence for 22593.
SEQ ID NO:433 is the cDNA sequence for 22594.
SEQ ID NO:434 is the cDNA sequence for 22595.
SEQ ID NO:435 is the cDNA sequence for 22596.
SEQ ID NO:436 is the cDNA sequence for 22847.
SEQ ID NO:437 is the cDNA sequence for 22848.
SEQ ID NO:438 is the cDNA sequence for 22849.
SEQ ID NO:439 is the cDNA sequence for 22851.
SEQ ID NO:440 is the cDNA sequence for 22852.
SEQ ID NO:441 is the cDNA sequence for 22853.
SEQ ID NO:442 is the cDNA sequence for 22854.
SEQ ID NO:443 is the cDNA sequence for 22855.
SEQ ID NO:444 is the cDNA sequence for 22856.
SEQ ID NO:445 is the cDNA sequence for 22857.
SEQ ID NO:446 is the cDNA sequence for 23601.
SEQ ID NO:447 is the cDNA sequence for 23602.
SEQ ID NO:448 is the cDNA sequence for 23605.
SEQ ID NO:449 is the cDNA sequence for 23606.
SEQ ID NO:450 is the cDNA sequence for 23612.
SEQ ID NO:451 is the cDNA sequence for 23614.
SEQ ID NO:452 is the cDNA sequence for 23618.
SEQ ID NO:453 is the cDNA sequence for 23622.
SEQ ID NO:454 is the cDNA sequence for folate hydrolase.
SEQ ID NO:455 is the cDNA sequence for LIM protein.
SEQ ID NO:456 is the cDNA sequence for a known gene.
SEQ ID NO:457 is the cDNA sequence for a known gene.
SEQ ID NO:458 is the cDNA sequence for a previously identified gene.
SEQ ID NO:459 is the cDNA sequence for 23045.
SEQ ID NO:460 is the cDNA sequence for 23032.
SEQ ID NO:461 is the cDNA sequence for 23054.
SEQ ID NOs:462–467 are cDNA sequences for known genes.
SEQ ID NOs:468–471 are cDNA sequences for P710P.
SEQ ID NO:472 is a cDNA sequence for P1001C.

DETAILED DESCRIPTION OF THE INVENTION

As noted above, the present invention is generally directed to compositions and methods for the therapy and diagnosis of cancer, such as prostate cancer. The compositions described herein may include prostate tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a prostate tumor protein or a variant thereof. A "prostate tumor protein" is a protein that is expressed in prostate tumor cells at a level that is at least two fold, and preferably at least five fold, greater than the level of expression in a normal tissue, as determined using a representative assay provided herein. Certain prostate tumor proteins are tumor proteins that react detectably (within an immunoassay, such as an ELISA or Western blot) with antisera of a patient afflicted with prostate cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human prostate tumor proteins. Sequences of polynucleotides encoding certain tumor proteins, or portions thereof, are provided in SEQ ID NOs:1–111, 115–171, 173–175, 177, 179–305, 307–315, 326, 328, 330, 332–335, 340–375, 381, 382 or 384–472. Sequences of polypeptides comprising at least a portion of a tumor protein are provided in SEQ ID NOs:112–114, 172, 176, 178, 327, 329, 331, 336, 339, 376–380 and 383.

PROSTATE TUMOR PROTEIN POLYNUCLEOTIDES

Any polynucleotide that encodes a prostate tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a prostate tumor protein. More preferably, a polynucleotide encodes an immunogenic portion of a prostate tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a prostate tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate tumor protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native prostate tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least five fold greater in a prostate tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad Sci. USA* 93:10614–10619, 1996 and Heller et al., *Proc. Natl. Acad Sci. USA* 94:2150–2155, 1997). Alternatively, polypeptides may be amplified from cDNA prepared from cells expressing the proteins described herein, such as prostate tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding at least a portion of a prostate tumor protein are provided in SEQ ID NOs:1–111, 115–171, 173–175, 177, 179–305, 307–315, 326, 328, 330, 332–335, 340–375, 381, 382 or 384–472. Isolation of these polynucleotides is described below. Each of these prostate tumor proteins was overexpressed in prostate tumor tissue.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a prostate tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a prostate tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al, In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

PROSTATE TUMOR POLYPEPTIDES

Within the context of the present invention, polypeptides may comprise at least an immunogenic portion of a prostate tumor protein or a variant thereof, as described herein. As noted above, a "prostate tumor protein" is a protein that is expressed by prostate tumor cells. Proteins that are prostate tumor proteins also react detectably within an immunoassay (such as an ELISA) with antisera from a patient with prostate cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostate tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundmental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native prostate tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native prostate tumor protein. A polypeptide "variant," as used herein, is a polypeptide that differs from a native prostate tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc*. 85:2149–2146, 1963. Equipment for automated synthesis of polypeptides is commercially available from suppliers such as Perkin Elmer/Applied BioSystems Division (Foster City, Calif.), and may be operated according to the manufacturers instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–100 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in E. coli (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of E. coli C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

BINDING AGENTS

The present invention further provides agents, such as antibodies and antigen-binding fragments thereof, that specifically bind to a prostate tumor protein. As used herein, an antibody, or antigen-binding fragment thereof, is said to "specifically bind" to a prostate tumor protein if it reacts at a detectable level (within, for example, an ELISA) with a prostate tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as prostate cancer, using the representative assays provided herein. In other words, antibodies or other binding agents that bind to a prostate tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T CELLS

Immunotherapeutic compositions may also, or alternatively, comprise T cells specific for a prostate tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a prostate tumor polypeptide, polynucleotide encoding a prostate tumor polypeptide and/or an antigen presenting cell (APC) that expresses such a polypeptide. Such stimulation is performed under conditions and for a time sufficient to permit the generation of T cells that are specific for the polypeptide. Preferably, a prostate tumor polypeptide or polynucleotide is present within a delivery vehicle, such as a microsphere, to facilitate the generation of specific T cells.

T cells are considered to be specific for a prostate tumor polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res*. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a prostate tumor polypeptide (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a prostate tumor polypeptide, polynucleotide or polypeptide-expressing APC may be CD4$^+$ and/or CD8$^+$. Prostate tumor protein-specific T cells may be expanded using standard techniques. Within preferred embodiments, the T cells are derived from either a patient or a related, or unrelated, donor and are administered to the patient following stimulation and expansion.

For therapeutic purposes, CD4$^+$ or CD8$^+$ T cells that proliferate in response to a prostate tumor polypeptide, polynucleotide or APC can be expanded in number either in vitro or in vivo. Proliferation of such T cells in vitro may be accomplished in a variety of ways. For example, the T cells can be re-exposed to a prostate tumor polypeptide, or a short peptide corresponding to an immunogenic portion of such a polypeptide, with or without the addition of T cell growth factors, such as interleukin-2, and/or stimulator cells that synthesize a prostate tumor polypeptide. Alternatively, one or more T cells that proliferate in the presence of a prostate tumor protein can be expanded in number by cloning. Methods for cloning cells are well known in the art, and include limiting dilution.

PHARMACEUTICAL COMPOSITIONS AND VACCINES

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad Sci. USA* 91:215–219, 1994; Kass-Eisler et al., *Proc. Natl. Acad. Sci. USA* 90:11498–11502, 1993; Guzman et al., *Circulation* 88:2838–2848. 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96102555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a prostate tumor protein (or portion or other variant thereof) such that the prostate tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the prostate tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

CANCER THERAPY

In further aspects of the present invention, the compositions described herein may be used for immunotherapy of cancer, such as prostate cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

METHODS FOR DETECTING CANCER

In general, a cancer may be detected in a patient based on the presence of one or more prostate tumor proteins and/or polynucleotides encoding such proteins in a biological sample (for example, blood, sera, urine and/or tumor biopsies) obtained from the patient. In other words, such proteins may be used as markers to indicate the presence or absence of a cancer such as prostate cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a prostate tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length prostate tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as prostate cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use prostate tumor polypeptides to detect antibodies that bind to such polypeptides in a biological sample. The detection of such prostate tumor protein specific antibodies may correlate with the presence of a cancer.

A cancer may also, or alternatively, be detected based on the presence of T cells that specifically react with a prostate tumor protein in a biological sample. Within certain methods, a biological sample comprising $CD4^+$ and/or $CD8^+$ T cells isolated from a patient is incubated with a prostate tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with prostate tumor polypeptide (e.g., 5–25 µg/ml). It may be desirable to incubate another aliquot of a T cell sample in the absence of prostate tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a prostate tumor protein in a biological sample. For example, at least two oligonucleotide primers may be employed in a polymerase chain reaction (PCR) based assay to amplify a portion of a prostate tumor cDNA derived from a biological sample, wherein at least one of the oligonucleotide primers is specific for (i.e., hybridizes to) a polynucleotide encoding the prostate tumor protein. The amplified cDNA is then separated and detected using techniques well known in the art, such as gel electrophoresis. Similarly, oligonucleotide probes that specifically hybridize to a polynucleotide encoding a prostate tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a prostate tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–111, 115–171, 173–175, 177, 179–305, 307–315, 326, 328, 330, 332–335, 340–375 and 381. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the noncancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple prostate tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

DIAGNOSTIC KITS

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a prostate tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a prostate tumor protein in a biological sample. Such kits generally comprise at least one oligonucleotide probe or primer, as described above, that hybridizes to a polynucleotide encoding a prostate tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a prostate tumor protein.

The following Examples are offered by way of illustration and not by way of limitation.

EXAMPLES

Example 1

Isolation and Characterization of Prostate Tumor Polypeptides

This Example describes the isolation of certain prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax $E.$ $coli$ DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination. cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 µg) was digested with EcoRi, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl $H_2O$ to form the driver DNA.

To form the tracer DNA, 10 µg prostate tumor cDNA library was digested with BamHI and XhoI, phenol chloroform extracted and passed through Chroma spin-400 columns (Clontech). Following ethanol precipitation, the tracer DNA was dissolved in 5 µl H$_2$O. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl H$_2$O, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax E. coli DH10B cells by electroporation to generate a prostate tumor specific subtracted cDNA library (referred to as "prostate subtraction 1").

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107; with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1µg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23 24–25, 26–27 and 28–29, respectively. The determined 3 cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1–48; SEQ ID NO:33) was determined to have some homology to R. norvegicus mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114. L1-12 is also referred to as P501S.

In a further experiment, four additional clones were identified by subtracting a prostate tumor cDNA library with normal prostate cDNA prepared from a pool of three normal prostate poly A$^+$ RNA (referred to as "prostate subtraction 2"). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (referred to as "prostate subtraction spike 2") was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively.

Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

Additional studies with prostate subtraction spike 2 resulted in the isolation of three more clones. Their sequences were determined as described above and compared to the most recent GenBank. All three clones were found to have homology to known genes, which are Cysteine-rich protein, KIAA0242, and KIAA0280 (SEQ ID NO: 317, 319, and 320, respectively). Further analysis of these clones by Synteni microarray (Synteni, Palo Alto, Calif.) demonstrated that all three clones were over-expressed in most prostate tumors and prostate BPH, as well as in the majority of normal prostate tissues tested, but low expression in all other normal tissues.

An additional subtraction was performed by subtracting a normal prostate cDNA library with normal pancreas cDNA (referred to as "prostate subtraction 3"). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA$^+$ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Additional, studies led to the isolation of the full-length cDNA sequence for P509S. This sequence is provided in SEQ ID NO: 332, with the corresponding predicted amino acid sequence being provided in SEQ ID NO: 339.

Example 2

Determination of Tissue Specificity of Prostate Tumor Polypeptides

Using gene specific primers, mRNA expression levels for the representative prostate tumor polypeptides F1-16, H1-1, J1-17 (also referred to as P502S), L1-12 (also referred to as P501S), F1-12 (also referred to as P504S) and N1-1862 (also referred to as P503S) were examined in a variety of normal and tumor tissues using RT-PCR.

Briefly, total RNA was extracted from a variety of normal and tumor tissues using Trizol reagent as described above. First strand synthesis was carried out using 1–2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 (P502S) and L1-12 (P501S) appear to be specifically over-expressed in prostate, with both genes being expressed at high levels in prostate tumor and normal prostate but at low to undetectable levels in all the other tissues examined. N1-1862 (P503S) was found to be over-expressed in 60% of prostate tumors and detectable in normal colon and kidney. The RT-PCR results thus indicate that F1-16, H1-1, J1-17 (P502S), N1-1862 (P503S)

and L1-12 (P501S) are either prostate specific or are expressed at significantly elevated levels in prostate.

Further RT-PCR studies showed that F1-12 (P504S) is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 (P501S) is over-expressed in prostate tumors and normal prostate, while being undetectable in other normal tissues tested. J1-17 (P502S) was detected in two prostate tumors and not in the other tissues tested. N1-1862 (P503S) was found to be over-expressed in three prostate tumors and to be expressed in normal prostate, colon and kidney, but not in other tissues tested. F1-12 (P504S) was found to be highly expressed in two prostate tumors and to be undetectable in all other tissues tested.

The microarray technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 (P501S) was found to be over-expressed in normal prostate and prostate tumor, with some expression being detected in normal skeletal muscle. Both J1-12 and F1-12 (P504S) were found to be over-expressed in prostate tumor, with expression being lower or undetectable in all other tissues tested. N1-1862 (P503S) was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Further microarray analysis to specifically address the extent to which P501S (SEQ ID NO: 110) was expressed in breast tumor revealed moderate over-expression not only in breast tumor, but also in metastatic breast tumor (2/31), with negligible to low expression in normal tissues. This data suggests that P501S may be over-expressed in various breast tumors as well as in prostate tumors.

The expression levels of 32 ESTs (expressed sequence tags) described by Vasmatzis et al. (*Proc. Natl. Acad. Sci. USA* 95:300–304, 1998) in a variety of tumor and normal tissues were examined by microarray technology as described above. Two of these clones (referred to as P1000C and P1001C) were found to be over-expressed in prostate tumor and normal prostate, and expressed at low to undetectable levels in all other tissues tested (normal aorta, thymus, resting and activated PBMC, epithelial cells, spinal cord, adrenal gland, fetal tissues, skin, salivary gland, large intestine, bone marrow, liver, lung, dendritic cells, stomach, lymph nodes, brain, heart, small intestine, skeletal muscle, colon and kidney. The determined cDNA sequences for P1000C and P1001C are provided in SEQ ID NO: 384 and 472, respectively. The sequence of P1001C was found to show some homology to the previously isolated Human mRNA for JM27 protein. No significant homologies were found to the sequence of P1000C.

The expression of the polypeptide encoded by the full length cDNA sequence for F1-12 (also referred to as P504S; SEQ ID NO: 108) was investigated by immunohistochemical analysis. Rabbit-anti-P504S polyclonal antibodies were generated against the full length P504S protein by standard techniques. Subsequent isolation and characterization of the polyclonal antibodies were also performed by techniques well known in the art. Immunohistochemical analysis showed that the P504S polypeptide was expressed in 100% of prostate carcinoma samples tested (n=5).

The rabbit-anti-P504S polyclonal antibody did not appear to label benign prostate cells with the same cytoplasmic granular staining, but rather with light nuclear staining. Analysis of normal tissues revealed that the encoded polypeptide was found to be expressed in some, but not all normal human tissues. Positive cytoplasmic staining with rabbit-anti-P504S polyclonal antibody was found in normal human kidney, liver, brain, colon and lung-associated macrophages, whereas heart and bone marrow were negative.

This data indicates that the P504S polypeptide is present in prostate cancer tissues, and that there are qualitative and quantitative differences in the staining between benign prostatic hyperplasia tissues and prostate cancer tissues, suggesting that this polypeptide may be detected selectively in prostate tumors and therefore be useful in the diagnosis of prostate cancer.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' *E. coli* (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO: 41–45, 47–52 and 54–65, respectively. P29, P47, P68, P80 and P82 (SEQ ID NO: 46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. Larger cDNA clones containing the P20 sequence represent splice variants of a gene referred to as P703P. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20, a portion of the P703P gene, was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA expression levels for these clones were determined using the micro-array technology described above. The clones 7-G6, 8-G3, 8-B5, 8-B6, 8-D4, 8-D9, 9-F3, 9-F12, 9-H3, 10-A2, 10-A4, 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

PCR and hybridization-based methodologies were employed to obtain longer cDNA sequences for clone P20 (also referred to as P703P), yielding three additional cDNA fragments that progressively extend the 5' end of the gene. These fragments, referred to as P7.03PDE5, P703P6.26, and P703PX-23 (SEQ ID NO: 326, 328 and 330, with the predicted corresponding amino acid sequences being provided in SEQ ID NO: 327, 329 and 331, respectively) contain additional 5' sequence. P703PDE5 was recovered by screening of a cDNA library (#141-26) with a portion of P703P as a probe. P703P6.26 was recovered from a mixture of three prostate tumor cDNAs and P703PX__23 was recovered from cDNA library (#438-48). Together, the additional sequences include all of the putative mature serine protease along with part of the putative signal sequence. Further studies using a PCR-based subtraction library of a prostate tumor pool subtracted against a pool of normal tissues (referred to as JP: PCR subtraction) resulted in the isolation of thirteen additional clones, seven of which did not share any significant homology to known GenBank sequences. The determined cDNA sequences for these seven clones (P711P, P712P, novel 23, P774P, P775P, P710P and P768P) are provided in SEQ ID NO: 307–311, 313 and 315, respectively. The remaining six clones (SEQ ID NO: 316 and 321–325) were shown to share some homology to known genes. By microarray analysis, all thirteen clones showed three or more fold over-expression in prostate tissues, including prostate tumors, BPH and normal prostate as compared to normal non-prostate tissues. Clones P711P, P712P, novel 23 and P768P showed over-expression in most prostate tumors and BPH tissues tested (n=29), and in the majority of normal prostate tissues (n=4), but background to low expression levels in all normal tissues. Clones P774P, P775P and P710P showed comparatively lower expression and expression in fewer prostate tumors and BPH samples, with negative to low expression in normal prostate.

The full-length cDNA for P711P was obtained by employing the partial sequence of SEQ ID NO: 307 to screen a prostate cDNA library. Specifically, a directionally cloned prostate cDNA library was prepared using standard techniques. One million colonies of this library were plated onto LB/Amp plates. Nylon membrane filters were used to lift these colonies, and the cDNAs which were picked up by these filters were denatured and cross-linked to the filters by UV light. The P711P cDNA fragment of SEQ ID NO: 307 was radio-labeled and used to hybridize with these filters. Positive clones were selected, and cDNAs were prepared and sequenced using an automatic Perkin Elmer/Applied Biosystems sequencer. The determined full-length sequence of P711P is provided in SEQ ID NO: 382, with the corresponding predicted amino acid sequence being provided in SEQ ID NO: 383.

Using PCR and hybridization-based methodologies, additional cDNA sequence information was derived for two clones described above, 11-C9 and 9-F3, herein after referred to as P707P and P714P, respectively (SEQ ID NO: 333 and 334). After comparison with the most recent GenBank, P707P was found to be a splice variant of the known gene HoxB13. In contrast, no significant homologies to P714P were found.

Clones 8-B3, P89, P98, P130 and P201 (as disclosed in U.S. patent application Ser. No. 09/020,956, filed Feb. 9, 1998) were found to be contained within one contiguous sequence, referred to as P705P (SEQ ID NO: 335, with the predicted amino acid sequence provided in SEQ ID NO: 336), which was determined to be a splice variant of the known gene NKX 3.1.

Example 4

Synthesis of Polypeptides

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Further Isolation and Characterization of Prostate Tumor Polypeptides by PCR-Based Subtraction A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven further clones were identified. Sequences of these partial cDNAs are provided in SEQ ID NO: 29 to 305. Most of these clones had no significant homology to database sequences. Exceptions were JPTPN23 (SEQ ID NO: 231; similarity to pig valosin-containing protein), JPTPN30 (SEQ ID NO: 234; similarity to rat mRNA for proteasome subunit), JPTPN45 (SEQ ID NO: 243; similarity to rat norvegicus cytosolic NADP-dependent isocitrate dehydrogenase), JPTPN46 (SEQ ID NO: 244; similarity to human subclone H8 4 d4 DNA sequence), JP1D6 (SEQ ID NO: 265; similarity to *G. gallus* dynein light chain-A), JP8D6 (SEQ ID NO: 288; similarity to human BAC clone RG016J04), JP8F5 (SEQ ID NO: 289; similarity to human subclone H8 3 b5 DNA sequence), and JP8E9 (SEQ ID NO: 299; similarity to human Alu sequence).

Additional studies using the PCR-based subtraction library consisting of a prostate tumor pool subtracted against a normal prostate pool (referred to as PT-PN PCR subtraction) yielded three additional clones. Comparison of the cDNA sequences of these clones with the most recent release of GenBank revealed no significant homologies to the two clones referred to as P715P and P767P (SEQ ID NO: 312 and 314). The remaining clone was found to show some homology to the known gene KIAA0056 (SEQ ID NO: 318). Using microarray analysis to measure mRNA expression levels in various tissues, all three clones were found to be over-expressed in prostate tumors and BPH tissues. Specifically, clone P715P was over-expressed in most prostate tumors and BPH tissues by a factor of three or greater, with elevated expression seen in the majority of normal prostate samples and in fetal tissue, but negative to low expression in all other normal tissues. Clone P767P was over-expressed in several prostate tumors and BPH tissues, with moderate expression levels in half of the normal prostate samples, and background to low expression in all other normal tissues tested.

Further analysis, by microarray as described above, of the PT-PN PCR subtraction library and of a DNA subtraction library containing cDNA from prostate tumor subtracted with a pool of normal tissue cDNAs, led to the isolation of 27 additional clones (SEQ ID NO: 340–365 and 381) which were determined to be over-expressed in prostate tumor. The clones of SEQ ID NO: 341, 342, 345, 347, 348, 349, 351, 355–359, 361, 362 and 364 were also found to be expressed in normal prostate. Expression of all 26 clones in a variety of normal tissues was found to be low or undetectable, with the exception of P544S (SEQ ID NO: 356) which was found to be expressed in small intestine. Of the 26 clones, 10 (SEQ ID NO: 340–349) were found to show some homology to previously identified sequences. No significant homologies were found to the clones of SEQ ID NO: 350–365.

Example 6

Peptide Priming of Mice and Propagation of CTL Lines 6.1. This Example illustrates the preparation of a CTL cell line specific for cells expressing the P502S gene.

Mice expressing the transgene for human HLA A2.1 (provided by Dr L. Sherman, The Scripps Research Institute, La Jolla, Calif.) were immunized with P2S#12 peptide (VLGWVAEL; SEQ ID NO: 306), which is derived from the P502S gene (also referred to herein as J1-17, SEQ ID NO: 8), as described by Theobald et al., *Proc. Natl. Acad Sci. USA* 92:11993–11997, 1995 with the following modifications. Mice were immunized with 100 μg of P2S#12 and 120 μg of an I-A$^b$ binding peptide derived from hepatitis B Virus protein emulsified in incomplete Freund's adjuvant. Three weeks later these mice were sacrificed and using a nylon mesh single cell suspensions prepared. Cells were then resuspended at 6 ×10$^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×10$^{-5}$ M 2-mercaptoethanol, 50 U/ml penicillin and streptomycin, and cultured in the presence of irradiated (3000 rads) P2S#12-pulsed (5 mg/ml P2S#12 and 10 mg/ml β2-microglobulin) LPS blasts (A2 transgenic spleens cells cultured in the presence of 7 μg/ml dextran sulfate and 25 μg/ml LPS for 3 days). Six days later, cells (5×10$^5$/ml) were restimulated with 2.5×10$^6$/ml peptide pulsed irradiated (20,000 rads) EL4A2Kb cells (Sherman et al, *Science* 258:815–818, 1992) and 3×10$^6$/ml A2 transgenic spleen feeder cells. Cells were cultured in the presence of 20 U/ml IL-2. Cells continued to be restimulated on a weekly basis as described, in preparation for cloning the line.

Figure 1:
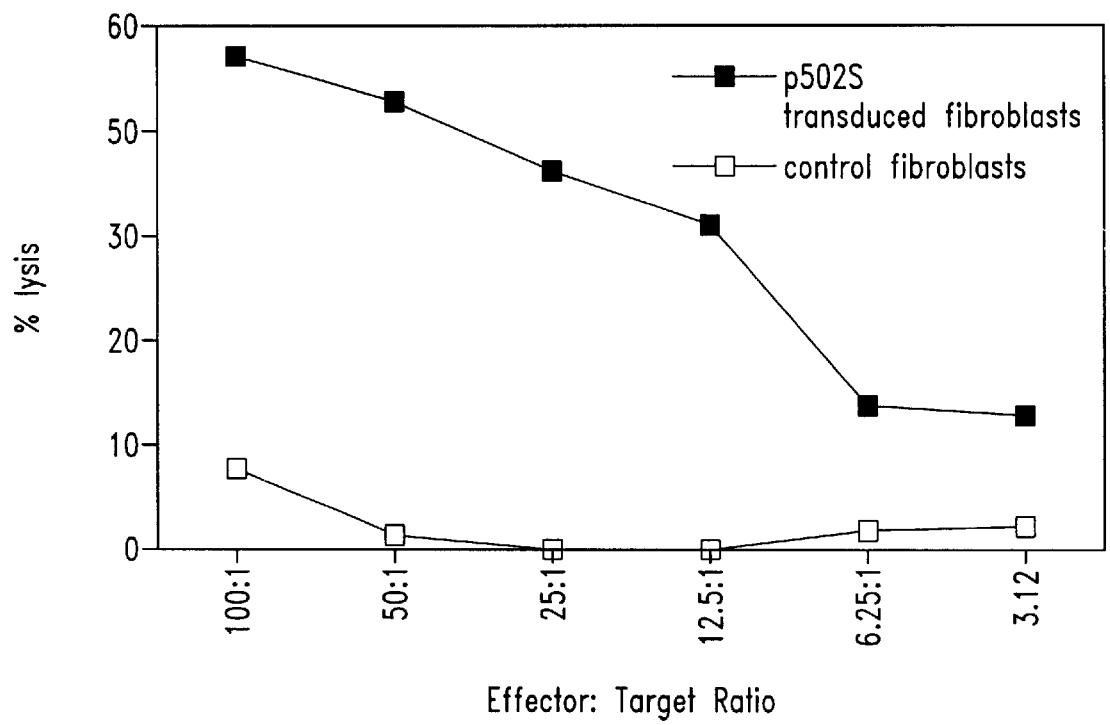

P2S#12 line was cloned by limiting dilution analysis with peptide pulsed EL4 A2Kb tumor cells (1×10$^4$ cells/well) as stimulators and A2 transgenic spleen cells as feeders (5×10$^5$ cells/well) grown in the presence of 30 U/ml IL-2. On day 14, cells were restimulated as before. On day 21, clones that were growing were isolated and maintained in culture. Several of these clones demonstrated significantly higher reactivity (lysis) against human fibroblasts (HLA A2.1 expressing) transduced with P502S than against control fibroblasts. An example is presented in FIG. 1.

This data indicates that P2S #12 represents a naturally processed epitope of the P502S protein that is expressed in the context of the human HLA A2.1 molecule.

6.2. This Example illustrates the preparation of murine CTL lines and CTL clones specific for cells expressing the P501S gene.

Figure 3:
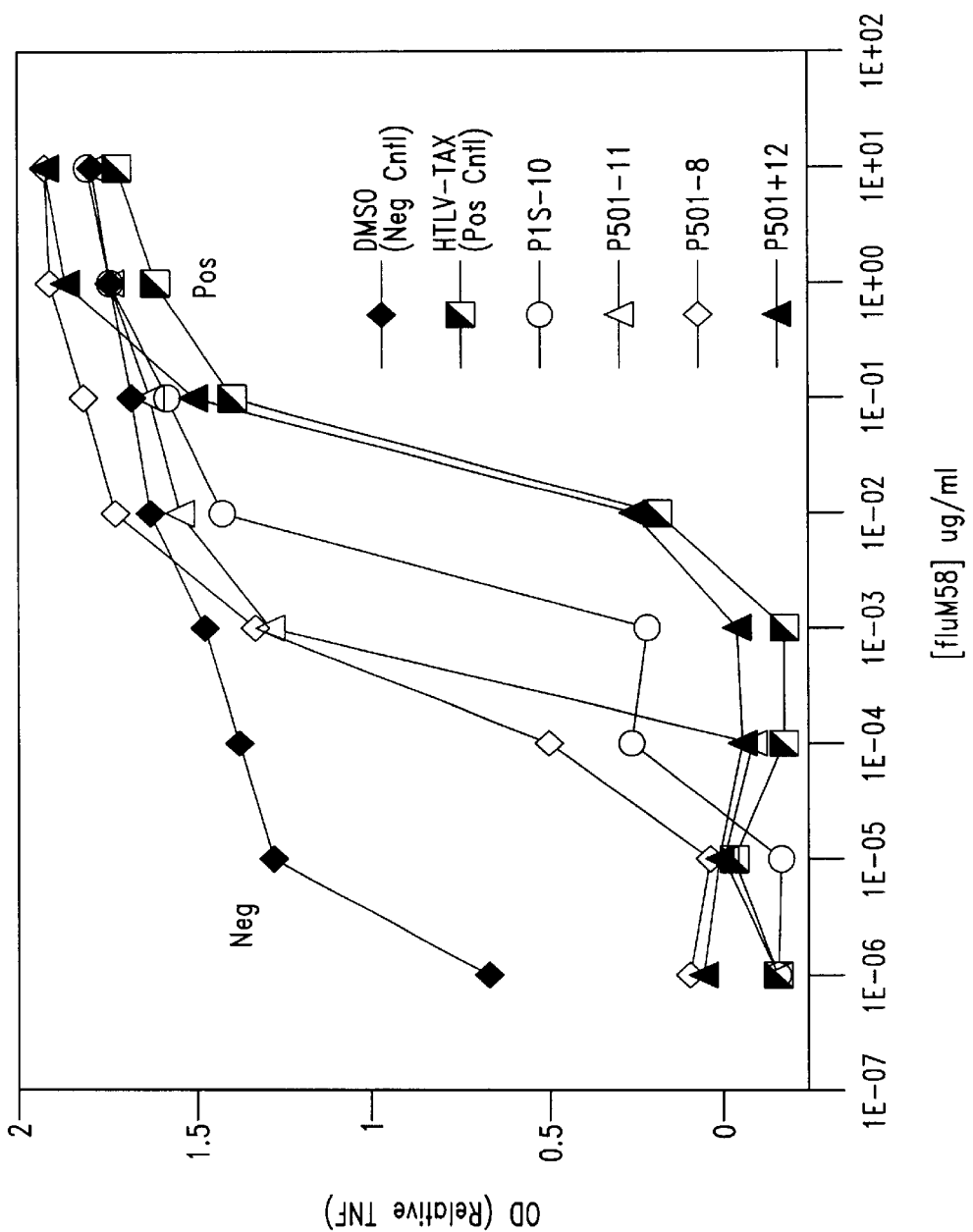

This series of experiments were performed similarly to that described above. Mice were immunized with the P1S#10 peptide (SEQ ID NO: 337), which is derived from the P501S gene (also referred to herein as L1-12, SEQ ID NO: 110). The P1S#10 peptide was derived by analysis of the predicted polypeptide sequence for P501 S for potential HLA-A2 binding sequences as defined by published HLA-A2 binding motifs (Parker, KC, et al, *J. Immunol.*, 152:163, 1994). P1S#10 peptide was synthesized as described in Example 4, and empirically tested for HLA-A2 binding using a T cell based competition assay. Predicted A2 binding peptides were tested for their ability to compete HLA-A2 specific peptide presentation to an HLA-A2 restricted CTL clone (D150M58), which is specific for the HLA-A2 binding influenza matrix peptide fluM58. D150M58 CTL secretes TNF in response to self-presentation of peptide fluM58. In the competition assay, test peptides at 100–200 μg/ml were added to cultures of D150M58 CTL in order to bind HLA-A2 on the CTL. After thirty minutes, CTL cultured with test peptides, or control peptides, were tested for their antigen dose response to the fluM58 peptide in a standard TNF bioassay. As shown in FIG. 3, peptide P1S#10 competes HLA-A2 restricted presentation of fluM58, demonstrating that peptide P1S#10 binds HLA-A2.

Figure 4:
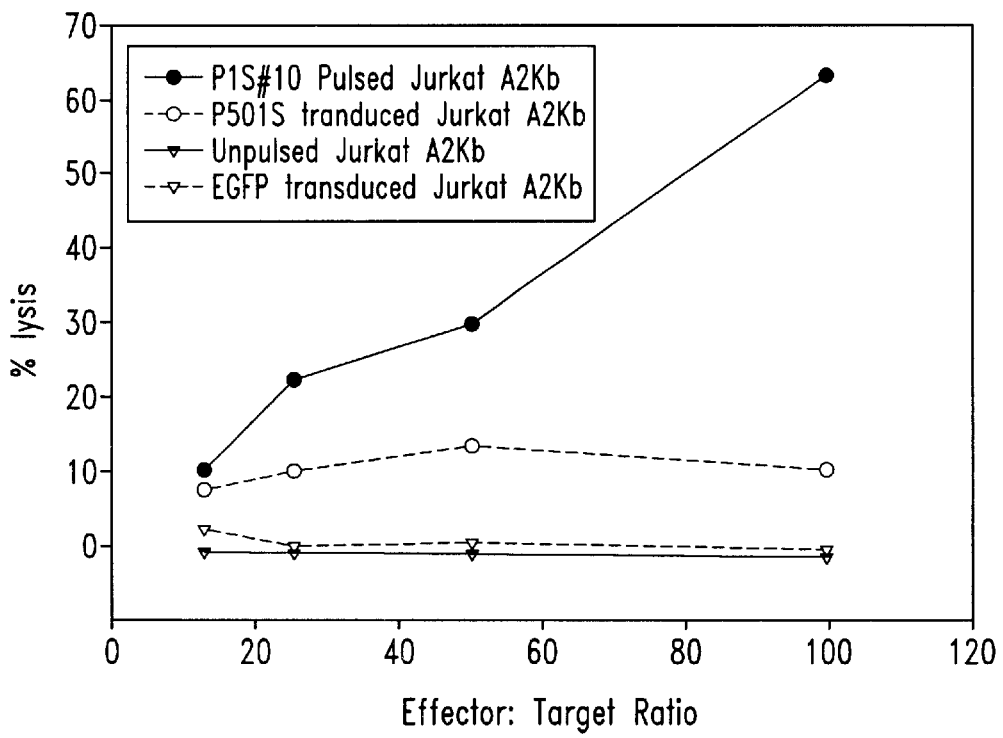
FIG. 4 illustrates the ability of T cell lines generated from P1S#10 immunized mice to specifically lyse P1S#10-pulsed Jurkat A2Kb targets and P501S-transduced Jurkat A2Kb targets, as compared to EGFP-transduced Jurkat A2Kb. The percent lysis is shown as a series of effector to target ratios, as indicated.

Mice expressing the transgene for human HLA A2.1 were immunized as described by Theobald et al. (*Proc. Natl. Acad Sci. USA* 92:11993–11997, 1995) with the following modifications. Mice were immunized with 62.5 μg of P1S#10 and 120 μg of an I-A$^b$ binding peptide derived from Hepatitis B Virus protein emulsified in incomplete Freund's adjuvant. Three weeks later these mice were sacrificed and single cell suspensions prepared using a nylon mesh. Cells were then resuspended at 6×10$^6$ cells/ml in complete media (as described above) and cultured in the presence of irradiated (3000 rads) P1S#10-pulsed (2 μg/ml P1S#10 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide-pulsed irradiated (20, 000 rads) EL4A2Kb cells, as described above, and 3×10$^6$/ml A2 transgenic spleen feeder cells. Cells were cultured in the presence of 20 U/ml IL-2. Cells were restimulated on a weekly basis in preparation for cloning. After three rounds of in vitro stimulations, one line was generated that recognized P1S#10-pulsed Jurkat A2Kb targets and P501S-transduced Jurkat targets as shown in FIG. 4.

Figure 5:
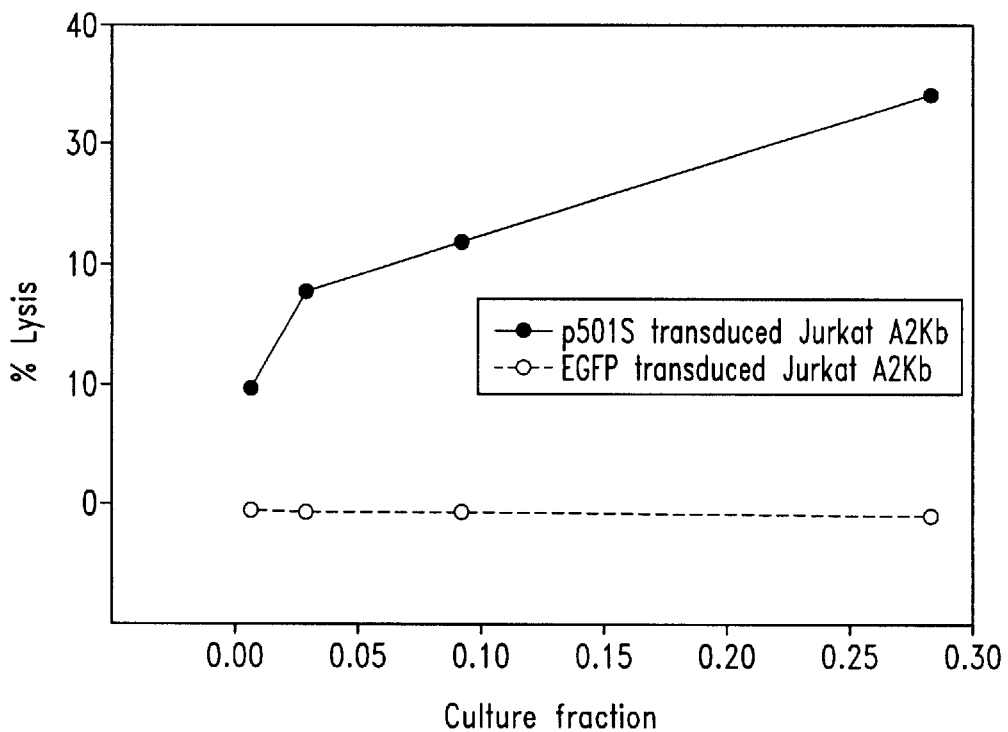
FIG. 5 illustrates the ability of a T cell clone to recognize and specifically lyse Jurkat A2Kb cells expressing the representative prostate tumor polypeptide P501S, thereby demonstrating that the P1S#10 peptide may be a naturally processed epitope of the P501S polypeptide.

A P1S#10-specific CTL line was cloned by limiting dilution analysis with peptide pulsed EL4 A2Kb tumor cells (1×10$^4$ cells/well) as stimulators and A2 transgenic spleen cells as feeders (5×10$^5$ cells/well) grown in the presence of 30 U/ml IL-2. On day 14, cells were restimulated as before. On day 21, viable clones were isolated and maintained in culture. As shown in FIG. 5, five of these clones demonstrated specific cytolytic reactivity against P501S-transduced Jurkat A2Kb targets. This data indicates that P1S#10 represents a naturally processed epitope of the P501S protein that is expressed in the context of the human HLA-A2.1 molecule.

Example 7

Ability of Human T Cells to Recognize Prostate Tumor Polypeptides

This Example illustrates the ability of T cells specific for a prostate tumor polypeptide to recognize human tumor.

Figure 2A:
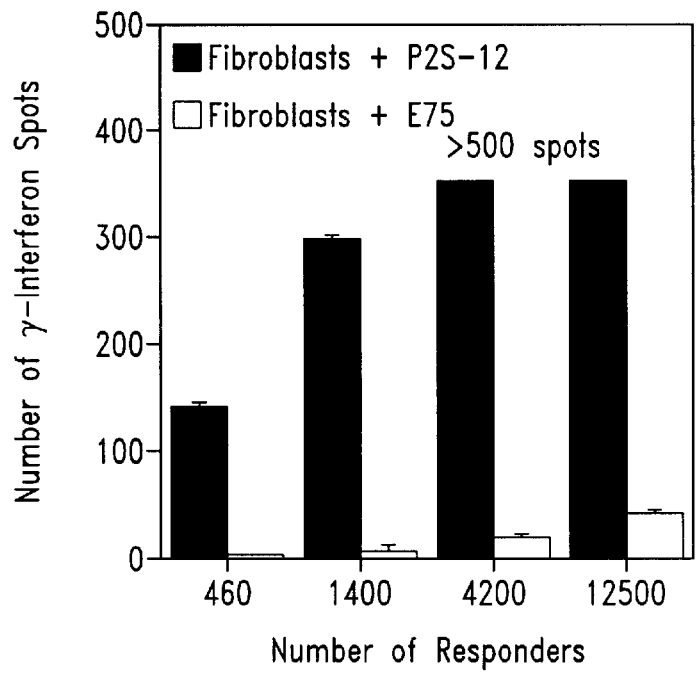
Figure 2B:
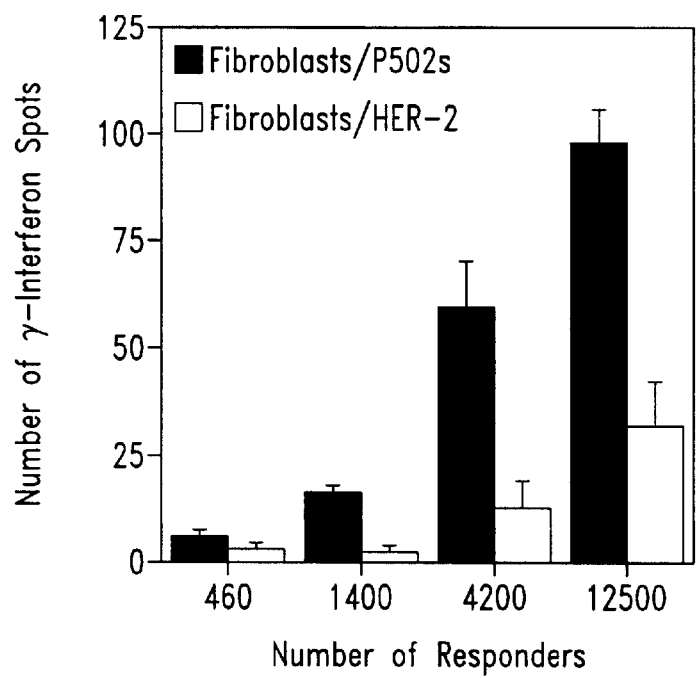

Human CD8$^+$ T cells were primed in vitro to the P2S-12 peptide (SEQ ID NO: 306) derived from P502S (also referred to as J1-17) using dendritic cells according to the protocol of Van Tsai et al. (*Critical Reviews in Immunology* 18:65–75, 1998). The resulting CD8$^+$ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Exp. Med.* 186:859–865, 1997). Briefly, titrating numbers of T cells were assayed in duplicate on $10^4$ fibroblasts in the presence of 3 µg/ml human $β_2$-microglobulin and 1 µg/ml P2S-12 peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. As shown in FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

Example 8

Priming of CTL In Vivo Using Naked DNA Immunization With a Prostate Antigen

The prostate tumor antigen L1-12, as described above, is also referred to as P501S. HLA A2Kb Tg mice (provided by Dr L. Sherman, The Scripps Research Institute, La Jolla, Calif.) were immunized with 100 µg VR10132-P501S either intramuscularly or intradermally. The mice were immunized three times, with a two week interval between immunizations. Two weeks after the last immunization, immune spleen cells were cultured with Jurkat A2Kb-P501S transduced stimulator cells. CTL lines were stimulated weekly. After two weeks of in vitro stimulation, CTL activity was assessed against P501S transduced targets. Two out of 8 mice developed strong anti-P501S CTL responses. These results demonstrate that P501S contains at least one naturally processed A2-restricted CTL epitope.

Example 9

Generation of Human CTL in Vitro Using Whole Gene Priming and Stimulation Techniques with Prostate Tumor Antigen Using in vitro whole-gene priming with P501S-retrovirally transduced autologous fibroblasts (see, for example, Yee et al, *The Journal of Immunology*, 157(9):4079–86, 1996), human CTL lines were derived that specifically recognize autologous fibroblasts transduced with P501S (also known as L1-12), as determined by interferon-γ ELISPOT analysis as described above. Using a panel of HLA-mismatched fibroblast lines transduced with P501S, these CTL lines were shown to be restricted HLA-A2 class I allele. Specifically, dendritic cells (DC) were differentiated from monocyte cultures derived from PBMC of normal human donors by growing for five days in RPMI medium containing 10% human serum, 50 ng/ml human GM-CSF and 30 ng/ml human IL-4. Following culture, DC were infected overnight with recombinant P501S vaccinia virus at a multiplicity of infection (M.O.I) of five, and matured overnight by the addition of 3 µg/ml CD40 ligand. Virus was inactivated by UV irradiation. CD8$^+$ T cells were isolated using a magnetic bead system, and priming cultures were initiated using standard culture techniques. Cultures were restimulated every 7–10 days using autologous primary fibroblasts retrovirally transduced with P501S. Following four stimulation cycles, CD8$^+$ T cell lines were identified that specifically produced interferon-γ when stimulated with P501S-transduced autologous fibroblasts. The P501S-specific activity could be sustained by the continued stimulation of the cultures with P501S-transduced fibroblasts in the presence of IL-15. A panel of HLA-mismatched fibroblast lines transduced with P501S were generated to define the restriction allele of the response. By measuring interferon-γ in an ELISPOT assay, the P501S specific response was shown to be restricted by HLA-A2. These results demonstrate that a CD8$^+$ CTL response to P501S can be elicited.

Example 10

Identification of a Naturally Processed CTL Epitope Contained within a Prostate Tumor Antigen The 9-mer peptide p5 (SEQ ID NO: 338) was derived from the P703P antigen (also referred to as P20). The p5 peptide is immunogenic in human HLA-A2 donors and is a naturally processed epitope. Antigen specific CD8$^+$ T cells can be primed following repeated in vitro stimulations with monocytes pulsed with p5 peptide. These CTL specifically recognize p5-pulsed target cells in both ELISPOT (as described above) and chromium release assays. Additionally, immunization of HLA-A2 transgenic mice with p5 leads to the generation of CTL lines which recognize a variety of P703P transduced target cells expressing either HLA-A2Kb or HLA-A2. Specifically, HLA-A2 transgenic mice were immunized subcutaneously in the footpad with 100 µg of p5 peptide together with 140 µg of hepatitis B virus core peptide (a Th peptide) in Freund's incomplete adjuvant. Three weeks post immunization, spleen cells from immunized mice were stimulated in vitro with peptide-pulsed LPS blasts. CTL activity was assessed by chromium release assay five days after primary in vitro stimulation. Retrovirally transduced cells expressing the control antigen P703P and HLA-A2Kb were used as targets. CTL lines that specifically recognized both p5-pulsed targets as well as P703P-expressing targets were identified.

Human in vitro priming experiments demonstrated that the p5 peptide is immunogenic in humans. Dendritic cells (DC) were differentiated from monocyte cultures derived from PBMC of normal human donors by culturing for five days in RPMI medium containing 10% human serum, 50 ng/ml human GM-CSF and 30 ng/ml human IL-4. Following culture, the DC were pulsed with p5 peptide and cultured with GM-CSF and IL-4 together with CD8+ T cell enriched PBMC. CTL lines were restimulated on a weekly basis with p5-pulsed monocytes. Five to six weeks after initiation of the CTL cultures, CTL recognition of p5-pulsed target cells was demonstrated.

Example 11

Expression of a Breast Tumor-Derived Antigen in Prostate

Isolation of the antigen B305D from breast tumor by differential display is described in U.S. patent application Ser. No. 08/700,014, filed Aug. 20, 1996. Several different splice forms of this antigen were isolated. The determined cDNA sequences for these splice forms are provided in SEQ ID NO: 366–375, with the predicted amino acid sequences corresponding to the sequences of SEQ ID NO: 292, 298 and 301–303 being provided in SEQ ID NO: 299–306, respectively.

The expression levels of B305D in a variety of tumor and normal tissues were examined by real time PCR and by Northern analysis. The results indicated that B305D is highly expressed in breast tumor, prostate tumor, normal prostate tumor and normal testes, with expression being low or undetectable in all other tissues examined (colon tumor, lung tumor, ovary tumor, and normal bone marrow, colon, kidney, liver, lung, ovary, skin, small intestine, stomach).

Example 12

Elicitation of Prostate Tumor Antigen-Specific CTL Responses in Human Blood

This Example illustrates the ability of a prostate tumor antigen to elicit a CTL response in blood of normal humans.

Autologous dendritic cells (DC) were differentiated from monocyte cultures derived from PBMC of normal donors by growth for five days in RPMI medium containing 10% human serum, 50 ng/ml GMCSF and 30 ng/ml IL-4. Following culture, DC were infected overnight with recombinant P501S-expressing vaccinia virus at an M.O.I. of 5 and matured for 8 hours by the addition of 2 micrograms/ml CD40 ligand. Virus was inactivated by UV irradiation, CD8+ cells were isolated by positive selection using magnetic beads, and priming cultures were initiated in 24-well plates. Following five stimulation cycles, CD8+ lines were identified that specifically produced interferon-gamma when stimulated with autologous P501S-transduced fibroblasts. The P501S-specific activity of cell line 3A-1 could be maintained following additional stimulation cycles on autologous B-LCL transduced with P501S. Line 3A-1 was shown to specifically recognize autologous B-LCL transduced to express P501S, but not EGFP-transduced autologous B-LCL, as measured by cytotoxity assays ($^{51}$Cr release) and interferon-gamma production (Interferon-gamma Elispot; see above and Lalvani et al., *J. Exp. Med.* 186:859–865, 1997). The results of these assays are presented in FIGS. 6A and 6B.

Example 13

Identification of Prostate Tumor Antigens by Microarray Analysis

This Example describes the isolation of certain prostate tumor polypeptides from a prostate tumor cDNA library.

A human prostate tumor cDNA expression library as described above was screened using microarray analysis to identify clones that display at least a three fold over-expression in prostate tumor and/or normal prostate tissue, as compared to non-prostate normal tissues (not including testis). 372 clones were identified, and 319 were successfully sequenced. Table I presents a summary of these clones, which are shown in SEQ ID NOs:385–400. Of these sequences SEQ ID NOs:386, 389, 390 and 392 correspond to novel genes, and SEQ ID NOs: 393 and 396 correspond to previously identified sequences. The others (SEQ ID NOs:385, 387, 388, 391, 394, 395 and 397–400) correspond to known sequences, as shown in Table I.

TABLE I

Summary of Prostate Tumor Antigens

| Known Genes | Previously identified Genes | Novel Genes |
|---|---|---|
| T-cell gamma chain | P504S | 23379 (SEQ ID NO:389) |
| Kallikrein | P1000C | 23399 (SEQ ID NO:392) |
| Vector | P501S | 23320 (SEQ ID NO:386) |
| CGI-82 protein mRNA (23319; SEQ ID NO:385) | P503S | 23381 (SEQ ID NO:390) |
| PSA | P510S | |
| Ald. 6 Dehyd. | P784P | |
| L-iditol-2 dehydrogenase (23376; SEQ ID NO:388) | P502S | |
| Ets transcription factor PDEF (22672; SEQ ID NO:398) | P706P | |
| hTGR (22678; SEQ ID NO:399) | 19142.2, bangur.seq (22621; SEQ ID NO:396) | |
| K1AA0295(22685; SEQ ID NO:400) | 5566.1 Wang (23404; SEQ ID NO:393) | |
| Prostatic Acid Phosphatase (22655; SEQ ID NO:397) | P712P | |
| transglutaminase (22611; SEQ ID NO:395) | P778P | |
| HDLBP (23508; SEQ ID NO:394) | | |
| CGI-69 Protein(23367; SEQ ID NO:387) | | |
| KIAA0122(23383; SEQ ID NO:391) | | |
| TEEG | | |

CGI-82 showed 4.06 fold over-expression in prostate tissues as compared to other normal tissues tested. It was over-expressed in 43% of prostate tumors, 25% normal prostate, not detected in other normal tissues tested. L-iditol-2 dehydrogenase showed 4.94 fold over-expression in prostate tissues as compared to other normal tissues tested. It was over-expressed in 90% of prostate tumors, 100% of normal prostate, and not detected in other normal tissues tested. Ets transcription factor PDEF showed 5.55 fold over-expression in prostate tissues as compared to other normal tissues tested. It was over-expressed in 47% prostate tumors, 25% normal prostate and not detected in other normal tissues tested. hTGR1 showed 9.11 fold over-expression in prostate tissues as compared to other normal tissues tested. It was over-expressed in 63% of prostate tumors and is not detected in normal tissues tested including normal prostate. KIAA0295 showed 5.59 fold over-expression in prostate tissues as compared to other normal tissues tested. It was over-expressed in 47% of prostate tumors, low to undetectable in normal tissues tested including normal prostate tissues. Prostatic acid phosphatase showed 9.14 fold over-expression in prostate tissues as compared to other normal tissues tested. It was over-expressed in 67% of prostate tumors, 50% of normal prostate, and not detected in other normal tissues tested. Transglutaminase showed 14.84 fold over-expression in prostate tissues as compared to other normal tissues tested. It was over-expressed in 30% of prostate tumors, 50% of normal prostate, and is not detected in other normal tissues tested. High density lipoprotein binding protein (HDLBP) showed 28.06 fold over-expression in prostate tissues as compared to other normal tissues tested. It was over-expressed in 97% of prostate tumors, 75% of normal prostate, and is undetectable in all other normal tissues tested. CGI-69 showed 3.56 fold over-expression in prostate tissues as compared to other normal tissues tested. It is a low abundant gene, detected in more than 90% of prostate tumors, and in 75% normal prostate tissues. The expression of this gene in normal tissues was very low. KIAA0122 showed 4.24 fold over-expression in prostate tissues as compared to other normal tissues tested. It was over-expressed in 57% of prostate tumors, it was undetectable in all normal tissues tested including normal prostate tissues. 19142.2 bangur showed 23.25 fold over-expression in prostate tissues as compared to other normal tissues tested. It was over-expressed in 97% of prostate tumors and 100% of normal prostate. It was undetectable in other normal tissues tested. 5566.1 Wang showed 3.31 fold over-expression in prostate tissues as compared to other normal tissues tested. It was over-expressed in 97% of prostate tumors, 75% normal prostate and was also over-expressed in normal bone marrow, pancreas, and activated PBMC. Novel clone 23379 showed 4.86 fold over-expression in prostate tissues as compared to other normal tissues tested. It was detectable in 97% of prostate tumors and 75% normal prostate and is undetectable in all other normal tissues tested. Novel clone 23399 showed 4.09 fold over-expression in prostate tissues as compared to other normal tissues tested. It was over-expressed in 27% of prostate tumors and was undetectable in all normal tissues tested including normal prostate tissues. Novel clone 23320 showed 3.15 fold over-expression in prostate tissues as compared to other normal tissues tested. It was detectable in all prostate tumors and 50% of normal prostate tissues. It was also expressed in normal colon and trachea. Other normal tissues do not express this gene at high level.

Example 14

Identification of Prostate Tumor Antigens by Electronic Subtraction

This Example describes the use of an electronic subtraction technique to identify prostate tumor antigens.

Potential prostate-specific genes present in the GenBank human EST database were identified by electronic subtraction (similar to that described by Vasmatizis et al., *Proc. Natl. Acad. Sci. USA* 95:300–304, 1998). The sequences of EST clones (43,482) derived from various prostate libraries were obtained from the GenBank public human EST database. Each prostate EST sequence was used as a query sequence in a BLASTN (National Center for Biotechnology Information) search against the human EST database. All matches considered identical (length of matching sequence >100 base pairs, density of identical matches over this region >70%) were grouped (aligned) together in a cluster. Clusters containing more than 200 ESTs were discarded since they probably represented repetitive elements or highly expressed genes such as those for ribosomal proteins. If two or more clusters shared common ESTs, those clusters were grouped together into a "supercluster," resulting in 4,345 prostate superclusters.

Records for the 479 human cDNA libraries represented in the GenBank release were downloaded to create a database of these cDNA library records. These 479 cDNA libraries were grouped into three groups, Plus (normal prostate and prostate tumor libraries, and breast cell lines, in which expression was desired), Minus (libraries from other normal adult tissues, in which expression was not desirable), and Other (fetal tissue, infant tissue, tissues found only in women, non-prostate tumors and cell lines other than prostate cell lines, in which expression was considered to be irrelevant). A summary of these library groups is presented in Table II.

TABLE II

Prostate cDNA Libraries and ESTs

| Library | # of Libraries | # of ESTs |
|---|---|---|
| Plus | 25 | 43,482 |
| Normal | 11 | 18,875 |
| Tumor | 11 | 21,769 |
| Cell lines | 3 | 2,838 |
| Minus | 166 | |
| Other | 287 | |

Each supercluster was analyzed in terms of the ESTs within the supercluster. The tissue source of each EST clone was noted and used to classify the superclusters into four groups: Type 1-EST clones found in the Plus group libraries only; no expression detected in Minus or Other group libraries; Type 2-EST clones found in the Plus and Other group libraries only; no expression detected in the Minus group; Type 3-EST clones found in the Plus, Minus and Other group libraries, but the expression in the Plus group is higher than in either the Minus or Other groups; and Type 4-EST clones found in Plus, Minus and Other group libraries, but the expression in the Plus group is higher than the expression in the Minus group. This analysis identified 4,345 breast clusters (see Table III). From these clusters, 3,172 EST clones were ordered from Research Genetics, Inc., and were received as frozen glycerol stocks in 96-well plates.

TABLE III

Prostate Cluster Summary

| Type | # of Superclusters | # of ESTs Ordered |
|---|---|---|
| 1 | 688 | 677 |
| 2 | 2899 | 2484 |
| 3 | 85 | 11 |
| 4 | 673 | 0 |
| Total | 4345 | 3172 |

The inserts were PCR-amplified using amino-linked PCR primers for Synteni microarray analysis. When more than one PCR product was obtained for a particular clone, that PCR product was not used for expression analysis. In total, 2,528 clones from the electronic subtraction method were analyzed by microarray analysis to identify electronic subtraction breast clones that had high tumor vs. normal tissue mRNA. Such screens were performed using a Synteni (Palo Alto, Calif.) microarray, according to the manufacturers instructions (and essentially as described by Schena et al., Proc. Natl. Acad. Sci. USA 93:10614–10619, 1996 and Heller et al., Proc. Natl. Acad. Sci. USA 94:2150–2155, 1997). Within these analyses, the clones were arrayed on the chip, which was then probed with fluorescent probes generated from normal and tumor prostate cDNA, as well as various other normal tissues. The slides were scanned and the fluorescence intensity was measured.

Clones with an expression ratio greater than 3 (i.e., the level in prostate tumor cDNA was at least three times the level in normal prostate cDNA) were identified as prostate tumor-specific sequences (Table IV). The sequences of these clones are provided in SEQ ID NOs:401–453, with certain novel sequences shown in SEQ ID NOs:407, 413, 416–419, 422, 426, 427 and 450.

TABLE IV

Prostate-tumor Specific Clones

| SEQ ID NO. | Sequence Designation | Comments |
|---|---|---|
| 401 | 22545 | previously identified P1000C |
| 402 | 22547 | previously identified P704P |
| 403 | 22548 | known |
| 404 | 22550 | known |
| 405 | 22551 | PSA |
| 406 | 22552 | prostate secretory protein 94 |
| 407 | 22553 | novel |
| 408 | 22558 | previously identified P509S |
| 409 | 22562 | glandular kallikrein |
| 410 | 22565 | previously identified P1000C |
| 411 | 22567 | PAP |
| 412 | 22568 | B1006C (breast tumor antigen) |
| 413 | 22570 | novel |
| 414 | 22571 | PSA |
| 415 | 22572 | previously identified P706P |
| 416 | 22573 | novel |
| 417 | 22574 | novel |
| 418 | 22575 | novel |
| 419 | 22580 | novel |
| 420 | 22581 | PAP |
| 421 | 22582 | prostatic secretory protein 94 |
| 422 | 22583 | novel |
| 423 | 22584 | prostatic secretory protein 94 |
| 424 | 22585 | prostatic secretory protein 94 |
| 425 | 22586 | known |
| 426 | 22587 | novel |
| 427 | 22588 | novel |
| 428 | 22589 | PAP |
| 429 | 22590 | known |
| 430 | 22591 | PSA |
| 431 | 22592 | known |
| 432 | 22593 | Previously identified P777P |
| 433 | 22594 | T cell receptor gamma chain |
| 434 | 22595 | Previously identified P705P |
| 435 | 22596 | Previously identified P707P |
| 436 | 22847 | PAP |
| 437 | 22848 | known |
| 438 | 22849 | prostatic secretory protein 57 |
| 439 | 22851 | PAP |
| 440 | 22852 | PAP |
| 441 | 22853 | PAP |
| 442 | 22854 | previously identified P509S |
| 443 | 22855 | previously identified P705P |

TABLE IV-continued

Prostate-tumor Specific Clones

| SEQ ID NO. | Sequence Designation | Comments |
|---|---|---|
| 444 | 22856 | previously identified P774P |
| 445 | 22857 | PSA |
| 446 | 23601 | previously identified P777P |
| 447 | 23602 | PSA |
| 448 | 23605 | PSA |
| 449 | 23606 | PSA |
| 450 | 23612 | novel |
| 451 | 23614 | PSA |
| 452 | 23618 | previously identified P1000C |
| 453 | 23622 | previously identified P705P |

Example 15

Further Identification of Prostate Tumor Antigens by Microarray Analysis

This Example describes the isolation of additional prostate tumor polypeptides from a prostate tumor cDNA library.

A human prostate tumor cDNA expression library as described above was screened using microarray analysis to identify clones that display at least a three fold overexpressed in prostate tumor and/or normal prostate tissue, as compared to non-prostate normal tissues (not including testis). 142 clones were identified and sequenced. Certain of these clones are shown in SEQ ID NOs:454–467. Of these sequences SEQ ID NOs:459–461 correspond to novel genes. The others (SEQ ID NOs:454–458 and 461–467) correspond to known sequences.

Example 16

Further Characterization of Prostate Tumor Antigen P710P

This Example describes the full length cloning of P710P.

The prostate cDNA library described above was screened with the P710P fragment described above. One million colonies were plated on LB/Ampicillin plates. Nylon membrane filters were used to lift these colonies, and the cDNAs picked up by these filters were then denatured and crosslinked to the filters by UV light. The P710P fragment was radiolabeled and used to hybridize with the filters. Positive cDNA clones were selected and their cDNAs recovered and sequenced by an automatic ABI Sequencer. Four sequences were obtained, and are presented in SEQ ID NOs:468–471.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

What is claimed is:

1. A fusion protein comprising SEQ ID NO:327.

2. A fusion protein comprising SEQ ID NO:327 and an expression enhancer that increases expression of the fusion protein in a host cell transfected with a polynucleotide encoding the fusion protein.

3. A fusion protein comprising SEQ ID NO:327 and a T helper epitope.

4. A composition comprising a fusion protein according to any one of claims 1–3 and a physiologically acceptable carrier.

5. An composition comprising a fusion protein according to any one of claims 1–3 and an adjuvant.

6. The composition of claim 5, wherein the adjuvant is capable of inducing a predominantly Type I immune response.

7. The composition of claim 5, wherein the adjuvant comprises at least one component selected from the group consisting of:

monophosphoryl lipid A, 3-de-O-acylated monophosphoryl lipid A, CpG-containing oligonucleotides, saponins, saponin derivatives and tocopherol.

8. The composition of claim 5, further comprising a delivery vehicle.

9. The composition of claim 8, wherein the delivery vehicle is selected from the group consisting of microspheres and antigen presenting cells.

10. The composition of claim 9, wherein the antigen, presenting cells are selected from the group consisting of dendritic cells, macrophages, B cells and monocytes.

* * * * *

UNITED STATES PATENT AND TRADEMARK OFFICE
CERTIFICATE OF CORRECTION

PATENT NO. : 6,395,278 B1
DATED : May 28, 2002
INVENTOR(S) : Jiangchun Xu et al.

It is certified that error appears in the above-identified patent and that said Letters Patent is hereby corrected as shown below:

Column 411,
Line 21, "An composition" should read -- A composition --.

Column 412,
Line 21, "wherein the antigen, presenting" should read -- wherein the antigen presenting --.

Signed and Sealed this

Fifteenth Day of October, 2002

Attest:

Attesting Officer

JAMES E. ROGAN
Director of the United States Patent and Trademark Office

SEQUENCE LISTING

<160> NUMBER OF SEQ ID NOS: 472

<210> SEQ ID NO 1
<211> LENGTH: 814

```
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1
tttttttttt tttttcacag tataacagct ctttatttct gtgagttcta ctaggaaatc    60
atcaaatctg agggttgtct ggaggacttc aatacacctc cccccatagt gaatcagctt   120 ccaggggtc cagtccctct ccttacttca tccccatccc atgccaaagg aagaccctcc    180
ctccttggct cacagccttc tctaggcttc ccagtgcctc caggacagag tgggttatgt   240
tttcagctcc atccttgctg tgagtgtctg gtgcgttgtg cctccagctt ctgctcagtg   300
cttcatggac agtgtccagc acatgtcact ctccactctc tcagtgtgga tccactagtt   360
ctagagcggc cgccaccgcg gtggagctcc agcttttgtt ccctttagtg agggttaatt   420
gcgcgcttgg cgtaatcatg gtcataactg tttcctgtgt gaaattgtta tccgctcaca   480
attccacaca acatacgagc cggaagcata agtgtaaag cctggggtgc ctaatgagtg    540
anctaactca cattaattgc gttgcgctca ctgnccgctt ccagtcngg aaaactgtcg    600 tgccagctgc attaatgaat cggccaacgc ncggggaaaa gcggtttgcg ttttgggggc   660
tcttccgctt ctcgctcact nantcctgcg ctcggtcntt cggctgcggg aacggtatc    720 actcctcaaa ggnggtatta cggttatccn naaatcnggg datacccngg aaaaaantt    780 aacaaaaggg cancaaaggg cngaaacgta aaaa                               814

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2
acagaaatgt tggatggtgg agcacctttc tatacgactt acaggacagc agatggggaa    60
ttcatggctg ttggagcaat agaaccccag ttctacgagc tgctgatcaa aggacttgga   120
ctaaagtctg atgaacttcc caatcagatg agcatggatg attggccaga atgaagaag    180 aagtttgcag atgtatttgc aaagaagacg aaggcagagt ggtgtcaaat ctttgacggc   240
acagatgcct gtgtgactcc ggttctgact tttgaggagg ttgttcatca tgatcacaac   300
aaggaacggg gctcgtttat caccagtgag gagcaggacg tgagccccg ccctgcacct    360 ctgctgttaa cacccccagc catcccttct ttcaaaaggg atccactagt tctagaagcg   420
gccgccaccg cggtggagct ccagcttttg ttccctttag tgagggttaa ttgcgcgctt   480
ggcgtaatca tggtcatagc tgtttcctgt gtgaaattgt tatccgctca caattccccc   540
aacatacgag ccggaacata agtgttaag cctggggtgc ctaatgantg agctaactcn    600
cattaattgc gttgcgctca ctgccgctt ccagtcggg aaaactgtcg tgccactgcn    660
ttantgaatc ngccaccccc cgggaaaagg cggttgcntt tgggcctct tccgcttcc    720 tcgctcattg atcctngcnc ccggtcttcg gctgcggnga acggttcact cctcaaaggc   780
ggtntnccgg ttatccccaa acnggggata cccnga                             816

<210> SEQ ID NO 3
```

<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3

```
cttttgaaag aagggatggc tggggtgttt aacagcagag gtgcagggcg ggggctcacg      60
tcctgctcct cactggtgat aaacgagccc cgttccttgt tgtgatcatg atgaacaacc     120
tcctcaaaag tcagaaccgg agtcacacag gcatctgtgc cgtcaaagat ttgacaccac     180
tctgccttcg tcttctttgc aaatacatct gcaaacttct tcttcatttc tggccaatca     240
tccatgctca tctgattggg aagttcatca gactttagtc canntccttt gatcagcagc     300
tcgtagaact ggggttctat tgctccaaca gccatgaatt ccccatctgc tgtcctgtaa     360
gtcgtataga aggtgctcc accatccaac atgttctgtc ctcgaggggg ggcccggtac     420
ccaattcgcc ctatantgag tcgtattacg cgcgctcact ggccgtcgtt ttacaacgtc     480
gtgactggga aaccctgggc gttaccaac ttaatcgcct tgcagcacat cccccttcg      540
ccagctgggc gtaatancga aaaggcccgc accgatcgcc cttccaacag ttgcgcacct     600
gaatgggnaa atgggacccc cctgttaccg cgcattnaac ccccgcnggg tttngttgtt     660
accccccacnt nnaccgctta cactttgcca gcgccttanc gccgctccc tttcnccttt     720
cttcccttcc tttcncnccn ctttccccg gggtttcccc cntcaaaccc cna           773
```

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4

```
cctcctgagt cctactgacc tgtgctttct ggtgtggagt ccaggctgc taggaaaagg      60
aatgggcaga cacaggtgta tgccaatgtt tctgaaatgg gtataatttc gtcctctcct     120
tcggaacact ggctgtctct gaagacttct cgctcagttt cagtgaggac acacacaaag     180
acgtgggtga ccatgttgtt tgtggggtgc agagatggga ggggtggggc ccaccctgga     240
agagtggaca gtgacacaag gtggacactc tctacagatc actgaggata agctggagcc     300
acaatgcatg aggcacacac acagcaagga tgacnctgta aacatagccc acgctgtcct     360
gngggcactg ggaagcctan atnaggccgt gagcanaaag aaggggagga tccactagtt     420
ctanagcggc cgccaccgcg gtgganctcc anctttttgt ccctttagtg agggttaatt     480
gcgcgcttgg cntaatcatg gtcatanctn tttcctgtgt gaaattgtta tccgctcaca     540
attccacaca acatacganc cggaaacata aantgtaaac ctgggggtgcc taatgantga     600
ctaactcaca ttaattgcgt tgcgctcact gcccgctttc caatcnggaa acctgtcttg     660
ccncttgcat tnatgaatcn gccaacccc ggggaaaagc gtttgcgttt gggcgctct      720
tccgcttcct cnctcantta ntccctncnc tcggtcattc cggctgcngc aaaccggttc     780
accnctcca aagggggtat tccggtttcc ccnaatccgg gganancc               828
```

<210> SEQ ID NO 5
<211> LENGTH: 834

```
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5
tttttttttt ttttactga tagatggaat ttattaagct tttcacatgt gatagcacat    60
agttttaatt gcatccaaag tactaacaaa aactctagca atcaagaatg gcagcatgtt   120
attttataac aatcaacacc tgtggctttt aaaatttggt tttcataaga taatttatac   180
tgaagtaaat ctagccatgc ttttaaaaaa tgctttaggt cactccaagc ttggcagtta   240
acatttggca taaacaataa taaaacaatc acaatttaat aaataacaaa tacaacattg   300
taggccataa tcatatacag tataaggaaa aggtggtagt gttgagtaag cagttattag   360
aatagaatac cttggcctct atgcaaatat gtctagacac tttgattcac tcagccctga   420
cattcagttt tcaaagtagg agacaggttc tacagtatca ttttacagtt ccaacacat    480
tgaaaacaag tagaaaatga tgagttgatt tttattaatg cattacatcc tcaagagtta   540
tcaccaaccc ctcagttata aaaaattttc aagttatatt agtcatataa cttggtgtgc   600
ttatttaaa ttagtgctaa atggattaag tgaagacaac aatggtcccc taatgtgatt    660
gatattggtc attttacca gcttctaaat ctnaactttc aggcttttga actggaacat    720
tgnatnacag tgttccanag ttncaaccta ctggaacatt acagtgtgct tgattcaaaa   780
tgttattttg ttaaaaatta aattttaacc tggtggaaaa ataatttgaa atna          834

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6
tttttttttt tttttttttt aagaccctca tcaatagatg gagacataca gaaatagtca    60
aaccacatct acaaaatgcc agtatcaggc ggcggcttcg aagccaaagt gatgtttgga   120
tgtaaagtga atattagtt ggcggatgaa gcagatagtg aggaaagttg agccaataat    180
gacgtgaagt ccgtggaagc ctgtggctac aaaaaatgtt gagccgtaga tgccgtcgga   240
aatggtgaag ggagactcga agtactctga ggcttgtagg agggtaaaat agagacccag   300
taaaattgta ataagcagtg cttgaattat ttggtttcgg ttgttttcta ttagactatg   360
gtgagctcag gtgattgata ctcctgatgc gagtaatacg gatgtgttta ggagtgggac   420
ttctagggga tttagcgggg tgatgcctgt tgggggccag tgccctccta gttgggggt    480
agggctagg ctggagtggt aaaaggctca gaaaatcct gcgaagaaaa aaacttctga    540
ggtaataaat aggattatcc cgtatcgaag gccttttgg acaggtggtg tgtggtggcc    600
ttggtatgtg ctttctcgtg ttacatcgcg ccatcattgg tatatggtta gtgtgttggg   660
ttantanggc ctantatgaa gaacttttgg antggaatta aatcaatngc ttggccggaa   720
gtcattanga nggctnaaaa ggccctgtta ngggtctggg ctnggtttta cccnacccat   780
ggaatncncc ccccggacna ntgnatccct attcttaa                            818

<210> SEQ ID NO 7
```

<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7

```
ttttttttttt tttttttttt tggctctaga gggggtagag gggtgctat agggtaaata    60
cgggccctat ttcaaagatt tttaggggaa ttaattctag gacgatgggt atgaaactgt   120
ggtttgctcc acagatttca gagcattgac cgtagtatac ccccggtcgt gtagcggtga   180
aagtggtttg gtttagacgt ccgggaattg catctgtttt taagcctaat gtggggacag   240
ctcatgagtg caagacgtct tgtgatgtaa ttattatacn aatgggggct tcaatcggga   300
gtactactcg attgtcaacg tcaaggagtc gcaggtcgcc tggttctagg aataatgggg   360
gaagtatgta ggaattgaag attaatccgc cgtagtcggt gttctcctag gttcaatacc   420
attggtggcc aattgatttg atggtaaggg gagggatcgt tgaactcgtc tgttatgtaa   480
aggatnccett ngggatggga aggcnataa ggactangga tnaatggcgg gcangatatt   540
tcaaacngtc tctanttcct gaaacgtctg aaatgttaat aanaattaan tttngttatt   600
gaatnttnng gaaaagggct tacaggacta gaaaccaaat angaaaanta atnntaangg   660
cnttatcntn aaaggtnata accnctccta tnatcccacc caatngnatt ccccacncnn   720
acnattggat ncccanttc canaaanggc cnccccccgg tgnannccnc cttttgttcc   780
cttnantgan ggttattcnc ccctngcntt atcancc                            817
```

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8

```
catttccggg tttactttct aaggaaagcc gagcggaagc tgctaacgtg ggaatcggtg    60
cataaggaga actttctgct ggcacgcgct agggacaagc gggagagcga ctccgagcgt   120
ctgaagcgca cgtcccagaa ggtggacttg gcactgaaac agctgggaca catccgcgag   180
tacgaacagc gcctgaaagt gctggagcgg gaggtccagc agtgtagccg cgtcctgggg   240
tgggtggccg angcctganc cgctctgcct tgctgccccc angtgggccg ccacccctg    300
acctgcctgg gtccaaacac tgagccctgc tggcggactt caagganaac ccccacangg   360
ggattttgct cctanantaa ggctcatctg ggcctcggcc cccccacctg gttggccttg   420
tctttgangt gagccccatg tccatctggg ccactgtcng gaccacctt ngggagtgtt   480
ctccttacaa ccacannatg cccggctcct cccggaaacc antcccancc tgngaaggat   540
caagnccctgn atccactnnt nctanaaccg gccncncncg cngtggaacc cnccttntgt   600
tccttttcnt tnagggttaa tnncgccttg gccttccan ngtcctncnc nttttccnnt   660
gttnaaattg ttangcnccc nccnntcccn cnncnncnan cccgacccnn annttnnann   720
ncctgggggt nccnncngat tgacccnncc ncctntant tgcnttnggg nncnntgccc   780
ctttccctct ngggannncg                                               799
```

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

| | | | | |
|---|---|---|---|---|
| acgccttgat | cctcccaggc | tgggactggt | tctgggagga | gccgggcatg | ctgtggtttg | 60 |
| taangatgac | actcccaaag | gtggtcctga | cagtggccca | gatggacatg | gggctcacct | 120 |
| caaggacaag | gccaccaggt | gcgggggccg | aagcccacat | gatccttact | ctatgagcaa | 180 |
| aatccctgt | gggggcttct | ccttgaagtc | cgccancagg | gctcagtctt | tggacccang | 240 |
| caggtcatgg | ggttgtngnc | caactggggg | ccncaacgca | aaanggcnca | gggcctcngn | 300 |
| cacccatccc | angacgcggc | tacactnctg | gacctcccnc | tccaccactt | tcatgcgctg | 360 |
| ttcntacccg | cgnatntgtc | ccanctgttt | cngtgccnac | tccancttct | nggacgtgcg | 420 |
| ctacatacgc | ccggantcnc | nctcccgctt | tgtccctatc | cacgtnccan | caacaaattt | 480 |
| cnccntantg | caccnattcc | cacntttnnc | agntttccnc | nncgngcttc | cttntaaaag | 540 |
| ggttganccc | cggaaaatnc | cccaaagggg | ggggccngg | tacccaactn | cccctnata | 600 |
| gctgaantcc | ccatnaccnn | gnctcnatgg | ancntcnt | tttaannacn | ttctnaactt | 660 |
| gggaanancc | ctcgnccntn | ccccnttaa | tcccnccttg | cnangnnct | ccccnntcc | 720 |
| ncccnnntng | gcntntnann | cnaaaaaggc | ccnnnancaa | tctcctnncn | cctcanttcg | 780 |
| ccanccctcg | aaatcggccn | c | | | | 801 |

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

| | | | | | | |
|---|---|---|---|---|---|---|
| cagtctatnt | ggccagtgtg | gcagctttcc | ctgtggctgc | cggtgccaca | tgcctgtccc | 60 |
| acagtgtggc | cgtggtgaca | gcttcagccg | ccctcaccgg | gttcaccttc | tcagccctgc | 120 |
| agatcctgcc | ctacacactg | gcctccctct | accaccggga | gaagcaggtg | ttcctgccca | 180 |
| aataccgagg | ggacactgga | ggtgctagca | gtgaggacag | cctgatgacc | agcttcctgc | 240 |
| caggccctaa | gcctggagct | cccttcccta | atggacacgt | gggtgctgga | ggcagtggcc | 300 |
| tgctcccacc | tccacccgcg | ctctgcgggg | cctctgcctg | tgatgtctcc | gtacgtgtgg | 360 |
| tggtgggtga | gcccaccgan | gccagggtgg | ttccggggccg | gggcatctgc | ctggacctcg | 420 |
| ccatcctgga | tagtgcttcc | tgctgtccca | ngtgccccca | tccctgttta | tgggctccat | 480 |
| tgtccagctc | agccagtctg | tcactgccta | tatggtgtct | gccgcaggcc | tgggtctggt | 540 |
| cccatttact | ttgctacaca | ggtantattt | gacaagaacg | anttggccaa | atactcagcg | 600 |
| ttaaaaaatt | ccagcaacat | tgggggtgga | aggcctgcct | cactgggtcc | aactccccgc | 660 |
| tcctgttaac | cccatggggc | tgccggcttg | gccgccaatt | tctgttgctg | ccaaantnat | 720 |
| gtggctctct | gctgccacct | gttgctggct | gaagtgcnta | cngcncanct | nggggggtng | 780 |
| ggngttccc | | | | | | 789 |

<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11

| | | | | | |
|---|---|---|---|---|---|
| cccaccctac | ccaaatatta | gacaccaaca | cagaaaagct | agcaatggat | tcccttctac | 60 |
| tttgttaaat | aaataagtta | aatatttaaa | tgcctgtgtc | tctgtgatgg | caacagaagg | 120 |
| accaacaggc | cacatcctga | taaaaggtaa | gaggggggtg | gatcagcaaa | agacagtgc | 180 |
| tgtgggctga | ggggacctgg | ttcttgtgtg | ttgcccctca | ggactcttcc | cctacaaata | 240 |
| actttcatat | gttcaaatcc | catggaggag | tgtttcatcc | tagaaactcc | catgcaagag | 300 |
| ctacattaaa | cgaagctgca | ggttaagggg | cttanagatg | ggaaaccagg | tgactgagtt | 360 |
| tattcagctc | ccaaaaaccc | ttctctaggt | gtgtctcaac | taggaggcta | gctgttaacc | 420 |
| ctgagcctgg | gtaatccacc | tgcagagtcc | ccgcattcca | gtgcatggaa | cccttctggc | 480 |
| ctccctgtat | aagtccagac | tgaaaccccc | ttggaaggnc | tccagtcagg | cagccctana | 540 |
| aactggggaa | aaagaaaag | gacgccccan | ccccagctg | tgcanctacg | cacctcaaca | 600 |
| gcacagggtg | gcagcaaaaa | aaccacttta | ctttggcaca | aacaaaaact | nggggggca | 660 |
| accccggcac | cccnangggg | gttaacagga | ancngggnaa | cntggaaccc | aattnaggca | 720 |
| ggcccnccac | cccnaatntt | gctgggaaat | ttttcctccc | ctaaattntt | tc | 772 |

<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12

| | | | | | |
|---|---|---|---|---|---|
| gccccaattc | cagctgccac | accacccacg | gtgactgcat | tagttcggat | gtcatacaaa | 60 |
| agctgattga | agcaaccctc | tacttttttgg | tcgtgagcct | tttgcttggt | gcaggtttca | 120 |
| ttggctgtgt | tggtgacgtt | gtcattgcaa | cagaatgggg | gaaaggcact | gttctctttg | 180 |
| aagtangggtg | agtcctcaaa | atccgtatag | ttggtgaagc | cacagcactt | gagccctttc | 240 |
| atggtggtgt | tccacacttg | agtgaagtct | tcctgggaac | cataatcttt | cttgatggca | 300 |
| ggcactacca | gcaacgtcag | ggaagtgctc | agccattgtg | gtgtacacca | aggcgaccac | 360 |
| agcagctgcn | acctcagcaa | tgaagatgan | gaggangatg | aagaagaacg | tcncgagggc | 420 |
| acacttgctc | tcagtcttan | caccatanca | gcccntgaaa | accaananca | aagaccacna | 480 |
| cnccggctgc | gatgaagaaa | tnacccccncg | ttgacaaact | tgcatggcac | tgggaaccac | 540 |
| agtggcccna | aaaatcttca | aaaaggatgc | cccatcnatt | gaccccccaa | atgcccactg | 600 |
| ccaacagggg | ctgccccacn | cncnnaacga | tganccnatt | gnacaagatc | tncntggtct | 660 |
| tnatnaacnt | gaaccctgcn | tngtggctcc | tgttcaggnc | cnnggcctga | cttctnaann | 720 |
| aangaactcn | gaagncccca | cnggananc | g | | | 751 |

<210> SEQ ID NO 13
<211> LENGTH: 729

```
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13
gagccaggcg tccctctgcc tgcccactca gtggcaacac ccgggagctg ttttgtcctt    60
tgtggancct cagcagtncc ctctttcaga actcantgcc aagancctg aacaggagcc     120 accatgcagt gcttcagctt cattaagacc atgatgatcc tcttcaattt gctcatcttt    180
ctgtgtggtg cagccctgtt ggcagtgggc atctgggtgt caatcgatgg ggcatccttt    240
ctgaagatct tcgggccact gtcgtccagt gccatgcagt ttgtcaacgt gggctacttc    300
ctcatcgcag ccggcgttgt ggtcttagct ctaggtttcc tgggctgcta tggtgctaag    360
actgagagca gtgtgccct cgtgacgttc ttcttcatcc tcctcctcat cttcattgct     420
gaggttgcaa tgctgtggtc gccttggtgt acaccacaat ggctgagcac ttcctgacgt    480
tgctggtaat gcctgccatc aanaaaagat tatgggttcc caggaanact tcactcaagt    540
gttggaacac caccatgaaa gggctcaagt gctgtggctt cnnccaacta tacggatttt    600
gaagantcac ctacttcaaa gaaaanagtg cctttccccc atttctgttg caattgacaa    660
acgtccccaa cacagccaat tgaaaacctg cacccaaccc aaangggtcc ccaaccanaa    720 attnaaggg                                                            729

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14
tgctcttcct caaagttgtt cttgttgcca taacaaccac cataggtaaa gcgggcgcag    60
tgttcgctga aggggttgta gtaccagcgc gggatgctct ccttgcagag tcctgtgtct    120
ggcaggtcca cgcagtgccc tttgtcactg gggaaatgga tgcgctggag ctcgtcaaag    180
ccactcgtgt atttttcaca ggcagcctcg tccgacgcgt cggggcagtt gggggtgtct    240
tcacactcca ggaaactgtc natgcagcag ccattgctgc agcggaactg ggtgggctga    300
cangtgccag agcacactgg atggcgcctt tccatgnnan gggccctgng gaaagtccc     360 tgancccan anctgcctct caaangcccc accttgcaca ccccgacagg ctagaatgga    420
atcttcttcc cgaaaggtag ttnttcttgt tgcccaance anccccntaa acaaactctt    480
gcanatctgc tccgnggggg tcntantacc ancgtgggaa aagaaccca ggcngcgaac     540 caancttgtt tggatncgaa gcnataatct nctnttctgc ttggtggaca gcaccantna    600
ctgtnnanct ttagnccntg gtcctcntgg gttgnncttg aacctaatcn ccnntcaact    660
gggacaaggt aantngccnt cctttnaatt cccnancntn ccccctggtt tggggttttn    720
cncnctccta ccccagaaan nccgtgttcc ccccaacta ggggccnaaa ccnnttnttc     780
cacaaccctn ccccacccac gggttcngnt ggttng                              816

<210> SEQ ID NO 15
<211> LENGTH: 783
<212> TYPE: DNA
```

```
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15
ccaaggcctg ggcaggcata nacttgaagg tacaacccca ggaaccctg gtgctgaagg        60 atgtggaaaa cacagattgg cgcctactgc ggggtgacac ggatgtcagg gtagagagga     120
aagacccaaa ccaggtggaa ctgtggggac tcaaggaang cacctacctg ttccagctga     180
cagtgactag ctcagaccac ccagaggaca cggccaacgt cacagtcact gtgctgtcca     240
ccaagcagac agaagactac tgcctcgcat ccaacaangt gggtcgctgc cggggctctt     300
tcccacgctg gtactatgac cccacggagc agatctgcaa gagtttcgtt tatggaggct     360
gcttgggcaa caagaacaac taccttcggg aagaagagtg cattctancc tgtcngggtg     420
tgcaaggtgg gcctttgana ngcanctctg gggctcangc gactttcccc cagggcccct     480
ccatggaaag gcgccatcca ntgttctctg gcacctgtca gcccacccag ttccgctgca     540
ncaatggctg ctgcatcnac antttcctng aattgtgaca acacccccca ntgccccaa     600 ccctcccaac aaagcttccc tgtttaaaaa tacnccantt ggcttttnac aaacnccgg     660 cnccctccntt ttccccnntn aacaagggc nctngcnttt gaactgcccn aaaccnggaa     720
tctnccnngg aaaaantncc ccccctggtt cctnnaaance cctccncnaa anctnccccc     780
ccc                                                                    783

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16
gccccaattc cagctgccac accacccacg gtgactgcat tagttcggat gtcatacaaa       60
agctgattga agcaaccctc tacttttgg tcgtgagcct tttgcttggt gcaggtttca     120
ttggctgtgt tggtgacgtt gtcattgcaa cagaatgggg gaaaggcact gttctctttg     180
aagtagggtg agtcctcaaa atccgtatag ttggtgaagc cacagcactt gagcccttc     240 atggtggtgt tccacacttg agtgaagtct tcctgggaac cataatcttt cttgatggca     300
ggcactacca gcaacgtcag gaagtgctca gccattgtgg tgtacaccaa ggcgaccaca     360
gcagctgcaa cctcagcaat gaagatgagg aggaggatga agaagaacgt cncgagggca     420
cacttgctct ccgtcttagc accatagcag cccangaaac caagagcaaa gaccacaacg     480
ccngctgcga atgaaagaaa ntacccacgt tgacaaactg catggccact ggacgacagt     540
tggcccgaan atcttcagaa aagggatgcc ccatcgattg aacacccana tgcccactgc     600
cnacagggct gcnccncncn gaaagaatga gccattgaag aaggatcntc ntggtcttaa     660
tgaactgaaa ccntgcatgg tggccctgt tcagggctct tggcagtgaa ttctganaaa     720
aaggaacngc ntnagccccc ccaaangana aaacaccccc gggtgttgcc ctgaattggc     780
ggccaaggan ccctgccccn g                                                801

<210> SEQ ID NO 17
<211> LENGTH: 740
```

```
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17
gtgagagcca ggcgtccctc tgcctgccca ctcagtggca acacccggga gctgttttgt      60
cctttgtgga gcctcagcag ttccctcttt cagaactcac tgccaagagc cctgaacagg     120
agccaccatg cagtgcttca gcttcattaa gaccatgatg atcctcttca atttgctcat     180
ctttctgtgt ggtgcagccc tgttggcagt gggcatctgg gtgtcaatcg atgggcatc      240 ctttctgaag atcttcgggc cactgtcgtc cagtgccatg cagtttgtca acgtgggcta     300
cttcctcatc gcagccggcg ttgtggtctt tgctcttggt ttcctgggct gctatggtgc     360
taagacggag agcaagtgtg ccctcgtgac gttcttcttc atcctcctcc tcatcttcat     420
tgctgaagtt gcagctgctg tggtcgcctt ggtgtacacc acaatggctg aaccattcct     480
gacgttgctg gtantgcctg ccatcaanaa agattatggg ttcccaggaa aaattcactc     540
aantntggaa caccnccatg aaaagggctc caatttctgn tggcttcccc aactataccg     600
gaattttgaa agantcnccc tacttccaaa aaaaaanant tgcctttncc cccnttctgt     660
tgcaatgaaa acntcccaan acngccaatn aaaacctgcc cnnncaaaaa ggntcncaaa     720
caaaaaaant nnaagggttn                                                 740

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18
ccgctggttg cgctggtcca gngnagccac gaagcacgtc agcatacaca gcctcaatca      60
caaggtcttc cagctgccgc acattacgca gggcaagagc ctccagcaac actgcatatg     120
ggatacactt tactttagca gccagggtga caactgagag gtgtcgaagc ttattcttct     180
gagcctctgt tagtggagga agattccggg cttcagctaa gtagtcagcg tatgtcccat     240
aagcaaacac tgtgagcagc cggaaggtag aggcaaagtc actctcagcc agctctctaa     300
cattgggcat gtccagcagt tctccaaaca cgtagacacc agnggcctcc agcacctgat     360
ggatgagtgt ggccagcgct gccccttgg ccgacttggc taggagcaga aattgctcct     420
ggttctgccc tgtcaccttc acttccgcac tcatcactgc actgagtgtg ggggacttgg     480
gctcaggatg tccagagacg tggttccgcc ccctcnctta atgacaccgn ccanncaacc     540
gtcggctccc gccgantgng ttcgtcgtnc ctgggtcagg gtctgctggc cnctacttgc     600
aancttcgtc nggcccatgg aattcaccnc accggaactn gtangatcca ctnnttctat     660
aaccggncgc caccgcnnnt ggaactccac tcttnttncc tttacttgag ggttaaggtc     720
acccttnncg ttaccttggt ccaaaccntc ccntgtgtcg anatngtnaa tcnggnccna     780
tnccanccnc atangaagcc ng                                              802

<210> SEQ ID NO 19
<211> LENGTH: 731
<212> TYPE: DNA
```

<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19

| | | | | | |
|---|---|---|---|---|---|
| cnaagcttcc | aggtnacggg | ccgcnaancc | tgacccnagg | tancanaang | cagncngcgg | 60 |
| gagcccaccg | tcacgnggng | gngtctttat | nggaggggc | ggagccacat | cnctggacnt | 120 |
| cntgacccca | actccccncc | ncncantgca | gtgatgagtg | cagaactgaa | ggtnacgtgg | 180 |
| caggaaccaa | gancaaannc | tgctccnntc | caagtcggcn | naggggcgg | ggctggccac | 240 |
| gcncatcct | cnagtgctgn | aaagcccnn | cctgtctact | tgtttggaga | acngcnnnga | 300 |
| catgcccagn | gttanataac | nggcnagag | tnantttgcc | tctcccttcc | ggctgcgcan | 360 |
| cgngtntgct | tagnggacat | aacctgacta | cttaactgaa | cccnngaatc | tnccncccct | 420 |
| ccactaagct | cagaacaaaa | aacttcgaca | ccactcantt | gtcacctgnc | tgctcaagta | 480 |
| aagtgtaccc | catncccaat | gtntgctnga | ngctctgncc | tgcnttangt | tcggtcctgg | 540 |
| gaagacctat | caattnaagc | tatgtttctg | actgcctctt | gctccctgna | acaancnacc | 600 |
| cnncnntcca | aggggggnc | ggcccccaat | ccccccaacc | ntnaattnan | tttanccccn | 660 |
| ccccnggcc | cggcctttta | cnancntcnn | nnacnggna | aaaccnngc | tttncccaac | 720 |
| nnaatccncc | t | | | | | 731 |

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20

| | | | | | |
|---|---|---|---|---|---|
| tttttttttt | tttttttttt | taaaaaccc | ctccattnaa | tgnaaacttc | cgaaattgtc | 60 |
| caaccccctc | ntccaaatnn | ccntttccgg | gnggggttc | caaacccaan | ttannttttgg | 120 |
| annttaaatt | aaatnttnnt | tggnggnnna | anccnaatgt | nangaaagtt | naacccanta | 180 |
| tnancttnaa | tncctggaaa | ccngtngntt | ccaaaaatnt | ttaaccctta | antccctccg | 240 |
| aaatngttna | nggaaaaccc | aanttctcnt | aaggttgttt | gaaggntnaa | tnaaaancc | 300 |
| nnccaattgt | ttttngccac | gcctgaatta | attggnttcc | gntgttttcc | nttaaaanaa | 360 |
| ggnnancccc | ggttantnaa | tcccccnnc | cccaattata | ccganttttt | ttngaattgg | 420 |
| ganccncgg | gaattaacgg | ggnnnntccc | tnttgggggg | cnggnncccc | cccntcggg | 480 |
| ggttngggnc | aggncnnaat | tgtttaaggg | tccgaaaaat | ccctccnaga | aaaaaanctc | 540 |
| ccaggntgag | nntgggttt | nccccccccc | canggcccct | ctcgnanagt | tggggtttgg | 600 |
| ggggcctggg | atttttnttc | ccctnttncc | tcccccccc | ccnggganag | aggttngngt | 660 |
| tttgntcnnc | ggccccncn | aaganctttn | ccganttnan | ttaaatcont | gcctnggcga | 720 |
| agtccnttgn | agggntaaan | ggccccctnn | cggg | | | 754 |

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

```
atcancccat gacccnaac nngggaccnc tcanccggnc nnncnaccnc cggccnatca      60
nngtnagnnc actncnnttn natcacnccc cnccnactac gcccncnanc cnacgcncta    120
nncanatncc actgannngcg cgangtngan ngagaaanct nataccanag ncaccanacn   180
ccagctgtcc nanaangcct nnatacngg nnatccaat ntgnaccctc cnaagtattn     240
nncnncanat gattttcctn anccgattac ccntnccccc tanccctcc cccccaacna    300
cgaaggcnct ggnccnaagg nngcgncnc ccgctagntc cccnncaagt cncncnccta    360
aactcanccn nattacncgc ttcntgagta tcactcccg aatctcaccc tactcaactc    420
aaaaanatcn gatacaaaat aatncaagcc tgnttatnac actntgactg ggtctctatt   480
ttagnggtcc ntnaancntc ctaatacttc cagtctncct tcnccaattt ccnaanggct   540
ctttcngaca gcatnttttg gttccnntt gggttcttan ngaattgccc ttcntngaac   600
gggctcntct tttccttcgg ttancctggn ttcnnccggc cagttattat ttcccntttt   660
aaattcntnc cntttanttt tggcnttcna aaccccggc cttgaaaacg gccccctggt    720
aaaggttgt ttganaaaa tttttgtttt gttcc                                755
```

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

```
tttttttttt ttttangtg tngtcgtgca ggtagaggct tactacaant gtgaanacgt    60
acgctnggan taangcgacc cganttctag ganncnccct aaaatcanac tgtgaagatn   120
atcctgnnna cggaanggtc accggnngat nntgctaggg tgnccnctcc cannncnttn   180
cataactcng nggccctgcc caccaccttc ggcggcccng ngccgggcc cgggtcattn    240
gnnttaaccn cactnngcna ncggtttccn ncccnncng accnggcga tccggggtnc    300
tctgtcttcc cctgnagncn anaaantggg ccncggnccc ctttaccct nnacaagcca   360
cngccntcta nccncngccc cccctccant nnggggact gccnanngct ccgttnctng   420
nnaccccnnn gggtncctcg gttgtcgant cnaccgnang ccanggattc cnaaggaagg   480
tgcgttnttg gccctaccc ttcgctncgg nncacccttc ccgacnanga nccgctcccg   540
cncnnngnng cctcnctcg caacacccgc nctcntcgt ncggnnnccc ccccacccgc   600
ncctcncnc ngncgnancn ctccnccncc gtctcannca ccaccccgcc ccgccaggcc   660
ntcanccacn ggnngacnng nagcncnntc gcnccgcgcn gcgncnccct cgcccncngaa  720
ctncntcngg ccantnncgc tcaanccnna cnaaacgccg ctgcgcggcc cgnagcgncc   780
ncctccncga gtcctcccgn cttccnaccc angnnttccn cgaggacacn nnaccccgcc   840
nncangcgg                                                           849
```

<210> SEQ ID NO 23
<211> LENGTH: 872
<212> TYPE: DNA
<213> ORGANISM: Homo sapien
<220> FEATURE:

<221> NAME/KEY: misc_feature
<222> LOCATION: (1)...(872)
<223> OTHER INFORMATION: n = A,T,C or G

<400> SEQUENCE: 23

```
gcgcaaacta tacttcgctc gnactcgtgc gcctcgctnc tcttttcctc cgcaaccatg    60
tctgacnanc ccgattnggc ngatatcnan aagntcganc agtccaaact gantaacaca   120
cacacncnan aganaaatcc nctgccttcc anagtanacn attgaacnng agaaccangc   180
nggcgaatcg taataggcg tgcgccgcca atntgtcncc gtttattntn ccagcntcnc    240
ctnccnaccc tacntcttcn nagctgtcnn accectngtn cgnaccccce naggtcggga   300
tcgggttttnn nntgaccgng cnnccectcc cccentccat nacgancenc cgcaccacc   360
nanngcncgc nccecgnnct cttcgccncc ctgtcctntn ccectgtngc ctggcncngn   420
accgcattga ccctcgccnn ctncnngaaa ncgnanacgt ccgggttgnn annancgctg   480
tgggnnngcg tctgcnccgc gttccttccn ncnncttcca ccatcttcnt tacngggtct   540
ccncgccntc tcnnncacnc cctgggacgc ntcctntgc cccccttnac tccccccctt   600
cgncgtgncc cgncecace ntcatttnca nacgntcttc acaanncct ggntnnctcc     660
cnancngncn gtcanccnag ggaagggngg ggnnccnntg nttgacgttg nggngangtc   720
cgaanantcc tcnccntcan nctaccect cgggcgnnct ctcngttncc aacttancaa    780
ntctccccg ngngcncntc tcagcctcnc ccncccnct ctctgcantg tnctctgctc     840
tnaccnntac gantnttcgn cnccctcttt cc                                 872
```

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

```
gcatgcaagc ttgagtattc tatagngtca cctaaatanc ttggcntaat catggtcnta    60
nctgncttcc tgtgtcaaat gtatacnaan tanatatgaa tctnatntga caagannnta   120
tcntncatta gtaacaantg tnntgtccat cctgtcngan canattccca tnnattncgn   180
cgcattcncn gcncatatn taatngggaa ntcnnntnnn ncaccnncat ctatcntncc    240
gcnccctgac tggnagagat ggatnanttc tnntntgacc nacatgttca tcttggattn   300
aananccecc cgcngnccac cggttngnng cnagccnntc ccaagacctc ctgtggaggt   360
aacctgcgtc aganncatca aacntgggaa acccgcnncc angtnnaagt ngnnncanan   420
gatcccgtcc aggnttnacc atccctcnc agcgcccct ttngtgcctt anagngnagc     480
gtgtccnanc cnctcaacat ganacgcgcc agnccanccg caattnggca caatgtcgnc   540
gaaccccta ggggantna tncaaancce caggattgtc cncncangaa atccencanc     600
cccncectac ccnnctttgg gacngtgacc aantccegga gtnccagtcc ggccngnctc   660
ccccaccggt nnccntgggg gggtgaanct cgnnntcanc cngncgaggn ntcgnaagga   720
accggncctn ggncgaanng ancnntcnga agngccncnt cgtataaccc ccctcncca    780
nccnacngnt agtnccccce cngggtncgg aangg                              815
```

<210> SEQ ID NO 25
<211> LENGTH: 775

```
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25
ccgagatgtc tcgctccgtg gccttagctg tgctcgcgct actctctctt tctggcctgg    60
aggctatcca gcgtactcca aagattcagg tttactcacg tcatccagca gagaatggaa   120
agtcaaattt cctgaattgc tatgtgtctg ggtttcatcc atccgacatt gaanttgact   180
tactgaagaa tgganagaga attgaaaaag tggagcattc agacttgtct ttcagcaagg   240
actggtcttt ctatctcntg tactacactg aattcacccc cactgaaaaa gatgagtatg   300
cctgccgtgt gaaccatgtg actttgtcac agcccaagat agttaagtgg gatcgagaca   360
tgtaagcagn cnncatggaa gtttgaagat gccgcatttg gattggatga attccaaatt   420
ctgcttgctt gcnttttaat antgatatgc ntatacaccc tacccttat gnccccaaat    480 tgtaggggtt acatnantgt tcncntngga catgatcttc ctttataant ccnccnttcg   540
aattgcccgt cncccngttn ngaatgtttc cnnaaccacg gttggctccc ccaggtcncc   600
tcttacggaa gggcctgggc cnctttcaa ggttggggga accnaaaatt tcncttntgc    660
ccncccncca cnntcttgng nncncanttt ggaacccttc cnattcccct tggcctcnna   720
nccttnncta anaaaacttn aaancgtngc naaanntttn acttcccccc ttacc        775

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26
anattantac agtgtaatct tttcccagag gtgtgtanag ggaacggggc ctagaggcat    60
cccanagata ncttatanca acagtgcttt gaccaagagc tgctgggcac atttcctgca   120
gaaaaggtgg cggtccccat cactcctcct ctcccatagc catcccagag gggtgagtag   180
ccatcangcc ttcggtggga gggagtcang gaaacaacan accacagagc anacagacca   240
ntgatgacca tgggcgggag cgagcctctt ccctgnaccg gggtggcana nganagccta   300
nctgaggggt cacactataa acgttaacga ccnagatnan cacctgcttc aagtgcaccc   360
ttcctacctg acnaccagng accnnnaact gcngcctggg gacagcnctg ggancagcta   420
acnnagcact cacctgcccc cccatggccg tncgcntccc tggtcctgnc aagggaagct   480
ccctgttgga attncggga naccaaggga nccccctcct ccanctgtga aggaaaaann   540
gatggaattt tncccttccg gccnntcccc tcttcccttta cacgcccct nntactcntc   600 tccctctntt ntcctgncnc acttttnacc ccnnnatttc ccttnattga tcggannctn   660
ganattccac tnncgcctnc cntcnatcng naanacnaaa nactntctna cccngggat    720 gggnncctcg ntcatcctct cttttcnct accnccnntt ctttgcctct ccttngatca    780
tccaaccntc gntggccntn cccccccnnn tcctttnccc                         820

<210> SEQ ID NO 27
<211> LENGTH: 818
<212> TYPE: DNA
```

<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27

| | | | | | |
|---|---|---|---|---|---|
| tctgggtgat | ggcctcttcc | tcctcaggga | cctctgactg | ctctgggcca | aagaatctct | 60 |
| tgtttcttct | ccgagcccca | ggcagcggtg | attcagccct | gcccaacctg | attctgatga | 120 |
| ctgcggatgc | tgtgacggac | ccaaggggca | atagggtcc | cagggtccag | ggaggggcgc | 180 |
| ctgctgagca | cttccgcccc | tcaccctgcc | cagcccctgc | catgagctct | gggctgggtc | 240 |
| tccgcctcca | gggttctgct | cttccangca | ngccancaag | tggcgctggg | ccacactggc | 300 |
| ttcttcctgc | cccntccctg | gctctgantc | tctgtcttcc | tgtcctgtgc | angcnccttg | 360 |
| gatctcagtt | tccctcnctc | anngaactct | gtttctgann | tcttcantta | actntgantt | 420 |
| tatnaccnan | tggnctgtnc | tgtcnnactt | taatgggccn | gaccggctaa | tccctccctc | 480 |
| nctcccttcc | anttcnnnna | accngcttnc | cntcntctcc | cntancccg | ccngggaanc | 540 |
| ctcctttgcc | ctnaccangg | gccnnnaccg | cccntnnctn | gggggcnng | gtnnctncnc | 600 |
| ctgntnnccc | cnctcncnnt | tncctcgtcc | cnncnncgcn | nngcannttc | ncngtcccnn | 660 |
| tnnctcttcn | ngtntcgnaa | ngntcncntn | tnnnnngncn | ngntnntncn | tccctctcnc | 720 |
| cnnntgnang | tnnttnnnnc | ncngnncccc | nnnncnnnn | nggnnntnnn | tctncncngc | 780 |
| cccnnccccc | ngnattaagg | cctccnntct | ccggccnc | | | 818 |

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28

| | | | | | |
|---|---|---|---|---|---|
| aggaagggcg | gagggatatt | gtangggatt | gagggatagg | agnataangg | gggaggtgtg | 60 |
| tcccaacatg | anggtgnngt | tctcttttga | angagggttg | ngtttttann | ccngtgggt | 120 |
| gattnaaccc | cattgtatgg | agnnaaaggn | tttnagggat | ttttcggctc | ttatcagtat | 180 |
| ntanattcct | gtnaatcgga | aaatnatntt | tcnncngga | aatnttgctc | ccatccgnaa | 240 |
| attnctcccg | ggtagtgcat | nttnggggn | cngccangtt | tcccaggctg | ctanaatcgt | 300 |
| actaaagntt | naagtgggan | tncaaatgaa | aacctnncac | agagnatccn | tacccgactg | 360 |
| tnnnttncct | tcgccctntg | actctgcnng | agcccaatac | ccnngngnat | gtcnccngn | 420 |
| nnngcgncnc | tgaaannnnc | tcgnggctnn | gancatcang | gggtttcgca | tcaaaagcnn | 480 |
| cgtttcncat | naaggcactt | tngcctcatc | caaccnctng | ccctcnncca | tttngccgtc | 540 |
| nggttcncct | acgctnnntg | cncctnnntn | ganattttnc | ccgcctngg | naancctcct | 600 |
| gnaatgggta | gggncttntc | ttttnaccnn | gnggtntact | aatcnnctnc | acgcntncctt | 660 |
| tctcnacccc | cccccttttt | caatcccanc | ggcnaatggg | gtctccccnn | cganggggg | 720 |
| nnncccannc | c | | | | | 731 |

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

```
actagtccag tgtggtggaa ttccattgtg ttggggncnc ttctatgant antnttagat      60
cgctcanacc tcacanccctc ccnacnangc ctataangaa nannaataga nctgtncnnt    120
atntntacnc tcatanncct cnnnacccac tccctcttaa cccntactgt gcctatngcn    180
tnnctantct ntgccgcctn cnanccaccn gtgggccnac cncnngnatt ctcnatctcc    240
tcnccatntn gcctananta ngtncatacc ctatacctac ccaatgcta nnnctaancn     300
tccatnantt annntaacta ccactgacnt ngactttcnc atnanctcct aatttgaatc    360
tactctgact cccacngcct annnattagc ancntccccc nacnatntct caaccaaatc    420
ntcaacaacc tatctanctg ttcnccaacc nttncctccg atccccnnac aaccccctc     480
ccaaatacc nccacctgac ncctaacccn caccatcccg gcaagccnan ggncatttan    540
ccactggaat cacnatngga naaaaaaaac ccnaactctc tancncnnat ctccctaana   600
aatnctcctn naatttactn ncantnccat caancccacn tgaaacnnaa ccctgtttt    660
tanatcccctt ctttcgaaaa ccnacccttt annncccaac ctttngggcc ccccncttnc   720
ccnaatgaag gncncccaat cnangaaacg nccntgaaaa ancnaggcna anannntccg   780
canatcctat cccttantn ggggnccctt nccngggcc cc                         822
```

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

```
cggccgcctg ctctggcaca tgcctcctga atggcatcaa aagtgatgga ctgcccattg      60
ctagagaaga ccttctctcc tactgtcatt atggagccct gcagactgag ggctcccctt    120
gtctgcagga tttgatgtct gaagtcgtgg agtgtggctt ggagctcctc atctacatna    180
gctggaagcc ctggagggcc tctctcgcca gcctccccct tctctccacg ctctccanggg  240
acaccagggg ctccaggcag cccattattc ccagnangac atggtgttc tccacgcgga    300
cccatggggc ctgnaaggcc agggtctcct ttgacaccat ctctcccgtc ctgcctggca   360
ggccgtggga tccactantt ctanaacggn cgccaccncg gtgggagctc cagcttttgt    420
tcccnttaat gaaggttaat tgcncgcttg gcgtaatcat nggtcanaac tntttcctgt   480
gtgaaattgt ttntcccctc ncnattccnc ncnacatacn aacccggaan cataaagtgt    540
taaagcctgg gggtngcctn nngaatnaac tnaactcaat taattgcgtt ggctcatggc   600
ccgctttccn ttcnggaaaa ctgtcntccc ctgcnttnnt gaatcggcca ccccccnggg   660
aaaagcggtt tgcnttttng ggggntcctt ccncttcccc cctcnctaan ccctncgcct   720
cggtcgttnc nggtngcggg gaangggnat nnnctcccnc naagggggng agnnngntat  780
ccccaaa                                                              787
```

<210> SEQ ID NO 31
<211> LENGTH: 799
<212> TYPE: DNA

<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31

| | | | | | |
|---|---|---|---|---|---|
| tttttttttt | tttttttggc | gatgctactg | tttaattgca | ggaggtgggg | gtgtgtgtac | 60 |
| catgtaccag | ggctattaga | agcaagaagg | aaggagggag | ggcagagcgc | cctgctgagc | 120 |
| aacaaaggac | tcctgcagcc | ttctctgtct | gtctcttggc | gcaggcacat | ggggaggcct | 180 |
| cccgcagggt | gggggccacc | agtccagggg | tgggagcact | acanggggtg | ggagtgggtg | 240 |
| gtggctggtn | cnaatggcct | gncacanatc | cctacgattc | ttgacacctg | gatttcacca | 300 |
| ggggaccttc | tgttctccca | nggnaacttc | ntnnatctcn | aaagaacaca | actgtttctt | 360 |
| cngcanttct | ggctgttcat | ggaaagcaca | ggtgtccnat | ttnggctggg | acttggtaca | 420 |
| tatggttccg | gcccacctct | cccntcnaan | aagtaattca | cccccccccn | cntctnttg | 480 |
| cctgggccct | taantaccca | caccggaact | canttantta | ttcatcttng | gntgggcttg | 540 |
| ntnatcnccn | cctgaangcg | ccaagttgaa | aggccacgcc | gtnccnctc | cccatagnan | 600 |
| nttttnncnt | canctaatgc | ccccccnggc | aacnatccaa | tccccccccn | tgggggcccc | 660 |
| agcccanggc | ccccgnctcg | ggnnnccngn | cncgnantcc | ccaggntctc | ccantcngnc | 720 |
| ccnnngcncc | cccgcacgca | gaacanaagg | ntngagccnc | cgcannnnnn | nggtnncnac | 780 |
| ctcgcccccc | ccnncgnng | | | | | 799 |

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32

| | | | | | |
|---|---|---|---|---|---|
| tttttttttt | tttttttttt | tttttttttt | tttttttttt | tttttttttt | tttttttttt | 60 |
| ttttnccnag | ggcaggttta | ttgacaacct | cncgggacac | aancaggctg | ggacaggac | 120 |
| ggcaacaggc | tccggcggcg | gcggcggcgg | ccctacctgc | ggtaccaaat | ntgcagcctc | 180 |
| cgctcccgct | tgatnttcct | ctgcagctgc | aggatgccnt | aaaacagggc | ctcggccntn | 240 |
| ggtgggcacc | ctgggatttn | aatttccacg | ggcacaatgc | ggtcgcancc | cctcaccacc | 300 |
| nattaggaat | agtggtntta | cccncncccg | ttggcncact | cccntggaa | accacttntc | 360 |
| gcggctccgg | catctggtct | taaaccttgc | aaacnctggg | gccctctttt | tggttantnt | 420 |
| nccngccaca | atcatnactc | agactggcnc | gggctggccc | caaaaaancn | ccccaaaacc | 480 |
| ggnccatgtc | ttnncggggt | tgctgcnatn | tncatcacct | cccgggcnca | ncaggncaac | 540 |
| ccaaagttc | ttgnggcccn | caaaaaanct | ccgggggnc | ccagtttcaa | caaagtcatc | 600 |
| ccccttggcc | cccaaatcct | cccccgntt | nctgggtttg | ggaacccacg | cctctnncctt | 660 |
| tggnnggcaa | gntggntccc | ccttcgggcc | cccggtgggc | ccnctctaa | ngaaaacncc | 720 |
| ntcctnnnca | ccatcccccc | nngnnacgnc | tancaangna | tcccttttt | tanaaacggg | 780 |
| ccccccncg | | | | | | 789 |

<210> SEQ ID NO 33
<211> LENGTH: 793

```
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33
gacagaacat gttggatggt ggagcacctt tctatacgac ttacaggaca gcagatgggg      60
aattcatggc tgttggagca atanaacccc agttctacga gctgctgatc aaaggacttg     120
gactaaagtc tgatgaactt cccaatcaga tgagcatgga tgattggcca gaaatgaana     180
agaagtttgc agatgtattt gcaaagaaga cgaaggcaga gtggtgtcaa atctttgacg     240
gcacagatgc ctgtgtgact ccggttctga cttttgagga ggttgttcat catgatcaca     300
acaangaacg gggctcgttt atcaccantg aggagcagga cgtgagcccc cgccctgcac     360
ctctgctgtt aaacacccca gccatccctt ctttcaaaag ggatccacta cttctagagc     420
ggncgccacc gcggtggagc tccagctttt gttcccttta gtgagggtta attgcgcgct     480
tggcgtaatc atggtcatan ctgtttcctg tgtgaaattg ttatccgctc acaattccac     540
acaacatacg anccggaagc atnaaatttt aaagcctggn ggtngcctaa tgantgaact     600
nactcacatt aattggcttt gcgctcactg cccgctttcc agtccggaaa acctgtcctt     660
gccagctgcc nttaatgaat cnggccaccc cccggggaaa aggcngtttg cttnttgggg     720
cgcncttccc gctttctcgc ttcctgaant ccttcccccc ggtctttcgg cttgcggcna     780
acggtatcna cct                                                        793

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34
gccgcgaccg gcatgtacga gcaactcaag ggcgagtgga accgtaaaag ccccaatctt      60
ancaagtgcg gggaanagct gggtcgactc aagctagttc ttctggagct caacttcttg     120
ccaaccacag ggaccaagct gaccaaaacag cagctaattc tggcccgtga catactggag     180
atcggggccc aatggagcat cctacgcaan gacatcccct ccttcgagcg ctacatggcc     240
cagctcaaat gctactactt tgattacaan gagcagctcc ccgagtcagc ctatatgcac     300
cagctcttgg gcctcaacct cctcttcctg ctgtcccaga accgggtggc tgantnccac     360
acgganttgg ancggctgcc tgcccaanga catacanacc aatgtctaca tcnaccacca     420
gtgtcctgga gcaatactga tgganggcag ctaccncaaa gtnttcctgg ccnagggtaa     480 catccccgc cgagagctac accttcttca ttgacatcct gctcgacact atcagggatg     540
aaaatcgcng ggttgctcca gaaaggctnc aanaanatcc ttttcnctga aggccccgg     600 atncnctagt nctagaatcg gcccgccatc gcggtgganc ctccaacctt tcgttnccct     660
ttactgaggg ttnattgccg cccttggcgt tatcatggtc acnccngttn cctgtgttga     720
aattnttaac cccccacaat tccacgccna cattng                               756

<210> SEQ ID NO 35
<211> LENGTH: 834
<212> TYPE: DNA
```

<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

| | | | | | |
|---|---|---|---|---|---|
| ggggatctct | anatcnacct | gnatgcatgg | ttgtcggtgt | ggtcgctgtc | gatgaanatg | 60 |
| aacaggatct | tgcccttgaa | gctctcggct | gctgtnttta | agttgctcag | tctgccgtca | 120 |
| tagtcagaca | cnctcttggg | caaaaaacan | caggatntga | gtcttgattt | cacctccaat | 180 |
| aatcttcngg | gctgtctgct | cggtgaactc | gatgacnang | ggcagctggt | tgtgtntgat | 240 |
| aaantccanc | angttctcct | tggtgacctc | cccttcaaag | ttgttccggc | cttcatcaaa | 300 |
| cttctnnaan | angannancc | canctttgtc | gagctggnat | ttgganaaca | cgtcactgtt | 360 |
| ggaaactgat | cccaaatggt | atgtcatcca | tcgcctctgc | tgcctgcaaa | aaacttgctt | 420 |
| ggcncaaatc | cgactccccn | tccttgaaag | aagccnatca | caccccctc | cctggactcc | 480 |
| nncaangact | ctnccgctnc | cccntccnng | cagggttggt | ggcannccgg | gcccntgcgc | 540 |
| ttcttcagcc | agttcacnat | nttcatcagc | ccctctgcca | gctgttntat | tccttggggg | 600 |
| ggaanccgtc | tctcccttcc | tgaannaact | ttgaccgtng | gaatagccgc | gcntcnccnt | 660 |
| acntnctggg | ccgggttcaa | antccctccn | ttgncnntcn | cctcgggcca | ttctggattt | 720 |
| nccnaacttt | ttccttcccc | cnccccncgg | ngtttggntt | tttcatnggg | cccaactct | 780 |
| gctnttggcc | antccctgg | gggcntntan | cnccccctnt | ggtcccntng | ggcc | 834 |

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

| | | | | | |
|---|---|---|---|---|---|
| cggncgcttt | ccngccgcgc | cccgtttcca | tgacnaaggc | tcccttcang | ttaaatacnn | 60 |
| cctagnaaac | attaatgggt | tgctctacta | atacatcata | cnaaccagta | agcctgccca | 120 |
| naacgccaac | tcaggccatt | cctaccaaag | gaagaaaggc | tggtctctcc | accccctgta | 180 |
| ggaaaggcct | gccttgtaag | acaccacaat | ncggctgaat | ctnaagtctt | gtgtttact | 240 |
| aatgaaaaa | aaaaataaac | aanaggtttt | gttctcatgg | ctgcccaccg | cagcctggca | 300 |
| ctaaaacanc | ccagcgctca | cttctgcttg | ganaaatatt | ctttgctctt | ttggacatca | 360 |
| ggcttgatgg | tatcactgcc | acntttccac | ccagctgggc | nccctttcccc | catntttgtc | 420 |
| antganctgg | aaggcctgaa | ncttagtctc | caaaagtctc | ngcccacaag | accggccacc | 480 |
| aggggangtc | ntttncagtg | gatctgccaa | anantacccn | tatcatcnnt | gaataaaaag | 540 |
| gcccctgaac | ganatgcttc | cancanccctt | taagacccat | aatcctngaa | ccatggtgcc | 600 |
| cttccggtct | gatccnaaag | gaatgttcct | gggtcccant | ccctcctttg | ttncttacgt | 660 |
| tgtnttggac | ccntgctngn | atnacccaan | tganatcccc | ngaagcaccc | tnccctggc | 720 |
| atttganttt | cntaaattct | ctgccctacn | nctgaaagca | cnattccctn | ggcnccnaan | 780 |
| ggngaactca | agaaggtctn | ngaaaaacca | cncn | | | 814 |

<210> SEQ ID NO 37
<211> LENGTH: 760

```
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37
gcatgctgct cttcctcaaa gttgttcttg ttgccataac aaccaccata ggtaaagcgg      60
gcgcagtgtt cgctgaaggg gttgtagtac cagcgcggga tgctctcctt gcagagtcct     120
gtgtctggca ggtccacgca atgccctttg tcactgggga aatggatgcg ctggagctcg     180
tcnaanccac tcgtgtattt ttcacangca gcctcctccg aagcntccgg gcagttgggg     240
gtgtcgtcac actccactaa actgtcgatn cancagccca ttgctgcagc ggaactgggt     300
gggctgacag gtgccagaac acactggatn ggcctttcca tggaagggcc tgggggaaat     360
cncctnancc caaactgcct ctcaaaggcc accttgcaca cccgacaggt ctagaaatgc     420
actcttcttc ccaaaggtag ttgttcttgt tgcccaagca ncctccanca aaccaaaanc     480
ttgcaaaatc tgctccgtgg gggtcatnnn taccanggtt ggggaaanaa acccggcngn     540
ganccncctt gttttgaatgc naaggnaata atcctcctgt cttgcttggg tggaanagca    600
caattgaact gttaacnttg ggccgngttc cnctngggtg gtctgaaact aatcaccgtc     660
actggaaaaa ggtangtgcc ttccttgaat tcccaaantt cccctngntt tgggtnnttt     720
ctcctctncc ctaaaaatcg tnttccccccc ccntanggcg                          760

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38
tttttttttt tttttttttt tttttttttt tttttaaaaa ccccctccat tgaatgaaaa      60
cttccnaaat tgtccaaccc cctcnnccaa atnnccattt ccgggggggg gttccaaacc     120
caaattaatt ttggantttta aattaaatnt tnattngggg aanaaccaa atgtnaagaa     180 aatttaaccc attataact taaatnccta gaaacccntg gnttccaaaa atttttaacc     240
cttaaatccc tccgaaattg ntaanggaaa accaaattcn cctaaggctn tttgaaggtt     300
ngatttaaac ccccttnant tnttttnacc cnngnctnaa ntatttngnt tccggtgttt     360
tcctnttaan cntnggtaac tcccgntaat gaannnccct aanccaatta aaccgaattt     420
tttttgaatt ggaaattccn nggaattna ccggggtttt tcccntttgg gggccatncc      480 cccntttcg gggtttgggn ntaggttgaa tttttnnang nccaaaaaa nccccccaana     540 aaaaaactcc caagnnttaa ttngaatntc cccccttccca ggcctttttgg gaaaggnggg    600 tttntggggg ccngggantt cnttccccccn ttnccncccc cccccngnt aanggttat     660 ngnntttggt ttttgggccc cttnanggac cttccggatn gaaattaaat ccccgggncg     720
gccg                                                                  724

<210> SEQ ID NO 39
<211> LENGTH: 751
<212> TYPE: DNA
<213> ORGANISM: Homo sapien
<220> FEATURE:
```

<221> NAME/KEY: misc_feature
<222> LOCATION: (1)...(751)
<223> OTHER INFORMATION: n = A,T,C or G

<400> SEQUENCE: 39

| | | | | | |
|---|---|---|---|---|---|
| tttttttttt | ttttctttg | ctcacattta | atttttattt | tgatttttt | taatgctgca | 60 |
| caacacaata | tttatttcat | ttgtttcttt | tatttcattt | tatttgtttg | ctgctgctgt | 120 |
| tttatttatt | tttactgaaa | gtgagaggga | acttttgtgg | cctttttcc | tttttctgta | 180 |
| ggccgcctta | agctttctaa | atttggaaca | tctaagcaag | ctgaanggaa | aaggggttt | 240 |
| cgcaaaatca | ctcgggggaa | nggaaaggtt | gctttgttaa | tcatgccta | tggtgggtga | 300 |
| ttaactgctt | gtacaattac | ntttcacttt | taattaattg | tgctnaangc | tttaattana | 360 |
| cttgggggtt | ccctccccan | accaaccccn | ctgacaaaaa | gtgccngccc | tcaaatnatg | 420 |
| tcccggcnnt | cnttgaaaca | cacngcngaa | ngttctcatt | ntccncnc | caggtnaaaa | 480 |
| tgaagggtta | ccatntttaa | cnccacctcc | acntggcnnn | gcctgaatcc | tcnaaaancn | 540 |
| ccctcaancn | aattnctnng | ccccggtcnc | gcntnngtcc | cnccccgggct | ccgggaantn | 600 |
| caccccnga | anncnntnnc | naacnaaatt | ccgaaaatat | tcccnntcnc | tcaattcccc | 660 |
| cnnagactnt | cctcnncnan | cncaattttc | ttttnntcac | gaacncgnnc | cnnaaaatgn | 720 |
| nnnncncctc | cnctngtccn | naatcnccan | c | | | 751 |

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | | | | | |
|---|---|---|---|---|---|
| gtggtatttt | ctgtaagatc | aggtgttcct | ccctcgtagg | tttagaggaa | acaccctcat | 60 |
| agatgaaaac | cccccgaga | cagcagcact | gcaactgcca | agcagccggg | gtaggagggg | 120 |
| cgccctatgc | acagctgggc | ccttgagaca | gcagggcttc | gatgtcaggc | tcgatgtcaa | 180 |
| tggtctggaa | gcggcggctg | tacctgcgta | ggggcacacc | gtcagggccc | accaggaact | 240 |
| tctcaaagtt | ccaggcaacn | tcgttgcgac | acaccggaga | ccaggtgatn | agcttggggt | 300 |
| cggtcataan | cgcggtggcg | tcgtcgctgg | gagctggcag | ggcctcccgc | aggaaggcna | 360 |
| ataaaaggtg | cgcccccgca | ccgttcanct | cgcacttctc | naanaccatg | angttgggct | 420 |
| cnaacccacc | accanncccgg | acttccttga | nggaattccc | aaatctcttc | gntcttgggc | 480 |
| ttctnctgat | gccctanctg | gttgcccngn | atgccaanca | ncccaancc | ccgggtcct | 540 |
| aaancacccn | cctcctcntt | tcatctgggt | tnttntcccc | ggaccntggt | tcctctcaag | 600 |
| ggancccata | tctcnaccan | tactcaccnt | ncccccccnt | gnnacccanc | cttctanngn | 660 |
| ttcccncccg | ncctctggcc | cntcaaanan | gcttncacna | cctgggtctg | ccttcccccc | 720 |
| tnccctatct | gnacccncn | tttgtctcan | tnt | | | 753 |

<210> SEQ ID NO 41
<211> LENGTH: 341
<212> TYPE: DNA
<213> ORGANISM: Homo sapien

<400> SEQUENCE: 41

| | | | | | |
|---|---|---|---|---|---|
| actatatcca | tcacaacaga | catgcttcat | cccatagact | tcttgacata | gcttcaaatg | 60 |

-continued

| | |
|---|---|
| agtgaaccca tccttgattt atatacatat atgttctcag tattttggga gcctttccac | 120 |
| ttctttaaac cttgttcatt atgaacactg aaaataggaa tttgtgaaga gttaaaaagt | 180 |
| tatagcttgt ttacgtagta agttttttgaa gtctacattc aatccagaca cttagttgag | 240 |
| tgttaaactg tgatttttaa aaaatatcat ttgagaatat tctttcagag gtattttcat | 300 |
| ttttactttt tgattaattg tgttttatat attagggtag t | 341 |

<210> SEQ ID NO 42
<211> LENGTH: 101
<212> TYPE: DNA
<213> ORGANISM: Homo sapien

<400> SEQUENCE: 42

| | |
|---|---|
| acttactgaa tttagttctg tgctcttcct tatttagtgt tgtatcataa atactttgat | 60 |
| gtttcaaaca ttctaaataa ataattttca gtggcttcat a | 101 |

<210> SEQ ID NO 43
<211> LENGTH: 305
<212> TYPE: DNA
<213> ORGANISM: Homo sapien

<400> SEQUENCE: 43

| | |
|---|---|
| acatctttgt tacagtctaa gatgtgttct taaatcacca ttccttcctg gtcctcaccc | 60 |
| tccagggtgg tctcacactg taattagagc tattgaggag tctttacagc aaattaagat | 120 |
| tcagatgcct tgctaagtct agagttctag agttatgttt cagaaagtct aagaaaccca | 180 |
| cctcttgaga ggtcagtaaa gaggacttaa tatttcatat ctacaaaatg accacaggat | 240 |
| tggatacaga acgagagtta tcctggataa ctcagagctg agtacctgcc cgggggccgc | 300 |
| tcgaa | 305 |

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

| | |
|---|---|
| acataaatat cagagaaaag tagtctttga aatatttacg tccaggagtt ctttgtttct | 60 |
| gattatttgg tgtgtgtttt ggtttgtgtc caaagtattg gcagcttcag ttttcattt | 120 |
| ctctccatcc tcgggcattc ttcccaaatt tatataccag tcttcgtcca tccacacgct | 180 |
| ccagaatttc tcttttgtag taatatctca tagctcggct gagcttttca taggtcatgc | 240 |
| tgctgttgtt cttcttttta ccccatagct gagccactgc ctctgatttc aagaacctga | 300 |
| agacgccctc agatcggtct tcccatttta ttaatcctgg gttcttgtct gggttcaaga | 360 |
| ggatgtcgcg gatgaattcc cataagtgag tccctctcgg gttgtgcttt ttggtgtggc | 420 |
| acttggcagg ggggtcttgc tccttttttca tatcaggtga ctctgcaaca ggaaggtgac | 480 |
| tggtggttgt catggagatc tgagcccggc agaaagtttt gctgtccaac aaatctactg | 540 |
| tgctaccata gttggtgtca tataaatagt tctngtcttt ccaggtgttc atgatggaag | 600 |
| gctcagtttg ttcagtcttg acaatgacat tgtgtgtgga ctggaacagg tcactactgc | 660 |
| actggccgtt ccacttcaga tgctgcaagt tgctgtagag gagntgcccc gccgtccctg | 720 |

| | |
|---|---|
| ccgcccgggt gaactcctgc aaactcatgc tgcaaaggtg ctcgccgttg atgtcgaact | 780 |
| cntggaaagg gatacaattg gcatccagct ggttggtgtc caggaggtga tggagccact | 840 |
| cccacacctg gt | 852 |

<210> SEQ ID NO 45
<211> LENGTH: 234
<212> TYPE: DNA
<213> ORGANISM: Homo sapien

<400> SEQUENCE: 45

| | |
|---|---|
| acaacagacc cttgctcgct aacgacctca tgctcatcaa gttggacgaa tccgtgtccg | 60 |
| agtctgacac catccggagc atcagcattg cttcgcagtg ccctaccgcg gggaactctt | 120 |
| gcctcgtttc tggctggggt ctgctggcga acggcagaat gcctaccgtg ctgcagtgcg | 180 |
| tgaacgtgtc ggtggtgtct gaggaggtct gcagtaagct ctatgacccg ctgt | 234 |

<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46

| | |
|---|---|
| acttttatt taaatgttta taaggcagat ctatgagaat gatagaaaac atggtgtgta | 60 |
| atttgatagc aatattttgg agattacaga gttttagtaa ttaccaatta cacagttaaa | 120 |
| aagaagataa tatattccaa gcanatacaa aatatctaat gaaagatcaa ggcaggaaaa | 180 |
| tgantataac taattgacaa tggaaaatca attttaatgt gaattgcaca ttatccttta | 240 |
| aaagctttca aaanaaanaa ttattgcagt ctanttaatt caaacagtgt taaatggtat | 300 |
| caggataaan aactgaaggg canaaagaat taattttcac ttcatgtaac ncacccanat | 360 |
| ttacaatggc ttaaatgcan ggaaaaagca gtggaagtag ggaagtantc aaggtctttc | 420 |
| tggtctctaa tctgccttac tctttgggtg tggctttgat cctctggaga cagctgccag | 480 |
| ggctcctgtt atatccacaa tcccagcagc aagatgaagg gatgaaaaag gacacatgct | 540 |
| gccttccttt gaggagactt catctcactg gccaacactc agtcacatgt | 590 |

<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47

| | |
|---|---|
| acaaggggc ataatgaagg agtggggana gattttaaag aaggaaaaaa aacgaggccc | 60 |
| tgaacagaat tttcctgnac aacggggctt caaaataatt ttcttgggga ggttcaagac | 120 |
| gcttcactgc ttgaaactta aatggatgtg ggacanaatt ttctgtaatg accctgaggg | 180 |
| cattacagac gggactctgg gaggaaggat aaacagaaag gggacaaagg ctaatcccaa | 240 |
| aacatcaaag aaaggaaggt ggcgtcatac ctcccagcct acacagttct ccagggctct | 300 |
| cctcatccct ggaggacgac agtggaggaa caactgacca tgtccccagg ctcctgtgtg | 360 |
| ctggctcctg gtcttcagcc cccagctctg gaagcccacc ctctgctgat cctgcgtggc | 420 |

-continued
ccacactcct tgaacacaca tccccaggtt atattcctgg acatggctga acctcctatt 480
cctacttccg agatgccttg ctccctgcag cctgtcaaaa tcccactcac cctccaaacc 540
acggcatggg aagcctttct gacttgcctg attactccag catcttggaa caatccctga 600
ttccccactc cttagaggca agatagggtg gttaagagta gggctggacc acttggagcc 660
aggctgctgg cttcaaattn tggctcattt acgagctatg ggaccttggg caagtnatct 720
tcacttctat gggcntcatt ttgttctacc tgcaaaatgg gggataataa tagt 774


<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48
canaaattga aattttataa aaaggcattt ttctcttata tccataaaat gatataattt 60
ttgcaantat anaaatgtgt cataaattat aatgttcctt aattacagct caacgcaact 120
tggt 124


<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt 60
tgtggctaca ggtggtgtct gactgcatna aaaanttttt tacgggtgat tgcaaaaatt 120
ttagggcacc catatcccaa gcantgt 147


<210> SEQ ID NO 50
<211> LENGTH: 107
<212> TYPE: DNA
<213> ORGANISM: Homo sapien

<400> SEQUENCE: 50
acattaaatt aataaaagga ctgttggggt tctgctaaaa cacatggctt gatatattgc 60
atggtttgag gttaggagga gttaggcata tgttttggga gaggggt 107


<210> SEQ ID NO 51
<211> LENGTH: 204
<212> TYPE: DNA
<213> ORGANISM: Homo sapien

<400> SEQUENCE: 51
gtcctaggaa gtctagggga cacacgactc tggggtcacg gggccgacac acttgcacgg 60
cgggaaggaa aggcagagaa gtgacaccgt caggggggaaa tgacagaaag gaaaatcaag 120
gccttgcaag gtcagaaagg ggactcaggg cttccaccac agccctgccc cacttggcca 180
cctccctttt gggaccagca atgt 204


<210> SEQ ID NO 52

<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52

```
acaaagataa catttatctt ataacaaaaa tttgatagtt ttaaaggtta gtattgtgta      60
gggtattttc caaaagacta agagataac tcaggtaaaa agttagaaat gtataaaaca     120
ccatcagaca ggttttttaaa aaacaacata ttacaaaatt agacaatcat ccttaaaaaa    180
aaaacttctt gtatcaattt cttttgttca aaatgactga cttaantatt tttaaatatt   240
tcanaaacac ttcctcaaaa attttcaana tggtagcttt canatgtncc ctcagtccca    300
atgttgctca gataaataaa tctcgtgaga acttaccacc caccacaagc tttctggggc    360
atgcaacagt gtcttttctt tncttttcct tttttttttt ttacaggcac agaaactcat   420
caattttatt tggataacaa agggtctcca aattatattg aaaaataaat ccaagttaat    480
atcactcttg t                                                          491
```

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53

```
acataattta gcagggctaa ttaccataag atgctattta ttaanaggtn tatgatctga      60
gtattaacag ttgctgaagt ttggtatttt tatgcagcat tttcttttg ctttgataac    120
actacagaac ccttaaggac actgaaaatt agtaagtaaa gttcagaaac attagctgct   180
caatcaaatc tctacataac actatagtaa ttaaaacgtt aaaaaaaagt gttgaaatct    240
gcactagtat anaccgctcc tgtcaggata anactgctt ggaacagaaa gggaaaaanc    300
agctttgant ttcttttgtgc tgatangagg aaaggctgaa ttaccttgtt gcctctccct    360
aatgattggc aggtcnggta aatnccaaaa catattccaa ctcaacactt cttttccncg    420
tancttgant ctgtgtattc caggancagg cggatggaat gggccagccc ncggatgttc    480
cant                                                                  484
```

<210> SEQ ID NO 54
<211> LENGTH: 151
<212> TYPE: DNA
<213> ORGANISM: Homo sapien

<400> SEQUENCE: 54

```
actaaacctc gtgcttgtga actccataca gaaaacggtg ccatccctga acacggctgg     60
ccactgggta tactgctgac aaccgcaaca acaaaaacac aaatccttgg cactggctag    120
tctatgtcct ctcaagtgcc ttttttgttg t                                   151
```

<210> SEQ ID NO 55
<211> LENGTH: 91
<212> TYPE: DNA
<213> ORGANISM: Homo sapien

<400> SEQUENCE: 55

```
acctggcttg tctccgggtg gttcccggcg cccccccacgg tccccagaac ggacactttc    60
gccctccagt ggatactcga gccaaagtgg t                                   91
```

<210> SEQ ID NO 56
<211> LENGTH: 133
<212> TYPE: DNA
<213> ORGANISM: Homo sapien

<400> SEQUENCE: 56

```
ggcggatgtg cgttggttat atacaaatat gtcattttat gtaagggact tgagtatact    60
tggatttttg gtatctgtgg gttgggggga cggtccagga accaataccc catggatacc   120
aagggacaac tgt                                                     133
```

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57

```
actctggaga acctgagccg ctgctccgcc tctgggatga ggtgatgcan gcngtggcgc    60
gactgggagc tgagcccttc cctttgcgcc tgcctcagag gattgttgcc gacntgcana   120
tctcantggg ctggatncat gcagggt                                      147
```

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58

```
acagggatat aggtttnaag ttattgtnat tgtaaaatac attgaatttt ctgtatactc    60
tgattacata catttatcct ttaaaaaaga tgtaaatctt aatttttatg ccatctatta   120
atttaccaat gagttacctt gtaaatgaga agtcatgata gcactgaatt ttaactagtt   180
ttgacttcta agtttggt                                                198
```

<210> SEQ ID NO 59
<211> LENGTH: 330
<212> TYPE: DNA
<213> ORGANISM: Homo sapien

<400> SEQUENCE: 59

```
acaacaaatg ggttgtgagg aagtcttatc agcaaaactg gtgatggcta ctgaaaagat    60
ccattgaaaa ttatcattaa tgattttaaa tgacaagtta tcaaaaactc actcaatttt   120
cacctgtgct agcttgctaa aatgggagtt aactctagag caaatatagt atcttctgaa   180
tacagtcaat aaaatgacaaa gccagggcct acaggtggtt tccagacttt ccagacccag   240
cagaaggaat ctattttatc acatggatct ccgtctgtgc tcaaaatacc taatgatatt   300 tttcgtctttt attggacttc tttgaagagt                                  330
```

<210> SEQ ID NO 60

```
<211> LENGTH: 175
<212> TYPE: DNA
<213> ORGANISM: Homo sapien

<400> SEQUENCE: 60
accgtgggtg ccttctacat tcctgacggc tccttcacca acatctggtt ctacttcggc      60
gtcgtgggct ccttcctctt catcctcatc cagctggtgc tgctcatcga ctttgcgcac     120
tcctggaacc agcggtggct gggcaaggcc gaggagtgcg attcccgtgc ctggt          175

<210> SEQ ID NO 61
<211> LENGTH: 154
<212> TYPE: DNA
<213> ORGANISM: Homo sapien

<400> SEQUENCE: 61
accccacttt tcctcctgtg agcagtctgg acttctcact gctacatgat gagggtgagt      60
ggttgttgct cttcaacagt atcctcccct ttccggatct gctgagccgg acagcagtgc     120
tggactgcac agccccgggg ctccacattg ctgt                                 154

<210> SEQ ID NO 62
<211> LENGTH: 30
<212> TYPE: DNA
<213> ORGANISM: Homo sapien

<400> SEQUENCE: 62
cgctcgagcc ctatagtgag tcgtattaga                                       30

<210> SEQ ID NO 63
<211> LENGTH: 89
<212> TYPE: DNA
<213> ORGANISM: Homo sapien

<400> SEQUENCE: 63
acaagtcatt tcagcaccct ttgctcttca aaactgacca tcttttatat ttaatgcttc      60
ctgtatgaat aaaaatggtt atgtcaagt                                        89

<210> SEQ ID NO 64
<211> LENGTH: 97
<212> TYPE: DNA
<213> ORGANISM: Homo sapien

<400> SEQUENCE: 64
accggagtaa ctgagtcggg acgctgaatc tgaatccacc aataaataaa ggttctgcag      60
aatcagtgca tccaggattg gtccttggat ctggggt                               97

<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 65
acaacaanaa ntcccttctt taggccactg atggaaacct ggaaccccct tttgatggca      60
gcatggcgtc ctaggccttg acacagcggc tggggtttgg gctntcccaa accgcacacc     120
ccaaccctgg tctacccaca nttctggcta tgggctgtct ctgccactga acatcagggt     180
tcggtcataa natgaaatcc caaggggac agaggtcagt agaggaagct caatgagaaa      240
```

```
ggtgctgttt gctcagccag aaaacagctg cctggcattc gccgctgaac tatgaacccg      300
tgggggtgaa ctaccccan gaggaatcat gcctgggcga tgcaaggtg ccaacaggag        360 gggcgggagg agcatgt                                                     377
```

<210> SEQ ID NO 66
<211> LENGTH: 305
<212> TYPE: DNA
<213> ORGANISM: Homo sapien

<400> SEQUENCE: 66

```
acgcctttcc ctcagaattc agggaagaga ctgtcgcctg ccttcctccg ttgttgcgtg       60
agaacccgtg tgcccttcc caccatatcc accctcgctc catctttgaa ctcaaacacg      120
aggaactaac tgcaccctgg tcctctcccc agtccccagt tcaccctcca tccctcacct     180
tcctccactc taagggatat caacactgcc agcacaggg gccctgaatt tatgtggttt      240
ttatatattt tttaataaga tgcactttat gtcatttttt aataaagtct gaagaattac     300
tgttt                                                                 305
```

<210> SEQ ID NO 67
<211> LENGTH: 385
<212> TYPE: DNA
<213> ORGANISM: Homo sapien

<400> SEQUENCE: 67

```
actacacaca ctccacttgc ccttgtgaga cactttgtcc cagcacttta ggaatgctga       60
ggtcggacca gccacatctc atgtgcaaga ttgcccagca gacatcaggt ctgagagttc     120 ccctttttaaa aaggggact tgcttaaaaa agaagtctag ccacgattgt gtagagcagc    180
tgtgctgtgc tggagattca cttttgagag agttctcctc tgagacctga tctttagagg     240
ctgggcagtc ttgcacatga gatggggctg gtctgatctc agcactcctt agtctgcttg     300
cctctcccag ggccccagcc tggccacacc tgcttacagg gcactctcag atgcccatac     360
catagtttct gtgctagtgg accgt                                           385
```

<210> SEQ ID NO 68
<211> LENGTH: 73
<212> TYPE: DNA
<213> ORGANISM: Homo sapien

<400> SEQUENCE: 68

```
acttaaccag atatatttt accccagatg gggatattct ttgtaaaaaa tgaaaataaa        60
gtttttttaa tgg                                                         73
```

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69

```
actagtccag tgtggtggaa ttccattgtg ttggggctc tcaccctcct ctcctgcagc       60
tccagctttg tgctctgcct ctgaggagac catggcccag catctgagta ccctgctgct     120
cctgctggcc accctagctg tggccctggc ctggagcccc aaggaggagg ataggataat     180
```

```
cccgggtggc atctataacg cagacctcaa tgatgagtgg gtacagcgtg cccttcactt    240
cgccatcagc gagtataaca aggccaccaa agatgactac tacagacgtc cgctgcgggt    300
actaagagcc aggcaacaga ccgttggggg ggtgaattac ttcttcgacg tagaggtggg    360
ccgaaccata tgtaccaagt cccagcccaa cttggacacc tgtgccttcc atgaacagcc    420
agaactgcag aagaaacagt tgtgctcttt cgagatctac gaagttccct ggggagaaca    480
gaangtccct gggtgaaatc caggtgtcaa gaaatcctan ggatctgttg ccaggc        536
```

<210> SEQ ID NO 70
<211> LENGTH: 477
<212> TYPE: DNA
<213> ORGANISM: Homo sapien

<400> SEQUENCE: 70

```
atgacccta acaggggccc tctcagccct cctaatgacc tccggcctag ccatgtgatt    60
tcacttccac tccataacgc tcctcatact aggcctacta accaacacac taaccatata    120
ccaatgatgg cgcgatgtaa cacgagaaag cataccaa ggccaccaca cacccctgt      180 ccaaaaaggc cttcgatacg ggataatcct atttattacc tcagaagttt ttttcttcgc    240
agggattttt ctgagccttt taccactcca gcctagcccc tacccccaa ctaggagggc     300 actgcccc aacaggcatc accccgctaa atcccctaga agtcccactc ctaaacacat      360
ccgtattact cgcatcagga gtatcaatca cctgagctca ccatagtcta atagaaaaca    420
accgaaacca aattattcaa agcactgctt attacaattt tactgggtct ctatttt       477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

```
agagctatag gtacagtgtg atctcagctt tgcaaacaca ttttctacat agatagtact    60
aggtattaat agatatgtaa agaaagaaat cacaccatta ataatggtaa gattggttta    120
tgtgatttta gtggtatttt tggcacccct atatatgttt tccaaacttt cagcagtgat    180
attatttcca taacttaaaa agtgagtttg aaaaagaaaa tctccagcaa gcatctcatt    240
taaataaagg tttgtcatct ttaaaaatac agcaatatgt gacttttaa aaaagctgtc     300 aaataggtgt gaccctacta ataattatta gaaatacatt taaaaacatc gagtacctca    360
agtcagtttg ccttgaaaaa tatcaaatat aactcttaga gaaatgtaca taaaagaatg    420
cttcgtaatt ttggagtang aggttccctc ctcaatttg tattttaaa aagtacatgg      480 taaaaaaaaa aattcacaac agtatataag gctgtaaaat gaagaattct gcc            533
```

<210> SEQ ID NO 72
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 72

```
tattacggaa aaacacacca cataattcaa ctancaaaga anactgcttc agggcgtgta    60
```

```
aaatgaaagg cttccaggca gttatctgat taaagaacac taaaagaggg acaaggctaa    120
aagccgcagg atgtctacac tatancaggc gctatttggg ttggctggag gagctgtgga    180
aaacatggan agattggtgc tgganatcgc cgtggctatt cctcattgtt attacanagt    240
gaggttctct gtgtgcccac tggtttgaaa accgttctnc aataatgata gaatagtaca    300
cacatgagaa ctgaaatggc ccaaacccag aaagaaagcc caactagatc ctcagaanac    360
gcttctaggg acaataaccg atgaagaaaa gatggcctcc ttgtgccccc gtctgttatg    420
atttctctcc attgcagcna naaacccgtt cttctaagca aacncaggtg atgatggcna    480
aaatacaccc cctcttgaag naccnggagg a                                  511
```

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73

```
cagtgccagc actggtgcca gtaccagtac caataacagt gccagtgcca gtgccagcac     60
cagtggtggc ttcagtgctg gtgccagcct gaccgccact ctcacatttg ggctcttcgc    120
tggccttggt ggagctggtg ccagcaccag tggcagctct ggtgcctgtg gtttctccta    180
caagtgagat tttagatatt gttaatcctg ccagtctttc tcttcaagcc agggtgcatc    240
ctcagaaacc tactcaacac agcactctag gcagccacta tcaatcaatt gaagttgaca    300
ctctgcatta aatctatttg ccatttctga aaaaaaaaaa aaaaaaggg cggccgctcg    360 antctagagg gcccgtttaa acccgctgat cagcctcgac tgtgccttct anttgccagc    420
catctgttgt ttgcccctcc cccgntgcct tccttgaccc tggaaagtgc cactcccact    480
gtcctttcct aantaaaat                                                499
```

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74

```
tttcatagga gaacacactg aggagatact tgaagaattt ggattcagcc gcgaagagat     60
ttatcagctt aactcagata aaatcattga agtaataag gtaaaagcta gtctctaact    120
tccaggccca cggctcaagt gaatttgaat actgcattta cagtgtagag taacacataa    180
cattgtatgc atggaaacat ggaggaacag tattacagtg tcctaccact ctaatcaaga    240
aaagaattac agactctgat tctacagtga tgattgaatt ctaaaatgg taatcattag    300 ggcttttgat ttataanact ttgggtactt atactaaatt atggtagtta tactgccttc    360
cagtttgctt gatatatttg ttgatattaa gattcttgac ttatattttg aatgggttct    420
actgaaaaan gaatgatata ttcttgaaga catcgatata catttattta cactcttgat    480
tctacaatgt agaaaatgaa ggaaatgccc caaattgtat ggtgataaaa gtcccgt       537
```

<210> SEQ ID NO 75

<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

| | | | | | |
|---|---|---|---|---|---|
| caaanacaat | tgttcaaaag | atgcaaatga | tacactactg | ctgcagctca | caaacacctc | 60 |
| tgcatattac | acgtacctcc | tcctgctcct | caagtagtgt | ggtctatttt | gccatcatca | 120 |
| cctgctgtct | gcttagaaga | acggctttct | gctgcaangg | agagaaatca | taacagacgg | 180 |
| tggcacaagg | aggccatctt | ttcctcatcg | gttattgtcc | ctagaagcgt | cttctgagga | 240 |
| tctagttggg | ctttctttct | gggtttgggc | catttcantt | ctcatgtgtg | tactattcta | 300 |
| tcattattgt | ataacggttt | tcaaaccngt | gggcacncag | agaacctcac | tctgtaataa | 360 |
| caatgaggaa | tagccacggt | gatctccagc | accaaatctc | tccatgttnt | tccagagctc | 420 |
| ctccagccaa | cccaaatagc | cgctgctatn | gtgtagaaca | tccctgn | | 467 |

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

| | | | | | |
|---|---|---|---|---|---|
| aagctgacag | cattcgggcc | gagatgtctc | gctccgtggc | cttagctgtg | ctcgcgctac | 60 |
| tctctctttc | tggcctggag | gctatccagc | gtactccaaa | gattcaggtt | tactcacgtc | 120 |
| atccagcaga | gaatggaaag | tcaaatttcc | tgaattgcta | tgtgtctggg | tttcatccat | 180 |
| ccgacattga | agttgactta | ctgaagaatg | gagagagaat | tgaaaaagtg | gagcattcag | 240 |
| acttgtcttt | cagcaaggac | tggtctttct | atctcttgta | ctacactgaa | ttcaccccca | 300 |
| ctgaaaaaga | tgagtatgcc | tgccgtgtga | accatgtgac | tttgtcacag | cccaagatng | 360 |
| ttnagtggga | tcganacatg | taagcagcan | catgggaggt | | | 400 |

<210> SEQ ID NO 77
<211> LENGTH: 248
<212> TYPE: DNA
<213> ORGANISM: Homo sapien

<400> SEQUENCE: 77

| | | | | | |
|---|---|---|---|---|---|
| ctggagtgcc | ttggtgtttc | aagcccctgc | aggaagcaga | atgcaccttc | tgaggcacct | 60 |
| ccagctgccc | cggcggggga | tgcgaggctc | ggagcaccct | tgcccggctg | tgattgctgc | 120 |
| caggcactgt | tcatctcagc | ttttctgtcc | ctttgctccc | ggcaagcgct | tctgctgaaa | 180 |
| gttcatatct | ggagcctgat | gtcttaacga | ataaaggtcc | catgctccac | ccgaaaaaaa | 240 |
| aaaaaaaa | | | | | | 248 |

<210> SEQ ID NO 78
<211> LENGTH: 201
<212> TYPE: DNA
<213> ORGANISM: Homo sapien

<400> SEQUENCE: 78

| | | | | | |
|---|---|---|---|---|---|
| actagtccag | tgtggtggaa | ttccattgtg | ttgggcccaa | cacaatggct | acctttaaca | 60 | tcacccagac cccgccctgc ccgtgcccca cgctgctgct aacgacagta tgatgcttac    120 tctgctactc ggaaactatt tttatgtaat taatgtatgc tttcttgttt ataaatgcct    180 gatttaaaaa aaaaaaaaaa a    201

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79
tccttttgtt aggtttttga gacaaccct a gacctaaact gtgtcacaga cttctgaatg    60
tttaggcagt gctagtaatt tcctcgtaat gattctgtta ttacttt cct attcttt att    120 cctctttctt ctgaagatta atgaagttga aaattgaggt ggataaatac aaaaaggtag    180
tgtgatagta taagtatcta agtgcagatg aaagtgtgtt atatatatcc attcaaaatt    240
atgcaagtta gtaattactc agggttaact aaattacttt aatatgctgt tgaacctact    300
ctgttccttg gctagaaaaa attataaaca ggactttgtt agtttgggaa gccaaattga    360
taatattcta tgttctaaaa gttgggctat acataaanta tnaagaaata tggaatttta    420
ttcccaggaa tatggggttc atttatgaat antacccggg anagaagttt tgantnaaac    480
cngttttggt taatacgtta atatgtcctn aatnaacaag gcntgactta tttccaaaaa    540
aaaaaaaaaa aa    552

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80
acagggattt gagatgctaa ggccccagag atcgtttgat ccaaccctct tattttcaga    60
ggggaaaatg gggcctagaa gttacagagc atctagctgg tgcgctggca cccctggcct    120
cacacagact cccgagtagc tgggactaca ggcacacagt cactgaagca ggccctgttt    180
gcaattcacg ttgccacctc caacttaaac attcttcata tgtgatgtcc ttagtcacta    240
aggtaaaact ttcccaccca gaaaaggcaa cttagataaa atcttagagt actttcatac    300
tcttctaagt cctcttccag cctcactttg agtcctcctt ggggttgat aggaantntc    360 tcttggcttt ctcaataaaa tctctatcca tctcatgttt aatttggtac gcntaaaaat    420
gctgaaaaaa ttaaaatgtt ctggtttcnc tttaaaaaaa aaaaaaaaa aaaaaa    476

<210> SEQ ID NO 81
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 81

```
tttttttttg tatgccntcn ctgtggngtt attgttgctg ccaccctgga ggagcccagt      60
ttcttctgta tctttctttt ctggggatc ttcctggctc tgcccctcca ttcccagcct     120
ctcatcccca tcttgcactt ttgctagggt tggaggcgct ttcctggtag ccctcagag     180 actcagtcag cggaataag tcctaggggt ggggggtgtg gcaagccggc ct             232
```

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82

```
aggcgggagc agaagctaaa gccaaagccc aagaagagtg gcagtgccag cactggtgcc      60
agtaccagta ccaataacat gccagtgcca gtgccagcac cagtggtggc ttcagtgctg     120
gtgccagcct gaccgccact ctcacatttg ggctcttcgc tggccttggt ggagctggtg     180
ccagcaccag tggcagctct ggtgcctgtg gtttctccta caagtgagat tttagatatt     240
gttaatcctg ccagtctttc tcttcaagcc agggtgcatc ctcagaaacc tactcaacac     300
agcactctng gcagccacta tcaatcaatt gaagttgaca ctctgcatta aatctatttg     360
ccatttcaaa aaaaaaaaaa aaa                                             383
```

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83

```
accgaattgg gaccgctggc ttataagcga tcatgtcctc cagtattacc tcaacgagca      60
gggagatcga gtctatacgc tgaagaaatt tgacccgatg ggacaacaga cctgctcagc     120
ccatcctgct cggttctccc cagatgacaa atactctcga caccgaatca ccatcaagaa     180
acgcttcaag gtgctcatga cccagcaacc gcgccctgtc ctctgagggt ccttaaactg     240
atgtcttttc tgccacctgt taccctcgg agactccgta accaaactct tcggactgtg     300
agccctgatg ccttttttgcc agccatactc tttggcntcc agtctctcgt ggcgattgat     360
tatgcttgtg tgaggcaatc atggtggcat caccatnaa gggaacacat ttganttttt     420
tttcncatat tttaaattac naccagaata nttcagaata aatgaattga aaaactctta     480
aaaaaaaaaa aaaa                                                       494
```

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 84

```
gctggtagcc tatggcgtgg ccacggangg gctcctgagg cacgggacag tgacttccca      60
agtatcctgc gccgcgtctt ctaccgtccc tacctgcaga tcttcgggca gattccccag     120
```

```
gaggacatgg acgtggccct catggagcac agcaactgct cgtcggagcc cggcttctgg      180
gcacaccctc ctggggccca ggcgggcacc tgcgtctccc agtatgccaa ctggctggtg      240
gtgctgctcc tcgtcatctt cctgctcgtg gccaacatct gctggtcac ttgctcattg       300 ccatgttcag ttacacattc ggcaaagtac agggcaacag cnatctctac tgggaaggcc      360
agcgttnccg cctcatccgg                                                  380

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85
gagttagctc ctccacaacc ttgatgaggt cgtctgcagt ggcctctcgc ttcataccgc       60
tnccatcgtc atactgtagg tttgccacca cctcctgcat cttggggcgg ctaatatcca      120
ggaaactctc aatcaagtca ccgtcnatna aacctgtggc tggttctgtc ttccgctcgg      180
tgtgaaagga tctccagaag gagtgctcga tcttccccac acttttgatg acttattga      240 gtcgattctg catgtccagc aggaggttgt accagctctc tgacagtgag gtcaccagcc      300
ctatcatgcc nttgaacgtg ccgaagaaca ccgagccttg tgtgggggt gnagtctcac       360 ccagattctg cattaccaga nagccgtggc aaaaganatt gacaactcgc ccaggnngaa     420
aaagaacacc tcctggaagt gctngccgct cctcgtccnt tggtggnngc gcntnccttt     480
t                                                                    481

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86
aacatcttcc tgtataatgc tgtgtaatat cgatccgatn ttgtctgctg agaattcatt       60
acttggaaaa gcaacttnaa gcctggacac tggtattaaa attcacaata tgcaacactt      120
taaacagtgt gtcaatctgc tcccttactt tgtcatcacc agtctgggaa taagggtatg      180
ccctattcac acctgttaaa agggcgctaa gcatttttga ttcaacatct ttttttttga     240
cacaagtccg aaaaaagcaa aagtaaacag ttnttaattt gttagccaat tcactttctt      300
catgggacag agccatttga tttaaaaagc aaattgcata atattgagct ttgggagctg      360
atatntgagc ggaagantag cctttctact tcaccagaca caactccttt catattggga     420
tgttnacnaa agtatgtgtct cttacagatg ggatgctttt gtggcaattc tg            472

<210> SEQ ID NO 87
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G
```

<400> SEQUENCE: 87

```
agaaaccagt atctctnaaa acaacctctc ataccttgtg gacctaattt tgtgtgcgtg      60
tgtgtgtgcg cgcatattat atagacaggc acatcttttt tacttttgta aaagcttatg     120
cctctttggt atctatatct gtgaaagttt taatgatctg ccataatgtc ttggggacct     180
ttgtcttctg tgtaaatggt actagagaaa cacctatnt tatgagtcaa tctagttngt      240
tttattcgac atgaaggaaa tttccagatn acaacactna caaactctcc cttgactagg     300
ggggacaaag aaaagcanaa ctgaacatna gaaacaattn cctggtgaga aattncataa     360
acagaaattg ggtngtatat tgaaananng catcattnaa acgttttttt ttt            413
```

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88

```
cgcagcgggt cctctctatc tagctccagc ctctcgcctg ccccactccc cgcgtcccgc      60
gtcctagccn accatggccg ggcccctgcg cgccccgctg ctcctgctgg ccatcctggc     120
cgtggccctg gccgtgagcc ccgcggccgg ctccagtccc ggcaagccgc cgcgcctggt     180
gggaggccca tggaccccgc gtggaagaag aaggtgtgcg cgtgcactg gactttgccg     240
tcggcnanta caacaaaccc gcaacnactt ttaccnagcn cgcgctgcag gttgtgccgc     300
cccaancaaa ttgttactng gggtaantaa ttcttggaag ttgaacctgg gccaaacnng     360
tttaccagaa ccnagccaat tngaacaatt nccctccat aacagcccct tttaaaaagg     420
gaancantcc tgntctttc caaatttt                                          448
```

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89

```
gaattttgtg cactggccac tgtgatggaa ccattgggcc aggatgcttt gagtttatca      60
gtagtgattc tgccaaagtt ggtgttgtaa catgagtatg taaaatgtca aaaaattagc     120
agaggtctag gtctgcatat cagcagacag tttgtccgtg tattttgtag ccttgaagtt     180
ctcagtgaca agttnnttct gatgcgaagt tctnattcca gtgttttagt cctttgcatc     240
tttnatgttn agacttgcct ctntnaaatt gcttttgtnt tctgcaggta ctatctgtgg     300
tttaacaaaa tagaannact tctctgcttn gaanatttga atatcttaca tctnaaaatn     360
aattctctcc ccatannaaa acccangccc ttgggananat ttgaaaaang gntccttcnn    420
aattcnnana anttcagntn tcatacaaca naacnggananc ccc                      463
```

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

| | | | | |
|---|---|---|---|---|
| agggattgaa | ggtctnttnt | actgtcggac | tgttcancca | ccaactctac | aagttgctgt | 60 |
| cttccactca | ctgtctgtaa | gcntnttaac | ccagactgta | tcttcataaa | tagaacaaat | 120 |
| tcttcaccag | tcacatcttc | taggacctt | tttggattcag | ttagtataag | ctcttccact | 180 |
| tcctttgtta | agacttcatc | tggtaaagtc | ttaagttttg | tagaaaggaa | tttaattgct | 240 |
| cgttctctaa | caatgtcctc | tccttgaagt | atttggctga | acaacccacc | tnaagtccct | 300 |
| ttgtgcatcc | attttaaata | tacttaatag | ggcattggtn | cactaggtta | aattctgcaa | 360 |
| gagtcatctg | tctgcaaaag | ttgcgttagt | atatctgcca | | | 400 |

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

| | | | | | | |
|---|---|---|---|---|---|---|
| gagctcggat | ccaataatct | ttgtctgagg | gcagcacaca | tatncagtgc | catggnaact | 60 |
| ggtctacccc | acatgggagc | agcatgccgt | agntatataa | ggtcattccc | tgagtcagac | 120 |
| atgcctcttt | gactaccgtg | tgccagtgct | ggtgattctc | acacacctcc | nnccgctctt | 180 |
| tgtggaaaaa | ctggcacttg | nctggaacta | gcaagacatc | acttacaaat | tcacccacga | 240 |
| gacacttgaa | aggtgtaaca | aagcgactct | tgcattgctt | tttgtccctc | cggcaccagt | 300 |
| tgtcaatact | aacccgctgg | tttgcctcca | tcacatttgt | gatctgtagc | tctggataca | 360 |
| tctcctgaca | gtactgaaga | acttcttctt | ttgtttcaaa | agcaactctt | ggtgcctgtt | 420 |
| ngatcaggtt | cccatttccc | agtccgaatg | ttcacatggc | atatnttact | tcccacaaaa | 480 |

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

| | | | | | | |
|---|---|---|---|---|---|---|
| atacagccca | natcccacca | cgaagatgcg | cttgttgact | gagaacctga | tgcggtcact | 60 |
| ggtcccgctg | tagccccagc | gactctccac | ctgctggaag | cggttgatgc | tgcactcctt | 120 |
| cccacgcagg | cagcagcggg | gccggtcaat | gaactccact | cgtggcttgg | ggttgacggt | 180 |
| taantgcagg | aagaggctga | ccacctcgcg | gtccaccagg | atgcccgact | gtgcgggacc | 240 |
| tgcagcgaaa | ctcctcgatg | gtcatgagcg | ggaagcgaat | gangcccagg | gccttgccca | 300 |
| gaaccttccg | cctgttctct | ggcgtcacct | gcagctgctg | ccgctnacac | tcggcctcgg | 360 |
| accagcggac | aaacggcgtt | gaacagccgc | acctcacgga | tgcccantgt | gtcgcgctcc | 420 |
| aggaacggcn | ccagcgtgtc | caggtcaatg | tcggtgaanc | ctccgcgggt | aatggcg | 477 |

<210> SEQ ID NO 93
<211> LENGTH: 377
<212> TYPE: DNA

<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93

| | | | | | |
|---|---|---|---|---|---|
| gaacggctgg | accttgcctc | gcattgtgct | gctggcagga | ataccttggc | aagcagctcc | 60 |
| agtccgagca | gccccagacc | gctgccgccc | gaagctaagc | ctgcctctgg | ccttcccctc | 120 |
| cgcctcaatg | cagaaccant | agtgggagca | ctgtgtttag | agttaagagt | gaacactgtn | 180 |
| tgattttact | tgggaatttc | ctctgttata | tagcttttcc | caatgctaat | ttccaaacaa | 240 |
| caacaacaaa | ataacatgtt | tgcctgttna | gttgtataaa | agtangtgat | tctgtatnta | 300 |
| aagaaaatat | tactgttaca | tatactgctt | gcaanttctg | tatttattgg | tnctctggaa | 360 |
| ataaatatat | tattaaa | | | | | 377 |

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94

| | | | | | |
|---|---|---|---|---|---|
| ccctttgagg | ggttagggtc | cagttcccag | tggaagaaac | aggccaggag | aantgcgtgc | 60 |
| cgagctgang | cagatttccc | acagtgaccc | cagagccctg | ggctatagtc | tctgaccect | 120 |
| ccaaggaaag | accaccttct | ggggacatgg | gctggagggc | aggacctaga | ggcaccaagg | 180 |
| gaaggcccca | ttccggggct | gttccccgag | gaggaaggga | aggggctctg | tgtgccccc | 240 |
| acgaggaana | ggccctgant | cctgggatca | nacaccectt | cacgtgtatc | cccacacaaa | 300 |
| tgcaagctca | ccaaggtccc | ctctcagtcc | cttccctaca | ccctgaacgg | ncactggccc | 360 |
| acacccaccc | agancancca | cccgccatgg | ggaatgtnct | caaggaatcg | cngggcaacg | 420 |
| tggactctng | tcccnnaagg | gggcagaatc | tccaatagan | ggannngaacc | cttgctnana | 480 |
| aaaaaaaana | aaaaa | | | | | 495 |

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95

| | | | | | |
|---|---|---|---|---|---|
| ggttacttgg | tttcattgcc | accacttagt | ggatgtcatt | tagaaccatt | ttgtctgctc | 60 |
| cctctggaag | ccttgcgcag | agcggacttt | gtaattgttg | gagaataact | gctgaattt | 120 |
| tagctgtttt | gagttgattc | gcaccactgc | accacaactc | aatatgaaaa | ctatttnact | 180 |
| tatttattat | cttgtgaaaa | gtatacaatg | aaaattttgt | tcatactgta | tttatcaagt | 240 |
| atgatgaaaa | gcaatagata | tatattcttt | tattatgttn | aattatgatt | gccattatta | 300 |
| atcggcaaaa | tgtggagtgt | atgttctttt | cacagtaata | tatgcctttt | gtaacttcac | 360 |
| ttggttattt | tattgtaaat | gaattacaaa | attcttaatt | taagaaaatg | gtangttata | 420 |
| tttanttcan | taatttcttt | ccttgtttac | gttaattttg | aaaagaatgc | at | 472 |

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

| | | | | | |
|---|---|---|---|---|---|
| ctgaagcatt | tcttcaaact | tntctacttt | tgtcattgat | acctgtagta | agttgacaat | 60 |
| gtggtgaaat | ttcaaaatta | tatgtaactt | ctactagttt | tactttctcc | cccaagtctt | 120 |
| ttttaactca | tgatttttac | acacacaatc | cagaacttat | tatatagcct | ctaagtcttt | 180 |
| attcttcaca | gtagatgatg | aaagagtcct | ccagtgtctt | gngcanaatg | ttctagntat | 240 |
| agctggatac | atacngtggg | agttctataa | actcatacct | cagtgggact | naaccaaaat | 300 |
| tgtgttagtc | tcaattccta | ccacactgag | ggagcctccc | aaatcactat | attcttatct | 360 |
| gcaggtactc | ctccagaaaa | acngacaggg | caggcttgca | tgaaaaagtn | acatctgcgt | 420 |
| tacaaagtct | atcttcctca | nangtctgtn | aaggaacaat | ttaatcttct | agcttt | 476 |

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

| | | | | | |
|---|---|---|---|---|---|
| actctttcta | atgctgatat | gatcttgagt | ataagaatgc | atatgtcact | agaatggata | 60 |
| aaataatgct | gcaaacttaa | tgttcttatg | caaaatggaa | cgctaatgaa | acacagctta | 120 |
| caatcgcaaa | tcaaaactca | caagtgctca | tctgttgtag | atttagtgta | ataagactta | 180 |
| gattgtgctc | cttcggatat | gattgtttct | canatcttgg | gcaatnttcc | ttagtcaaat | 240 |
| caggctacta | gaattctgtt | attggatatn | tgagagcatg | aaattttttaa | naatacactt | 300 |
| gtgattatna | aattaatcac | aaatttcact | tatacctgct | atcagcagct | agaaaaacat | 360 |
| ntnnttttta | natcaaagta | ttttgtgttt | ggaantgtnn | aaatgaaatc | tgaatgtggg | 420 |
| ttcnatctta | ttttttcccn | gacnactant | tncttttta | gggnctattc | tganccatc | 479 |

<210> SEQ ID NO 98
<211> LENGTH: 461
<212> TYPE: DNA
<213> ORGANISM: Homo sapien

<400> SEQUENCE: 98

| | | | | | |
|---|---|---|---|---|---|
| agtgacttgt | cctccaacaa | aaccccttga | tcaagtttgt | ggcactgaca | atcagaccta | 60 |
| tgctagttcc | tgtcatctat | tcgctactaa | atgcagactg | gaggggacca | aaaaggggca | 120 |
| tcaactccag | ctggattatt | ttggagcctg | caaatctatt | cctacttgta | cggactttga | 180 |
| agtgattcag | tttcctctac | ggatgagaga | ctggctcaag | aatatcctca | tgcagcttta | 240 |
| tgaagccact | ctgaacacgc | tggttatcta | gatgagaaca | gagaaataaa | gtcagaaaat | 300 |
| ttacctggag | aaaagaggct | ttggctgggg | accatcccat | tgaaccttct | cttaaggact | 360 |
| ttaagaaaaa | ctaccacatg | ttgtgtatcc | tggtgccggc | cgtttatgaa | ctgaccaccc | 420 |

-continued

```
tttggaataa tcttgacgct cctgaacttg ctcctctgcg a                461
```

<210> SEQ ID NO 99
<211> LENGTH: 171
<212> TYPE: DNA
<213> ORGANISM: Homo sapien

<400> SEQUENCE: 99

```
gtggccgcgc gcaggtgttt cctcgtaccg cagggccccc tcccttcccc aggcgtccct    60
cggcgcctct gcgggcccga ggaggagcgg ctggcgggtg gggggagtgt gacccaccct   120
cggtgagaaa agccttctct agcgatctga gaggcgtgcc ttgggggtac c            171
```

<210> SEQ ID NO 100
<211> LENGTH: 269
<212> TYPE: DNA
<213> ORGANISM: Homo sapien

<400> SEQUENCE: 100

```
cggccgcaag tgcaactcca gctgggggccg tgcggacgaa gattctgcca gcagttggtc    60
cgactgcgac gacggcggcg gcgacagtcg caggtgcagc gcggcgcct gggtcttgc    120
aaggctgagc tgacgccgca gaggtcgtgt cacgtccac gaccttgacg ccgtcgggga   180
cagccggaac agagcccggt gaagcgggag gcctcgggga gccctcggg aagggcggcc   240
cgagagatac gcaggtgcag gtggccgcc                                     269
```

<210> SEQ ID NO 101
<211> LENGTH: 405
<212> TYPE: DNA
<213> ORGANISM: Homo sapien

<400> SEQUENCE: 101

```
tttttttttt ttttggaatc tactgcgagc acagcaggtc agcaacaagt ttattttgca    60
gctagcaagg taacagggta gggcatggtt acatgttcag gtcaacttcc tttgtcgtgg   120
ttgattggtt tgtcttatg ggggcggggt gggtagggg aaacgaagca ataacatgg    180
agtgggtgca ccctccctgt agaacctggt tacaaagctt ggggcagttc acctggtctg   240
tgaccgtcat tttcttgaca tcaatgttat tagaagtcag gatatctttt agagagtcca   300
ctgttctgga gggagattag ggtttcttgc caaatccaac aaaatccact gaaaaagttg   360
gatgatcagt acgaataccg aggcatattc tcatatcggt ggcca                  405
```

<210> SEQ ID NO 102
<211> LENGTH: 470
<212> TYPE: DNA
<213> ORGANISM: Homo sapien

<400> SEQUENCE: 102

```
tttttttttt tttttttttt tttttttttt tttttttttt tttttttttt tttttttttt    60
ggcacttaat ccatttttat ttcaaaatgt ctacaaattt aatcccatta tacggtattt   120
tcaaaatcta aattattcaa attagccaaa tccttaccaa ataatcccca aaaatcaaaa   180
atatacttct ttcagcaaac ttgttacata aattaaaaaa atatatacgg ctggtgtttt   240
caaagtacaa ttatcttaac actgcaaaca ttttaaggaa ctaaaataaa aaaaaacact   300
ccgcaaaggt taagggaac aacaaattct tttacaacac cattataaaa atcatatctc   360
aaatcttagg ggaatatata cttcacacgg gatcttaact tttactcact ttgtttattt   420
ttttaaacca ttgtttgggc ccaacacaat ggaatccccc ctggactagt              470
```

<210> SEQ ID NO 103
<211> LENGTH: 581
<212> TYPE: DNA
<213> ORGANISM: Homo sapien

<400> SEQUENCE: 103

| | | | | | |
|---|---|---|---|---|---|
| tttttttttt | ttttttttga | ccccctctt | ataaaaaaca | agttaccatt | ttatttact | 60 |
| tacacatatt | tattttataa | ttggtattag | atattcaaaa | ggcagctttt | aaaatcaaac | 120 |
| taaatggaaa | ctgccttaga | tacataattc | ttaggaatta | gcttaaaatc | tgcctaaagt | 180 |
| gaaaatcttc | tctagctctt | ttgactgtaa | atttttgact | cttgtaaaac | atccaaattc | 240 |
| attttcttg | tctttaaaat | tatctaatct | ttccatttt | tccctattcc | aagtcaattt | 300 |
| gcttctctag | cctcatttcc | tagctcttat | ctactattag | taagtggctt | ttttcctaaa | 360 |
| agggaaaaca | ggaagagaaa | tggcacacaa | aacaaacatt | ttatattcat | atttctacct | 420 |
| acgttaataa | aatagcattt | tgtgaagcca | gctcaaaaga | aggcttagat | ccttttatgt | 480 |
| ccattttagt | cactaaacga | tatcaaagtg | ccagaatgca | aaaggtttgt | gaacatttat | 540 |
| tcaaaagcta | atataagata | tttcacatac | tcatctttct | g | | 581 |

<210> SEQ ID NO 104
<211> LENGTH: 578
<212> TYPE: DNA
<213> ORGANISM: Homo sapien

<400> SEQUENCE: 104

| | | | | | |
|---|---|---|---|---|---|
| tttttttttt | ttttttttt | tttttctctt | cttttttttt | gaaatgagga | tcgagttttt | 60 |
| cactctctag | atagggcatg | aagaaaactc | atctttccag | ctttaaaata | acaatcaaat | 120 |
| ctcttatgct | atatcatatt | ttaagttaaa | ctaatgagtc | actggcttat | cttctcctga | 180 |
| aggaaatctg | ttcattcttc | tcattcatat | agttatatca | agtactacct | tgcatattga | 240 |
| gaggttttc | ttctctattt | acacatatat | ttccatgtga | atttgtatca | aacctttatt | 300 |
| ttcatgcaaa | ctagaaaata | atgtttcttt | tgcataagag | aagagaacaa | tatagcatta | 360 |
| caaaactgct | caaattgttt | gttaagttat | ccattataat | tagttggcag | gagctaatac | 420 |
| aaatcacatt | tacgacagca | ataataaaac | tgaagtacca | gttaaatatc | caaataatt | 480 |
| aaaggaacat | tttagcctg | ggtataatta | gctaattcac | tttacaagca | tttattagaa | 540 |
| tgaattcaca | tgttattatt | cctagcccaa | cacaatgg | | | 578 |

<210> SEQ ID NO 105
<211> LENGTH: 538
<212> TYPE: DNA
<213> ORGANISM: Homo sapien

<400> SEQUENCE: 105

| | | | | | |
|---|---|---|---|---|---|
| tttttttttt | tttttcagta | ataatcagaa | caatatttat | ttttatattt | aaaattcata | 60 |
| gaaaagtgcc | ttcatttaa | taaagtttg | tttctcaaag | tgatcagagg | aattagatat | 120 |
| gtcttgaaca | ccaatattaa | tttgaggaaa | atacaccaaa | atacattaag | taaattattt | 180 |
| aagatcatag | agcttgtaag | tgaaaagata | aaatttgacc | tcagaaactc | tgagcattaa | 240 |
| aaatccacta | ttagcaaata | aattactatg | gacttcttgc | tttaattttg | tgatgaatat | 300 |
| ggggtgtcac | tggtaaacca | acacattctg | aaggatacat | tacttagtga | tagattctta | 360 |
| tgtactttgc | taatacgtgg | atatgagttg | acaagtttct | cttcttcaa | tcttttaagg | 420 |

```
ggcgagaaat gaggaagaaa agaaaaggat tacgcatact gttctttcta tggaaggatt    480
agatatgttt cctttgccaa tattaaaaaa ataataatgt ttactactag tgaaaccc      538

<210> SEQ ID NO 106
<211> LENGTH: 473
<212> TYPE: DNA
<213> ORGANISM: Homo sapien

<400> SEQUENCE: 106
tttttttttt tttttagtc aagtttctat ttttattata attaaagtct tggtcatttc      60
atttattagc tctgcaactt acatatttaa attaaagaaa cgttttagac aactgtacaa     120
tttataaatg taaggtgcca ttattgagta atatattcct ccaagagtgg atgtgtccct    180
tctcccacca actaatgaac agcaacatta gtttaatttt attagtagat atacactgct    240
gcaaacgcta attctcttct ccatccccat gtgatattgt gtatatgtgt gagttggtag    300
aatgcatcac aatctacaat caacagcaag atgaagctag gctgggcttt cggtgaaaat    360
agactgtgtc tgtctgaatc aaatgatctg acctatcctc ggtggcaaga actcttcgaa    420
ccgcttcctc aaaggcgctg ccacatttgt ggctctttgc acttgtttca aaa           473

<210> SEQ ID NO 107
<211> LENGTH: 1621
<212> TYPE: DNA
<213> ORGANISM: Homo sapien

<400> SEQUENCE: 107
cgccatggca ctgcagggca tctcggtcat ggagctgtcc ggcctggccc cgggcccgtt     60
ctgtgctatg gtcctggctg actcggggc gcgtgtggta cgcgtggacc ggcccggctc    120
ccgctacgac gtgagccgct gggccggggg caagcgctcg ctagtgctgg acctgaagca    180
gccgcgggga gccgccgtgc tgcggcgtct gtgcaagcgg tcggatgtgc tgctggagcc    240
cttccgccgc ggtgtcatgg agaaactcca gctgggccca gagattctgc agcgggaaaa    300
tccaaggctt atttatgcca ggctgagtgg atttggccag tcaggaagct tctgccggtt    360
agctggccac gatatcaact atttggcttt gtcaggtgtt ctctcaaaaa ttggcagaag    420
tggtgagaat ccgtatgccc cgctgaatct cctggctgac tttgctggtg gtggccttat    480
gtgtgcactg ggcattataa tggctctttt tgaccgcaca cgcactgaca agggtcaggt    540
cattgatgca aatatggtgg aaggaacagc atatttaagt tcttttctgt ggaaaactca    600
gaaatcgagt ctgtgggaag cacctcgagg acagaacatg ttggatggtg gagcaccttt    660
ctatacgact tacaggacag cagatgggga attcatggct gttggagcaa tagaaccca    720 gttctacgag ctgctgatca aggacttgg actaaagtct gatgaacttc ccaatcagat    780
gagcatggat gattggccag aaatgaagaa gaagtttgca gatgtatttg caaagaagac    840
gaaggcagag tggtgtcaaa tctttgacgg cacagatgcc tgtgtgactc cggttctgac    900
ttttgaggag gttgttcatc atgatcacaa caaggaacgg ggctcgttta tcaccagtga    960
ggagcaggac gtgagccccc gcctgcacc tctgctgtta aacacccag ccatcccttc    1020 tttcaaaagg gatcctttca taggagaaca cactgaggag atacttgaag aatttggatt    1080
cagccgcgaa gagatttatc agcttaactc agataaaatc attgaaagta ataaggtaaa    1140
agctagtctc taacttccag gcccacggct caagtgaatt tgaatactgc atttacagtg    1200
tagagtaaca cataacattg tatgcatgga aacatggagg aacagtatta cagtgtccta    1260
ccactctaat caagaaaaga attacagact ctgattctac agtgatgatt gaattctaaa    1320
```

-continued

```
aatggttatc attagggctt ttgatttata aaactttggg tacttatact aaattatggt    1380
agttattctg ccttccagtt tgcttgatat atttgttgat attaagattc ttgacttata    1440
ttttgaatgg gttctagtga aaaggaatg atatattctt gaagacatcg atatacattt     1500
atttacactc ttgattctac aatgtagaaa atgaggaaat gccacaaatt gtatggtgat    1560
aaaagtcacg tgaaacaaaa aaaaaaaaaa aaaaaaaaaa aaaaaaaaaa aaaaaaaaa     1620 a                                                                    1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
  1               5                  10                  15

Gly Pro Phe Cys Ala Met Val Leu Ala Asp Phe Gly Ala Arg Val Val
                 20                  25                  30

Arg Val Asp Arg Pro Gly Ser Arg Tyr Asp Val Ser Arg Leu Gly Arg
             35                  40                  45

Gly Lys Arg Ser Leu Val Leu Asp Leu Lys Gln Pro Arg Gly Ala Ala
         50                  55                  60

Val Leu Arg Arg Leu Cys Lys Arg Ser Asp Val Leu Leu Glu Pro Phe
 65                  70                  75                  80

Arg Arg Gly Val Met Glu Lys Leu Gln Leu Gly Pro Glu Ile Leu Gln
                 85                  90                  95

Arg Glu Asn Pro Arg Leu Ile Tyr Ala Arg Leu Ser Gly Phe Gly Gln
                100                 105                 110

Ser Gly Ser Phe Cys Arg Leu Ala Gly His Asp Ile Asn Tyr Leu Ala
            115                 120                 125

Leu Ser Gly Val Leu Ser Lys Ile Gly Arg Ser Gly Glu Asn Pro Tyr
        130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270

Asp Val Phe Ala Lys Lys Thr Lys Ala Glu Trp Cys Gln Ile Phe Asp
        275                 280                 285

Gly Thr Asp Ala Cys Val Thr Pro Val Leu Thr Phe Glu Glu Val Val
    290                 295                 300

His His Asp His Asn Lys Glu Arg Gly Ser Phe Ile Thr Ser Glu Glu
```

```
305                 310                 315                 320
Gln Asp Val Ser Pro Arg Pro Ala Pro Leu Leu Asn Thr Pro Ala
                325                 330                 335
Ile Pro Ser Phe Lys Arg Asp Pro Phe Ile Gly Glu His Thr Glu Glu
                340                 345                 350
Ile Leu Glu Glu Phe Gly Phe Ser Arg Glu Glu Ile Tyr Gln Leu Asn
                355                 360                 365
Ser Asp Lys Ile Ile Glu Ser Asn Lys Val Lys Ala Ser Leu
                370                 375                 380

<210> SEQ ID NO 109
<211> LENGTH: 1524
<212> TYPE: DNA
<213> ORGANISM: Homo sapien

<400> SEQUENCE: 109
ggcacgaggc tgcgccaggg cctgagcgga ggcgggggca gcctcgccag cgggggcccc      60
gggcctggcc atgcctcact gagccagcgc ctgcgcctct acctcgccga cagctggaac     120
cagtgcgacc tagtggctct cacctgcttc ctcctgggcg tgggctgccg gctgaccccg     180
ggtttgtacc acctgggccg cactgtcctc tgcatcgact tcatggtttt cacggtgcgg     240
ctgcttcaca tcttcacggt caacaaacag ctggggccca gatcgtcat cgtgagcaag      300 atgatgaagg acgtgttctt cttcctcttc ttcctcggcg tgtggctggt agcctatggc     360
gtggccacgg aggggctcct gaggccacgg gacagtgact cccaagtat cctgcgccgc      420 gtcttctacc gtccctacct gcagatcttc gggcagattc cccaggagga catggacgtg     480
gccctcatgg agcacagcaa ctgctcgtcg gagcccggct ctgggcaca ccctcctggg      540 gcccaggcgg gcacctgcgt ctcccagtat gccaactggc tggtggtgct gctcctcgtc     600
atcttcctgc tcgtggccaa catcctgctg gtcaacttgc tcattgccat gttcagttac     660
acattcggca agtacaggg caacagcgat ctctactgga aggcgcagcg ttaccgcctc      720
atccgggaat tccactctcg gcccgcgctg gccccgccct ttatcgtcat ctcccacttg     780
cgcctcctgc tcaggcaatt gtgcaggcga ccccggagcc cccagccgtc ctccccggcc     840
ctcgagcatt tccgggttta ccttctaag gaagccgagc ggaagctgct aacgtgggaa      900
tcggtgcata aggagaactt tctgctggca cgcgctaggg acaagcggga gagcgactcc     960
gagcgtctga gcgcacgtc ccagaaggtg gacttggcac tgaaacagct gggacacatc     1020
cgcgagtacg aacagcgcct gaaagtgctg gagcgggagg tccagcagtg tagccgcgtc    1080
ctggggtggg tggccgaggc cctgagccgc tctgccttgc tgccccagg tgggccgcca    1140 cccctgacc tgcctgggtc caaagactga gccctgctgg cggacttcaa ggagaagccc     1200
ccacagggga ttttgctcct agagtaaggc tcatctgggc ctcggccccc gcacctggtg    1260
gccttgtcct tgaggtgagc cccatgtcca tctgggccac tgtcaggacc acctttggga    1320
gtgtcatcct tacaaaccac agcatgcccg gctcctccca gaaccagtcc cagcctggga    1380
ggatcaaggc ctggatcccg ggccgttatc catctggagg ctgcagggtc cttggggtaa    1440
cagggaccac agacccctca ccactcacag attcctcaca ctggggaaat aaagccattt    1500
cagaggaaaa aaaaaaaaa aaaa                                            1524

<210> SEQ ID NO 110
<211> LENGTH: 3410
<212> TYPE: DNA
<213> ORGANISM: Homo sapien
```

<400> SEQUENCE: 110

```
gggaaccagc ctgcacgcgc tggctccggg tgacagccgc gcgcctcggc caggatctga      60
gtgatgagac gtgtccccac tgaggtgccc cacagcagca ggtgttgagc atgggctgag     120
aagctggacc ggcaccaaag ggctggcaga atgggcgcc tggctgattc ctaggcagtt      180
ggcggcagca aggaggagag gccgcagctt ctggagcaga gccgagacga agcagttctg     240
gagtgcctga acggcccct gagccctacc cgcctggccc actatggtcc agaggctgtg      300
ggtgagccgc ctgctgcggc accggaaagc ccagctcttg ctggtcaacc tgctaacctt     360
tggcctggag gtgtgtttgg ccgcaggcat cacctatgtg ccgcctctgc tgctggaagt     420
gggggtagag gagaagttca tgaccatggt gctgggcatt ggtccagtgc tgggcctggt     480
ctgtgtcccg ctcctaggct cagccagtga ccactggcgt ggacgctatg ccgccgccg      540
gcccttcatc tgggcactgt ccttgggcat cctgctgagc ctctttctca tcccaagggc     600
cggctggcta gcagggctgc tgtgcccgga tcccaggccc ctggagctgg cactgctcat     660
cctgggcgtg gggctgctgg acttctgtgg ccaggtgtgc ttcactccac tggaggccct     720
gctctctgac ctcttccggg acccggacca ctgtcgccag gcctactctg tctatgcctt     780
catgatcagt cttgggggct gcctgggcta cctcctgcct gccattgact gggacaccag     840
tgccctggcc ccctacctgg gcacccagga ggagtgcctc tttggcctgc tcaccctcat     900
cttcctcacc tgcgtagcag ccacactgct ggtggctgag gaggcagcgc tgggccccac     960
cgagccagca gaagggctgt cggcccctc cttgtcgccc cactgctgtc catgccgggc    1020
ccgcttggct ttccggaacc tgggcgccct gcttccccgg ctgcaccagc tgtgctgccg    1080
catgccccgc accctgcgcc ggctcttcgt ggctgagctg tgcagctgga tggcactcat    1140
gaccttcacg ctgttttaca cggatttcgt gggcagggg ctgtaccagg gcgtgcccag    1200
agctgagccg ggcaccgagg cccggagaca ctatgatgaa ggcgttcgga tgggcagcct    1260
ggggctgttc ctgcagtgcg ccatctccct ggtcttctct ctggtcatgg accggctggt    1320
gcagcgattc ggcactcgag cagtctattt ggccagtgtg gcagctttcc ctgtggctgc    1380
cggtgccaca tgcctgtccc acagtgtggc cgtggtgaca gcttcagccg ccctcaccgg    1440
gttcaccttc tcagccctgc agatcctgcc ctacacactg gcctccctct accaccggga    1500
gaagcaggtg ttcctgccca ataccgagg ggacactgga ggtgctagca gtgaggacag    1560
cctgatgacc agcttcctgc caggccctaa gcctggagct cccttcccta atggacacgt    1620
gggtgctgga ggcagtggcc tgctcccacc tccacccgcg ctctgcgggg cctctgcctg    1680
tgatgtctcc gtacgtgtgg tggtgggtga gcccaccgag gccagggtgg ttccgggccg    1740
gggcatctgc ctggacctcg ccatcctgga tagtgccttc ctgctgtccc aggtggcccc    1800
atccctgttt atgggctcca ttgtccagct cagccagtct gtcactgcct atatggtgtc    1860
tgccgcaggc ctgggtctgg tcgccattta ctttgctaca caggtagtat ttgacaagag    1920
cgacttggcc aaatactcag cgtagaaaac ttccagcaca ttggggtgga gggcctgcct    1980
cactgggtcc cagctccccg ctcctgttag ccccatgggg ctgccgggct ggccgccagt    2040
ttctgttgct gccaaagtaa tgtggctctc tgctgccacc ctgtgctgct gaggtgcgta    2100
gctgcacagc tgggggctgg ggcgtccctc tcctctctcc ccagtctcta gggctgcctg    2160
actgaggcc ttccaagggg gtttcagtct ggacttatac agggaggcca gaagggctcc    2220
atgcactgga atgcggggac tctgcaggtg gattacccag gctcagggtt aacagctagc    2280
```

```
ctcctagttg agacacacct agagaagggt ttttgggagc tgaataaact cagtcacctg    2340
gtttcccatc tctaagcccc ttaacctgca gcttcgttta atgtagctct tgcatgggag    2400
tttctaggat gaaacactcc tccatgggat ttgaacatat gacttatttg taggggaaga    2460
gtcctgaggg gcaacacaca agaaccaggt cccctcagcc cacagcactg tcttttttgct   2520 gatccacccc cctcttacct tttatcagga gtgtggcctgt tggtccttct gttgccatca    2580
cagagacaca ggcatttaaa tatttaactt atttatttaa caaagtagaa gggaatccat    2640
tgctagcttt tctgtgttgg tgtctaatat ttgggtaggg tggggatcc caacaatca     2700 ggtcccctga gatagctggt cattgggctg atcattgcca gaatcttctt ctcctggggt    2760
ctggcccccc aaaatgccta acccaggacc ttggaaattc tactcatccc aaatgataat    2820
tccaaatgct gttacccaag gttagggtgt tgaaggaagg tagagggtgg ggcttcaggt    2880
ctcaacggct tccctaacca cccctcttct cttggcccag cctggttccc cccacttcca    2940
ctcccctcta ctctctctag gactgggctg atgaaggcac tgcccaaaat ttcccctacc    3000
cccaactttc ccctacccc aactttcccc accagctcca caaccctgtt tggagctact    3060
gcaggaccag aagcacaaag tgcggtttcc caagcctttg tccatctcag cccccagagt    3120
atatctgtgc ttggggaatc tcacacagaa actcaggagc accccctgcc tgagctaagg    3180
gaggtcttat ctctcagggg gggtttaagt gccgtttgca ataatgtcgt cttatttatt    3240
tagcggggtg aatattttat actgtaagtg agcaatcaga gtataatgtt tatggtgaca    3300
aaattaaagg ctttcttata tgtttaaaaa aaaaaaaaaa aaaaaaaaaa aaaaaaaaaa    3360
aaaaaaaara aaaaaaaaaa aaaaaaaaaa aaaaaataa aaaaaaaaaa               3410
```

<210> SEQ ID NO 111
<211> LENGTH: 1289
<212> TYPE: DNA
<213> ORGANISM: Homo sapien

<400> SEQUENCE: 111

```
agccaggcgt ccctctgcct gcccactcag tggcaacacc cgggagctgt tttgtccttt      60
gtggagcctc agcagttccc tctttcagaa ctcactgcca agagccctga acaggagcca    120
ccatgcagtg cttcagcttc attaagacca tgatgatcct cttcaatttg ctcatctttc    180
tgtgtggtgc agccctgttg gcagtgggca tctgggtgtc aatcgatggg gcatcctttc    240
tgaagatctt cgggccactg tcgtccagtg ccatgcagtt tgtcaacgtg ggctacttcc    300
tcatcgcagc cggcgttgtg gtctttgctc ttggtttcct gggctgctat ggtgctaaga    360
ctgagagcaa gtgtgccctc gtgacgttct tcttcatcct cctcctcatc ttcattgctg    420
aggttgcagc tgctgtggtc gccttggtgt acaccacaat ggctgagcac ttcctgacgt    480
tgctggtagt gcctgccatc aagaaagatt atggttccca ggaagacttc actcaagtgt    540
ggaacaccac catgaaaggg ctcaagtgct gtggcttcac caactatacg gattttgagg    600
actcacccta cttcaaagag aacagtgcct ttccccatt ctgttgcaat gacaacgtca    660
ccaacacagc caatgaaacc tgcaccaagc aaaaggctca cgaccaaaaa gtagagggtt    720
gcttcaatca gcttttgtat gacatccgaa ctaatgcagt caccgtgggt ggtgtggcag    780
ctggaattgg gggcctcgag ctggctgcca tgattgtgtc catgtatctg tactgcaatc    840
tacaataagt ccacttctgc ctctgccact actgctgcca catgggaact gtgaagaggc    900
accctggcaa gcagcagtga ttgggggagg ggacaggatc taacaatgtc acttgggcca    960
gaatggacct gcccttctg ctccagactt ggggctagat agggaccact cctttttagcg   1020
```

```
atgcctgact tccttccat tggtgggtgg atgggtgggg ggcattccag agcctctaag    1080
gtagccagtt ctgttgccca ttcccccagt ctattaaacc cttgatatgc ccctaggcc    1140 tagtggtgat cccagtgctc tactggggga tgagagaaag gcattttata gcctgggcat   1200
aagtgaaatc agcagagcct ctgggtggat gtgtagaagg cacttcaaaa tgcataaacc   1260
tgttacaatg ttaaaaaaaa aaaaaaaaa                                     1289
```

```
<210> SEQ ID NO 112
<211> LENGTH: 315
<212> TYPE: PRT
<213> ORGANISM: Homo sapien

<400> SEQUENCE: 112
```

```
Met Val Phe Thr Val Arg Leu Leu His Ile Phe Thr Val Asn Lys Gln
 1               5                  10                  15

Leu Gly Pro Lys Ile Val Ile Val Ser Lys Met Met Lys Asp Val Phe
                20                  25                  30

Phe Phe Leu Phe Phe Leu Gly Val Trp Leu Val Ala Tyr Gly Val Ala
            35                  40                  45

Thr Glu Gly Leu Leu Arg Pro Arg Asp Ser Asp Phe Pro Ser Ile Leu
 50                  55                  60

Arg Arg Val Phe Tyr Arg Pro Tyr Leu Gln Ile Phe Gly Gln Ile Pro
 65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Pro Ala Leu Glu
        195                 200                 205

His Phe Arg Val Tyr Leu Ser Lys Glu Ala Glu Arg Lys Leu Leu Thr
210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285

Trp Val Ala Glu Ala Leu Ser Arg Ser Ala Leu Leu Pro Pro Gly Gly
    290                 295                 300

Pro Pro Pro Pro Asp Leu Pro Gly Ser Lys Asp
305                 310                 315
```

```
<210> SEQ ID NO 113
<211> LENGTH: 553
<212> TYPE: PRT
<213> ORGANISM: Homo sapien

<400> SEQUENCE: 113
```

| | | | | | | | | | | | | | | |
|---|---|---|---|---|---|---|---|---|---|---|---|---|---|---|
| Met | Val | Gln | Arg | Leu | Trp | Val | Ser | Arg | Leu | Leu | Arg | His | Arg | Lys | Ala |
| 1 | | | | 5 | | | | | 10 | | | | | 15 | |
| Gln | Leu | Leu | Val | Asn | Leu | Leu | Thr | Phe | Gly | Leu | Glu | Val | Cys | Leu | |
| | | | 20 | | | | | 25 | | | | | 30 | | |
| Ala | Ala | Gly | Ile | Thr | Tyr | Val | Pro | Leu | Leu | Glu | Val | Gly | Val | | |
| | | | 35 | | | | 40 | | | | 45 | | | | |
| Glu | Glu | Lys | Phe | Met | Thr | Met | Val | Leu | Gly | Ile | Gly | Pro | Val | Leu | Gly |
| | 50 | | | | | 55 | | | | | 60 | | | | |
| Leu | Val | Cys | Val | Pro | Leu | Leu | Gly | Ser | Ala | Ser | Asp | His | Trp | Arg | Gly |
| 65 | | | | | 70 | | | | | 75 | | | | | 80 |
| Arg | Tyr | Gly | Arg | Arg | Pro | Phe | Ile | Trp | Ala | Leu | Ser | Leu | Gly | Ile | |
| | | | | 85 | | | | | 90 | | | | | 95 | |
| Leu | Leu | Ser | Leu | Phe | Leu | Ile | Pro | Arg | Ala | Gly | Trp | Leu | Ala | Gly | Leu |
| | | | 100 | | | | | 105 | | | | | 110 | | |
| Leu | Cys | Pro | Asp | Pro | Arg | Pro | Leu | Glu | Leu | Ala | Leu | Leu | Ile | Leu | Gly |
| | | | 115 | | | | | 120 | | | | | 125 | | |
| Val | Gly | Leu | Leu | Asp | Phe | Cys | Gly | Gln | Val | Cys | Phe | Thr | Pro | Leu | Glu |
| | 130 | | | | | 135 | | | | | 140 | | | | |
| Ala | Leu | Leu | Ser | Asp | Leu | Phe | Arg | Asp | Pro | Asp | His | Cys | Arg | Gln | Ala |
| 145 | | | | | 150 | | | | | 155 | | | | | 160 |
| Tyr | Ser | Val | Tyr | Ala | Phe | Met | Ile | Ser | Leu | Gly | Gly | Cys | Leu | Gly | Tyr |
| | | | | 165 | | | | | 170 | | | | | 175 | |
| Leu | Leu | Pro | Ala | Ile | Asp | Trp | Asp | Thr | Ser | Ala | Leu | Ala | Pro | Tyr | Leu |
| | | | 180 | | | | | 185 | | | | | 190 | | |
| Gly | Thr | Gln | Glu | Glu | Cys | Leu | Phe | Gly | Leu | Leu | Thr | Leu | Ile | Phe | Leu |
| | | | 195 | | | | | 200 | | | | | 205 | | |
| Thr | Cys | Val | Ala | Ala | Thr | Leu | Leu | Val | Ala | Glu | Ala | Ala | Leu | Gly | |
| | 210 | | | | | 215 | | | | | 220 | | | | |
| Pro | Thr | Glu | Pro | Ala | Glu | Gly | Leu | Ser | Ala | Pro | Ser | Leu | Ser | Pro | His |
| 225 | | | | | 230 | | | | | 235 | | | | | 240 |
| Cys | Cys | Pro | Cys | Arg | Ala | Arg | Leu | Ala | Phe | Arg | Asn | Leu | Gly | Ala | Leu |
| | | | | 245 | | | | | 250 | | | | | 255 | |
| Leu | Pro | Arg | Leu | His | Gln | Leu | Cys | Cys | Arg | Met | Pro | Arg | Thr | Leu | Arg |
| | | | 260 | | | | | 265 | | | | | 270 | | |
| Arg | Leu | Phe | Val | Ala | Glu | Leu | Cys | Ser | Trp | Met | Ala | Leu | Met | Thr | Phe |
| | | | 275 | | | | | 280 | | | | | 285 | | |
| Thr | Leu | Phe | Tyr | Thr | Asp | Phe | Val | Gly | Glu | Gly | Leu | Tyr | Gln | Gly | Val |
| | | | 290 | | | | | 295 | | | | | 300 | | |
| Pro | Arg | Ala | Glu | Pro | Gly | Thr | Glu | Ala | Arg | Arg | His | Tyr | Asp | Glu | Gly |
| 305 | | | | | 310 | | | | | 315 | | | | | 320 |
| Val | Arg | Met | Gly | Ser | Leu | Gly | Leu | Phe | Leu | Gln | Cys | Ala | Ile | Ser | Leu |
| | | | | 325 | | | | | 330 | | | | | 335 | |
| Val | Phe | Ser | Leu | Val | Met | Asp | Arg | Leu | Val | Gln | Arg | Phe | Gly | Thr | Arg |
| | | | 340 | | | | | 345 | | | | | 350 | | |
| Ala | Val | Tyr | Leu | Ala | Ser | Val | Ala | Ala | Phe | Pro | Val | Ala | Ala | Gly | Ala |
| | | | 355 | | | | | 360 | | | | | 365 | | |
| Thr | Cys | Leu | Ser | His | Ser | Val | Ala | Val | Thr | Ala | Ser | Ala | Ala | Leu | |
| | 370 | | | | | 375 | | | | | 380 | | | | |

```
Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
            405                 410                 415

Asp Thr Gly Gly Ala Ser Ser Glu Asp Ser Leu Met Thr Ser Phe Leu
        420                 425                 430

Pro Gly Pro Lys Pro Gly Ala Pro Phe Pro Asn Gly His Val Gly Ala
        435                 440                 445

Gly Gly Ser Gly Leu Leu Pro Pro Pro Ala Leu Cys Gly Ala Ser
    450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
                500                 505                 510

Ile Val Gln Leu Ser Gln Ser Val Thr Ala Tyr Met Val Ser Ala Ala
            515                 520                 525

Gly Leu Gly Leu Val Ala Ile Tyr Phe Ala Thr Gln Val Val Phe Asp
        530                 535                 540

Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
  1               5                  10                  15

Leu Ile Phe Leu Cys Gly Ala Ala Leu Leu Ala Val Gly Ile Trp Val
                20                  25                  30

Ser Ile Asp Gly Ala Ser Phe Leu Lys Ile Phe Gly Pro Leu Ser Ser
            35                  40                  45

Ser Ala Met Gln Phe Val Asn Val Gly Tyr Phe Leu Ile Ala Ala Gly
        50                  55                  60

Val Val Val Phe Ala Leu Gly Phe Leu Gly Cys Tyr Gly Ala Lys Thr
 65                  70                  75                  80

Glu Ser Lys Cys Ala Leu Val Thr Phe Phe Ile Leu Leu Leu Ile
                85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
            115                 120                 125

Asp Tyr Gly Ser Gln Glu Asp Phe Thr Gln Val Trp Asn Thr Thr Met
        130                 135                 140

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
```

```
              195                 200                 205
Arg Thr Asn Ala Val Thr Val Gly Gly Val Ala Ala Gly Ile Gly Gly
    210                 215                 220

Leu Glu Leu Ala Ala Met Ile Val Ser Met Tyr Leu Tyr Cys Asn Leu
225                 230                 235                 240

Gln
```

<210> SEQ ID NO 115
<211> LENGTH: 366
<212> TYPE: DNA
<213> ORGANISM: Homo sapien

<400> SEQUENCE: 115

```
gctctttctc tcccctcctc tgaatttaat tctttcaact tgcaatttgc aaggattaca      60
catttcactg tgatgtatat tgtgttgcaa aaaaaaaaa gtgtctttgt ttaaaattac      120
ttggtttgtg aatccatctt gcttttccc cattggaact agtcattaac ccatctctga     180
actggtagaa aaacatctga agagctagtc tatcagcatc tgacaggtga attggatggt     240
tctcagaacc atttcaccca gacagcctgt ttctatcctg tttaataaat tagtttgggt    300
tctctacatg cataacaaac cctgctccaa tctgtcacat aaaagtctgt gacttgaagt    360
ttagtc                                                                366
```

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116

```
acaaagatga accatttcct atattatagc aaaattaaaa tctacccgta ttctaatatt      60
gagaaatgag atnaaacaca atnttataaa gtctacttag agaagatcaa gtgacctcaa    120
agactttact attttcatat tttaagacac atgatttatc ctattttagt aacctggttc    180
atacgttaaa caaggataa tgtgaacagc agagaggatt tgttggcaga aaatctatgt     240
tcaatctnga actatctana tcacagacat ttctattcct tt                       282
```

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117

```
acacatgtcg cttcactgcc ttcttagatg cttctggtca acatanagga acagggacca      60
tatttatcct ccctcctgaa acaattgcaa ataanacaa atatatgaa acaattgcaa     120 aataaggcaa atatatgaa acaacaggtc tcgagatatt ggaaatcagt caatgaagga    180
tactgatccc tgatcactgt cctaatgcag gatgtgggaa acagatgagg tcacctctgt    240
gactgcccca gcttactgcc tgtagagagt ttctangctg cagttcagac agggagaaat   300
tgggt                                                                305
```

```
<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118
accaaggtgt ntgaatctct gacgtgggga tctctgattc ccgcacaatc tgagtggaaa      60
aantcctggg t                                                          71

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119
actccggttg gtgtcagcag cacgtggcat tgaacatngc aatgtggagc ccaaaccaca      60
gaaaatgggg tgaaattggc caactttcta tnaacttatg ttggcaantt tgccaccaac     120
agtaagctgg cccttctaat aaaagaaaat tgaaaggttt ctcactaanc ggaattaant     180
aatggantca aganactccc aggcctcagc gt                                   212

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120
actcgttgca natcaggggc cccccagagt caccgttgca ggagtccttc tggtcttgcc      60
ctccgccggc gcagaacatg ctggggtggt                                      90

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121
tgtancgtga anacgacaga nagggttgtc aaaaatggag aanccttgaa gtcattttga      60
gaataagatt tgctaaaaga tttggggcta aaacatggtt attgggagac atttctgaag     120
atatncangt aaaattangga atgaattcat ggttctttg ggaattcctt tacgatngcc     180
agcatanact tcatgtgggg atancagcta cccttgta                             218

<210> SEQ ID NO 122
<211> LENGTH: 171
<212> TYPE: DNA
<213> ORGANISM: Homo sapien

<400> SEQUENCE: 122
``` tagggggtgta tgcaactgta aggacaaaaa ttgagactca actggcttaa ccaataaagg    60
catttgttag ctcatggaac aggaagtcgg atggtggggc atcttcagtg ctgcatgagt    120
caccaccccg gcggggtcat ctgtgccaca ggtccctgtt gacagtgcgg t             171

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123
tgtagcgtga agacnacaga atggtgtgtg ctgtgctatc caggaacaca tttattatca    60
ttatcaanta ttgtgt                                                    76

<210> SEQ ID NO 124
<211> LENGTH: 131
<212> TYPE: DNA
<213> ORGANISM: Homo sapien

<400> SEQUENCE: 124
acctttcccc aaggccaatg tcctgtgtgc taactggccg gctgcaggac agctgcaatt    60
caatgtgctg ggtcatatgg aggggaggag actctaaaat agccaatttt attctcttgg    120
ttaagatttg t                                                         131

<210> SEQ ID NO 125
<211> LENGTH: 432
<212> TYPE: DNA
<213> ORGANISM: Homo sapien

<400> SEQUENCE: 125
actttatcta ctggctatga aatagatggt ggaaaattgc gttaccaact ataccactgg    60
cttgaaaaag aggtgatagc tcttcagagg acttgtgact tttgctcaga tgctgaagaa    120
ctacagtctg catttggcag aaatgaagat gaatttggat taaatgagga tgctgaagat    180
ttgcctcacc aaacaaaagt gaaacaactg agagaaaatt tcaggaaaaa agacagtgg    240 ctcttgaagt atcagtcact tttgagaatg tttcttagtt actgcatact tcatggatcc    300
catggtgggg gtcttgcatc tgtaagaatg gaattgattt tgcttttgca agaatctcag    360
caggaaacat cagaaccact attttctagc cctctgtcag agcaaacctc agtgcctctc    420
ctctttgctt gt                                                        432

<210> SEQ ID NO 126
<211> LENGTH: 112
<212> TYPE: DNA
<213> ORGANISM: Homo sapien

<400> SEQUENCE: 126
acacaacttg aatagtaaaa tagaaactga gctgaaattt ctaattcact ttctaaccat    60
agtaagaatg atatttcccc ccagggatca ccaaatattt ataaaaattt gt            112

<210> SEQ ID NO 127
<211> LENGTH: 54
<212> TYPE: DNA
<213> ORGANISM: Homo sapien

<400> SEQUENCE: 127

```
accacgaaac cacaaacaag atggaagcat caatccactt gccaagcaca gcag          54
```

<210> SEQ ID NO 128
<211> LENGTH: 323
<212> TYPE: DNA
<213> ORGANISM: Homo sapien

<400> SEQUENCE: 128

```
acctcattag taattgtttt gttgtttcat ttttttctaa tgtctcccct ctaccagctc    60
acctgagata acagaatgaa aatggaagga cagccagatt tctcctttgc tctctgctca   120
ttctctctga agtctaggtt acccattttg gggacccatt ataggcaata aacacagttc   180
ccaaagcatt tggacagttt cttgttgtgt tttagaatgg ttttcctttt tcttagcctt   240
ttcctgcaaa aggctcactc agtcccttgc ttgctcagtg gactgggctc cccagggcct   300
aggctgcctt cttttccatg tcc                                           323
```

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

```
acatacatgt gtgtatattt ttaaatatca cttttgtatc actctgactt tttagcatac    60
tgaaaacaca ctaacataat ttntgtgaac catgatcaga tacaacccaa atcattcatc   120
tagcacattc atctgtgata naaagatagg tgagtttcat ttccttcacg ttggccaatg   180
gataaacaaa gt                                                       192
```

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

```
ccctttttta tggaatgagt agactgtatg tttgaanatt tanccacaac ctctttgaca    60
tataatgacg caacaaaaag gtgctgttta gtcctatggt tcagtttatg ccctgacaa    120
gtttccattg tgttttgccg atcttctggc taatcgtggt atcctccatg ttattagtaa   180
ttctgtattc cattttgtta acgcctggta gatgtaacct gctangaggc taactttata   240
cttatttaaa agctcttatt ttgtggtcat taaaatggca atttatgtgc agcactttat   300
tgcagcagga agcacgtgtg ggttggttgt aaagctcttt gctaatctta aaaagtaatg   360
gg                                                                  362
```

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

```
cttttttgaaa gatcgtgtcc actcctgtgg acatcttgtt ttaatggagt ttcccatgca        60
gtangactgg tatggttgca gctgtccaga taaaaacatt tgaagagctc caaaatgaga       120
gttctcccag gttcgccctg ctgctccaag tctcagcagc agcctctttt aggaggcatc       180
ttctgaacta gattaaggca gcttgtaaat ctgatgtgat ttggtttatt atccaactaa       240
cttccatctg ttatcactgg agaaagccca gactccccan gacnggtacg gattgtgggc       300
atanaaggat tgggtgaagc tggcgttgtg gt                                     332
```

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

```
acttttgcca ttttgtatat ataaacaatc ttgggacatt ctcctgaaaa ctaggtgtcc        60
agtggctaag agaactcgat ttcaagcaat tctgaaagga aaaccagcat gacacagaat       120
ctcaaattcc caaacagggg ctctgtggga aaaatgaggg aggacctttg tatctcgggt       180
tttagcaagt taaatgaan atgacaggaa aggcttattt atcaacaaag agaagagttg       240
ggatgcttct aaaaaaaact ttggtagaga aaataggaat gctnaatcct agggaagcct       300
gtaacaatct acaattggtc ca                                                322
```

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

```
acaagccttc acaagtttaa ctaaattggg attaatcttt ctgtanttat ctgcataatt        60
cttgtttttc tttccatctg gctcctgggt tgacaatttg tggaaacaac tctattgcta       120
ctatttaaaa aaaatcacaa atctttccct ttaagctatg ttnaattcaa actattcctg       180
ctattcctgt tttgtcaaag aaattatatt tttcaaaata tgtntatttg tttgatgggt       240
cccacgaaac actaataaaa accacagaga ccagcctg                               278
```

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G

<400> SEQUENCE: 134

```
gtttanaaaa cttgtttagc tccatagagg aaagaatgtt aaactttgta ttttaaaaca        60
tgattctctg aggttaaact tggttttcaa atgttatttt tacttgtatt ttgcttttgg       120
t                                                                       121
```

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135

```
acttanaacc atgcctagca catcagaatc cctcaaagaa catcagtata atcctatacc      60
atancaagtg gtgactggtt aagcgtgcga caaaggtcag ctggcacatt acttgtgtgc     120
aaacttgata cttttgttct aagtaggaac tagtatacag tncctaggan tggtactcca     180
gggtgccccc caactcctgc agccgctcct ctgtgccagn ccctgnaagg aactttcgct     240
ccacctcaat caagccctgg gccatgctac ctgcaattgg ctgaacaaac gtttgctgag     300
ttcccaagga tgcaaagcct ggtgctcaac tcctggggcg tcaactcagt                350
```

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136

```
tgtaccgtga agacgacaga agttgcatgg cagggacagg gcagggccga ggccagggtt      60
gctgtgattg tatccgaata ntcctcgtga gaaaagataa tgagatgacg tgagcagcct     120
gcagacttgt gtctgccttc aanaagccag acaggaaggc cctgcctgcc ttggctctga     180
cctggcggcc agccagccag ccacaggtgg gcttcttcct tttgtggtga caacnccaag     240
aaaactgcag aggcccaggg tcaggtgtna gtgggtangt gaccataaaa caccaggtgc     300
tcccaggaac ccgggcaaag gccatcccca cctacagcca gcatgcccac tggcgtgatg     360
ggtgcagang gatgaagcag ccagntgttc tgctgtggt                            399
```

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137

```
actggtgtgg tnggggtga tgctggtggt anaagttgan gtgacttcan gatggtgtgt      60
ggaggaagtg tgtgaacgta gggatgtaga ngttttggcc gtgctaaatg agcttcggga    120
ttggctggtc ccactggtgg tcactgtcat tggtggggtt cctgt                    165
```

<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138

```
actcactgga atgccacatt cacaacagaa tcagaggtct gtgaaaacat taatggctcc    60
ttaacttctc cagtaagaat cagggacttg aaatggaaac gttaacagcc acatgcccaa   120
tgctgggcag tctcccatgc cttccacagt gaaagggctt gagaaaaatc acatccaatg   180
tcatgtgttt ccagccacac caaaaggtgc ttggggtgga gggctggggg catananggt   240
cangcctcag gaagcctcaa gttccattca gctttgccac tgtacattcc ccatntttaa   300
aaaaactgat gccttttttt ttttttttg taaaattc                            338

<210> SEQ ID NO 139
<211> LENGTH: 382
<212> TYPE: DNA
<213> ORGANISM: Homo sapien

<400> SEQUENCE: 139
gggaatcttg gtttttggca tctggtttgc ctatagccga ggccactttg acagaacaaa    60
gaaagggact tcgagtaaga aggtgattta cagccagcct agtgcccgaa gtgaaggaga   120
attcaaacag acctcgtcat tcctggtgtg agcctggtcg gctcaccgcc tatcatctgc   180
atttgcctta ctcaggtgct accggactct ggcccctgat gtctgtagtt tcacaggatg   240
ccttatttgt cttctacacc ccacagggcc cctacttct tcggatgtgt ttttaataat    300
gtcagctatg tgccccatcc tccttcatgc cctccctccc tttcctacca ctgctgagtg   360
gcctggaact tgtttaaagt gt                                            382

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140
accaaanctt ctttctgttg tgttngattt tactataggg gtttngcttn ttctaaanat    60
acttttcatt taacancttt tgttaagtgt caggctgcac tttgctccat anaattattg   120
ttttcacatt tcaacttgta tgtgtttgtc tcttanagca ttggtgaaat cacatatttt   180
atattcagca taaaggagaa                                               200

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141
actttatttt caaacactc atatgttgca aaaacacat agaaaaataa agtttggtgg      60
gggtgctgac taaacttcaa gtcacagact tttatgtgac agattggagc agggtttgtt   120
atgcatgtag agaacccaaa ctaatttatt aaacaggata gaaacaggct gtctgggtga   180
aatggttctg agaaccatcc aattcacctg tcagatgctg atanactagc tcttcagatg   240
tttttctacc agttcagaga tnggttaatg actanttcca atggggaaaa agcaagatgg   300
attcacaaac caagtaattt taaacaaaga cactt                              335
```

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

| | | | | | |
|---|---|---|---|---|---|
| accaggttaa | tattgccaca | tatatccttt | ccaattgcgg | gctaaacaga cgtgtatttta | 60 |
| gggttgttta | aagacaaccc | agcttaatat | caagagaaat | tgtgaccttt catggagtat | 120 |
| ctgatggaga | aaacactgag | ttttgacaaa | tcttatttta | ttcagatagc agtctgatca | 180 |
| cacatggtcc | aacaacactc | aaataataaa | tcaaatatna | tcagatgtta aagattggtc | 240 |
| ttcaaacatc | atagccaatg | atgccccgct | tgcctataat | ctctccgaca taaaaccaca | 300 |
| tcaacacctc | agtggccacc | aaaccattca | gcacagcttc | cttaactgtg agctgtttga | 360 |
| agctaccagt | ctgagcacta | ttgactatnt | ttttcangct | ctgaatagct ctagggatct | 420 |
| cagcangggt | gggaggaacc | agctcaacct | tggcgtant | | 459 |

<210> SEQ ID NO 143
<211> LENGTH: 140
<212> TYPE: DNA
<213> ORGANISM: Homo sapien

<400> SEQUENCE: 143

| | | | | | |
|---|---|---|---|---|---|
| acatttcctt | ccaccaagtc | aggactcctg | gcttctgtgg | gagttcttat cacctgaggg | 60 |
| aaatccaaac | agtctctcct | agaaaggaat | agtgtcacca | accccaccca tctccctgag | 120 |
| accatccgac | ttccctgtgt | | | | 140 |

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

| | | | | | |
|---|---|---|---|---|---|
| acttcagtaa | caacatacaa | taacaacatt | aagtgtatat | tgccatcttt gtcattttct | 60 |
| atctatacca | ctctcccttc | tgaaaacaan | aatcactanc | caatcactta tacaaatttg | 120 |
| aggcaattaa | tccatatttg | ttttcaataa | ggaaaaaaag | atgt | 164 |

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145

| | | | | | |
|---|---|---|---|---|---|
| acgtagacca | tccaactttg | tatttgtaat | ggcaaacatc | cagnagcaat tcctaaacaa | 60 |
| actggagggt | atttatacccc | aattatccca | ttcattaaca | tgccctcctc ctcaggctat | 120 |
| gcaggacagc | tatcataagt | cggcccaggc | atccagatac | taccatttgt ataaacttca | 180 |
| gtagggggagt | ccatccaagt | gacaggtcta | atcaaaggag | gaaatggaac ataagcccag | 240 |

```
tagtaaaatn ttgcttagct gaaacagcca caaaagactt accgccgtgg tgattaccat    300
caa                                                                  303
```

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

```
actgcagctc aattagaagt ggtctctgac tttcatcanc ttctccctgg gctccatgac     60
actggcctgg agtgactcat tgctctggtt ggttgagaga gctcctttgc caacaggcct    120
ccaagtcagg gctgggattt gtttcctttc cacattctag caacaatatg ctggccactt    180
cctgaacagg gagggtggga ggagccagca tggaacaagc tgccactttc taaagtagcc    240
agacttgccc ctgggcctgt cacacctact gatgaccttc tgtgcctgca ggatggaatg    300 tagggtgag ctgtgtgact ctatggt                                          327
```

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

```
acattgtttt tttgagataa agcattgana gagctctcct taacgtgaca caatggaagg     60 actgaacac atacccacat ctttgttctg agggataatt ttctgataaa gtcttgctgt    120
atattcaagc acatatgtta tatattattc agttccatgt ttatagccta gtt           173
```

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

```
acaaccactt tatctcatcg aatttttaac ccaaactcac tcactgtgcc tttctatcct     60
atgggatata ttatttgatg ctccatttca tcacacatat atgaataata cactcatact    120
gccctactac ctgctgcaat aatcacattc ccttcctgtc ctgaccctga agccattggg    180
gtggtcctag tggccatcag tccangcctg caccttgagc ccttgagctc cattgctcac    240 nccanccac ctcaccgacc ccatcctctt acacagctac ctccttgctc tctaaccccca    300 tagattatnt ccaaattcag tcaattaagt tactattaac actctacccg acatgtccag    360
caccactggt aagccttctc cagccaacac acacacacac acacncacac acacacatat    420
ccaggcacag gctacctcat cttcacaatc accccttttaa ttaccatgct atggtgg       477
```

<210> SEQ ID NO 149
<211> LENGTH: 207
<212> TYPE: DNA
<213> ORGANISM: Homo sapien

```
<400> SEQUENCE: 149
acagttgtat tataatatca agaaataaac ttgcaatgag agcatttaag agggaagaac      60
taacgtattt tagagagcca aggaaggttt ctgtggggag tgggatgtaa ggtggggcct     120
gatgataaat aagagtcagc caggtaagtg ggtggtgtgg tatgggcaca gtgaagaaca    180
tttcaggcag agggaacagc agtgaaa                                         207

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150
accttgattt cattgctgct ctgatggaaa cccaactatc taatttagct aaaacatggg      60
cacttaaatg tggtcagtgt ttggacttgt taactantgg catctttggg t             111

<210> SEQ ID NO 151
<211> LENGTH: 196
<212> TYPE: DNA
<213> ORGANISM: Homo sapien

<400> SEQUENCE: 151
agcgcggcag gtcatattga acattccaga tacctatcat tactcgatgc tgttgataac      60
agcaagatgg cttttgaactc aggtcacca ccagctattg gaccttacta tgaaaaccat    120
ggataccaac cggaaaaccc ctatcccgca cagcccactg tggtccccac tgtctacgag    180
gtgcatccgg ctcagt                                                    196

<210> SEQ ID NO 152
<211> LENGTH: 132
<212> TYPE: DNA
<213> ORGANISM: Homo sapien

<400> SEQUENCE: 152
acagcacttt cacatgtaag aagggagaaa ttcctaaatg taggagaaag ataacagaac      60
cttccccttt tcatctagtg gtggaaacct gatgctttat gttgacagga atagaaccag    120
gagggagttt gt                                                         132

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153
acaanaccca nganaggcca ctggccgtgg tgtcatggcc tccaaacatg aaagtgtcag      60
cttctgctct tatgtcctca tctgacaact ctttaccatt tttatcctcg ctcagcagga    120
gcacatcaat aaagtccaaa gtcttggact tggccttggc ttggaggaag tcatcaacac    180
cctggctagt gagggtgcgg cgccgctcct ggatgacggc atctgtgaag tcgtgcacca    240
gtctgcaggc cctgtggaag cgccgtccac acggagtnag gaatt                    285
```

<210> SEQ ID NO 154
<211> LENGTH: 333
<212> TYPE: DNA
<213> ORGANISM: Homo sapien

<400> SEQUENCE: 154

| | | | | |
|---|---|---|---|---|
| accacagtcc | tgttgggcca | gggcttcatg | acccttcctg | tgaaaagcca | tattatcacc | 60 |
| accccaaatt | tttccttaaa | tatctttaac | tgaagggtc | agcctcttga | ctgcaaagac | 120 |
| cctaagccgg | ttacacagct | aactcccact | ggccctgatt | tgtgaaattg | ctgctgcctg | 180 |
| attggcacag | gagtcgaagg | tgttcagctc | ccctcctccg | tggaacgaga | ctctgatttg | 240 |
| agtttcacaa | attctcgggc | cacctcgtca | ttgctcctct | gaaataaaat | ccggagaatg | 300 |
| gtcaggcctg | tctcatccat | atggatcttc | cgg | | | 333 |

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155

| | | | | | | |
|---|---|---|---|---|---|---|
| actggaaata | ataaaaccca | catcacagtg | ttgtgtcaaa | gatcatcagg | gcatggatgg | 60 |
| gaaagtgctt | tgggaactgt | aaagtgccta | acacatgatc | gatgattttt | gttataatat | 120 |
| ttgaatcacg | gtgcatacaa | actctcctgc | ctgctcctcc | tgggcccag | ccccagcccc | 180 |
| atcacagctc | actgctctgt | tcatccaggc | ccagcatgta | gtggctgatt | cttcttggct | 240 |
| gcttttagcc | tccanaagtt | tctctgaagc | caaccaaacc | tctangtgta | aggcatgctg | 300 |
| gccctggt | | | | | | 308 |

<210> SEQ ID NO 156
<211> LENGTH: 295
<212> TYPE: DNA
<213> ORGANISM: Homo sapien

<400> SEQUENCE: 156

| | | | | | | |
|---|---|---|---|---|---|---|
| accttgctcg | gtgcttggaa | catattagga | actcaaaata | tgagatgata | acagtgccta | 60 |
| ttattgatta | ctgagagaac | tgttagacat | ttagttgaag | attttctaca | caggaactga | 120 |
| gaataggaga | ttatgtttgg | ccctcatatt | ctctcctatc | ctccttgcct | cattctatgt | 180 |
| ctaatatatt | ctcaatcaaa | taaggttagc | ataatcagga | aatcgaccaa | ataccaatat | 240 |
| aaaaccagat | gtctatcctt | aagattttca | aatagaaaac | aaattaacag | actat | 295 |

<210> SEQ ID NO 157
<211> LENGTH: 126
<212> TYPE: DNA
<213> ORGANISM: Homo sapien

<400> SEQUENCE: 157

| | | | | | | |
|---|---|---|---|---|---|---|
| acaagtttaa | atagtgctgt | cactgtgcat | gtgctgaaat | gtgaaatcca | ccacatttct | 60 |
| gaagagcaaa | acaaattctg | tcatgtaatc | tctatcttgg | gtcgtgggta | tatctgtccc | 120 |
| cttagt | | | | | | 126 |

<210> SEQ ID NO 158
<211> LENGTH: 442

```
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158
acccactggt cttggaaaca cccatcctta atacgatgat ttttctgtcg tgtgaaaatg    60
aanccagcag gctgcccta gtcagtcctt ccttccagag aaaaagagat ttgagaaagt    120
gcctgggtaa ttcaccatta atttcctccc ccaaactctc tgagtcttcc cttaatattt    180
ctggtggttc tgaccaaagc aggtcatggt ttgttgagca tttgggatcc cagtgaagta    240
natgtttgta gccttgcata cttagcccct cccacgcaca aacggagtgg cagagtggtg    300
ccaaccctgt tttcccagtc cacgtagaca gattcacagt gcggaattct ggaagctgga    360
nacagacggg ctctttgcag agccgggact ctgagangga catgagggcc tctgcctctg    420
tgttcattct ctgatgtcct gt                                            442

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159
acttccaggt aacgttgttg tttccgttga gcctgaactg atgggtgacg ttgtaggttc    60
tccaacaaga actgaggttg cagagcgggt agggaagagt gctgttccag ttgcacctgg    120
gctgctgtgg actgttgttg attcctcact acggcccaag gttgtggaac tggcanaaag    180
gtgtgttgtt gganttgagc tcgggcggct gtggtaggtt gtgggctctt caacagggc    240 tgctgtggtg ccgggangtg aangtgttgt gtcacttgag cttggccagc tctgaaagt    300 antanattct tcctgaaggc cagcgcttgt ggagctggca ngggtcantg ttgtgtgtaa    360
cgaaccagtg ctgctgtggg tgggtgtana tcctccacaa agcctgaagt tatggtgtcn    420
tcaggtaana atgtggtttc agtgtccctg ggcngctgtg gaaggttgta nattgtcacc    480
aagggaataa gctgtggt                                                 498

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160
acctgcatcc agcttccctg ccaaactcac aaggagacat caacctctag acagggaaac    60
agcttcagga tacttccagg agacagagcc accagcagca aaacaaatat tcccatgcct    120
ggagcatggc atagaggaag ctganaaatg tggggtctga ggaagccatt tgagtctggc    180
cactagacat ctcatcagcc acttgtgtga agagatgccc catgacccca gatgcctctc    240
ccacccttac ctccatctca cacacttgag ctttccactc tgtataattc taacatcctg    300
gagaaaaatg gcagtttgac cgaacctgtt cacaacggta gaggctgatt tctaacgaaa    360
```
cttgtagaat gaagcctgga                                                      380

<210> SEQ ID NO 161
<211> LENGTH: 114
<212> TYPE: DNA
<213> ORGANISM: Homo sapien

<400> SEQUENCE: 161
actccacatc ccctctgagc aggcggttgt cgttcaaggt gtatttggcc ttgcctgtca          60
cactgtccac tggcccctta tccacttggt gcttaatccc tcgaaagagc atgt               114

<210> SEQ ID NO 162
<211> LENGTH: 177
<212> TYPE: DNA
<213> ORGANISM: Homo sapien

<400> SEQUENCE: 162
actttctgaa tcgaatcaaa tgatacttag tgtagtttta atatcctcat atatatcaaa          60
gttttactac tctgataatt ttgtaaacca ggtaaccaga acatccagtc atacagcttt          120
tggtgatata taacttggca ataacccagt ctggtgatac ataaaactac tcactgt            177

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163
catttataca gacaggcgtg aagacattca cgacaaaaac gcgaaattct atcccgtgac          60
canagaaggc agctacggct actcctacat cctggcgtgg gtggccttcg cctgcacctt         120
catcagcggc atgatgt                                                         137

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164
cttatcacaa tgaatgttct cctgggcagc gttgtgatct ttgccacctt cgtgactta          60 tgcaatgcat catgctattt catacctaat gagggagttc caggagattc aaccaggaaa         120
tgcatggatc tcaaaggaaa caaacaccca ataaactcgg agtggcagac tgacaactgt         180
gagacatgca cttgctacga aacagaaatt tcatgttgca cccttgtttc tacacctgtg         240
ggttatgaca agacaactg ccaagaatc ttcaagaagg aggactgcaa gtatatcgtg           300
gtggagaaga aggacccaaa aaagacctgt tctgtcagtg aatggataat ctaatgtgct         360
tctagtaggc acagggctcc caggccaggc tcattctcc tctggcctct aatagtcaat         420
gattgtgtag ccatgcctat cagtaaaaag atntttgagc aaacacttt                    469

<210> SEQ ID NO 165
<211> LENGTH: 195
<212> TYPE: DNA
<213> ORGANISM: Homo sapien

```
<220> FEATURE:
<221> NAME/KEY: misc_feature
<222> LOCATION: (1)...(195)
<223> OTHER INFORMATION: n = A,T,C or G

<400> SEQUENCE: 165
acagtttttt atanatatcg acattgccgg cacttgtgtt cagtttcata aagctggtgg      60
atccgctgtc atccactatt ccttggctag agtaaaaatt attcttatag cccatgtccc     120
tgcaggccgc ccgcccgtag ttctcgttcc agtcgtcttg cacacaggg tgccaggact      180 tcctctgaga tgagt                                                      195

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166
acatcttagt agtgtggcac atcagggggc catcagggtc acagtcactc atagcctcgc      60
cgaggtcgga gtccacacca ccggtgtagg tgtgctcaat cttgggcttg gcgcccacct    120
ttggagaagg gatatgctgc acacacatgt ccacaaagcc tgtgaactcg ccaaagaatt    180
tttgcagacc agcctgagca aggggcggat gttcagcttc agctcctcct tcgtcaggtg    240
gatgccaacc tcgtctangg tccgtgggaa gctggtgtcc acntcaccta caacctgggc    300
gangatctta taaagaggct ccnagataaa ctccacgaaa cttctctggg agctgctagt    360 ngggccttt ttggtgaact ttc                                             383

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167
acagagccag accttggcca taaatgaanc agagattaag actaaacccc aagtcganat      60
tggagcagaa actggagcaa gaagtgggcc tggggctgaa gtagagacca aggccactgc    120
tatanccata cacagagcca actctcaggc caaggcnatg gttggggcag anccagagac    180
tcaatctgan tccaaagtgg tggctggaac actggtcatg acanaggcag tgactctgac    240 tgangtc                                                              247

<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G

<400> SEQUENCE: 168
acttctaagt tttctagaag tggaaggatt gtantcatcc tgaaaatggg tttacttcaa      60
aatccctcan ccttgttctt cacnactgtc tatactgana gtgtcatgtt tccacaaagg    120
```

-continued

| | |
|---|---|
| gctgacacct gagcctgnat tttcactcat ccctgagaag ccctttccag tagggtgggc | 180 |
| aattcccaac ttccttgcca caagcttccc aggctttctc ccctggaaaa ctccagcttg | 240 |
| agtcccagat acactcatgg gctgccctgg gca | 273 |

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

| | |
|---|---|
| acagccttgg cttccccaaa ctccacagtc tcagtgcaga aagatcatct tccagcagtc | 60 |
| agctcagacc agggtcaaag gatgtgacat caacagtttc tggtttcaga acaggttcta | 120 |
| ctactgtcaa atgaccccc atacttcctc aaaggctgtg gtaagttttg cacaggtgag | 180 |
| ggcagcagaa aggggtant tactgatgga caccatcttc tctgtatact ccacactgac | 240 |
| cttgccatgg gcaaaggccc ctaccacaaa acaataggca tcactgctgg gcaccagctc | 300 |
| acgcacatca ctgacaaccg ggatggaaaa agaantgcca actttcatac atccaactgg | 360 |
| aaagtgatct gatactggat tcttaattac cttcaaaagc ttctggggc catcagctgc | 420 |
| tcgaacactg a | 431 |

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

| | |
|---|---|
| acctgtgggc tgggctgtta tgcctgtgcc ggctgctgaa agggagttca gaggtggagc | 60 |
| tcaaggagct ctgcaggcat tttgccaanc ctctccanag canagggagc aacctacact | 120 |
| ccccgctaga aagacaccag attggagtcc tgggaggggg agttgggtg ggcatttgat | 180 |
| gtatacttgt cacctgaatg aangagccag agaggaanga gacgaanatg anattggcct | 240 |
| tcaaagctag gggtctggca ggtgga | 266 |

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

| | |
|---|---|
| ggcagccaaa tcataaacgg cgaggactgc agcccgcact cgcagccctg gcaggcggca | 60 |
| ctggtcatgg aaaacgaatt gttctgctcg ggcgtcctgg tgcatccgca gtgggtgctg | 120 |
| tcagccgcac actgtttcca gaagtgagtg cagagctcct acaccatcgg gctgggcctg | 180 |
| cacagtcttg aggccgacca agagccaggg agccagatgg tggaggccag cctctccgta | 240 |
| cggcacccag agtacaacag acccttgctc gctaacgacc tcatgctcat caagttggac | 300 |
| gaatccgtgt ccgagtctga caccatccgg agcatcagca ttgcttcgca gtgccctacc | 360 |

```
gcggggaact cttgcctcgt ttctggctgg ggtctgctgg cgaacggcag aatgcctacc    420
gtgctgcagt gcgtgaacgt gtcggtggtg tctgaggagg tctgcagtaa gctctatgac    480
ccgctgtacc accccagcat gttctgcgcc ggcggagggc aagaccagaa ggactcctgc    540
aacggtgact ctgggggggcc cctgatctgc aacgggtact tgcagggcct tgtgtctttc    600
ggaaaagccc cgtgtggcca agttggcgtg ccaggtgtct acaccaacct ctgcaaattc    660
actgagtgga tagagaaaac cgtccaggcc agttaactct ggggactggg aacccatgaa    720
attgacccccc aaatacatcc tgcggaagga attcaggaat atctgttccc agcccctcct    780
ccctcaggcc caggagtcca ggcccccagc ccctcctccc tcaaaccaag ggtacagatc    840
cccagcccct cctccctcag acccaggagt ccagaccccc cagcccctcc tccctcagac    900
ccaggagtcc agcccctcct ccctcagacc caggagtcca gacccccag ccccctcctcc    960
ctcagaccca ggggtccagg ccccaaccc ctcctccctc agactcagag gtccaagccc   1020
ccaacccntc attccccaga cccagaggtc caggtcccag ccctctntcc ctcagaccca   1080
gcggtccaat gccacctaga ctntccctgt acacagtgcc cccttgtggc acgttgaccc   1140
aaccttacca gttggttttt cattttttngt cccttttcccc tagatccaga aataaagttt   1200
aagagaagng caaaaaaaaa aaaaaaaaaa aaaaaaaaa aaaaaaaa                1248
```

```
<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

Met Val Glu Ala Ser Leu Ser Val Arg His Pro Glu Tyr Asn Arg Pro
 1               5                  10                  15

Leu Leu Ala Asn Asp Leu Met Leu Ile Lys Leu Asp Glu Ser Val Ser
                20                  25                  30

Glu Ser Asp Thr Ile Arg Ser Ile Ser Ile Ala Ser Gln Cys Pro Thr
            35                  40                  45

Ala Gly Asn Ser Cys Leu Val Ser Gly Trp Gly Leu Leu Ala Asn Gly
        50                  55                  60

Arg Met Pro Thr Val Leu Gln Cys Val Asn Val Ser Val Val Ser Glu
 65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

```
<210> SEQ ID NO 173
<211> LENGTH: 1265
<212> TYPE: DNA
<213> ORGANISM: Homo sapien
<220> FEATURE:
```

<221> NAME/KEY: misc_feature
<222> LOCATION: (1)...(1265)
<223> OTHER INFORMATION: n = A,T,C or G

<400> SEQUENCE: 173

```
ggcagcccgc actcgcagcc ctggcaggcg gcactggtca tggaaaacga attgttctgc      60
tcgggcgtcc tggtgcatcc gcagtgggtg ctgtcagccg cacactgttt ccagaactcc     120
tacaccatcg ggctgggcct gcacagtctt gaggccgacc aagagccagg gagccagatg     180
gtggaggcca gcctctccgt acggcaccca gagtacaaca gaccccttgct cgctaacgac     240
ctcatgctca tcaagttgga cgaatccgtg tccgagtctg acaccatccg gagcatcagc     300
attgcttcgc agtgccctac cgcggggaac tcttgcctcg tttctggctg gggtctgctg     360
gcgaacggtg agctcacggg tgtgtgtctg ccctcttcaa ggaggtcctc tgcccagtcg     420
cgggggctga cccagagctc tgcgtcccag gcagaatgcc taccgtgctg cagtgcgtga     480
acgtgtcggt ggtgtctgag gaggtctgca gtaagctcta tgacccgctg taccacccca     540
gcatgttctg cgccggcgga gggcaagacc agaaggactc ctgcaacggt gactctgggg     600
ggccctgat ctgcaacggg tacttgcagg gccttgtgtc tttcggaaaa gccccgtgtg     660
gccaagttgg cgtgccaggt gtctacacca acctctgcaa attcactgag tggatagaga     720
aaaccgtcca ggccagttaa ctctggggac tgggaaccca tgaaattgac ccccaaatac     780
atcctgcgga aggaattcag gaatatctgt tcccagcccc cctccctca ggcccaggag     840
tccaggcccc cagcccctcc tccctcaaac caagggtaca gatccccagc cctcctcccc     900
tcagacccag gagtccagac ccccagcccc ctcctccctc agaccaggag gtccagcccc     960
tcctccntca gacccaggag tccagacccc ccagcccctc tccctcaga cccaggggtt    1020
gaggccccca acccctcctc cttcagagtc agaggtccaa gccccaaccc cctcgttccc    1080
cagacccaga ggtnnaggtc ccagcccctc ttccntcaga cccagnggtc caatgccacc    1140
tagatttttcc ctgnacacag tgccccctg tggnangttg acccaacctt accagttggt    1200
ttttcatttt tngtcccttt cccctagatc cagaaataaa gtttaagaga ngngcaaaaa    1260
aaaaa                                                                1265
```

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

```
ggtcagccgc acactgtttc agaagtgag tgcagagctc ctacaccatc gggctgggcc      60
tgcacagtct tgaggccgac caagagccag ggagccagat ggtggaggcc agcctctccg     120
tacggcaccc agagtacaac agaccccttgc tcgctaacga cctcatgctc atcaagttgg     180
acgaatccgt gtccgagtct gacaccatcc ggagcatcag cattgcttcg cagtgcccta     240
ccgcggggaa ctcttgcctc gtttctggct ggggtctgct ggcgaacggt gagctcacgg     300
gtgtgtgtct gccctcttca aggaggtcct ctgcccagtc gcgggggctg acccagagct     360
ctgcgtccca ggcagaatgc ctaccgtgct gcagtgcgtg aacgtgtcgg tggtgtctga     420
ngaggtctgc antaagctct atgacccgct gtaccacccc ancatgttct gcgccggcgg     480
agggcaagac cagaaggact cctgcaacgt gagagagggg aagggagg gcaggcgact     540
```

```
cagggaaggg tggagaaggg ggagacagag acacacaggg ccgcatggcg agatgcagag    600
atggagagac acacagggag acagtgacaa ctagagagag aaactgagag aaacagagaa    660
ataaacacag gaataaagag aagcaaagga agagagaaac agaaacagac atggggaggc    720
agaaacacac acacatagaa atgcagttga ccttccaaca gcatgggcc tgagggcggt     780 gacctccacc caatagaaaa tcctcttata acttttgact ccccaaaaac ctgactagaa    840
atagcctact gttgacgggg agccttacca ataacataaa tagtcgattt atgcatacgt    900
tttatgcatt catgatatac ctttgttgga attttttgat atttctaagc tacacagttc    960
gtctgtgaat ttttttaaat tgttgcaact ctcctaaaat ttttctgatg tgtttattga   1020
aaaaatccaa gtataagtgg acttgtgcat tcaaaccagg gttgttcaag ggtcaactgt   1080
gtacccagag ggaaacagtg acacagattc atagaggtga acacgaaga gaaacaggaa    1140 aaatcaagac tctacaaaga ggctgggcag ggtggctcat gcctgtaatc ccagcacttt   1200
gggaggcgag gcaggcagat cacttgaggt aaggagttca agaccagcct ggccaaaatg   1260
gtgaaatcct gtctgtacta aaaatacaaa agttagctgg atatggtggc aggcgcctgt   1320
aatcccagct acttgggagg ctgaggcagg agaattgctt gaatatggga ggcagaggtt   1380
gaagtgagtt gagatcacac cactatactc cagctggggc aacagagtaa gactctgtct   1440
caaaaaaaaa aaaaaaaa                                                 1459

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175
gcgcagccct ggcaggcggc actggtcatg gaaaacgaat tgttctgctc gggcgtcctg     60
gtgcatccgc agtgggtgct gtcagccgca cactgtttcc agaactccta caccatcggg    120
ctgggcctgc acagtcttga ggccgaccaa gagccaggga ccagatggt ggaggccagc     180 ctctccgtac ggcacccaga gtacaacaga ctcttgctcg ctaacgacct catgctcatc    240
aagttggacg aatccgtgtc cgagtctgac accatccgga gcatcagcat tgcttcgcag    300
tgccctaccg cggggaactc ttgcctcgtn tctggctggg gtctgctggc gaacggcaga    360
atgcctaccg tgctgcactg cgtgaacgtg tcggtggtgt ctgaggangt ctgcagtaag    420
ctctatgacc cgctgtacca ccccagcatg ttctgcgccg gcggagggca agaccagaag    480
gactcctgca acggtgactc tgggggcc ctgatctgca acgggtactt gcagggcctt     540
gtgtctttcg gaaaagcccc gtgtggccaa cttggcgtgc caggtgtcta caccaacctc    600
tgcaaattca ctgagtggat agagaaaacc gtccagncca gttaactctg gggactggga    660
acccatgaaa ttgaccccca aatacatcct gcggaangaa ttcaggaata tctgttccca    720
gcccctcctc cctcaggccc aggagtccag gccccagcc cctcctccct caaaccaagg    780
gtacagatcc ccagcccctc ctccctcaga cccaggagtc cagaccccc agcccctcnt    840 ccntcagacc caggagtcca gcccctcctc cntcagacgc aggagtccag acccccagc    900 ccntcntccg tcagacccag gggtgcaggc ccccaacccc tcntccntca gagtcagagg    960
tccaagcccc caaccctcg ttccccagac ccagaggtnc aggtcccagc cctcctccc    1020
```

-continued

| | |
|---|---|
| tcagacccag cggtccaatg ccacctagan tntccctgta cacagtgccc ccttgtggca | 1080 |
| ngttgaccca accttaccag ttggtttttc attttttgtc cctttcccct agatccagaa | 1140 |
| ataaagtnta agagaagcgc aaaaaaa | 1167 |

<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

```
Met Glu Asn Glu Leu Phe Cys Ser Gly Val Leu Val His Pro Gln Trp
 1               5                  10                  15
Val Leu Ser Ala Ala His Cys Phe Gln Asn Ser Tyr Thr Ile Gly Leu
            20                  25                  30
Gly Leu His Ser Leu Glu Ala Asp Gln Glu Pro Gly Ser Gln Met Val
        35                  40                  45
Glu Ala Ser Leu Ser Val Arg His Pro Glu Tyr Asn Arg Leu Leu Leu
    50                  55                  60
Ala Asn Asp Leu Met Leu Ile Lys Leu Asp Glu Ser Val Ser Glu Ser
65                  70                  75                  80
Asp Thr Ile Arg Ser Ile Ser Ile Ala Ser Gln Cys Pro Thr Ala Gly
                85                  90                  95
Asn Ser Cys Leu Val Ser Gly Trp Gly Leu Leu Ala Asn Gly Arg Met
            100                 105                 110
Pro Thr Val Leu His Cys Val Asn Val Ser Val Val Ser Glu Xaa Val
        115                 120                 125
Cys Ser Lys Leu Tyr Asp Pro Leu Tyr His Pro Ser Met Phe Cys Ala
    130                 135                 140
Gly Gly Gly Gln Asp Gln Lys Asp Ser Cys Asn Gly Asp Ser Gly Gly
145                 150                 155                 160
Pro Leu Ile Cys Asn Gly Tyr Leu Gln Gly Leu Val Ser Phe Gly Lys
                165                 170                 175
Ala Pro Cys Gly Gln Leu Gly Val Pro Gly Val Tyr Thr Asn Leu Cys
            180                 185                 190
Lys Phe Thr Glu Trp Ile Glu Lys Thr Val Gln Xaa Ser
        195                 200                 205
```

<210> SEQ ID NO 177
<211> LENGTH: 1119
<212> TYPE: DNA
<213> ORGANISM: Homo sapien

<400> SEQUENCE: 177

| | |
|---|---|
| gcgcactcgc agccctggca ggcggcactg gtcatggaaa acgaattgtt ctgctcgggc | 60 |
| gtcctggtgc atccgcagtg ggtgctgtca gccgcacact gtttccagaa ctcctacacc | 120 |
| atcgggctgg gcctgcacag tcttgaggcc gaccaagagc cagggagcca gatggtggag | 180 |
| gccagcctct ccgtacggca cccagagtac aacagaccct tgctcgctaa cgacctcatg | 240 |
| ctcatcaagt tggacgaatc cgtgtccgag tctgacacca tccggagcat cagcattgct | 300 |
| tcgcagtgcc ctaccgcggg gaactcttgc ctcgtttctg gctggggtct gctggcgaac | 360 |
| gatgctgtga ttgccatcca gtcccagact gtgggaggct gggagtgtga aagctttcc | 420 |

-continued

```
caaccctggc agggttgtac catttcggca acttccagtg caaggacgtc ctgctgcatc        480
ctcactgggt gctcactact gctcactgca tcacccggaa cactgtgatc aactagccag        540
caccatagtt ctccgaagtc agactatcat gattactgtg ttgactgtgc tgtctattgt        600
actaaccatg ccgatgttta ggtgaaatta gcgtcacttg gcctcaacca tcttggtatc        660
cagttatcct cactgaattg agatttcctg cttcagtgtc agccattccc acataatttc        720
tgacctacag aggtgaggga tcatatagct cttcaaggat gctggtactc ccctcacaaa        780
ttcatttctc ctgttgtagt gaaaggtgcg ccctctggag cctcccaggg tgggtgtgca        840
ggtcacaatg atgaatgtat gatcgtgttc ccattaccca aagcctttaa atccctcatg        900
ctcagtacac cagggcaggt ctagcatttc ttcatttagt gtatgctgtc cattcatgca        960
accacctcag gactcctgga ttctctgcct agttgagctc ctgcatgctg cctccttggg       1020
gaggtgaggg agagggccca tggttcaatg ggatctgtgc agttgtaaca cattaggtgc       1080
ttaataaaca gaagctgtga tgttaaaaaa aaaaaaaaa                              1119
```

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Leu Thr Ala Ser
145                 150                 155                 160

Pro Gly Thr Leu
```

<210> SEQ ID NO 179
<211> LENGTH: 250
<212> TYPE: DNA
<213> ORGANISM: Homo sapien

<400> SEQUENCE: 179

```
ctggagtgcc ttggtgtttc aagcccctgc aggaagcaga atgcaccttc tgaggcacct         60
ccagctgccc ccggccgggg gatgcgaggc tcggagcacc cttgcccggc tgtgattgct        120
```

```
gccaggcact gttcatctca gcttttctgt cccttttgctc ccggcaagcg cttctgctga    180
aagttcatat ctggagcctg atgtcttaac gaataaaggt cccatgctcc acccgaaaaa    240
aaaaaaaaaa                                                           250

<210> SEQ ID NO 180
<211> LENGTH: 202
<212> TYPE: DNA
<213> ORGANISM: Homo sapien

<400> SEQUENCE: 180
actagtccag tgtggtggaa ttccattgtg ttgggcccaa cacaatggct acctttaaca     60
tcacccagac cccgcccctg cccgtgcccc acgctgctgc taacgacagt atgatgctta    120
ctctgctact cggaaactat ttttatgtaa ttaatgtatg ctttcttgtt tataaatgcc    180
tgatttaaaa aaaaaaaaaa aa                                             202

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181
tccytttgkt naggttttkkg agacamcccck agacctwaan ctgtgtcaca gacttcyngg    60
aatgtttagg cagtgctagt aatttcytcg taatgattct gttattactt tcctnattct    120
ttattcctct ttcttctgaa gattaatgaa gttgaaaatt gaggtggata aatacaaaaa    180
ggtagtgtga tagtataagt atctaagtgc agatgaaagt gtgttatata tatccattca    240
aaattatgca agttagtaat tactcagggt taactaaatt actttaatat gctgttgaac    300
ctactctgtt ccttggctag aaaaaattat aaacaggact tgttagtttt gggaagccaa    360
attgataata ttctatgttc taaaagttgg gctatacata aattattaag aaatatggaw    420
ttttattccc aggaatatgg kgttcatttt atgaatatta cscrggatag awgtwtgagt    480
aaaaycagtt ttggtwaata ygtwaatatg tcmtaaataa acaakgcttt gacttatttc    540
caaaaaaaaa aaaaaaaa                                                  558

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182
acagggwttk grggatgcta agsccccrga rwtygtttga tccaaccctg gcttwttttc     60 agagggaaa atggggccta gaagttacag mscatytagy tggtgcgmtg gcacccctgg    120
cstcacacag astcccgagt agctgggact acaggcacac agtcactgaa gcaggccctg    180
ttwgcaattc acgttgccac ctccaactta acattcttc atatgtgatg tccttagtca    240
ctaaggttaa actttcccac ccagaaaagg caacttagat aaaatcttag agtactttca    300
tactmttcta agtcctcttc cagcctcact kkgagtcctm cytgggggtt gataggaant    360
```

```
ntctcttggc tttctcaata aartctctat ycatctcatg tttaatttgg tacgcatara      420
awtgstgara aaattaaaat gttctggtty mactttaaaa araaaaaaaa aaaaaaaaa      479
```

<210> SEQ ID NO 183
<211> LENGTH: 384
<212> TYPE: DNA
<213> ORGANISM: Homo sapien

<400> SEQUENCE: 183

```
aggcgggagc agaagctaaa gccaaagccc aagaagagtg gcagtgccag cactggtgcc       60
agtaccagta ccaataacag tgccagtgcc agtgccagca ccagtggtgg cttcagtgct      120
ggtgccagcc tgaccgccac tctcacattt gggctcttcg ctggccttgg tggagctggt      180
gccagcacca gtggcagctc tggtgcctgt ggtttctcct acaagtgaga ttttagatat      240
tgttaatcct gccagtcttt ctcttcaagc cagggtgcat cctcagaaac ctactcaaca      300
cagcactcta ggcagccact atcaatcaat tgaagttgac actctgcatt aratctattt      360
gccatttcaa aaaaaaaaaa aaaa                                             384
```

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

```
accgaattgg gaccgctggc ttataagcga tcatgtyynt ccrgtatkac ctcaacgagc       60
agggagatcg agtctatacg ctgaagaaat ttgacccgat gggacaacag acctgctcag      120
cccatcctgc tcggttctcc ccagatgaca aatactctsg acaccgaatc accatcaaga      180
aacgcttcaa ggtgctcatg acccagcaac cgcgccctgt cctctgaggg tcccttaaac      240
tgatgtcttt tctgccacct gttacccctc ggagactccg taaccaaact cttcggactg      300
tgagccctga tgccttttg ccagccatac tctttggcat ccagtctctc gtggcgattg      360
attatgcttg tgtgaggcaa tcatggtggc atcacccata aagggaacac atttgactttt     420 tttttctcat attttaaatt actacmagaw tattwmagaw waaatgawtt gaaaaactst      480
taaaaaaaaa aaaaaa                                                      496
```

<210> SEQ ID NO 185
<211> LENGTH: 384
<212> TYPE: DNA
<213> ORGANISM: Homo sapien

<400> SEQUENCE: 185

```
gctggtagcc tatggcgkgg cccacggagg ggctcctgag gccacggrac agtgacttcc       60
caagtatcyt cgcsgcgtc ttctaccgtc cctacctgca gatcttcggg cagattcccc       120
aggaggacat ggacgtggcc ctcatggagc acagcaactg ytcgtcggag cccggcttct      180
gggcacaccc tcctgggggcc caggcgggca cctgcgtctc ccagtatgcc aactggctgg      240
tggtgctgct cctcgtcatc ttcctgctcg tggccaacat cctgctggtc aacttgctca      300
ttgccatgtt cagttacaca ttcggcaaag tacagggcaa cagcgatctc tactgggaag      360
gcgcagcgtt accgcctcat ccgg                                             384
```

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

| | | | | | | |
|---|---|---|---|---|---|---|
| gagttagctc | ctccacaacc | ttgatgaggt | cgtctgcagt | ggcctctcgc | ttcataccgc | 60 |
| tnccatcgtc | atactgtagg | tttgccacca | cytcctggca | tcttggggcg | gcntaatatt | 120 |
| ccaggaaact | ctcaatcaag | tcaccgtcga | tgaaacctgt | gggctggttc | tgtcttccgc | 180 |
| tcggtgtgaa | aggatctccc | agaaggagtg | ctcgatcttc | cccacacttt | tgatgacttt | 240 |
| attgagtcga | ttctgcatgt | ccagcaggag | gttgtaccag | ctctctgaca | gtgaggtcac | 300 |
| cagccctatc | atgccgttga | mcgtgccgaa | garcaccgag | ccttgtgtgg | gggkkgaagt | 360 |
| ctcacccaga | ttctgcatta | ccagagagcc | gtggcaaaag | acattgacaa | actcgcccag | 420 |
| gtggaaaaag | amcamctcct | ggargtgctn | gccgctcctc | gtcmgttggt | ggcagcgctw | 480 |
| tcctttgac | acacaaacaa | gttaaaggca | ttttcagccc | ccagaaantt | gtcatcatcc | 540 |
| aagatntcgc | acagcactna | tccagttggg | attaaat | | | 577 |

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

| | | | | | | |
|---|---|---|---|---|---|---|
| aacatcttcc | tgtataatgc | tgtgtaatat | cgatccgatn | ttgtctgstg | agaatycatw | 60 |
| actkggaaaa | gmaacattaa | agcctggaca | ctggtattaa | aattcacaat | atgcaacact | 120 |
| ttaaacagtg | tgtcaatctg | ctcccyynac | tttgtcatca | ccagtctggg | aakaagggta | 180 |
| tgccctattc | acacctgtta | aaagggcgct | aagcattttt | gattcaacat | cttttttttt | 240 |
| gacacaagtc | cgaaaaaagc | aaaagtaaac | agttatyaat | ttgttagcca | attcactttc | 300 |
| ttcatgggac | agagccatyt | gatttaaaaa | gcaaattgca | taatattgag | cttygggagc | 360 |
| tgatatttga | gcggaagagt | agcctttcta | cttcaccaga | cacaactccc | tttcatattg | 420 |
| ggatgttnac | naaagtwatg | tctctwacag | atgggatgct | tttgtggcaa | ttctgttctg | 480 |
| aggatctccc | agtttattta | ccacttgcac | aagaaggcgt | tttcttcctc | aggc | 534 |

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188

| | | | | | | |
|---|---|---|---|---|---|---|
| agaaaccagt | atctctnaaa | acaacctctc | ataccttgtg | gacctaattt | tgtgtgcgtg | 60 |
| tgtgtgtgcg | cgcatattat | atagacaggc | acatcttttt | tacttttgta | aaagcttatg | 120 |
| cctctttggt | atctatatct | gtgaaagttt | taatgatctg | ccataatgtc | ttggggacct | 180 |

-continued

| | |
|---|---|
| ttgtcttctg tgtaaatggt actagagaaa acacctatnt tatgagtcaa tctagttngt | 240 |
| tttattcgac atgaaggaaa tttccagatn acaacactna caaactctcc ctkgackarg | 300 |
| ggggacaaag aaaagcaaaa ctgamcataa raaacaatwa cctggtgaga arttgcataa | 360 |
| acagaaatwr ggtagtatat tgaarnacag catcattaaa rmgttwtktt wttctcccct | 420 |
| gcaaaaaaca tgtacngact tcccgttgag taatgccaag ttgtttttt tatnataaaa | 480 |
| cttgcccttc attacatgtt tnaaagtggt gtggtgggcc aaaatattga aatgatggaa | 540 |
| ctgactgata aagctgtaca aataagcagt gtgcctaaca agcaacacag taatgttgac | 600 |
| atgcttaatt cacaaatgct aatttcatta taaatgtttg ctaaaataca ctttgaacta | 660 |
| tttttctgtn ttcccagagc tgagatntta gattttatgt agtataagt gaaaaantac | 720 |
| gaaaataata acattgaaga aaaananaaa aaanaaaaaa a | 761 |

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

| | |
|---|---|
| tttttttttt tttgccgatn ctactatttt attgcaggan gtgggggtgt atgcaccgca | 60 |
| caccggggct atnagaagca agaaggaagg agggagggca cagcccttg ctgagcaaca | 120 |
| aagccgcctg ctgccttctc tgtctgtctc ctggtgcagg cacatgggga gaccttcccc | 180 |
| aaggcagggg ccaccagtcc aggggtggga atacagggg tgggangtgt gcataagaag | 240 |
| tgataggcac aggccacccg gtacagaccc ctcggctcct gacaggtnga tttcgaccag | 300 |
| gtcattgtgc cctgcccagg cacagcgtan atctggaaaa gacagaatgc tttccttttc | 360 |
| aaatttggct ngtcatngaa ngggcantt tccaanttng gctnggtctt ggtacncttg | 420 |
| gttcggccca gctccncgtc caaaaantat tcaccnnct ccnaattgct tgcnggnccc | 480 |
| cc | 482 |

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190

| | |
|---|---|
| tttttttttt ttttaaaaca gttttcaca acaaaattta ttagaagaat agtggttttg | 60 |
| aaaactctcg catccagtga gaactaccat acaccacatt acagctngga atgtnctcca | 120 |
| aatgtctggt caaatgatac aatgaaacca ttcaatctta cacatgcacg aaagaacaag | 180 |
| cgcttttgac atacaatgca caaaaaaaaa agggggggg gaccacatgg attaaaattt | 240 |
| taagtactca tcacatacat taagacacag ttctagtcca gtcnaaaatc agaactgcnt | 300 |
| tgaaaaattt catgtatgca atccaaccaa agaacttnat tggtgatcat gantnctcta | 360 |
| ctacatcnac cttgatcatt gccaggaacn aaaagttnaa ancacncngt acaaaaanaa | 420 |
| tctgtaattn anttcaacct ccgtacngaa aaatnttnnt tatacactcc c | 471 |

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

```
gagggattga aggtctgttc tastgtcggm ctgttcagcc accaactcta acaagttgct    60
gtcttccact cactgtctgt aagcttttta acccagacwg tatcttcata aatagaacaa   120
attcttcacc agtcacatct tctaggacct ttttggattc agttagtata agctcttcca   180
cttcctttgt taagacttca tctggtaaag tcttaagttt tgtagaaagg aattyaattg   240
ctcgttctct aacaatgtcc tctccttgaa gtatttggct gaacaaccca cctaaagtcc   300
ctttgtgcat ccattttaaa tatacttaat agggcattgk tncactaggt taaattctgc   360
aagagtcatc tgtctgcaaa agttgcgtta gtatatctgc ca                     402
```

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

```
gagctcggat ccaataatct ttgtctgagg gcagcacaca tatncagtgc catggnaact    60
ggtctacccc acatgggagc agcatgccgt agntatataa ggtcattccc tgagtcagac   120
atgcytyttt gaytaccgtg tgccaagtgc tggtgattct yaacacacyt ccatcccgyt   180
cttttgtgga aaaactggca cttktctgga actagcarga catcacttac aaattcaccc   240
acgagacact tgaaaggtgt aacaaagcga ytcttgcatt gcttttttgtc cctccggcac   300
cagttgtcaa tactaacccg ctggtttgcc tccatcacat ttgtgatctg tagctctgga   360
tacatctcct gacagtactg aagaacttct tcttttgttt caaaagcarc tcttggtgcc   420
tgttggatca ggttcccatt tcccagtcyg aatgttcaca tggcatattt wacttcccac   480
aaaacattgc gatttgaggc tcagcaacag caaatcctgt tccggcattg gctgcaagag   540
cctcgatgta gccggccagc gccaaggcag gcgccgtgag ccccaccagc agcagaagca   600
g                                                                  601
```

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

```
atacagccca natcccacca cgaagatgcg cttgttgact gagaacctga tgcggtcact    60
ggtcccgctg tagccccagc gactctccac ctgctggaag cggttgatgc tgcactcytt   120
cccaacgcag gcagmagcgg gsccggtcaa tgaactccay tcgtggcttg gggtkgacgg   180
tkaagtgcag gaagaggctg accacctcgc ggtccaccag gatgcccgac tgtgcgggac   240
```

```
ctgcagcgaa actcctcgat ggtcatgagc gggaagcgaa tgaggcccag ggccttgccc      300
agaaccttcc gcctgttctc tggcgtcacc tgcagctgct gccgctgaca ctcggcctcg      360
gaccagcgga caaacggcrt tgaacagccg cacctcacgg atgcccagtg tgtcgcgctc      420
caggammgsc accagcgtgt ccaggtcaat gtcggtgaag ccctccgcgg gtratggcgt      480
ctgcagtgtt tttgtcgatg ttctccaggc acaggctggc cagctgcggt tcatcgaaga      540
gtcgcgcctg cgtgagcagc atgaaggcgt tgtcggctcg cagttcttct tcaggaactc      600
cacgcaat                                                              608

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194
gaacggctgg accttgcctc gcattgtgct tgctggcagg gaataccttg gcaagcagyt       60
ccagtccgag cagccccaga ccgctgccgc ccgaagctaa gcctgcctct ggccttcccc      120
tccgcctcaa tgcagaacca gtagtgggag cactgtgttt agagttaaga gtgaacactg      180
tttgatttta cttgggaatt tcctctgtta tatagctttt cccaatgcta atttccaaac      240
aacaacaaca aaataacatg tttgcctgtt aagttgtata aaagtaggtg attctgtatt      300
taaagaaaat attactgtta catatactgc ttgcaatttc tgtatttatt gktnctstgg      360
aaataaatat agttattaaa ggttgtcant cc                                   392

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195
ccsttkgagg ggtkaggkyc cagttyccga gtggaagaaa caggccagga gaagtgcgtg       60
ccgagctgag gcagatgttc ccacagtgac ccccagagcc stgggstata gtytctgacc      120
cctcncaagg aaagaccacs ttctggggac atgggctgga gggcaggacc tagaggcacc      180
aagggaaggc cccattccgg ggstgttccc gaggaggaa gggaagggc tctgtgtgcc       240 ccccasgagg aagaggccct gagtcctggg atcagacacc ccttcacgtg tatccccaca      300
caaatgcaag ctcaccaagg tccctctca gtccccttcc stacaccctg amcggccact      360
gscscacacc cacccagagc acgccacccg ccatggggar tgtgctcaag gartcgcngg      420
gcarcgtgga catctngtcc cagaagggg cagaatctcc aatagangga ctgarcmstt      480
gctnanaaaa aaaaanaaaa aa                                              502

<210> SEQ ID NO 196
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G
```

<400> SEQUENCE: 196

```
ggttacttgg tttcattgcc accacttagt ggatgtcatt tagaaccatt ttgtctgctc    60
cctctggaag ccttgcgcag agcggacttt gtaattgttg gagaataact gctgaatttt   120
wagctgttk gagttgatts gcaccactgc acccacaact tcaatatgaa aacyawttga    180
actwatttat tatcttgtga aaagtataac aatgaaaatt ttgttcatac tgtattkatc   240
aagtatgatg aaaagcaawa gatatatatt ctttttattat gttaaattat gattgccatt  300
attaatcggc aaaatgtgga gtgtatgttc ttttcacagt aatatatgcc ttttgtaact   360
tcacttggtt attttattgt aaatgartta caaaattctt aatttaagar aatggtatgt   420
watatttatt tcattaattt ctttcctkgt ttacgtwaat tttgaaaaga wtgcatgatt   480
tcttgacaga aatcgatctt gatgctgtgg aagtagtttg acccacatcc ctatgagttt   540
ttcttagaat gtataaaggt tgtagcccat cnaacttcaa agaaaaaaat gaccacatac   600
tttgcaatca ggctgaaatg tggcatgctn ttctaattcc aactttataa actagcaaan   660
aagtg                                                               665
```

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197

```
ttttnttttt ttttttttgc aggaaggatt ccatttattg tggatgcatt ttcacaatat    60
atgtttattg gagcgatcca ttatcagtga aaagtatcaa gtgtttataa nattttagg    120
aaggcagatt cacagaacat gctngtcngc ttgcagtttt acctcgtana gatnacagag   180
aattatagtc naaccagtaa acnaggaatt tacttttcaa aagattaaat ccaaactgaa   240
caaaattcta ccctgaaact tactccatcc aaatattgga ataanagtca gcagtgatac   300
attctcttct gaactttaga ttttctagaa aaatatgtaa tagtgatcag gaagagctct   360
tgttcaaaag tacaacnaag caatgttccc ttaccatagg ccttaattca aactttgatc   420
catttcactc ccatcacggg agtcaatgct acctgggaca cttgtatttt gttcatnctg   480
ancntggctt aa                                                       492
```

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198

```
tttnttttgn atttcantct gtannaanta ttttcattat gtttattana aaaatatnaa    60
tgtntccacn acaaatcatn ttacntnagt aagaggccan ctacattgta caacatacac   120
tgagtatatt ttgaaaagga caagtttaaa gtanacncat attgccganc atancacatt   180
tatacatggc ttgattgata tttagcacag cnaaaactga gtgagttacc agaaanaaat   240
natatatgtc aatcngattt aagatacaaa acagatccta tggtacatan catcntgtag   300
```

```
gagttgtggc tttatgttta ctgaaagtca atgcagttcc tgtacaaaga gatggccgta      360
agcattctag tacctctact ccatggttaa gaatcgtaca cttatgttta catatgtnca      420
gggtaagaat tgtgttaagt naanttatgg agaggtccan gagaaaaatt tgatncaa        478
```

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

```
agtgacttgt cctccaacaa aaccccttga tcaagtttgt ggcactgaca atcagaccta       60
tgctagttcc tgtcatctat tcgctactaa atgcagactg gaggggacca aaaaggggca      120
tcaactccag ctggattatt ttggagcctg caaatctatt cctacttgta cggactttga      180
agtgattcag tttcctctac ggatgagaga ctggctcaag aatatcctca tgcagcttta      240
tgaagccnac tctgaacacg ctggttatct nagatgagaa ncagagaaat aaagtcnaga      300
aaatttacct ggangaaaag aggctttngg ctggggacca tcccattgaa ccttctctta      360
anggacttta agaanaaact accacatgtn tgtngtatcc tggtgccngg ccgtttantg      420
aacntngacn ncacccttnt ggaatanant cttgacngcn tcctgaactt gctcctctgc      480
ga                                                                    482
```

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

```
cggccgcaag tgcaactcca gctggggccg tgcggacgaa gattctgcca gcagttggtc       60
cgactgcgac gacggcggcg gcgacagtcg caggtgcagc gcgggcgcct ggggtcttgc      120
aaggctgagc tgacgccgca gaggtcgtgt cacgtcccac gaccttgacg ccgtcgggga      180
cagccggaac agagcccggt gaangcggga ggcctcgggg agcccctcgg aagggcggc       240 ccgagagata cgcaggtgca ggtggccgcc                                      270
```

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

```
tttttttttt ttttggaatc tactgcgagc acagcaggtc agcaacaagt ttattttgca       60
gctagcaagg taacagggta gggcatggtt acatgttcag gtcaacttcc tttgtcgtgg      120
ttgattggtt tgtctttatg ggggcggggt ggggtagggg aaancgaagc anaantaaca      180
tggagtgggt gcaccctccc tgtagaacct ggttacnaaa gctggggca gttcacctgg       240 tctgtgaccg tcatttcctt gacatcaatg ttattagaag tcaggatatc ttttagagag      300
```

```
tccactgtnt ctggagggag attagggttt cttgccaana tccaancaaa atccacntga    360
aaaagttgga tgatncangt acngaatacc ganggcatan ttctcatant cggtggcca     419
```

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

```
tttntttttt tttttttttt tttttttttt tttttttttt tttttttttt tttttttttt     60
tggcacttaa tccattttta tttcaaaatg tctacaaant ttnaatncnc cattatacng    120
gtnattttnc aaaatctaaa nnttattcaa atntnagcca aantccttac ncaaatnnaa    180
tacncncaaa atcaaaaat atacntntct ttcagcaaac ttngttacat aaattaaaaa     240
aatatatacg gctggtgttt tcaaagtaca attatcttaa cactgcaaac atntttnnaa    300
ggaactaaaa taaaaaaaaa cactnccgca aaggttaaag ggaacaacaa attcntttta    360
caacancnnc nattataaaa atcatatctc aaatcttagg ggaatatata cttcacacng    420
ggatcttaac ttttactnca ctttgtttat tttttttanaa ccattgtntt gggcccaaca    480
caatggnaat nccnccncnc tggactagt                                      509
```

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

```
tttttttttt ttttttttga ccccccctctt ataaaaaaca agttaccatt ttattttact     60
tacacatatt tattttataa ttggtattag atattcaaaa ggcagctttt aaaatcaaac    120
taaatggaaa ctgccttaga tacataattc ttaggaatta gcttaaaatc tgcctaaagt    180
gaaaatcttc tctagctctt ttgactgtaa atttttgact cttgtaaaac atccaaattc    240 attttttcttg tctttaaaat tatctaatct ttccattttt tccctattcc aagtcaattt    300
gcttctctag cctcatttcc tagctcttat ctactattag taagtggctt ttttcctaaa    360
agggaaaaca ggaagagana atggcacaca aaacaaacat tttatattca tatttctacc    420
tacgttaata aaatagcatt ttgtgaagcc agctcaaaag aaggcttaga tccttttatg    480
tccattttag tcactaaacg atatcnaaag tgccagaatg caaaggtttt gtgaacattt    540
attcaaaagc taatataaga tatttcacat actcatcttt ctg                      583
```

<210> SEQ ID NO 204
<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204

```
tttttttttnt tttttttttt tttttttnctc ttctttttttt ttganaatga ggatcgagtt      60
tttcactctc tagatagggc atgaagaaaa ctcatctttc cagctttaaa ataacaatca        120
aatctcttat gctatatcat attttaagtt aaactaatga gtcactggct tatcttctcc        180
tgaaggaaat ctgttcattc ttctcattca tatagttata tcaagtacta ccttgcatat        240
tgagaggttt ttcttctcta tttacacata tatttccatg tgaatttgta tcaaacctttt      300 attttcatgc aaactagaaa ataatgtntt cttttgcata agagaagaga acaatatnag        360
cattacaaaa ctgctcaaat tgtttgttaa gnttatccat tataattagt tnggcaggag        420
ctaatacaaa tcacatttac ngacnagcaa taataaaact gaagtaccag ttaaatatcc        480
aaaataatta aaggaacatt tttagcctgg gtataattag ctaattcact ttacaagcat        540
ttattnagaa tgaattcaca tgttattatt ccntagccca acacaatgg                   589

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205 ttttntttt tttttcagt aataatcaga acaatattta ttttatatt taaaattcat           60 agaaaagtgc cttacattta ataaagttt gtttctcaaa gtgatcagag gaattagata        120
tngtcttgaa caccaatatt aatttgagga aaatacacca aaatacatta agtaaattat       180
ttaagatcat agagcttgta agtgaaaaga taaaatttga cctcagaaac tctgagcatt       240
aaaaatccac tattagcaaa taaattacta tggacttctt gctttaattt tgtgatgaat      300 atgggtgtc actggtaaac caacacattc tgaaggatac attacttagt gatagattct       360
tatgtacttt gctanatnac gtggatatga gttgacaagt ttctctttct tcaatctttt      420 aagggcnga ngaaatgagg aagaaaagaa aaggattacg catactgttc tttctatngg       480
aaggattaga tatgtttcct ttgccaatat taaaaaaata ataatgttta ctactagtga      540
aaccc                                                                   545

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206
tttttttttt tttttagtc aagtttctna tttttattat aattaaagtc ttggtcattt        60
catttattag ctctgcaact tacatattta aattaaagaa acgttntttag acaactgtna     120 caatttataa atgtaaggtg ccattattga gtanatatat tcctccaaga gtggatgtgt      180
cccttctccc accaactaat gaancagcaa cattagttta atttattag tagatnatac       240 actgctgcaa acgctaattc tcttctccat ccccatgtng atattgtgta tatgtgtgag      300
ttggtnagaa tgcatcanca atctnacaat caacagcaag atgaagctag gcntgggctt      360
tcggtgaaaa tagactgtgt ctgtctgaat caaatgatct gacctatcct cggtggcaag      420
aactcttcga accgcttcct caaaggcngc tgccacattt gtggcntctn ttgcacttgt      480
``` ttcaaaa                                                                    487

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207
tgaattggct aaaagactgc atttttanaa ctagcaactc ttatttcttt cctttaaaaa    60
tacatagcat taaatcccaa atcctattta aagacctgac agcttgagaa ggtcactact   120
gcatttatag gaccttctgg tggttctgct gttacntttg aantctgaca atccttgana   180
atctttgcat gcagaggagg taaaaggtat tggattttca cagaggaana acacagcgca   240
gaaatgaagg ggccaggctt actgagcttg tccactggag ggctcatggg tgggacatgg   300
aaaagaaggc agcctaggcc ctggggagcc ca                                 332

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208
agggcgtggt gcggagggcg ttactgtttt gtctcagtaa caataaatac aaaaagactg    60
gttgtgttcc ggccccatcc aaccacgaag ttgatttctc ttgtgtgcag agtgactgat   120
tttaaaggac atggagcttg tcacaatgtc acaatgtcac agtgtgaagg gcacactcac   180
tcccgcgtga ttcacattta gcaaccaaca atagctcatg agtccatact tgtaaatact   240
tttggcagaa tacttnttga aacttgcaga tgataactaa gatccaagat atttcccaaa   300
gtaaatagaa gtgggtcata atattaatta cctgttcaca tcagcttcca tttacaagtc   360
atgagcccag acactgacat caaactaagc ccacttagac tcctcaccac cagtctgtcc   420
tgtcatcaga caggaggctg tcaccttgac caaattctca ccagtcaatc atctatccaa   480
aaaccattac ctgatccact tccggtaatg caccaccttg gtga                    524

<210> SEQ ID NO 209
<211> LENGTH: 159
<212> TYPE: DNA
<213> ORGANISM: Homo sapien

<400> SEQUENCE: 209
gggtgaggaa atccagagtt gccatggaga aaattccagt gtcagcattc ttgctccttg    60
tggccctctc ctacactctg gccagagata ccacagtcaa acctggagcc aaaaaggaca   120
caaaggactc tcgacccaaa ctgccccaga ccctctcca                          159

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)

<223> OTHER INFORMATION: n = A,T,C or G

<400> SEQUENCE: 210

| actccctggc agacaaaggc agaggagaga gctctgttag ttctgtgttg ttgaactgcc | 60 |
|---|---|
| actgaatttc tttccacttg gactattaca tgccanttga gggactaatg gaaaaacgta | 120 |
| tggggagatt ttanccaatt tangtntgta aatgggagag ctggggcagg cgggagagat | 180 |
| ttgcagggtg naaatgggan ggctggtttg ttanatgaac agggacatag gaggtaggca | 240 |
| ccaggatgct aaatca | 256 |

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

| acattgtttt tttgagataa agcattgaga gagctctcct taacgtgaca caatggaagg | 60 |
|---|---|
| actggaacac atacccacat ctttgttctg agggataatt ttctgataaa gtcttgctgt | 120 |
| atattcaagc acatatgtta tatattattc agttccatgt ttatagccta gttaaggaga | 180 |
| ggggagatac attcngaaag aggactgaaa gaaatactca agtnggaaaa cagaaaaga | 240 |
| aaaaaggag caaatgagaa gcct | 264 |

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

| acccaaaaat ccaatgctga atatttggct tcattattcc canattcttt gattgtcaaa | 60 |
|---|---|
| ggatttaatg ttgtctcagc ttgggcactt cagttaggac ctaaggatgc cagccggcag | 120 |
| gtttatatat gcagcaacaa tattcaagcg cgacaacagg ttattgaact tgcccgccag | 180 |
| ttnaatttca ttcccattga cttgggatcc ttatcatcag ccagagagat tgaaaattta | 240 |
| cccctacnac tctttactct ctgganaggg ccagtggtgg tagctataag cttggccaca | 300 |
| ttttttttc ctttattcct ttgtcaga | 328 |

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

| acttatgagc agagcgacat atccnagtgt agactgaata aaactgaatt ctctccagtt | 60 |
|---|---|
| taaagcattg ctcactgaag ggatagaagt gactgccagg agggaaagta agccaaggct | 120 |
| cattatgcca aagganatat acatttcaat tctccaaact tcttcctcat tccaagagtt | 180 |
| ttcaatattt gcatgaacct gctgataanc catgttaana aacaaatatc tctctnacct | 240 | tctcatcggt 250

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214
acccagaatc caatgctgaa tatttggctt cattattccc agattctttg attgtcaaag    60
gatttaatgt tgtctcagct tgggcacttc agtaggacc taaggatgcc agccggcagg    120
tttatatatg cagcaacaat attcaagcgc gacaacaggt tattgaactt gcccgccagt   180
tgaatttcat tcccattgac ttgggatcct tatcatcagc canagagatt gaaaatttac   240
ccctacgact ctttactctc tggagagggc cagtggtggt agctataagc ttggccacat   300 tttttttttcc tttattcctt tgtcagagat gcgattcatc catatgctan aaaccaacag   360
agtgactttt acaaaattcc tataganatt gtgaataaaa ccttacctat agttgccatt   420
actttgctct ccctaatata cctc                                          444

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215
acttatgagc agagcgacat atccaagtgt anactgaata aaactgaatt ctctccagtt    60
taaagcattg ctcactgaag ggatagaagt gactgccagg agggaaagta agccaaggct   120
cattatgcca aagganatat acatttcaat tctccaaact tcttcctcat tccaagagtt   180
ttcaatattt gcatgaacct gctgataagc catgttgaga acaaatatc tctctgacct    240 tctcatcggt aagcagaggc tgtaggcaac atggaccata gcgaanaaaa aacttagtaa   300
tccaagctgt tttctacact gtaaccaggt ttccaaccaa ggtggaaatc tcctatactt   360
ggtgcc                                                              366

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216
ctgtataaac agaactccac tgcangaggg agggccgggc caggagaatc tccgcttgtc    60
caagacaggg gcctaaggag ggtctccaca ctgctnntaa gggctnttnc attttttttat  120 taataaaaag tnnaaaaggc ctcttctcaa cttttttccc ttnggctgga aaatttaaaa   180
atcaaaaatt tcctnaagtt ntcaagctat catatatact ntatcctgaa aaagcaacat   240
aattcttcct tccctccttt                                               260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217

| | | | | |
|---|---|---|---|---|
| acctacgtgg gtaagtttan aaatgttata atttcaggaa naggaacgca tataattgta | | | | 60 |
| tcttgcctat aattttctat tttaataagg aaatagcaaa ttggggtggg gggaatgtag | | | | 120 |
| ggcattctac agtttgagca aaatgcaatt aaatgtggaa ggacagcact gaaaaatttt | | | | 180 |
| atgaataatc tgtatgatta tatgtctcta gagtagattt ataattagcc acttacccta | | | | 240 |
| atatccttca tgcttgtaaa gt | | | | 262 |

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218

| | | | | |
|---|---|---|---|---|
| accaaggtgg tgcattaccg gaantggatc aangacacca tcgtggccaa cccctgagca | | | | 60 |
| cccctatcaa ctccctttg tagtaaactt ggaaccttgg aaatgaccag gccaagactc | | | | 120 |
| aggcctcccc agttctactg acctttgtcc ttangtntna ngtccagggt tgctaggaaa | | | | 180 |
| anaaatcagc agacacaggt gtaaa | | | | 205 |

<210> SEQ ID NO 219
<211> LENGTH: 114
<212> TYPE: DNA
<213> ORGANISM: Homo sapien

<400> SEQUENCE: 219

| | | | | |
|---|---|---|---|---|
| tactgttttg tctcagtaac aataaataca aaaagactgg ttgtgttccg gccccatcca | | | | 60 |
| accacgaagt tgatttctct tgtgtgcaga gtgactgatt ttaaaggaca tgga | | | | 114 |

<210> SEQ ID NO 220
<211> LENGTH: 93
<212> TYPE: DNA
<213> ORGANISM: Homo sapien

<400> SEQUENCE: 220

| | | | | |
|---|---|---|---|---|
| actagccagc acaaaaggca gggtagcctg aattgctttc tgctctttac atttcttta | | | | 60 |
| aaataagcat ttagtgctca gtccctactg agt | | | | 93 |

<210> SEQ ID NO 221
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 221

| | | | | |
|---|---|---|---|---|
| actangtgca ggtgcgcaca aatatttgtc gatattccct tcatcttgga ttccatgagg | | | | 60 |

```
tcttttgccc agcctgtggc tctactgtag taagtttctg ctgatgagga gccagnatgc    120 ccccactac cttccctgac gctccccana aatcacccaa cctctgt                    167
```

<210> SEQ ID NO 222
<211> LENGTH: 351
<212> TYPE: DNA
<213> ORGANISM: Homo sapien

<400> SEQUENCE: 222

```
agggcgtggt gcggagggcg gtactgacct cattagtagg aggatgcatt ctggcacccc    60
gttcttcacc tgtcccccaa tccttaaaag gccatactgc ataaagtcaa caacagataa   120
atgtttgctg aattaaagga tggatgaaaa aaattaataa tgaatttttg cataatccaa   180
ttttctcttt tatatttcta gaagaagttt ctttgagcct attagatccc gggaatcttt   240
taggtgagca tgattagaga gcttgtaggt tgcttttaca tatatctggc atatttgagt   300
ctcgtatcaa aacaatagat tggtaaaggt ggtattattg tattgataag t            351
```

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223

```
aaaacaaaca aacaaaaaaa acaattcttc attcagaaaa attatcttag ggactgatat    60
tggtaattat ggtcaattta atwrtrttkt ggggcatttc cttacattgt cttgacaaga   120
ttaaaatgtc tgtgccaaaa ttttgtattt tatttggaga cttcttatca aaagtaatgc   180
tgccaaagga agtctaagga attagtagtg ttcccmtcac ttgtttggag tgtgctattc   240
taaaagattt tgatttcctg gaatgacaat tatattttaa ctttggtggg ggaaanagtt   300
ataggaccac agtcttcact tctgatactt gtaaattaat cttttattgc acttgttttg   360
accattaagc tatatgttta aaa                                            383
```

<210> SEQ ID NO 224
<211> LENGTH: 320
<212> TYPE: DNA
<213> ORGANISM: Homo sapien

<400> SEQUENCE: 224

```
cccctgaagg cttcttgtta gaaaatagta cagttacaac caataggaac aacaaaaga     60 aaaagtttgt gacattgtag tagggagtgt gtacccctta ctccccatca aaaaaaaaat   120
ggatacatgg ttaaaggata raagggcaat attttatcat atgttctaaa agagaaggaa   180
gagaaaatac tactttctcr aaatggaagc ccttaaaggt gctttgatac tgaaggacac   240
aaatgtggcc gtccatcctc ctttaragtt gcatgacttg gacacggtaa ctgttgcagt   300
tttaractcm gcattgtgac                                                320
```

<210> SEQ ID NO 225
<211> LENGTH: 1214
<212> TYPE: DNA
<213> ORGANISM: Homo sapien

<400> SEQUENCE: 225

-continued

```
gaggactgca gcccgcactc gcagccctgg caggcggcac tggtcatgga aaacgaattg      60
ttctgctcgg gcgtcctggt gcatccgcag tgggtgctgt cagccgcaca ctgtttccag     120
aactcctaca ccatcgggct gggcctgcac agtcttgagg ccgaccaaga gccagggagc     180
cagatggtgg aggccagcct ctccgtacgg cacccagagt acaacagacc cttgctcgct     240
aacgacctca tgctcatcaa gttggacgaa tccgtgtccg agtctgacac catccggagc     300
atcagcattg cttcgcagtg ccctaccgcg gggaactctt gcctcgtttc tggctggggt     360
ctgctggcga acggcagaat gcctaccgtg ctgcagtgcg tgaacgtgtc ggtggtgtct     420
gaggaggtct gcagtaagct ctatgacccg ctgtaccacc ccagcatgtt ctgcgccggc     480
ggagggcaag accagaagga ctcctgcaac ggtgactctg gggggcccct gatctgcaac     540
gggtacttgc agggccttgt gtctttcgga aaagcccgt gtggccaagt tggcgtgcca      600
ggtgtctaca ccaacctctg caaattcact gagtggatag agaaaaccgt ccaggccagt     660
taactctggg gactgggaac ccatgaaatt gaccccccaaa tacatcctgc ggaaggaatt    720
caggaatatc tgttcccagc ccctcctccc tcaggcccag gagtccaggc ccccagcccc    780
tcctccctca accaagggt acagatcccc agcccctcct ccctcagacc caggagtcca     840
gaccccccag cccctcctcc ctcagaccca ggagtccagc ccctcctccc tcagacccag     900
gagtccagac ccccagcccc ctcctccctc agacccaggg tccaggccc caacccctc     960 ctccctcaga ctcagaggtc caagccccca ccctccttt cccagaccc agaggtccag    1020 gtcccagccc ctcctccctc agaccagcg gtccaatgcc acctagactc tccctgtaca    1080
cagtgccccc ttgtggcacg ttgacccaac cttaccagtt ggttttcat tttttgtccc    1140 tttccctag atccagaaat aaagtctaag agaagcgcaa aaaaaaaaa aaaaaaaaa     1200 aaaaaaaaaa aaaa                                                    1214
```

<210> SEQ ID NO 226
<211> LENGTH: 119
<212> TYPE: DNA
<213> ORGANISM: Homo sapien

<400> SEQUENCE: 226

```
acccagtatg tgcagggaga cggaaccccca tgtgacagcc cactccacca gggttcccaa      60
agaacctggc ccagtcataa tcattcatcc tgacagtggc aataatcacg ataaccagt      119
```

<210> SEQ ID NO 227
<211> LENGTH: 818
<212> TYPE: DNA
<213> ORGANISM: Homo sapien

<400> SEQUENCE: 227

```
acaattcata gggacgacca atgaggacag ggaatgaacc cggctctccc ccagccctga      60
tttttgctac atatggggtc ccttttcatt cttttgcaaaa acactgggtt ttctgagaac     120
acggacggtt cttagcacaa tttgtgaaat ctgtgtaraa ccgggctttg caggggagat     180
aattttcctc ctctggagga aggtggtga ttgacaggca gggagacagt gacaaggcta     240
gagaaagcca cgctcggcct tctctgaacc aggatggaac ggcagacccc tgaaaacgaa     300
gcttgtcccc ttccaatcag ccacttctga gaaccccat ctaacttcct actggaaaag     360
agggcctcct caggagcagt ccaagagttt tcaaagataa cgtgacaact accatctaga     420
ggaaagggtg cacccctcagc agagaagccg agagcttaac tctggtcgtt tccagagaca     480
acctgctggc tgtcttggga tgcgcccagc cttttgagagg ccactacccc atgaacttct     540
```

```
gccatccact ggacatgaag ctgaggacac tgggcttcaa cactgagttg tcatgagagg    600
gacaggctct gccctcaagc cggctgaggg cagcaaccac tctcctcccc tttctcacgc    660
aaagccattc ccacaaatcc agaccatacc atgaagcaac gagacccaaa cagtttggct    720
caagaggata tgaggactgt ctcagcctgg ctttgggctg acaccatgca cacacacaag    780
gtccacttct aggttttcag cctagatggg agtcgtgt                            818

<210> SEQ ID NO 228
<211> LENGTH: 744
<212> TYPE: DNA
<213> ORGANISM: Homo sapien

<400> SEQUENCE: 228
actggagaca ctgttgaact tgatcaagac ccagaccacc ccaggtctcc ttcgtgggat     60
gtcatgacgt ttgacatacc tttgaacga gcctcctcct tggaagatgg aagaccgtgt    120
tcgtggccga cctggcctct cctggcctgt ttcttaagat gcggagtcac atttcaatgg    180
taggaaaagt ggcttcgtaa aatagaagag cagtcactgt ggaactacca aatggcgaga    240
tgctcggtgc acattggggt gctttgggat aaaagattta tgagccaact attctctggc    300
accagattct aggccagttt gttccactga agcttttccc acagcagtcc acctctgcag    360
gctggcagct gaatggcttg ccggtggctc tgtggcaaga tcacactgag atcgatgggt    420
gagaaggcta ggatgcttgt ctagtgttct tagctgtcac gttggctcct tccaggttgg    480
ccagacggtg ttggccactc ccttctaaaa cacaggcgcc ctcctggtga cagtgacccg    540
ccgtggtatg ccttggccca ttccagcagt cccagttatg catttcaagt ttggggtttg    600
ttcttttcgt taatgttcct ctgtgttgtc agctgtcttc atttcctggg ctaagcagca    660
ttgggagatg tggaccagag atccactcct taagaaccag tggcgaaaga cactttcttt    720
cttcactctg aagtagctgg tggt                                          744

<210> SEQ ID NO 229
<211> LENGTH: 300
<212> TYPE: DNA
<213> ORGANISM: Homo sapien

<400> SEQUENCE: 229
cgagtctggg ttttgtctat aaagtttgat ccctcctttt ctcatccaaa tcatgtgaac     60
cattacacat cgaaataaaa gaaaggtggc agacttgccc aacgccaggc tgacatgtgc    120 tgcaggggttg ttgtttttta attattattg ttagaaacgt cacccacagt ccctgttaat    180
ttgtatgtga cagccaactc tgagaaggtc ctatttttcc acctgcagag gatccagtct    240
cactaggctc ctccttgccc tcacactgga gtctccgcca gtgtgggtgc ccactgacat    300

<210> SEQ ID NO 230
<211> LENGTH: 301
<212> TYPE: DNA
<213> ORGANISM: Homo sapien

<400> SEQUENCE: 230
cagcagaaca aatacaaata tgaagagtgc aaagatctca taaaatctat gctgaggaat     60
gagcgacagt tcaaggagga gaagcttgca gagcagctca agcaagctga ggagctcagg    120
caatataaag tcctggttca cactcaggaa cgagagctga cccagttaag ggagaagttg    180
cgggaaggga gagatgcctc cctctcattg aatgagcatc tccaggccct cctcactccg    240
```

-continued

| | |
|---|---|
| gatgaaccgg acaagtccca ggggcaggac ctccaagaaa cagacctcgg ccgcgaccac | 300 |
| g | 301 |

<210> SEQ ID NO 231
<211> LENGTH: 301
<212> TYPE: DNA
<213> ORGANISM: Homo sapien

<400> SEQUENCE: 231

| | |
|---|---|
| gcaagcacgc tggcaaatct ctgtcaggtc agctccagag aagccattag tcattttagc | 60 |
| caggaactcc aagtccacat ccttggcaac tggggacttg cgcaggttag ccttgaggat | 120 |
| ggcaacacgg gacttctcat caggaagtgg gatgtagatg agctgatcaa gacggccagg | 180 |
| tctgaggatg gcaggatcaa tgatgtcagg ccggttggta ccgccaatga tgaacacatt | 240 |
| ttttttgtg gacatgccat ccatttctgt caggatctgg ttgatgactc ggtcagcagc | 300 |
| c | 301 |

<210> SEQ ID NO 232
<211> LENGTH: 301
<212> TYPE: DNA
<213> ORGANISM: Homo sapien

<400> SEQUENCE: 232

| | |
|---|---|
| agtaggtatt tcgtgagaag ttcaacacca aaactggaac atagttctcc ttcaagtgtt | 60 |
| ggcgacagcg gggcttcctg attctggaat ataactttgt gtaaattaac agccacctat | 120 |
| agaagagtcc atctgctgtg aaggagagac agagaactct ggttccgtc gtcctgtcca | 180 |
| cgtgctgtac caagtgctgg tgccagcctg ttacctgttc tcactgaaaa tctggctaat | 240 |
| gctcttgtgt atcacttctg attctgacaa tcaatcaatc aatggcctag agcactgact | 300 |
| g | 301 |

<210> SEQ ID NO 233
<211> LENGTH: 301
<212> TYPE: DNA
<213> ORGANISM: Homo sapien

<400> SEQUENCE: 233

| | |
|---|---|
| atgactgact tcccagtaag gctctctaag gggtaagtag gaggatccac aggatttgag | 60 |
| atgctaaggc cccagagatc gtttgatcca accctcttat tttcagaggg gaaaatgggg | 120 |
| cctagaagtt acagagcatc tagctggtgc gctggcaccc ctggcctcac acagactccc | 180 |
| gagtagctgg gactacaggc acacagtcac tgaagcaggc cctgttagca attctatgcg | 240 |
| tacaaattaa catgagatga gtagagactt tattgagaaa gcaagagaaa atcctatcaa | 300 |
| c | 301 |

<210> SEQ ID NO 234
<211> LENGTH: 301
<212> TYPE: DNA
<213> ORGANISM: Homo sapien

<400> SEQUENCE: 234

| | |
|---|---|
| aggtcctaca catcgagact catccatgat tgatatgaat ttaaaaatta caagcaaaga | 60 |
| cattttattc atcatgatgc tttcttttgt ttcttctttt cgtttctcc tttttctttt | 120 |
| tcaatttcag caacatactt ctcaatttct tcaggattta aaatcttgag ggattgatct | 180 |
| cgcctcatga cagcaagttc aatgttttg ccacctgact gaaccacttc caggagtgcc | 240 | ttgatcacca gcttaatggt cagatcatct gcttcaatgg cttcgtcagt atagttcttc    300 t                                                                    301

<210> SEQ ID NO 235
<211> LENGTH: 283
<212> TYPE: DNA
<213> ORGANISM: Homo sapien

<400> SEQUENCE: 235
tggggctgtg catcaggcgg gtttgagaaa tattcaattc tcagcagaag ccagaatttg     60
aattccctca tcttttaggg aatcatttac caggtttgga gaggattcag acagctcagg    120
tgctttcact aatgtctctg aacttctgtc cctctttgtt catggatagt ccaataaata    180
atgttatctt tgaactgatg ctcataggag agaatataag aactctgagt gatatcaaca    240
ttagggattc aaagaaatat tagatttaag ctcacactgg tca                      283

<210> SEQ ID NO 236
<211> LENGTH: 301
<212> TYPE: DNA
<213> ORGANISM: Homo sapien

<400> SEQUENCE: 236
aggtcctcca ccaactgcct gaagcacggt taaaattggg aagaagtata gtgcagcata     60
aatactttta aatcgatcag atttccctaa cccacatgca atcttcttca ccagaagagg    120
tcggagcagc atcattaata ccaagcagaa tgcgtaatag ataaatacaa tggtatatag    180
tgggtagacg gcttcatgag tacagtgtac tgtggtatcg taatctggac ttgggttgta    240
aagcatcgtg taccagtcag aaagcatcaa tactcgacat gaacgaatat aaagaacacc    300
a                                                                    301

<210> SEQ ID NO 237
<211> LENGTH: 301
<212> TYPE: DNA
<213> ORGANISM: Homo sapien

<400> SEQUENCE: 237
cagtggtagt ggtggtggac gtggcgttgg tcgtggtgcc tttttggtg cccgtcacaa      60 actcaatttt tgttcgctcc tttttggcct tttccaattt gtccatctca attttctggg    120
ccttggctaa tgcctcatag taggagtcct cagaccagca tggggatca aacatatcct     180 ttgggtagtt ggtgccaagc tcgtcaatgg cacagaatgg atcagcttct cgtaaatcta    240
gggttccgaa attctttctt cctttggata atgtagttca tatccattcc ctcctttatc    300
t                                                                    301

<210> SEQ ID NO 238
<211> LENGTH: 301
<212> TYPE: DNA
<213> ORGANISM: Homo sapien

<400> SEQUENCE: 238
gggcaggttt tttttttttt tttttgatg gtgcagaccc ttgctttatt tgtctgactt      60
gttcacagtt cagcccctg ctcagaaaac caacgggcca gctaaggaga ggaggaggca     120
ccttgagact tccggagtcg aggctctcca gggttcccca gcccatcaat cattttctgc    180
accccctgcc tgggaagcag ctccctgggg ggtgggaatg ggtgactaga agggatttca    240

-continued

```
gtgtgggacc cagggtctgt tcttcacagt aggaggtgga agggatgact aatttcttta    300
t                                                                   301

<210> SEQ ID NO 239
<211> LENGTH: 239
<212> TYPE: DNA
<213> ORGANISM: Homo sapien

<400> SEQUENCE: 239
ataagcagct agggaattct ttatttagta atgtcctaac ataaaagttc acataactgc     60
ttctgtcaaa ccatgatact gagctttgtg acaacccaga ataactaag agaaggcaaa    120
cataatacct tagagatcaa gaaacattta cacagttcaa ctgtttaaaa atagctcaac   180
attcagccag tgagtagagt gtgaatgcca gcatacacag tatacaggtc cttcaggga    239

<210> SEQ ID NO 240
<211> LENGTH: 300
<212> TYPE: DNA
<213> ORGANISM: Homo sapien

<400> SEQUENCE: 240
ggtcctaatg aagcagcagc ttccacattt taacgcaggt ttacggtgat actgtccttt     60
gggatctgcc ctccagtgga accttttaag gaagaagtgg gcccaagcta agttccacat   120
gctgggtgag ccagatgact tctgttccct ggtcactttc ttcaatgggg cgaatggggg   180
ctgccaggtt tttaaaatca tgcttcatct tgaagcacac ggtcacttca ccctcctcac   240
gctgtgggtg tactttgatg aaaatacca ctttgttggc cttctgaag ctataatgtc     300

<210> SEQ ID NO 241
<211> LENGTH: 301
<212> TYPE: DNA
<213> ORGANISM: Homo sapien

<400> SEQUENCE: 241
gaggtctggt gctgaggtct ctgggctagg aagaggagtt ctgtggagct ggaagccaga    60
cctctttgga ggaaactcca gcagctatgt tggtgtctct gagggaatgc aacaaggctg   120
ctcctccatg tattggaaaa ctgcaaactg gactcaactg gaaggaagtg ctgctgccag   180
tgtgaagaac cagcctgagg tgacagaaac ggaagcaaac aggaacagcc agtcttttct   240
tcctcctcct gtcatacggt ctctctcaag catccttttgt tgtcagggc ctaaaaggga   300
g                                                                   301

<210> SEQ ID NO 242
<211> LENGTH: 301
<212> TYPE: DNA
<213> ORGANISM: Homo sapien

<400> SEQUENCE: 242
ccgaggtcct gggatgcaac caatcactct gtttcacgtg acttttatca ccatacaatt     60
tgtggcattt cctcattttc tacattgtag aatcaagagt gtaaataaat gtatatcgat   120
gtcttcaaga atatatcatt ccttttttcac tagaacccat tcaaaatata agtcaagaat   180
cttaatatca acaaatatat caagcaaact ggaaggcaga ataactacca taatttagta   240
taagtaccca agttttata aatcaaaagc cctaatgata accattttta gaattcaatc   300
a                                                                   301
```

<210> SEQ ID NO 243
<211> LENGTH: 301
<212> TYPE: DNA
<213> ORGANISM: Homo sapien

<400> SEQUENCE: 243

| aggtaagtcc cagtttgaag ctcaaaagat ctggtatgag cataggctca tcgacgacat | 60 |
| ggtggcccaa gctatgaaat cagagggagg cttcatctgg gcctgtaaaa actatgatgg | 120 |
| tgacgtgcag tcggactctg tggcccaagg gtatggctct ctcggcatga tgaccagcgt | 180 |
| gctggtttgt ccagatggca agacagtaga agcagaggct gcccacggga ctgtaacccg | 240 |
| tcactaccgc atgttccaga aggacagga gacgtccacc aatcccattg cttccatttt | 300 |
| t | 301 |

<210> SEQ ID NO 244
<211> LENGTH: 300
<212> TYPE: DNA
<213> ORGANISM: Homo sapien

<400> SEQUENCE: 244

| gctggtttgc aagaatgaaa tgaatgattc tacagctagg acttaacctt gaaatggaaa | 60 |
| gtcatgcaat cccatttgca ggatctgtct gtgcacatgc ctctgtagag agcagcattc | 120 |
| ccagggacct tggaaacagt tgacactgta aggtgcttgc tccccaagac acatcctaaa | 180 |
| aggtgttgta atggtgaaaa cgtcttcctt ctttattgcc ccttcttatt tatgtgaaca | 240 |
| actgtttgtc ttttgtgtat cttttttaaa ctgtaaagtt caattgtgaa atgaatatc | 300 |

<210> SEQ ID NO 245
<211> LENGTH: 301
<212> TYPE: DNA
<213> ORGANISM: Homo sapien

<400> SEQUENCE: 245

| gtctgagtat ttaaaatgtt attgaaatta tccccaacca atgttagaaa agaaagaggt | 60 |
| tatatactta gataaaaaat gaggtgaatt actatccatt gaaatcatgc tcttagaatt | 120 |
| aaggccagga gatattgtca ttaatgtara cttcaggaca ctagagtata gcagccctat | 180 |
| gttttcaaag agcagagatg caattaaata ttgtttagca tcaaaaggc cactcaatac | 240 |
| agctaataaa atgaaagacc taatttctaa agcaattctt tataatttac aaagttttaa | 300 |
| g | 301 |

<210> SEQ ID NO 246
<211> LENGTH: 301
<212> TYPE: DNA
<213> ORGANISM: Homo sapien

<400> SEQUENCE: 246

| ggtctgtcct acaatgcctg cttcttgaaa gaagtcggca ctttctagaa tagctaaata | 60 |
| acctgggctt attttaaaga actatttgta gctcagattg gttttcctat ggctaaaata | 120 |
| agtgcttctt gtgaaaatta ataaaacag ttaattcaaa gccttgatat atgttaccac | 180 |
| taacaatcat actaaatata ttttgaagta caaagtttga catgctctaa agtgacaacc | 240 |
| caaatgtgtc ttacaaaaca cgttcctaac aaggtatgct ttacactacc aatgcagaaa | 300 |
| c | 301 |

<210> SEQ ID NO 247

```
<211> LENGTH: 301
<212> TYPE: DNA
<213> ORGANISM: Homo sapien

<400> SEQUENCE: 247
aggtcctttg gcagggctca tggatcagag ctcaaactgg agggaaaggc atttcgggta      60
gcctaagagg gcgactggcg gcagcacaac caaggaaggc aaggttgttt cccccacgct     120
gtgtcctgtg ttcaggtgcg acacacaatc ctcatgggaa caggatcacc catgcgctgc    180
ccttgatgat caaggttggg gcttaagtgg attaagggag gcaagttctg ggttccttgc    240
cttttcaaac catgaagtca ggctctgtat ccctcctttt cctaactgat attctaacta    300
a                                                                    301

<210> SEQ ID NO 248
<211> LENGTH: 301
<212> TYPE: DNA
<213> ORGANISM: Homo sapien

<400> SEQUENCE: 248
aggtccttgg agatgccatt tcagccgaag gactcttctw ttcggaagta caccctcact     60
attaggaaga ttcttagggg taatttttct gaggaaggag aactagccaa cttaagaatt    120
acaggaagaa agtggtttgg aagacagcca agaaataaa agcagattaa attgtatcag    180
gtacattcca gcctgttggc aactccataa aaacatttca gattttaatc ccgaatttag    240
ctaatgagac tggattttttg tttttatgt tgtgtgtcgc agagctaaaa actcagttcc    300
c                                                                    301

<210> SEQ ID NO 249
<211> LENGTH: 301
<212> TYPE: DNA
<213> ORGANISM: Homo sapien

<400> SEQUENCE: 249
gtccagagga agcacctggt gctgaactag gcttgccctg ctgtgaactt gcacttggag     60
ccctgacgct gctgttctcc ccgaaaaacc cgaccgacct ccgcgatctc cgtcccgccc    120
ccagggagac acagcagtga ctcagagctg gtcgcacact gtgcctccct cctcaccgcc    180
catcgtaatg aattattttg aaaattaatt ccaccatcct ttcagattct ggatggaaag    240
actgaatctt tgactcagaa ttgtttgctg aaaagaatga tgtgactttc ttagtcattt    300
a                                                                    301

<210> SEQ ID NO 250
<211> LENGTH: 301
<212> TYPE: DNA
<213> ORGANISM: Homo sapien

<400> SEQUENCE: 250
ggtctgtgac aaggacttgc aggctgtggg aggcaagtga cccttaacac tacacttctc     60
cttatcttta ttggcttgat aaacataatt atttctaaca ctagcttatt tccagttgcc    120
cataagcaca tcagtacttt tctctggctg aatagtaaaa ctaaagtatg gtacatctac    180
ctaaaagact actatgtgga ataatacata ctaatgaagt attacatgat ttaaagacta    240
caataaaacc aaacatgctt ataacattaa gaaaacaat aaagatacat gattgaaacc    300
a                                                                    301
```

<210> SEQ ID NO 251
<211> LENGTH: 301
<212> TYPE: DNA
<213> ORGANISM: Homo sapien

<400> SEQUENCE: 251

| gccgaggtcc tacatttggc ccagtttccc cctgcatcct ctccagggcc cctgcctcat | 60 |
| agacaacctc atagagcata ggagaactgg ttgccctggg ggcaggggga ctgtctggat | 120 |
| ggcagggtc ctcaaaaatg ccactgtcac tgccaggaaa tgcttctgag cagtacacct | 180 |
| cattgggatc aatgaaaagc ttcaagaaat cttcaggctc actctcttga aggcccggaa | 240 |
| cctctggagg ggggcagtgg aatcccagct ccaggacgga tcctgtcgaa aagatatcct | 300 |
| c | 301 |

<210> SEQ ID NO 252
<211> LENGTH: 301
<212> TYPE: DNA
<213> ORGANISM: Homo sapien

<400> SEQUENCE: 252

| gcaaccaatc actctgtttc acgtgacttt tatcaccata caatttgtgg catttcctca | 60 |
| ttttctacat tgtagaatca agagtgtaaa taaatgtata tcgatgtctt caagaatata | 120 |
| tcattccttt tcactagga acccattcaa aatataagtc aagaatctta atatcaacaa | 180 |
| atatatcaag caaactggaa ggcagaataa ctaccataat ttagtataag tacccaaagt | 240 |
| tttataaatc aaaagcccta atgataacca tttttagaat tcaatcatca ctgtagaatc | 300 |
| a | 301 |

<210> SEQ ID NO 253
<211> LENGTH: 301
<212> TYPE: DNA
<213> ORGANISM: Homo sapien

<400> SEQUENCE: 253

| ttccctaaga agatgttatt tgttgggtt ttgttccccc tccatctcga ttctcgtacc | 60 |
| caactaaaaa aaaaaaataa agaaaaaatg tgctgcgttc tgaaaaataa ctccttagct | 120 |
| tggtctgatt gttttcagac cttaaaatat aaacttgttt cacaagctttt aatccatgtg | 180 |
| gattttttt cttagagaac cacaaaacat aaaaggagca agtcggactg aatacctgtt | 240 |
| tccatagtgc ccacagggta ttcctcacat tttctccata ggaaaatgct ttttcccaag | 300 |
| g | 301 |

<210> SEQ ID NO 254
<211> LENGTH: 301
<212> TYPE: DNA
<213> ORGANISM: Homo sapien

<400> SEQUENCE: 254

| cgctgcgcct ttcccttggg ggaggggcaa ggccagaggg ggtccaagtg cagcacgagg | 60 |
| aacttgacca attcccttga agcgggtggg ttaaaccctg taaatgggaa caaaatcccc | 120 |
| ccaaatctct tcatcttacc ctggtggact cctgactgta gaatttttg gttgaaacaa | 180 |
| gaaaaaata aagctttgga cttttcaagg ttgcttaaca ggtactgaaa gactggcctc | 240 |
| acttaaactg agccaggaaa agctgcagat ttattaatgg gtgtgttagt gtgcagtgcc | 300 |
| t | 301 |

<210> SEQ ID NO 255
<211> LENGTH: 302
<212> TYPE: DNA
<213> ORGANISM: Homo sapien

<400> SEQUENCE: 255

```
agcttttttt tttttttttt tttttttttt ttcattaaaa aatagtgctc tttattataa      60
attactgaaa tgtttctttt ctgaatataa atataaatat gtgcaaagtt tgacttggat     120
tgggattttg ttgagttctt caagcatctc ctaataccct caagggcctg agtaggggg     180
aggaaaaagg actggaggtg gaatctttat aaaaaacaag agtgattgag gcagattgta    240
aacattatta aaaacaaga aacaaacaaa aaatagaga aaaaaaccac cccaacacac      300
aa                                                                   302
```

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256

```
gttccagaaa acattgaagg tggcttccca aagtctaact agggataccc cctctagcct     60
aggaccctcc tccccacacc tcaatccacc aaaccatcca taatgcaccc agataggccc    120
accccaaaa gcctggacac cttgagcaca cagttatgac caggacagac tcatctctat    180
aggcaaatag ctgctggcaa actggcatta cctggtttgt ggggatgggg gggcaagtgt    240
gtggcctctc ggcctggtta gcaagaacat tcagggtagg cctaagttan tcgtgttagt    300
t                                                                    301
```

<210> SEQ ID NO 257
<211> LENGTH: 301
<212> TYPE: DNA
<213> ORGANISM: Homo sapien

<400> SEQUENCE: 257

```
gttgtggagg aactctggct tgctcattaa gtcctactga ttttcactat cccctgaatt     60
tccccactta ttttgtctt tcactatcgc aggccttaga agaggtctac ctgcctccag    120
tcttacctag tccagtctac cccctggagt tagaatggcc atcctgaagt gaaaagtaat    180
gtcacattac tcccttcagt gatttcttgt agaagtgcca atccctgaat gccaccaaga    240
tcttaatctt cacatcttta atcttatctc tttgactcct ctttacaccg gagaaggctc    300
c                                                                    301
```

<210> SEQ ID NO 258
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 258

```
cagcagtagt agatgccgta tgccagcacg cccagcactc ccaggatcag caccagcacc     60
aggggcccag ccaccaggcg cagaagcaag ataaacagta ggctcaagac cagagccacc    120
```

```
cccagggcaa caagaatcca ataccaggac tgggcaaaat cttcaaagat cttaacactg        180
atgtctcggg cattgaggct gtcaataana cgctgatccc ctgctgtatg gtggtgtcat        240
tggtgatccc tgggagcgcc ggtggagtaa cgttggtcca tggaaagcag cgcccacaac        300
t                                                                       301

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259
tcatatatgc aaacaaatgc agactangcc tcaggcagag actaaaggac atctcttggg         60
gtgtcctgaa gtgatttgga cccctgaggg cagacaccta agtaggaatc ccagtgggaa        120
gcaaagccat aaggaagccc aggattcctt gtgatcagga agtgggccag gaaggtctgt        180
tccagctcac atctcatctg catgcagcac ggaccggatg cgcccactgg gtcttggctt        240
ccctcccatc ttctcaagca gtgtccttgt tgagccattt gcatccttgg ctccaggtgg        300
c                                                                       301

<210> SEQ ID NO 260
<211> LENGTH: 301
<212> TYPE: DNA
<213> ORGANISM: Homo sapien

<400> SEQUENCE: 260 tttttttct ccctaaggaa aaagaaggaa caagtctcat aaaaccaaat aagcaatggt          60
aaggtgtctt aacttgaaaa agattaggag tcactggttt acaagttata attgaatgaa        120
agaactgtaa cagccacagt tggccatttc atgccaatgg cagcaaacaa caggattaac        180
tagggcaaaa taaataagtg tgtggaagcc ctgataagtg cttaataaac agactgattc        240
actgagacat cagtacctgc ccgggcggcc gctcgagccg aattctgcag atatccatca        300
c                                                                       301

<210> SEQ ID NO 261
<211> LENGTH: 301
<212> TYPE: DNA
<213> ORGANISM: Homo sapien

<400> SEQUENCE: 261
aaatattcga gcaaatcctg taactaatgt gtctccataa aaggctttga actcagtgaa         60
tctgcttcca tccacgattc tagcaatgac ctctcggaca tcaaagctcc tcttaaggtt        120
agcaccaact attccataca attcatcagc aggaaataaa ggctcttcag aaggttcaat        180
ggtgacatcc aatttcttct gataatttag attcctcaca accttcctag ttaagtgaag        240
ggcatgatga tcatccaaag cccagtggtc acttactcca gactttctgc aatgaagatc        300
a                                                                       301

<210> SEQ ID NO 262
<211> LENGTH: 301
<212> TYPE: DNA
<213> ORGANISM: Homo sapien
```

<400> SEQUENCE: 262

```
gaggagagcc tgttacagca tttgtaagca cagaatactc caggagtatt tgtaattgtc      60
tgtgagcttc ttgccgcaag tctctcagaa atttaaaaag atgcaaatcc ctgagtcacc     120
cctagacttc ctaaaccaga tcctctgggg ctggaacctg gcactctgca tttgtaatga     180
gggctttctg gtgcacacct aattttgtgc atctttgccc taaatcctgg attagtgccc     240
catcattacc cccacattat aatgggatag attcagagca gatactctcc agcaaagaat     300
c                                                                     301
```

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263

```
tttagcttgt ggtaaatgac tcacaaaact gattttaaaa tcaagttaat gtgaattttg      60
aaaattacta cttaatccta attcacaata acaatggcat taaggtttga cttgagttgg     120
ttcttagtat tatttatggt aaataggctc ttaccacttg caaataactg gccacatcat     180
taatgactga cttcccagta aggctctcta agggtaagt angaggatcc acaggatttg      240
agatgctaag gccccagaga tcgtttgatc caaccctctt attttcagag gggaaaatgg     300
g                                                                     301
```

<210> SEQ ID NO 264
<211> LENGTH: 301
<212> TYPE: DNA
<213> ORGANISM: Homo sapien

<400> SEQUENCE: 264

```
aaagacgtta aaccactcta ctaccacttg tggaactctc aaagggtaaa tgacaaascc      60
aatgaatgac tctaaaaaca atatttacat ttaatggttt gtagacaata aaaaaacaag     120
gtggatagat ctagaattgt aacattttaa gaaaaccata scatttgaca gatgagaaag     180
ctcaattata gatgcaaagt tataactaaa ctactatagt agtaaagaaa tacatttcac     240
acccttcata taaattcact atcttggctt gaggcactcc ataaaatgta tcacgtgcat     300
a                                                                     301
```

<210> SEQ ID NO 265
<211> LENGTH: 301
<212> TYPE: DNA
<213> ORGANISM: Homo sapien

<400> SEQUENCE: 265

```
tgcccaagtt atgtgtaagt gtatccgcac ccagaggtaa aactacactg tcatctttgt      60
cttcttgtga cgcagtattt cttctctggg gagaagccgg gaagtcttct cctggctcta     120
catattcttg gaagtctcta atcaactttt gttccatttg tttcatttct tcaggaggga     180
ttttcagttt gtcaacatgt tctctaacaa cacttgccca tttctgtaaa gaatccaaag     240
cagtccaagg ctttgacatg tcaacaacca gcataactag agtatccttc agagatacgg     300
c                                                                     301
```

<210> SEQ ID NO 266
<211> LENGTH: 301
<212> TYPE: DNA
<213> ORGANISM: Homo sapien

<400> SEQUENCE: 266

| taccgtctgc | ccttcctccc | atccaggcca | tctgcgaatc | tacatgggtc | ctcctattcg | 60 |
| acaccagatc | actctttcct | ctacccacag | gcttgctatg | agcaagagac | acaacctcct | 120 |
| ctcttctgtg | ttccagcttc | ttttcctgtt | cttcccaccc | cttaagttct | attcctgggg | 180 |
| atagagacac | caatacccat | aacctctctc | ctaagcctcc | ttataaccca | gggtgcacag | 240 |
| cacagactcc | tgacaactgg | taaggccaat | gaactgggag | ctcacagctg | ctgtgcctg  | 300 |
| a | | | | | | 301 |

<210> SEQ ID NO 267
<211> LENGTH: 301
<212> TYPE: DNA
<213> ORGANISM: Homo sapien

<400> SEQUENCE: 267

| aaagagcaca | ggccagctca | gcctgccctg | gccatctaga | ctcagcctgg | ctccatgggg | 60 |
| gttctcagtg | ctgagtccat | ccaggaaaag | ctcacctaga | ccttctgagg | ctgaatcttc | 120 |
| atcctcacag | gcagcttctg | agagcctgat | attcctagcc | ttgatggtct | ggagtaaagc | 180 |
| ctcattctga | ttcctctcct | tcttttcttt | caagttggct | ttcctcacat | ccctctgttc | 240 |
| aattcgcttc | agcttgtctg | ctttagccct | catttccaga | agcttcttct | ctttggcatc | 300 |
| t | | | | | | 301 |

<210> SEQ ID NO 268
<211> LENGTH: 301
<212> TYPE: DNA
<213> ORGANISM: Homo sapien

<400> SEQUENCE: 268

| aatgtctcac | tcaactactt | cccagcctac | cgtggcctaa | ttctgggagt | tttcttctta | 60 |
| gatcttggga | gagctggttc | ttctaaggag | aaggaggaag | gacagatgta | actttggatc | 120 |
| tcgaagagga | agtctaatgg | aagtaattag | tcaacggtcc | ttgtttagac | tcttggaata | 180 |
| tgctgggtgg | ctcagtgagc | cctttggag  | aaagcaagta | ttattcttaa | ggagtaacca | 240 |
| cttcccattg | ttctactttc | taccatcatc | aattgtatat | tatgtattct | ttggagaact | 300 |
| a | | | | | | 301 |

<210> SEQ ID NO 269
<211> LENGTH: 301
<212> TYPE: DNA
<213> ORGANISM: Homo sapien

<400> SEQUENCE: 269

| taacaatata | cactagctat | cttttaact  | gtccatcatt | agcaccaatg | aagattcaat | 60 |
| aaaattacct | ttattcacac | atctcaaaac | aattctgcaa | attcttagtg | aagtttaact | 120 |
| atagtcacag | accttaaata | ttcacattgt | tttctatgtc | tactgaaaat | aagttcacta | 180 |
| ctttctgga  | tattctttac | aaaatcttat | taaaattcct | ggtattatca | ccccaatta  | 240 |
| tacagtagca | caaccacctt | atgtagtttt | tacatgatag | ctctgtagaa | gtttcacatc | 300 |
| t | | | | | | 301 |

<210> SEQ ID NO 270
<211> LENGTH: 301
<212> TYPE: DNA
<213> ORGANISM: Homo sapien

<400> SEQUENCE: 270

| | | | | | |
|---|---|---|---|---|---|
| cattgaagag | cttttgcgaa | acatcagaac | acaagtgctt | ataaaattaa | ttaagcctta | 60 |
| cacaagaata | catattcctt | ttatttctaa | ggagttaaac | atagatgtag | ctgatgtgga | 120 |
| gagcttgctg | gtgcagtgca | tattggataa | cactattcat | ggccgaattg | atcaagtcaa | 180 |
| ccaactcctt | gaactggatc | atcagaagaa | gggtggtgca | cgatatactg | cactagataa | 240 |
| tggaccaacc | aactaaattc | tctcaccagg | ctgtatcagt | aaactggctt | aacagaaaac | 300 |
| a | | | | | | 301 |

<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271

| | | | | | |
|---|---|---|---|---|---|
| aaaaggttct | cataagatta | acaatttaaa | taaatatttg | atagaacatt | ctttctcatt | 60 |
| tttatagctc | atctttaggg | ttgatattca | gttcatgctt | cccttgctgt | tcttgatcca | 120 |
| gaattgcaat | cacttcatca | gcctgtattc | gctccaattc | tctataaagt | gggtccaagg | 180 |
| tgaaccacag | agccacagca | cacctctttc | ccttggtgac | tgccttcacc | ccatganggt | 240 |
| tctctcctcc | agatganaac | tgatcatgcg | cccacatttt | gggttttata | gaagcagtca | 300 |
| c | | | | | | 301 |

<210> SEQ ID NO 272
<211> LENGTH: 301
<212> TYPE: DNA
<213> ORGANISM: Homo sapien

<400> SEQUENCE: 272

| | | | | | |
|---|---|---|---|---|---|
| taaattgcta | agccacagat | aacaccaatc | aaatggaaca | aatcactgtc | ttcaaatgtc | 60 |
| ttatcagaaa | accaaatgag | cctggaatct | tcataatacc | taaacatgcc | gtatttagga | 120 |
| tccaataatt | ccctcatgat | gagcaagaaa | aattctttgc | gcacccctcc | tgcatccaca | 180 |
| gcatcttctc | caacaaatat | aaccttgagt | ggcttcttgt | aatctatgtt | ctttgttttc | 240 |
| ctaaggactt | ccattgcatc | tcctacaata | ttttctctac | gcaccactag | aattaagcag | 300 |
| g | | | | | | 301 |

<210> SEQ ID NO 273
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 273

| | | | | | |
|---|---|---|---|---|---|
| acatgtgtgt | atgtgtatct | ttgggaaaan | aanaagacat | cttgtttayt | attttttttgg | 60 |
| agagangctg | ggacatggat | aatcacwtaa | tttgctayta | tyactttaat | ctgactygaa | 120 |

```
gaaccgtcta aaaataaaat ttaccatgtc dtatattcct tatagtatgc ttatttcacc       180
ttytttctgt ccagagagag tatcagtgac ananatttma gggtgaaamac atgmattggt      240 gggacttnty tttacngagm accctgcccg sgcgccctcg makcngantt ccgcsananc       300
t                                                                       301
```

```
<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274
cttatatact ctttctcaga ggcaaaagag gagatgggta atgtagacaa ttctttgagg       60
aacagtaaat gattattaga gagaangaat ggaccaagga gacagaaatt aacttgtaaa      120
tgattctctt tggaatctga atgagatcaa gaggccagct ttagcttgtg aaaagtcca       180 tctaggtatg gttgcattct cgtcttcttt tctgcagtag ataatgaggt aaccgaaggc      240
aattgtgctt cttttgataa gaagctttct tggtcatatc aggaaattcc aganaaagtc      300
c                                                                       301
```

```
<210> SEQ ID NO 275
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275
tcggtgtcag cagcacgtgg cattgaacat tgcaatgtgg agcccaaacc acagaaaatg       60
gggtgaaatt ggccaacttt ctattaactt atgttggcaa ttttgccacc aacagtaagc      120
tggcccttct aataaaagaa aattgaaagg tttctcacta aacggaatta agtagtggag      180
tcaagagact cccaggcctc agcgtacctg cccgggcggc cgctcgaagc cgaattctgc      240
agatatccat cacactggcg gncgctcgan catgcatcta gaaggnccaa ttcgccctat      300
a                                                                       301
```

```
<210> SEQ ID NO 276
<211> LENGTH: 301
<212> TYPE: DNA
<213> ORGANISM: Homo sapien

<400> SEQUENCE: 276
tgtacacata ctcaataaat aaatgactgc attgtggtat tattactata ctgattatat       60
ttatcatgtg acttctaatt agaaaatgta tccaaaagca aaacagcaga tatacaaaat      120
taaagagaca gaagatagac attaacagat aaggcaactt atacattgag aatccaaatc      180
caatacattt aaacatttgg gaatgagggg ggacaaatgg aagccagatc aaatttgtgt      240
aaaactattc agtatgtttc ccttgcttca tgtctgagaa ggctctcctt caatggggat      300
g                                                                       301
```

```
<210> SEQ ID NO 277
```

```
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277
tttgttgatg tcagtatttt attacttgcg ttatgagtgc tcacctggga aattctaaag      60
atacagagga cttggaggaa gcagagcaac tgaatttaat ttaaaagaag gaaaacattg     120
gaatcatggc actcctgata ctttcccaaa tcaacactct caatgcccca ccctcgtcct     180
caccatagtg gggagactaa agtggccacg gatttgcctt angtgtgcag tgcgttctga     240
gttcnctgtc gattacatct gaccagtctc cttttccga agtccntccg ttcaatcttg     300
c                                                                     301

<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278
taccactaca ctccagcctg ggcaacagag caagacctgt ctcaaagcat aaaatggaat      60
aacatatcaa atgaaacagg gaaaatgaag ctgacaattt atggaagcca gggcttgtca     120
cagtctctac tgttattatg cattacctgg gaatttatat aagcccttaa taataatgcc     180
aatgaacatc tcatgtgtgc tcacaatgtt ctggcactat tataagtgct tcacaggttt     240
tatgtgttct tcgtaacttt atggantagg tactcggccg cgaacacgct aagccgaatt     300
c                                                                     301

<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279
aaagcaggaa tgacaaagct tgcttttctg gtatgttcta ggtgtattgt gacttttact      60
gttatattaa ttgccaatat aagtaaatat agattatata tgtatagtgt ttcacaaagc     120
ttagaccttt accttccagc caccccacag tgcttgatat ttcagagtca gtcattggtt     180
atacatgtgt agttccaaag cacataagct agaanaanaa atatttctag ggagcactac     240
catctgtttt cacatgaaat gccacacaca tagaactcca acatcaattt cattgcacag     300
a                                                                     301

<210> SEQ ID NO 280
<211> LENGTH: 301
<212> TYPE: DNA
<213> ORGANISM: Homo sapien

<400> SEQUENCE: 280
ggtactggag ttttcctccc ctgtgaaaac gtaactactg ttgggagtga attgaggatg      60
```

```
tagaaaggtg gtggaaccaa attgtggtca atggaaatag gagaatatgg ttctcactct    120
tgagaaaaaa acctaagatt agcccaggta gttgcctgta acttcagttt ttctgcctgg    180
gtttgatata gtttagggtt ggggttagat taagatctaa attacatcag gacaaagaga    240
cagactatta actccacagt taattaagga ggtatgttcc atgtttattt gttaaagcag    300
t                                                                    301
```

<210> SEQ ID NO 281
<211> LENGTH: 301
<212> TYPE: DNA
<213> ORGANISM: Homo sapien

<400> SEQUENCE: 281

```
aggtacaaga aggggaatgg gaaagagctg ctgctgtggc attgttcaac ttggatattc     60
gccgagcaat ccaaatcctg aatgaagggg catcttctga aaaggagat ctgaatctca     120 atgtggtagc aatggcttta tcgggttata cggatgagaa gaactcccct tggagagaaa    180
tgtgtagcac actgcgatta cagctaaata acccgtattt gtgtgtcatg tttgcatttc    240
tgacaagtga aacaggatct tacgatggag ttttgtatga aaacaaagtt gcagtaccctc   300 g                                                                    301
```

<210> SEQ ID NO 282
<211> LENGTH: 301
<212> TYPE: DNA
<213> ORGANISM: Homo sapien

<400> SEQUENCE: 282

```
caggtactac agaattaaaa tactgacaag caagtagttt cttggcgtgc acgaattgca     60
tccagaaccc aaaaattaag aaattcaaaa agacattttg tgggcacctg ctagcacaga    120
agcgcagaag caaagcccag gcagaaccat gctaaccttca cagctcagcc tgcacagaag    180
cgcagaagca aagcccaggc agaaccatgc taaccttaca gctcagcctg cacagaagcg    240
cagaagcaaa gcccaggcag aacatgctaa ccttacagct cagcctgcac agaagcacag    300
a                                                                    301
```

<210> SEQ ID NO 283
<211> LENGTH: 301
<212> TYPE: DNA
<213> ORGANISM: Homo sapien

<400> SEQUENCE: 283

```
atctgtatac ggcagacaaa ctttatarag tgtagagagg tgagcgaaag gatgcaaaag     60
cactttgagg gctttataat aatatgctgc ttgaaaaaaa aaatgtgtag ttgatactca    120
gtgcatctcc agacatagta aggggttgct ctgaccaatc aggtgatcat ttttctatc     180 acttcccagg tttatgcaa aaatttgtt aaattctata atggtgatat gcatctttta    240
ggaaacatat acatttttaa aaatctattt tatgtaagaa ctgacagacg aatttgcttt    300
g                                                                    301
```

<210> SEQ ID NO 284
<211> LENGTH: 301
<212> TYPE: DNA
<213> ORGANISM: Homo sapien

<400> SEQUENCE: 284

```
caggtacaaa acgctattaa gtggcttaga atttgaacat ttgtggtctt tatttacttt    60
gcttcgtgtg tgggcaaagc aacatcttcc ctaaatatat attaccaaga aaagcaagaa   120
gcagattagg ttttttgacaa aacaaacagg ccaaaagggg gctgacctgg agcagagcat   180
ggtgagaggc aaggcatgag agggcaagtt tgttgtggac agatctgtgc ctactttatt   240
actggagtaa agaaaacaa agttcattga tgtcgaagga tatatacagt gttagaaatt   300
a                                                                   301
```

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285

```
acatcaccat gatcggatcc cccacccatt atacgttgta tgtttacata aatactcttc    60
aatgatcatt agtgttttaa aaaaaatact gaaaactcct tctgcatccc aatctctaac   120
caggaaagca aatgctattt acagacctgc aagccctccc tcaaacnaaa ctatttctgg   180
attaaatatg tctgacttct tttgaggtca cacgactagg caaatgctat ttacgatctg   240
caaaagctgt tgaagagtc aaagccccca tgtgaacacg atttctggac cctgtaacag   300
t                                                                   301
```

<210> SEQ ID NO 286
<211> LENGTH: 301
<212> TYPE: DNA
<213> ORGANISM: Homo sapien

<400> SEQUENCE: 286

```
taccactgca ttccagcctg ggtgacagag tgagactccg tctccaaaaa aaactttgct    60
tgtatattat ttttgcctta cagtggatca ttctagtagg aaaggacagt aagattttt   120 atcaaaatgt gtcatgccag taagagatgt tatattcttt tctcatttct tccccaccca   180 aaataagct accatatagc ttataagtct caaattttg cctttactta aaatgtgatt    240
gtttctgttc attgtgtatg cttcatcacc tatattaggc aaattccatt ttttccttg   300 t                                                                   301
```

<210> SEQ ID NO 287
<211> LENGTH: 301
<212> TYPE: DNA
<213> ORGANISM: Homo sapien

<400> SEQUENCE: 287

```
tacagatctg ggaactaaat attaaaaatg agtgtggctg gatatatgga gaatgttggg    60
cccagaagga acgtagagat cagatattac aacagctttg ttttgagggt tagaaatatg   120
aaatgatttg gttatgaacg cacagtttag gcagcagggc cagaatcctg accctctgcc   180
ccgtggttat ctcctcccca gcttggctgc ctcatgttat cacagtattc cattttgttt   240
gttgcatgtc ttgtgaagcc atcaagattt tctcgtctgt tttcctctca ttggtaatgc   300
t                                                                   301
```

<210> SEQ ID NO 288
<211> LENGTH: 301
<212> TYPE: DNA

<213> ORGANISM: Homo sapien

<400> SEQUENCE: 288

| gtacacctaa ctgcaaggac agctgaggaa tgtaatgggc agccgctttt aaagaagtag | 60 |
| agtcaatagg aagacaaatt ccagttccag ctcagtctgg gtatctgcaa agctgcaaaa | 120 |
| gatctttaaa gacaatttca agagaatatt tccttaaagt tggcaatttg agatcatac | 180 |
| aaaagcatct gcttttgtga tttaatttag ctcatctggc cactggaaga atccaaacag | 240 |
| tctgccttaa ttttggatga atgcatgatg gaaattcaat aatttagaaa gttaaaaaaa | 300 |
| a | 301 |

<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

| ggtacactgt ttccatgtta tgtttctaca cattgctacc tcagtgctcc tggaaactta | 60 |
| gcttttgatg tctccaagta gtccaccttc atttaactct ttgaaactgt atcatctttg | 120 |
| ccaagtaaga gtggtggcct atttcagctg cttttgacaaa atgactggct cctgacttaa | 180 |
| cgttctataa atgaatgtgc tgaagcaaag tgcccatggt ggcggcgaan aagagaaaga | 240 |
| tgtgttttgt tttggactct ctgtggtccc ttccaatgct gtgggtttcc aaccagngga | 300 |
| a | 301 |

<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290

| acactgagct cttcttgata aatatacaga atgcttggca tatacaagat tctatactac | 60 |
| tgactgatct gttcatttct ctcacagctc ttaccccccaa aagcttttcc accctaagtg | 120 |
| ttctgacctc cttttctaat cacagtaggg atagaggcag anccacctac aatgaacatg | 180 |
| gagttctatc aagaggcaga aacagcacag aatcccagtt ttaccattcg ctagcagtgc | 240 |
| tgccttgaac aaaaacattt ctccatgtct cattttcttc atgcctcaag taacagtgag | 300 |
| a | 301 |

<210> SEQ ID NO 291
<211> LENGTH: 301
<212> TYPE: DNA
<213> ORGANISM: Homo sapien

<400> SEQUENCE: 291

| caggtaccaa tttcttctat cctagaaaca tttcatttta tgttgttgaa acataacaac | 60 |
| tatatcagct agatttttt tctatgcttt acctgctatg gaaaatttga cacattctgc | 120 |
| tttactcttt tgtttatagg tgaatcacaa aatgtatttt tatgtattct gtagttcaat | 180 |
| agccatggct gtttacttca tttaatttat ttagcataaa gacattatga aaaggcctaa | 240 |

```
acatgagctt cacttcccca ctaactaatt agcatctgtt atttcttaac cgtaatgcct    300
a                                                                    301

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292 acctttagt agtaatgtct aataataaat aagaaatcaa ttttataagg tccatatagc      60
tgtattaaat aattttaag tttaaaagat aaataccat catttaaat gttggtattc       120 aaaccaaag natataaccg aaaggaaaaa cagatgagac ataaatgat ttgcnagatg      180 ggaaatatag tasttyatga atgttnatta aattccagtt ataatagtgg ctacacactc    240
tcactacaca cacagacccc acagtcctat atgccacaaa cacatttcca taacttgaaa    300
a                                                                    301

<210> SEQ ID NO 293
<211> LENGTH: 301
<212> TYPE: DNA
<213> ORGANISM: Homo sapien

<400> SEQUENCE: 293
ggtaccaagt gctggtgcca gcctgttacc tgttctcact gaaaagtctg gctaatgctc     60
ttgtgtagtc acttctgatt ctgacaatca atcaatcaat ggcctagagc actgactgtt    120
aacacaaacg tcactagcaa agtagcaaca gctttaagtc taaatacaaa gctgttctgt    180
gtgagaattt tttaaaaggc tacttgtata ataacccttg tcatttttaa tgtacctcgg    240
ccgcgaccac gctaagccga attctgcaga tatccatcac actggcggcc gctcgagcat    300
g                                                                    301

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294
tgacccataa caatatacac tagctatctt tttaactgtc catcattagc accaatgaag     60
attcaataaa attaccttta ttcacacatc tcaaaacaat tctgcaaatt cttagtgaag    120
tttaactata gtcacaganc ttaaatattc acattgtttt ctatgtctac tgaaaataag    180
ttcactactt ttctgggata ttctttacaa aatcttatta aaattcctgg tattatcacc    240
cccaattata cagtagcaca accaccttat gtagttttta catgatagct ctgtagaggt    300
t                                                                    301

<210> SEQ ID NO 295
<211> LENGTH: 305
<212> TYPE: DNA
<213> ORGANISM: Homo sapien
```

<400> SEQUENCE: 295

```
gtactctttc tctcccctcc tctgaattta attctttcaa cttgcaattt gcaaggatta      60
cacatttcac tgtgatgtat attgtgttgc aaaaaaaaaa gtgtctttgt ttaaaattac     120
ttggtttgtg aatccatctt gcttttccc cattggaact agtcattaac ccatctctga     180
actggtagaa aaacrtctga agagctagtc tatcagcatc tgacaggtga attggatggt     240
tctcagaacc atttcaccca gacagcctgt ttctatcctg tttaataaat tagtttgggt     300
tctct                                                                305
```

<210> SEQ ID NO 296
<211> LENGTH: 301
<212> TYPE: DNA
<213> ORGANISM: Homo sapien

<400> SEQUENCE: 296

```
aggtactatg ggaagctgct aaataatat ttgatagtaa aagtatgtaa tgtgctatct      60
cacctagtag taaactaaaa ataaactgaa actttatgga atctgaagtt attttccttg     120
attaaataga attaataaac caatatgagg aaacatgaaa ccatgcaatc tactatcaac     180
tttgaaaaag tgattgaacg aaccacttag ctttcagatg atgaacactg ataagtcatt     240
tgtcattact ataaatttta aaatctgtta ataagatggc ctatagggag gaaaaagggg     300
c                                                                    301
```

<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297

```
actgagtttt aactggacgc caagcaggca aggctggaag gttttgctct ctttgtgcta      60
aaggttttga aaaccttgaa ggagaatcat tttgacaaga agtacttaag agtctagaga     120
acaaagangt gaaccagctg aaagctctcg ggggaanctt acatgtgttg ttaggcctgt     180
tccatcattg ggagtgcact ggccatccct caaaatttgt ctgggctggc ctgagtggtc     240
accgcacctc ggccgcgacc acgctaagcc gaattctgca gatatccatc acactggcgg     300
```

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298

```
tatggggttt gtcacccaaa agctgatgct gagaaaggcc tccctggggc ccctcccgcg      60
ggcatctgag agacctggtg ttccagtgtt tctggaaatg ggtcccagtg ccgccggctg     120
tgaagctctc agatcaatca cgggaagggc ctggcggtgg tggccacctg gaaccaccct     180
gtcctgtctg tttacatttc actaycaggt tttctctggg cattacnatt tgttcccta     240
caacagtgac ctgtgcattc tgctgtggcc tgctgtgtct gcaggtggct ctcagcgagg     300
t                                                                    301
```

<210> SEQ ID NO 299
<211> LENGTH: 301
<212> TYPE: DNA
<213> ORGANISM: Homo sapien

<400> SEQUENCE: 299

```
gttttgagac ggagtttcac tcttgttgcc cagactggac tgcaatggca gggtctctgc      60
tcactgcacc ctctgcctcc caggttcgag caattctcct gcctcagcct cccaggtagc     120
tgggattgca ggctcacgcc accatacccca gctaattttt tgtatttttt agtagagacg     180
gagtttcgcc atgttggcca gctggtctca aactcctgac ctcaagcgac ctgcctgcct     240
cggcctccca agtgctgga attataggca tgagtcaaca cgcccagcct aaagatattt      300
t                                                                     301
```

<210> SEQ ID NO 300
<211> LENGTH: 301
<212> TYPE: DNA
<213> ORGANISM: Homo sapien

<400> SEQUENCE: 300

```
attcagtttt atttgctgcc ccagtatctg taaccaggag tgccacaaaa tcttgccaga      60
tatgtcccac acccactggg aaaggctccc acctggctac ttcctctatc agctgggtca     120
gctgcattcc acaaggttct cagcctaatg agtttcacta cctgccagtc tcaaaactta     180
gtaaagcaag accatgacat tcccccacgg aaatcagagt ttgccccacc gtcttgttac     240
tataaagcct gcctctaaca gtccttgctt cttcacacca atcccgagcg catcccccat     300
g                                                                     301
```

<210> SEQ ID NO 301
<211> LENGTH: 301
<212> TYPE: DNA
<213> ORGANISM: Homo sapien

<400> SEQUENCE: 301

```
ttaaattttt gagaggataa aaaggacaaa taatctagaa atgtgtcttc ttcagtctgc      60
agaggacccc aggtctccaa gcaaccacat ggtcaagggc atgaataatt aaaagttggt     120
gggaactcac aaagaccctc agagctgaga cacccacaac agtgggagct cacaaagacc     180
ctcagagctg agacacccac aacagtggga gctcacaaag accctcagag ctgagacacc     240
cacaacagca cctcgttcag ctgccacatg tgtgaataag gatgcaatgt ccagaagtgt     300
t                                                                     301
```

<210> SEQ ID NO 302
<211> LENGTH: 301
<212> TYPE: DNA
<213> ORGANISM: Homo sapien

<400> SEQUENCE: 302

```
aggtacacat ttagcttgtg gtaaatgact cacaaaactg attttaaaat caagttaatg      60
tgaattttga aaattactac ttaatcctaa ttcacaataa caatggcatt aaggtttgac     120
ttgagttggt tcttagtatt atttatggta aataggctct taccacttgc aaataactgg     180
ccacatcatt aatgactgac ttcccagtaa ggctctctaa ggggtaagta ggaggatcca     240
caggatttga gatgctaagg ccccagagat cgtttgatcc aaccctctta ttttcagagg     300
```

<210> SEQ ID NO 303
<211> LENGTH: 301
<212> TYPE: DNA
<213> ORGANISM: Homo sapien

<400> SEQUENCE: 303

```
aggtaccaac tgtggaaata ggtagaggat catttttct ttccatatca actaagttgt    60
atattgtttt ttgacagttt aacacatctt cttctgtcag agattctttc acaatagcac   120
tggctaatgg aactaccgct tgcatgttaa aaatggtggt ttgtgaaatg atcataggcc   180
agtaacgggt atgtttttct aactgatctt ttgctcgttc caaagggacc tcaagacttc   240
catcgatttt atatctgggg tctagaaaag gagttaatct gttttccctc ataaattcac   300
c                                                                   301
```

<210> SEQ ID NO 304
<211> LENGTH: 301
<212> TYPE: DNA
<213> ORGANISM: Homo sapien

<400> SEQUENCE: 304

```
acatggatgt tattttgcag actgtcaacc tgaatttgta tttgcttgac attgcctaat    60
tattagtttc agtttcagct tacccacttt ttgtctgcaa catgcaraas agacagtgcc   120
ctttttagtg tatcatatca ggaatcatct cacattggtt tgtgccatta ctggtgcagt   180
gactttcagc cacttgggta aggtggagtt ggccatatgt ctccactgca aaattactga   240
ttttcctttt gtaattaata agtgtgtgtg tgaagattct tgagatgag gtatatatct    300
c                                                                   301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag    60
caggggggaca gacctggaca gacacgttgt catttgctgc tgtgggtagg aaaatgggcg   120
taaggagga gaaacagata caaatctcc aactcagtat taaggtattc tcatgcctag     180
aatattggta gaaacaagaa tacattcata tggcaaataa ctaaccatgg tggaacaaaa   240
ttctgggatt taagttggat accaangaaa ttgtattaaa agagctgttc atggaataag   300
a                                                                   301
```

<210> SEQ ID NO 306
<211> LENGTH: 8
<212> TYPE: PRT
<213> ORGANISM: Homo sapien

<400> SEQUENCE: 306

Val Leu Gly Trp Val Ala Glu Leu
 1               5

<210> SEQ ID NO 307

<211> LENGTH: 637
<212> TYPE: DNA
<213> ORGANISM: Homo sapien

<400> SEQUENCE: 307

```
acagggratg aagggaaagg gagaggatga ggaagccccc ctggggattt ggtttggtcc      60
ttgtgatcag gtggtctatg ggcttatcc ctacaaagaa gaatccagaa ataggggcac     120
attgaggaat gatacttgag cccaaagagc attcaatcat tgttttattt gccttmtttt    180
cacaccattg gtgagggagg gattaccacc ctggggttat gaagatggtt gaacacccca    240
cacatagcac cggagatatg agatcaacag tttcttagcc atagagattc acagcccaga    300
gcaggaggac gcttgcacac catgcaggat gacatggggg atgcgctcgg gattggtgtg    360
aagaagcaag gactgttaga ggcaggcttt atagtaacaa gacggtgggg caaactctga    420
tttccgtggg ggaatgtcat ggtcttgctt tactaagttt tgagactggc aggtagtgaa    480
actcattagg ctgagaacct tgtggaatgc acttgaccca sctgatagag gaagtagcca    540
ggtgggagcc tttcccagtg ggtgtgggac atatctggca agattttgtg gcactcctgg    600
ttacagatac tggggcagca aataaaactg aatcttg                             637
```

<210> SEQ ID NO 308
<211> LENGTH: 647
<212> TYPE: DNA
<213> ORGANISM: Homo sapien
<220> FEATURE:
<221> NAME/KEY: misc_feature
<222> LOCATION: (1)...(647)
<223> OTHER INFORMATION: n = A,T,C or G

<400> SEQUENCE: 308

```
acgattttca ttatcatgta aatcgggtca ctcaaggggc caaccacagc tgggagccac      60
tgctcagggg aaggttcata tgggactttc tactgcccaa ggttctatac aggatataaa    120
ggngcctcac agtatagatc tggtagcaaa gaagaagaaa caaacactga tctctttctg    180
ccacccctct gaccctttgg aactcctctg acccttttaga acaagcctac ctaatatctg    240
ctagagaaaa gaccaacaac ggcctcaaag gatctcttac catgaaggtc tcagctaatt    300
cttggctaag atgtgggttc cacattaggt tctgaatatg gggggaaggg tcaatttgct    360
cattttgtgt gtggataaag tcaggatgcc caggggccag agcaggggc tgcttgcttt     420
gggaacaatg gctgagcata taaccatagg ttatggggaa caaacaaca tcaaagtcac     480
tgtatcaatt gccatgaaga cttgagggac ctgaatctac cgattcatct taaggcagca    540
ggaccagttt gagtggcaac aatgcagcag cagaatcaat ggaaacaaca gaatgattgc    600
aatgtccttt tttttctcct gcttctgact tgataaaagg ggaccgt                  647
```

<210> SEQ ID NO 309
<211> LENGTH: 460
<212> TYPE: DNA
<213> ORGANISM: Homo sapien

<400> SEQUENCE: 309

```
actttatagt ttaggctgga cattggaaaa aaaaaaagc cagaacaaca tgtgatagat      60
aatatgattg gctgcacact tccagactga tgaatgatga acgtgatgga ctattgtatg    120
gagcacatct tcagcaagag ggggaaatac tcatcatttt tggccagcag ttgtttgatc    180
accaaacatc atgccagaat actcagcaaa ccttcttagc tcttgagaag tcaaagtccg    240
ggggaattta ttcctggcaa ttttaattgg actccttatg tgagagcagc ggctacccag    300
```

```
ctggggtggt ggagcgaacc cgtcactagt ggacatgcag tggcagagct cctggtaacc    360
acctagagga atacacaggc acatgtgtga tgccaagcgt gacacctgta gcactcaaat    420
ttgtcttgtt tttgtctttc ggtgtgtaag attcttaagt                          460
```

<210> SEQ ID NO 310
<211> LENGTH: 539
<212> TYPE: DNA
<213> ORGANISM: Homo sapien

<400> SEQUENCE: 310

```
acgggactta tcaaataaag ataggaaaag aagaaaactc aaatattata ggcagaaatg     60
ctaaaggttt taaaatatgt caggattgga agaaggcatg gataaagaac aaagttcagt    120
taggaaagag aaacacagaa ggaagagaca caataaaagt cattatgtat tctgtgagaa    180
gtcagacagt aagatttgtg ggaaatgggt tggtttgttg tatggtatgt attttagcaa    240
taatctttat ggcagagaaa gctaaaatcc tttagcttgc gtgaatgatc acttgctgaa    300
ttcctcaagg taggcatgat gaaggagggt ttagaggaga cacagacaca atgaactgac    360
ctagatagaa agccttagta tactcagcta ggaatagtga ttctgagggc acactgtgac    420
atgattatgt cattacatgt atggtagtga tggggatgat aggaaggaag aacttatggc    480
atattttcac ccccacaaaa gtcagttaaa tattgggaca ctaaccatcc aggtcaaga    539
```

<210> SEQ ID NO 311
<211> LENGTH: 526
<212> TYPE: DNA
<213> ORGANISM: Homo sapien
<220> FEATURE:
<221> NAME/KEY: misc_feature
<222> LOCATION: (1)...(526)
<223> OTHER INFORMATION: n = A,T,C or G

<400> SEQUENCE: 311

```
caaatttgag ccaatgacat agaatttac aaatcaagaa gcttattctg gggccatttc      60
ttttgacgtt ttctctaaac tactaaagag gcattaatga tccataaatt atattatcta    120
catttacagc atttaaaatg tgttcagcat gaaatattag ctacagggga agctaaataa    180
attaaacatg gaataaagat ttgtccttaa atataatcta caagaagact ttgatatttg    240
tttttcacaa gtgaagcatt cttataaagt gtcataacct ttttggggaa actatgggaa    300
aaaatgggga aactctgaag ggtttaagt atcttacctg aagctacaga ctccataacc     360
tctctttaca gggagctcct gcagcccta cagaaatgag tggctgagat tcttgattgc     420
acagcaagag cttctcatct aaacccttc cctttttagt atctgtgtat caagtataaa     480
agttctataa actgtagtnt acttatttta atccccaaag cacagt                  526
```

<210> SEQ ID NO 312
<211> LENGTH: 500
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 312

```
cctctctctc cccacccct gactctagag aactgggttt tctcccagta ctccagcaat      60
tcatttctga aagcagttga gccactttat tccaaagtac actgcagatg ttcaaactct    120
```

```
ccatttctct ttcccttcca cctgccagtt ttgctgactc tcaacttgtc atgagtgtaa      180
gcattaagga cattatgctt cttcgattct gaagacaggc cctgctcatg gatgactctg      240
gcttcttagg aaaatatttt tcttccaaaa tcagtaggaa atctaaactt atcccctctt      300
tgcagatgtc tagcagcttc agacatttgg ttaagaaccc atgggaaaaa aaaaaatcct      360
tgctaatgtg gtttcctttg taaaccanga ttcttatttg nctggtatag aatatcagct      420
ctgaacgtgt ggtaaagatt tttgtgtttg aatataggag aaatcagttt gctgaaaagt      480
tagtcttaat tatctattgg                                                   500

<210> SEQ ID NO 313
<211> LENGTH: 718
<212> TYPE: DNA
<213> ORGANISM: Homo sapien
<220> FEATURE:
<221> NAME/KEY: misc_feature
<222> LOCATION: (1)...(718)
<223> OTHER INFORMATION: n = A,T,C or G

<400> SEQUENCE: 313
ggagatttgt gtggtttgca gccgagggag accaggaaga tctgcatggt gggaaggacc       60
tgatgataca gaggtgagaa ataagaaagg ctgctgactt taccatctga ggccacacat      120
ctgctgaaat ggagataatt aacatcacta gaaacagcaa gatgacaata taatgtctaa      180
gtagtgacat gtttttgcac atttccagcc cttttaaata tccacacaca caggaagcac      240
aaaaggaagc acagagatcc ctgggagaaa tgcccggccg ccatcttggg tcatcgatga      300
gcctcgccct gtgcctgntc ccgcttgtga gggaaggaca ttagaaaatg aattgatgtg      360
ttccttaaag gatggcagga aaacagatcc tgttgtggat atttatttga acgggattac      420
agatttgaaa tgaagtcaca aagtgagcat taccaatgag aggaaaacag acgagaaaat      480
cttgatggtt cacaagacat gcaacaaaca aaatggaata ctgtgatgac acgagcagcc      540
aactggggag gagataccac ggggcagagg tcaggattct ggccctgctg cctaactgtg      600
cgttatacca atcatttcta tttctaccct caaacaagct gtngaatatc tgacttacgg      660
ttcttntggc ccacattttc atnatccacc ccntcnttt aannttantc caaantgt       718

<210> SEQ ID NO 314
<211> LENGTH: 358
<212> TYPE: DNA
<213> ORGANISM: Homo sapien

<400> SEQUENCE: 314
gtttatttac attacagaaa aaacatcaag acaatgtata ctatttcaaa tatatccata       60
cataatcaaa tatagctgta gtacatgttt tcattggtgt agattaccac aaatgcaagg      120
caacatgtgt agatctcttg tcttattctt ttgtctataa tactgtattg tgtagtccaa      180
gctctcggta gtccagccac tgtgaaacat gctcccttta gattaacctc gtggacgctc      240
ttgttgtatt gctgaactgt agtgccctgt attttgcttc tgtctgtgaa ttctgttgct      300 tctgggcat ttccttgtga tgcagaggac caccacacag atgacagcaa tctgaatt        358

<210> SEQ ID NO 315
<211> LENGTH: 341
<212> TYPE: DNA
<213> ORGANISM: Homo sapien

<400> SEQUENCE: 315
taccacctcc ccgctggcac tgatgagccg catcaccatg gtcaccagca ccatgaaggc       60
```

```
ataggtgatg atgaggacat ggaatgggcc cccaaggatg gtctgtccaa agaagcgagt        120 gaccccatt ctgaagatgt ctggaacctc taccagcagg atgatgatag ccccaatgac         180
agtcaccagc tccccgacca gccggatatc gtccttaggg gtcatgtagg cttcctgaag        240
tagcttctgc tgtaagaggg tgttgtcccg ggggctcgtg cggttattgg tcctgggctt        300 gaggggcgg tagatgcagc acatggtgaa gcagatgatg t                             341

<210> SEQ ID NO 316
<211> LENGTH: 151
<212> TYPE: DNA
<213> ORGANISM: Homo sapien

<400> SEQUENCE: 316
agactgggca agactcttac gccccacact gcaatttggt cttgttgccg tatccattta         60
tgtgggcctt tctcgagttt ctgattataa acaccactgg agcgatgtgt tgactggact        120
cattcaggga gctctggttg caatattagt t                                       151

<210> SEQ ID NO 317
<211> LENGTH: 151
<212> TYPE: DNA
<213> ORGANISM: Homo sapien

<400> SEQUENCE: 317
agaactagtg gatcctaatg aaatacctga aacatatatt ggcatttatc aatggctcaa         60
atcttcattt atctctggcc ttaaccctgg ctcctgaggc tgcggccagc agatcccagg        120
ccagggctct gttcttgcca cacctgcttg a                                       151

<210> SEQ ID NO 318
<211> LENGTH: 151
<212> TYPE: DNA
<213> ORGANISM: Homo sapien

<400> SEQUENCE: 318
actggtggga ggcgctgttt agttggctgt tttcagaggg gtctttcgga gggacctcct         60
gctgcaggct ggagtgtctt tattcctggc gggagaccgc acattccact gctgaggctg        120
tgggggcggt ttatcaggca gtgataaaca t                                       151

<210> SEQ ID NO 319
<211> LENGTH: 151
<212> TYPE: DNA
<213> ORGANISM: Homo sapien

<400> SEQUENCE: 319
aactagtgga tccagagcta taggtacagt gtgatctcag ctttgcaaac acattttcta         60
catagatagt actaggtatt aatagatatg taaagaaaga atcacacca ttaataatgg         120 taagattggg tttatgtgat tttagtgggt a                                       151

<210> SEQ ID NO 320
<211> LENGTH: 150
<212> TYPE: DNA
<213> ORGANISM: Homo sapien

<400> SEQUENCE: 320
aactagtgga tccactagtc cagtgtggtg gaattccatt gtgttggggt tctagatcgc         60
gagcggctgc cctttttttt tttttttttg gggggaatt tttttttttt aatagttatt        120
```
gagtgttcta cagcttacag taaataccat                                          150

<210> SEQ ID NO 321
<211> LENGTH: 151
<212> TYPE: DNA
<213> ORGANISM: Homo sapien

<400> SEQUENCE: 321
agcaactttg tttttcatcc aggttatttt aggcttagga tttcctctca cactgcagtt          60
tagggtggca ttgtaaccag ctatggcata ggtgttaacc aaaggctgag taaacatggg         120
tgcctctgag aaatcaaagt cttcatacac t                                        151

<210> SEQ ID NO 322
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 322
atccagcatc ttctcctgtt tcttgccttc cttttctcttc ttcttasatt ctgcttgagg         60
tttgggcttg gtcagtttgc cacagggctt ggagatggtg acagtcttct ggcattcggc        120
attgtgcagg gctcgcttca nacttccagt t                                        151

<210> SEQ ID NO 323
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 323
tgaggacttg tkttcttttt ctttatttt aatcctctta ckttgtaaat atattgccta          60
nagactcant tactacccag tttgtggttt twtgggagaa atgtaactgg acagttagct        120
gttcaatyaa aaagacactt anccatgtg g                                         151

<210> SEQ ID NO 324
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 324
acctgtgtgg aatttcagct ttcctcatgc aaaaggattt tgtatccccg gcctacttga         60
agaagtggtc agctaaagga atccaggttg ttggttggac tgttaatacc tttgatgaaa        120
agagttacta cgaatcccat cttggttcca gctatatcac tgacagcatg gtagaagact        180
gcgaacctca cttctagact ttcacggtgg acgaaacgg gttcagaaac tgccaggggc         240
ctcatacagg gatatcaaaa taccctttgt gctacccagg ccctggggaa tcaggtgact        300
cacacaaatg caatagttgg tcactgcatt tttacctgaa ccaaagctaa acccggtgtt        360
gccaccatgc accatggcat gccagagttc aacactgttg ctcttgaaaa ttgggtctga        420
aaaaacgcac aagagcccct gccctgccct agctgangca c                            461

<210> SEQ ID NO 325
<211> LENGTH: 400
<212> TYPE: DNA
<213> ORGANISM: Homo sapien

<400> SEQUENCE: 325

```
acactgtttc catgttatgt ttctacacat tgctacctca gtgctcctgg aaacttagct      60
tttgatgtct ccaagtagtc caccttcatt taactctttg aaactgtatc atctttgcca     120
agtaagagtg gtggcctatt tcagctgctt tgacaaaatg actggctcct gacttaacgt     180
tctataaatg aatgtgctga agcaaagtgc ccatggtggc ggcgaagaag agaaagatgt     240
gttttgtttt ggactctctg tggtcccttc caatgctgtg ggtttccaac caggggaagg     300
gtccctttg cattgccaag tgccataacc atgagcacta cgctaccatg gttctgcctc      360
ctggccaagc aggctggttt gcaagaatga aatgaatgat                           400
```

<210> SEQ ID NO 326
<211> LENGTH: 1215
<212> TYPE: DNA
<213> ORGANISM: Homo sapien

<400> SEQUENCE: 326

```
ggaggactgc agcccgcact cgcagccctg gcaggcggca ctggtcatgg aaaacgaatt      60
gttctgctcg ggcgtcctgg tgcatccgca gtgggtgctg tcagccgcac actgtttcca     120
gaactcctac accatcgggc tgggcctgca cagtcttgag gccgaccaag agccagggag     180
ccagatggtg gaggccagcc tctccgtacg gcacccagag tacaacagac ccttgctcgc     240
taacgacctc atgctcatca gttggacgag atccgtgtcc gagtctgaca ccatccggag     300
catcagcatt gcttcgcagt gccctaccgc ggggaactct tgcctcgttt ctggctgggg     360
tctgctggcg aacggcagaa tgcctaccgt gctgcagtgc gtgaacgtgt cggtggtgtc     420
tgaggaggtc tgcagtaagc tctatgaccc gctgtaccac cccagcatgt tctgcgccgg     480
cggagggcaa gaccagaagg actcctgcaa cggtgactct gggggccccc tgatctgcaa     540
cgggtacttg cagggccttg tgtctttcgg aaaagcccg tgtggccaag ttggcgtgcc      600
aggtgtctac accaacctct gcaaattcac tgagtggata gagaaaaccg tccaggccag     660
ttaactctgg ggactgggaa cccatgaaat tgaccccaa atacatcctg cggaaggaat      720
tcaggaatat ctgttcccag cccctcctcc ctcaggccca ggagtccagg cccccagccc     780
ctcctccctc aaaccaaggg tacagatccc cagccctcc tccctcagac ccaggagtcc      840
agaccccca gcccctcctc cctcagaccc aggagtccag ccctcctcc ctcagaccca      900
ggagtccaga cccccagcc cctcctccct cagacccagg gtccaggcc cccaacccct      960
cctccctcag actcagaggt ccaagccccc aaccctcct tccccagacc cagaggtcca    1020
ggtcccagcc cctcctccct cagacccagc ggtccaatgc cacctagact ctccctgtac    1080
acagtgcccc cttgtggcac gttgacccaa ccttaccagt tggttttca tttttgtcc     1140
ctttccccta gatccagaaa taaagtctaa gagaagcgca aaaaaaaaaa aaaaaaaaa     1200
aaaaaaaaaa aaaaa                                                     1215
```

<210> SEQ ID NO 327
<211> LENGTH: 220
<212> TYPE: PRT
<213> ORGANISM: Homo sapien

```
<400> SEQUENCE: 327

Glu Asp Cys Ser Pro His Ser Gln Pro Trp Gln Ala Ala Leu Val Met
 1               5                  10                  15

Glu Asn Glu Leu Phe Cys Ser Gly Val Leu Val His Pro Gln Trp Val
            20                  25                  30

Leu Ser Ala Ala His Cys Phe Gln Asn Ser Tyr Thr Ile Gly Leu Gly
        35                  40                  45

Leu His Ser Leu Glu Ala Asp Gln Glu Pro Gly Ser Gln Met Val Glu
    50                  55                  60

Ala Ser Leu Ser Val Arg His Pro Glu Tyr Asn Arg Pro Leu Leu Ala
65                  70                  75                  80

Asn Asp Leu Met Leu Ile Lys Leu Asp Glu Ser Val Ser Glu Ser Asp
                85                  90                  95

Thr Ile Arg Ser Ile Ser Ile Ala Ser Gln Cys Pro Thr Ala Gly Asn
            100                 105                 110

Ser Cys Leu Val Ser Gly Trp Gly Leu Leu Ala Asn Gly Arg Met Pro
        115                 120                 125

Thr Val Leu Gln Cys Val Asn Val Ser Val Val Ser Glu Glu Val Cys
    130                 135                 140

Ser Lys Leu Tyr Asp Pro Leu Tyr His Pro Ser Met Phe Cys Ala Gly
145                 150                 155                 160

Gly Gly Gln Asp Gln Lys Asp Ser Cys Asn Gly Asp Ser Gly Gly Pro
                165                 170                 175

Leu Ile Cys Asn Gly Tyr Leu Gln Gly Leu Val Ser Phe Gly Lys Ala
            180                 185                 190

Pro Cys Gly Gln Val Gly Val Pro Gly Val Tyr Thr Asn Leu Cys Lys
        195                 200                 205

Phe Thr Glu Trp Ile Glu Lys Thr Val Gln Ala Ser
    210                 215                 220

<210> SEQ ID NO 328
<211> LENGTH: 234
<212> TYPE: DNA
<213> ORGANISM: Homo sapien

<400> SEQUENCE: 328
cgctcgtctc tggtagctgc agccaaatca taaacggcga ggactgcagc ccgcactcgc      60
agccctggca ggcggcactg gtcatggaaa acgaattgtt ctgctcgggc gtcctggtgc     120
atccgcagtg ggtgctgtca gccacacact gtttccagaa ctcctacacc atcgggctgg     180
gcctgcacag tcttgaggcc gaccaagagc cagggagcca gatggtggag gcca           234

<210> SEQ ID NO 329
<211> LENGTH: 77
<212> TYPE: PRT
<213> ORGANISM: Homo sapien

<400> SEQUENCE: 329

Leu Val Ser Gly Ser Cys Ser Gln Ile Ile Asn Gly Glu Asp Cys Ser
 1               5                  10                  15

Pro His Ser Gln Pro Trp Gln Ala Ala Leu Val Met Glu Asn Glu Leu
            20                  25                  30

Phe Cys Ser Gly Val Leu Val His Pro Gln Trp Val Leu Ser Ala Thr
        35                  40                  45

His Cys Phe Gln Asn Ser Tyr Thr Ile Gly Leu Gly Leu His Ser Leu
```

Glu Ala Asp Gln Glu Pro Gly Ser Gln Met Val Glu Ala
65                  70                  75

<210> SEQ ID NO 330
<211> LENGTH: 70
<212> TYPE: DNA
<213> ORGANISM: Homo sapien

<400> SEQUENCE: 330
cccaacacaa tggcccgatc ccatccctga ctccgccctc aggatcgctc gtctctggta    60
gctgcagcca                                                           70

<210> SEQ ID NO 331
<211> LENGTH: 22
<212> TYPE: PRT
<213> ORGANISM: Homo sapien

<400> SEQUENCE: 331

Gln His Asn Gly Pro Ile Pro Ser Leu Thr Pro Pro Ser Gly Ser Leu
 1               5                  10                  15

Val Ser Gly Ser Cys Ser
            20

<210> SEQ ID NO 332
<211> LENGTH: 2507
<212> TYPE: DNA
<213> ORGANISM: Homo sapien

<400> SEQUENCE: 332
tggtgccgct gcagccggca gagatggttg agctcatgtt cccgctgttg ctcctccttc    60
tgcccttcct tctgtatatg gctgcgcccc aaatcaggaa aatgctgtcc agtggggtgt   120
gtacatcaac tgttcagctt cctgggaaag tagttgtggt cacaggagct aatacaggta   180
tcgggaagga gacagccaaa gagctggctc agagaggagc tcgagtatat ttagcttgcc   240
gggatgtgga aaaggggaa ttggtggcca agagatcca gaccacgaca gggaaccagc    300
aggtgttggt gcggaaactg gacctgtctg tactaagtc tattcgagct tttgctaagg    360
gcttcttagc tgaggaaaag cacctccacg ttttgatcaa caatgcagga gtgatgatgt    420
gtccgtactc gaagacagca gatggctttg agatgcacat aggagtcaac cacttgggtc    480
acttcctcct aacccatctg ctgctagaga aactaaagga atcagcccca tcaaggatag    540
taaatgtgtc ttccctcgca catcacctgg aaggatcca cttccataac ctgcagggcg    600
agaaattcta caatgcaggc ctggcctact gtcacacgaa gctagccaac atcctcttca    660
cccaggaact ggcccggaga ctaaaaggct ctggcgttac gacgtattct gtacaccctg    720
gcacagtcca atctgaactg gttcggcact catctttcat gagatggatg tggtggcttt    780
tctccttttt catcaagact cctcagcagg gagcccagac cagcctgcac tgtgccttaa    840
cagaaggtct tgagattcta agtgggaatc atttcagtga ctgtcatgtg gcatgggtct    900
ctgcccaagc tcgtaatgag actatagcaa ggcggctgtg ggacgtcagt tgtgacctgc    960
tgggcctccc aatagactaa caggcagtgc cagttggacc caagagaaga ctgcagcaga   1020
ctacacagta cttcttgtca aaatgattct ccttcaaggt tttcaaaacc tttagcacaa   1080
agagagcaaa accttccagc cttgcctgct ggtgtccag ttaaaactca gtgtactgcc    1140
agattcgtct aaatgtctgt catgtccaga tttactttgc ttctgttact gccagagtta   1200

```
ctagagatat cataatagga taagaagacc ctcatatgac ctgcacagct cattttcctt      1260
ctgaaagaaa ctactaccta ggagaatcta agctatagca gggatgattt atgcaaattt      1320
gaactagctt ctttgttcac aattcagttc ctcccaacca accagtcttc acttcaagag      1380
ggccacactg caacctcagc ttaacatgaa taacaaagac tggctcagga gcagggcttg      1440
cccaggcatg gtggatcacc ggaggtcagt agttcaagac cagcctggcc aacatggtga      1500
aaccccacct ctactaaaaa ttgtgtatat ctttgtgtgt cttcctgttt atgtgtgcca      1560
agggagtatt ttcacaaagt tcaaaacagc acaataatc agagatggag caaaccagtg       1620
ccatccagtc tttatgcaaa tgaaatgctg caaagggaag cagattctgt atatgttggt      1680
aactacccac caagagcaca tgggtagcag ggaagaagta aaaaaagaga aggagaatac      1740
tggaagataa tgcacaaaat gaagggacta gttaaggatt aactagccct ttaaggatta      1800
actagttaag gattaatagc aaaagayatt aaatatgcta acatagctat ggaggaattg      1860
agggcaagca cccaggactg atgaggtctt aacaaaaacc agtgtggcaa aaaaaaaaaa      1920
aaaaaaaaaa aaaatcctaa aaacaaaca aacaaaaaaa acaattcttc attcagaaaa       1980
attatcttag ggactgatat tggtaattat ggtcaattta ataatatttt ggggcatttc      2040
cttacattgt cttgacaaga ttaaaatgtc tgtgccaaaa ttttgtattt tatttggaga      2100
cttcttatca aaagtaatgc tgccaaagga agtctaagga attagtagtg ttcccatcac      2160
ttgtttggag tgtgctattc taaaagattt tgatttcctg gaatgacaat tatattttaa      2220 cttttggtggg ggaaagagtt ataggaccac agtcttcact tctgatactt gtaaattaat     2280
cttttattgc acttgttttg accattaagc tatatgttta gaaatggtca ttttacggaa      2340
aaattagaaa aattctgata atagtgcaga ataaatgaat taatgttta cttaatttat       2400 attgaactgt caatgacaaa taaaaattct ttttgattat tttttgtttt catttaccag      2460
aataaaaacg taagaattaa aagtttgatt acaaaaaaaa aaaaaaa                    2507
```

<210> SEQ ID NO 333
<211> LENGTH: 3030
<212> TYPE: DNA
<213> ORGANISM: Homo sapien

<400> SEQUENCE: 333

```
gcaggcgact tgcgagctgg gagcgattta aaacgctttg gattcccccg gcctgggtgg       60
ggagagcgag ctgggtgccc cctagattcc ccgcccccgc acctcatgag ccgaccctcg      120
gctccatgga gcccggcaat tatgccacct tggatggagc caaggatatc gaaggcttgc      180
tgggagcggg aggggggcgg aatctggtcg cccactcccc tctgaccagc cacccagcgg      240
cgcctacgct gatgcctgct gtcaactatg ccccttgga tctgccaggc tcggcggagc       300
cgccaaagca atgccaccca tgccctgggg tgccccaggg gacgtcccca gctcccgtgc      360
cttatggtta ctttggaggc gggtactact cctgccgagt gtcccggagc tcgctgaaac      420
cctgtgccca ggcagccacc ctggccgcgt acccgcgga gactcccacg gccggggaag       480
agtaccccag ycgccccact gagtttgcct tctatccggg atatccggga acctaccagc      540
ctatggccaa ttacctggac gtgtctgtgg tgcagactct gggtgctcct ggagaaccgc      600
gacatgactc cctgttgcct gtggacagtt accagtcttg ggctctcgct ggtggctgga      660
acagccagat gtgttgccag ggagaacaga acccaccagg tccctttggg aaggcagcat      720
ttgcagactc cagcgggcag caccctcctg acgcctcgc ctttcgtcgc ggccgcaaga      780
aacgcattcc gtacagcaag gggcagttgc gggagctgga gcgggagtat gcggctaaca      840
```

```
agttcatcac caaggacaag aggcgcaaga tctcggcagc caccagcctc tcggagcgcc    900
agattaccat ctggtttcag aaccgccggg tcaaagagaa gaaggttctc gccaaggtga    960
agaacagcgc taccccttaa gagatctcct tgcctggtgt ggaggagcga aagtgggggt   1020
gtcctgggga gaccaggaac ctgccaagcc caggctgggg ccaaggactc tgctgagagg   1080
cccctagaga caacacccct tcccaggcca ctggctgctgg actgttcctc aggagcggcc   1140
tgggtaccca gtatgtgcag ggagacggaa ccccatgtga cagcccactc caccagggtt   1200
cccaaagaac ctggcccagt cataatcatt catcctgaca gtggcaataa tcacgataac   1260
cagtactagc tgccatgatc gttagcctca tattttctat ctagagctct gtagagcact   1320
ttagaaaccg ctttcatgaa ttgagctaat tatgaataaa tttggaaggc gatccctttg   1380
cagggaagct ttctctcaga ccccccttcca ttacacctct caccctggta acagcaggaa   1440
gactgaggag aggggaacgg gcagattcgt tgtgtggctg tgatgtccgt ttagcatttt   1500
tctcagctga cagctgggta ggtggacaat tgtagaggct gtctcttcct ccctccttgt   1560
ccaccccata gggtgtaccc actggtcttg gaagcaccca tccttaatac gatgattttt   1620
ctgtcgtgtg aaaatgaagc cagcaggctg ccctagtca gtccttcctt ccagagaaaa     1680
agagatttga gaaagtgcct gggtaattca ccattaattt cctcccccaa actctctgag   1740
tcttccctta atatttctgg tggttctgac caaagcaggt catggtttgt tgagcatttg   1800
ggatcccagt gaagtagatg tttgtagcct tgcatactta gccttccca ggcacaaacg    1860
gagtggcaga gtggtgccaa ccctgttttc ccagtccacg tagacagatt cacagtgcgg   1920
aattctggaa gctggagaca gacgggctct ttgcagagcc gggactctga gagggacatg   1980
agggcctctg cctctgtgtt cattctctga tgtcctgtac ctgggctcag tgcccggtgg   2040
gactcatctc ctggccgcgc agcaaagcca gcgggttcgt gctggtcctt cctgcacctt    2100
aggctggggg tgggggggcct gccggcgcat tctccacgat tgagcgcaca ggcctgaagt   2160
ctggacaacc cgcagaaccg aagctccgag cagcgggtcg gtggcgagta gtgggtgcgg    2220
tggcgagcag ttggtggtgg gccgcggccg ccactacctc gaggacattt ccctcccgga   2280
gccagctctc ctagaaaccc cgcggcggcc gccgcagcca agtgtttatg gcccgcggtc   2340
gggtgggatc ctagccctgt ctcctctcct gggaaggagt gagggtggga cgtgacttag   2400
acacctacaa atctatttac caaagaggag cccgggactg agggaaaagg ccaaagagtg   2460
tgagtgcatg cggactgggg gttcagggga agaggacgag gaggaggaag atgaggtcga   2520
tttcctgatt taaaaaatcg tccaagcccc gtggtccagc ttaaggtcct cggttacatg   2580
cgccgctcag agcaggtcac tttctgcctt ccacgtcctc cttcaaggaa gccccatgtg   2640
ggtagctttc aatatcgcag gttcttactc ctctgcctct ataagctcaa acccaccaac   2700
gatcgggcaa gtaaaccccc tccctcgccg acttcggaac tggcgagagt tcagcgcaga   2760
tgggcctgtg gggagggggc aagatagatg aggggagcg gcatggtgcg gggtgacccc    2820
ttggagagag gaaaaaggcc acaagagggg ctgccaccgc cactaacgga gatgccctg    2880
gtagagacct tgggggtct ggaacctctg gactccccat gctctaactc ccacactctg    2940
ctatcagaaa cttaaacttg aggatttcct ctgttttca ctcgcaataa aytcagagca    3000
aacaaaaaaa aaaaaaaaa aaaactcgag                                     3030
```

<210> SEQ ID NO 334
<211> LENGTH: 2417
<212> TYPE: DNA

<213> ORGANISM: Homo sapien

<400> SEQUENCE: 334

| | | | | | |
|---|---|---|---|---|---|
| ggcggccgct | ctagagctag | tgggatcccc | cgggctgcac | gaattcggca | cgagtgagtt | 60 |
| ggagttttac | ctgtattgtt | ttaatttcaa | caagcctgag | gactagccac | aaatgtaccc | 120 |
| agtttacaaa | tgaggaaaca | ggtgcaaaaa | ggttgttacc | tgtcaaaggt | cgtatgtggc | 180 |
| agagccaaga | tttgagccca | gttatgtctg | atgaacttag | cctatgctct | ttaaacttct | 240 |
| gaatgctgac | cattgaggat | atctaaactt | agatcaattg | cattttccct | ccaagactat | 300 |
| ttacttatca | atacaataat | accacccttta | ccaatctatt | gttttgatac | gagactcaaa | 360 |
| tatgccagat | atatgtaaaa | gcaacctaca | agctctctaa | tcatgctcac | ctaaaagatt | 420 |
| cccgggatct | aataggctca | agaaacttc | ttctagaaat | ataaaagaga | aaattggatt | 480 |
| atgcaaaaat | tcattattaa | ttttttcat | ccatccttta | attcagcaaa | catttatctg | 540 |
| ttgttgactt | tatgcagtat | ggccttttaa | ggattggggg | acaggtgaag | aacggggtgc | 600 |
| cagaatgcat | cctcctacta | atgaggtcag | tacacatttg | cattttaaaa | tgccctgtcc | 660 |
| agctgggcat | ggtggatcat | gcctgtaatc | tcaacattgg | aaggccaagg | caggaggatt | 720 |
| gcttcagccc | aggagttcaa | gaccagcctg | ggcaacatag | aaagacccca | tctctcaatc | 780 |
| aatcaatcaa | tgccctgtct | ttgaaaataa | aactctttaa | gaaaggttta | atgggcaggg | 840 |
| tgtggtagct | catgcctata | atacagcact | ttgggaggct | gaggcaggag | gatcacttta | 900 |
| gcccagaagt | tcaagaccag | cctgggcaac | aagtgacacc | tcatctcaat | tttttaataa | 960 |
| aatgaataca | tacataagga | aagataaaaa | gaaaagttta | atgaaagaat | acagtataaa | 1020 |
| acaaatctct | tggacctaaa | agtatttttg | ttcaagccaa | atattgtgaa | tcacctctct | 1080 |
| gtgttgagga | tacagaatat | ctaagcccag | gaaactgagc | agaaagttca | tgtactaact | 1140 |
| aatcaacccg | aggcaaggca | aaatgagac | taactaatca | atccgaggca | aggggcaaat | 1200 |
| tagacggaac | ctgactctgg | tctattaagc | gacaactttc | cctctgttgt | attttctttt | 1260 |
| tattcaatgt | aaaaggataa | aaactctcta | aaactaaaaa | caatgtttgt | caggagttac | 1320 |
| aaaccatgac | caactaatta | tggggaatca | taaaatatga | ctgtatgaga | tcttgatggt | 1380 |
| ttacaaagtg | tacccactgt | taatcacttt | aaacattaat | gaacttaaaa | atgaatttac | 1440 |
| ggagattgga | atgtttcttt | cctgttgtat | tagttggctc | aggctgccat | aacaaaatac | 1500 |
| cacagactgg | gaggcttaag | taacagaaat | tcatttctca | cagttctggg | ggctggaagt | 1560 |
| ccacgatcaa | ggtgcaggaa | aggcaggctt | cattctgagg | ccctctctt | ggctcacatg | 1620 |
| tggccaccct | cccactgcgt | gctcacatga | cctctttgtg | ctcctggaaa | gagggtgtgg | 1680 |
| gggacagagg | gaaagagaag | gagagggaac | tctctggtgt | ctcgtctttc | aaggaccta | 1740 |
| acctgggcca | ctttggccca | ggcactgtgg | ggtgggggt | tgtggctgct | ctgctctgag | 1800 |
| tggccaagat | aaagcaacag | aaaaatgtcc | aaagctgtgc | agcaaagaca | agccaccgaa | 1860 |
| cagggatctg | ctcatcagtg | tggggacctc | caagtcggcc | accctggagg | caagccccca | 1920 |
| cagagcccat | gcaaggtggc | agcagcagaa | gaagggaatt | gtccctgtcc | ttggcacatt | 1980 |
| cctcaccgac | ctggtgatgc | tggacactgc | gatgaatggt | aatgtggatg | agaatatgat | 2040 |
| ggactcccag | aaaaggagac | ccagctgctc | aggtggctgc | aaatcattac | agccttcatc | 2100 |
| ctggggagga | actgggggcc | tggttctggg | tcagagagca | gcccagtgag | ggtgagagct | 2160 |
| acagcctgtc | ctgccagctg | gatccccagt | cccggtcaac | cagtaatcaa | ggctgagcag | 2220 |
| atcaggcttc | ccggagctgg | tcttgggaag | ccagccctgg | ggtgagttgg | ctcctgctgt | 2280 |

```
ggtactgaga caatattgtc ataaattcaa tgcgcccttg tatccctttt tcttttttat   2340
ctgtctacat ctataatcac tatgcatact agtctttgtt agtgtttcta ttcmacttaa   2400
tagagatatg ttatact                                                  2417

<210> SEQ ID NO 335
<211> LENGTH: 2984
<212> TYPE: DNA
<213> ORGANISM: Homo sapien

<400> SEQUENCE: 335
atccctcctt ccccactctc ctttccagaa ggcacttggg gtcttatctg ttggactctg     60
aaaacacttc aggcgccctt ccaaggcttc cccaaacccc taagcagccg cagaagcgct    120
cccgagctgc cttctcccac actcaggtga tcgagttgga gaggaagttc agccatcaga    180
agtacctgtc ggcccctgaa cgggcccacc tggccaagaa cctcaagctc acggagaccc    240
aagtgaagat atggttccag aacagacgct ataagactaa gcgaaagcag ctctcctcgg    300
agctgggaga cttggagaag cactcctctt tgccggccct gaaagaggag ccttctccc     360 gggcctccct ggtctccgtg tataacagct atccttacta cccatacctg tactgcgtgg    420
gcagctggag cccagctttt tggtaatgcc agctcaggtg acaaccatta tgatcaaaaa    480
ctgccttccc cagggtgtct ctatgaaaag cacaaggggc caggtcagg gagcaagagg    540 tgtgcacacc aaagctattg gagatttgcg tggaaatctc asattcttca ctggtgagac    600
aatgaaacaa cagagacagt gaaagtttta atacctaagt cattcccccca gtgcatactg    660 taggtcattt ttttttgcttc tggctacctg tttgaagggg agagagggaa atcaagtgg    720 tatttttccag cactttgtat gattttggat gagctgtaca cccaaggatt ctgttctgca   780
actccatcct cctgtgtcac tgaatatcaa ctctgaaaga gcaaacctaa caggagaaag   840 acaaccagg atgaggatgt caccaactga attaaactta agtccagaag cctcctgttg    900
gccttggaat atggccaagg ctctctctgt ccctgtaaaa gagaggggca atagagagt    960 ctccaagaga acgccctcat gctcagcaca tatttgcatg ggaggggag atgggtggga   1020 ggagatgaaa atatcagctt ttcttattcc ttttattcc ttttaaaatg gtatgccaac   1080
ttaagtattt acagggtggc ccaaatagaa caagatgcac tcgctgtgat tttaagacaa   1140
gctgtataaa cagaactcca ctgcaagagg gggggccggg ccaggagaat ctccgcttgt   1200
ccaagacagg ggcctaagga gggtctccac actgctgcta ggggctgttg catttttta    1260 ttagtagaaa gtgaaaggc ctcttctcaa ctttttttccc ttgggctgga gaatttagaa   1320
tcagaagttt cctggagttt tcaggctatc atatatactg tatcctgaaa ggcaacataa   1380
ttcttccttc cctccttta aaattttgtg ttcctttttg cagcaattac tcactaaagg    1440
gcttcatttt agtccagatt tttagtctgg ctgcacctaa cttatgcctc gcttatttag   1500
cccgagatct ggtctttttt tttttttttt ttttccgtc tccccaaagc tttatctgtc   1560 ttgactttt aaaaaagttt gggggcagat tctgaattgg ctaaagaca tgcatttta     1620 aaactagcaa ctcttatttc tttccttaa aaatacatag cattaaatcc caatcctat     1680 ttaaagacct gacagcttga gaaggtcact actgcattta taggaccttc tggtggttct   1740
gctgttacgt ttgaagtctg acaatccttg agaatctttg catgcagagg aggtaagagg   1800
tattggattt tcagagagga agaacacagc gcagaatgaa gggccaggct tactgagctg   1860
tccagtggag ggctcatggg tgggacatgg aaaagaaggc agcctaggcc ctggggagcc   1920
```

```
cagtccactg agcaagcaag ggactgagtg agccttttgc aggaaaaggc taagaaaaag    1980
gaaaaccatt ctaaaacaca acaagaaact gtccaaatgc tttgggaact gtgtttattg    2040
cctataatgg gtccccaaaa tgggtaacct agacttcaga gagaatgagc agagagcaaa    2100
ggagaaatct ggctgtcctt ccattttcat tctgttatct caggtgagct ggtagagggg    2160
agacattaga aaaaaatgaa acaacaaaac aattactaat gaggtacgct gaggcctggg    2220
agtctcttga ctccactact taattccgtt tagtgagaaa cctttcaatt ttcttttatt    2280
agaagggcca gcttactgtt ggtggcaaaa ttgccaacat aagttaatag aaagttggcc    2340
aatttcaccc cattttctgt ggtttgggct ccacattgca atgttcaatg ccacgtgctg    2400
ctgacaccga ccggagtact agccagcaca aaaggcaggg tagcctgaat tgctttctgc    2460
tctttacatt tcttttaaaa taagcattta gtgctcagtc cctactgagt actctttctc    2520
tcccctcctc tgaatttaat tctttcaact tgcaatttgc aaggattaca catttcactg    2580
tgatgtatat tgtgttgcaa aaaaaaaaaa aagtgtcttt gtttaaaatt acttggtttg    2640
tgaatccatc ttgcttttc cccattggaa ctagtcatta acccatctct gaactggtag    2700
aaaaacatct gaagagctag tctatcagca tctgacaggt gaattggatg gttctcagaa    2760
ccatttcacc cagacagcct gtttctatcc tgtttaataa attagtttgg gttctctaca    2820
tgcataacaa accctgctcc aatctgtcac ataaaagtct gtgacttgaa gtttagtcag    2880
cacccccacc aaactttatt tttctatgtg ttttttgcaa catatgagtg ttttgaaaat    2940
aaagtaccca tgtctttatt agaaaaaaaa aaaaaaaaa aaaa                      2984
```

<210> SEQ ID NO 336
<211> LENGTH: 147
<212> TYPE: PRT
<213> ORGANISM: Homo sapien

<400> SEQUENCE: 336

```
Pro Ser Phe Pro Thr Leu Leu Ser Arg Arg His Leu Gly Ser Tyr Leu
 1               5                  10                  15

Leu Asp Ser Glu Asn Thr Ser Gly Ala Leu Pro Arg Leu Pro Gln Thr
            20                  25                  30

Pro Lys Gln Pro Gln Lys Arg Ser Arg Ala Ala Phe Ser His Thr Gln
        35                  40                  45

Val Ile Glu Leu Glu Arg Lys Phe Ser His Gln Lys Tyr Leu Ser Ala
    50                  55                  60

Pro Glu Arg Ala His Leu Ala Lys Asn Leu Lys Leu Thr Glu Thr Gln
65                  70                  75                  80

Val Lys Ile Trp Phe Gln Asn Arg Arg Tyr Lys Thr Lys Arg Lys Gln
                85                  90                  95

Leu Ser Ser Glu Leu Gly Asp Leu Glu Lys His Ser Ser Leu Pro Ala
            100                 105                 110

Leu Lys Glu Glu Ala Phe Ser Arg Ala Ser Leu Val Ser Val Tyr Asn
        115                 120                 125

Ser Tyr Pro Tyr Tyr Pro Tyr Leu Tyr Cys Val Gly Ser Trp Ser Pro
    130                 135                 140

Ala Phe Trp
145
```

<210> SEQ ID NO 337
<211> LENGTH: 9
<212> TYPE: PRT
<213> ORGANISM: Homo sapien

-continued

```
<400> SEQUENCE: 337

Ala Leu Thr Gly Phe Thr Phe Ser Ala
1               5

<210> SEQ ID NO 338
<211> LENGTH: 9
<212> TYPE: PRT
<213> ORGANISM: Homo sapien

<400> SEQUENCE: 338

Leu Leu Ala Asn Asp Leu Met Leu Ile
1               5

<210> SEQ ID NO 339
<211> LENGTH: 318
<212> TYPE: PRT
<213> ORGANISM: Homo sapien

<400> SEQUENCE: 339

Met Val Glu Leu Met Phe Pro Leu Leu Leu Leu Leu Pro Phe Leu
1               5                   10                  15

Leu Tyr Met Ala Ala Pro Gln Ile Arg Lys Met Leu Ser Ser Gly Val
                20                  25                  30

Cys Thr Ser Thr Val Gln Leu Pro Gly Lys Val Val Val Thr Gly
            35                  40                  45

Ala Asn Thr Gly Ile Gly Lys Glu Thr Ala Lys Glu Leu Ala Gln Arg
    50                  55                  60

Gly Ala Arg Val Tyr Leu Ala Cys Arg Asp Val Glu Lys Gly Glu Leu
65                  70                  75                  80

Val Ala Lys Glu Ile Gln Thr Thr Gly Asn Gln Gln Val Leu Val
                85                  90                  95

Arg Lys Leu Asp Leu Ser Asp Thr Lys Ser Ile Arg Ala Phe Ala Lys
                100                 105                 110

Gly Phe Leu Ala Glu Glu Lys His Leu His Val Leu Ile Asn Asn Ala
            115                 120                 125

Gly Val Met Met Cys Pro Tyr Ser Lys Thr Ala Asp Gly Phe Glu Met
    130                 135                 140

His Ile Gly Val Asn His Leu Gly His Phe Leu Leu Thr His Leu Leu
145                 150                 155                 160

Leu Glu Lys Leu Lys Glu Ser Ala Pro Ser Arg Ile Val Asn Val Ser
                165                 170                 175

Ser Leu Ala His His Leu Gly Arg Ile His Phe His Asn Leu Gln Gly
            180                 185                 190

Glu Lys Phe Tyr Asn Ala Gly Leu Ala Tyr Cys His Ser Lys Leu Ala
        195                 200                 205

Asn Ile Leu Phe Thr Gln Glu Leu Ala Arg Arg Leu Lys Gly Ser Gly
    210                 215                 220

Val Thr Thr Tyr Ser Val His Pro Gly Thr Val Gln Ser Glu Leu Val
225                 230                 235                 240

Arg His Ser Ser Phe Met Arg Trp Met Trp Trp Leu Phe Ser Phe Phe
                245                 250                 255

Ile Lys Thr Pro Gln Gln Gly Ala Gln Thr Ser Leu His Cys Ala Leu
            260                 265                 270

Thr Glu Gly Leu Glu Ile Leu Ser Gly Asn His Phe Ser Asp Cys His
        275                 280                 285
```

Val Ala Trp Val Ser Ala Gln Ala Arg Asn Glu Thr Ile Ala Arg Arg
    290                 295                 300

Leu Trp Asp Val Ser Cys Asp Leu Leu Gly Leu Pro Ile Asp
305                 310                 315

<210> SEQ ID NO 340
<211> LENGTH: 483
<212> TYPE: DNA
<213> ORGANISM: Homo sapien

<400> SEQUENCE: 340

| | | | | | |
|---|---|---|---|---|---|
| gccgaggtct | gccttcacac | ggaggacacg | agactgcttc | ctcaagggct | cctgcctgcc | 60 |
| tggacactgg | tgggaggcgc | tgtttagttg | gctgttttca | gagggtcttt | tcggagggac | 120 |
| ctcctgctgc | aggctggagt | gtctttattc | ctggcgggag | accgcacatt | ccactgctga | 180 |
| ggttgtgggg | gcggtttatc | aggcagtgat | aaacataaga | tgtcatttcc | ttgactccgg | 240 |
| ccttcaattt | tctctttggc | tgacgacgga | gtccgtggtg | tcccgatgta | actgaccect | 300 |
| gctccaaacg | tgacatcact | gatgctcttc | tcggggtgc | tgatggcccg | cttggtcacg | 360 |
| tgctcaatct | cgccattcga | ctcttgctcc | aaactgtatg | aagacacctg | actgcacgtt | 420 |
| ttttctgggc | ttccagaatt | taaagtgaaa | ggcagcactc | ctaagctccg | actccgatgc | 480 |
| ctg | | | | | | 483 |

<210> SEQ ID NO 341
<211> LENGTH: 344
<212> TYPE: DNA
<213> ORGANISM: Homo sapien

<400> SEQUENCE: 341

| | | | | | |
|---|---|---|---|---|---|
| ctgctgctga | gtcacagatt | tcattataaa | tagcctccct | aaggaaaata | cactgaatgc | 60 |
| tatttttact | aaccattcta | tttttataga | aatagctgag | agtttctaaa | ccaactctct | 120 |
| gctgccttac | aagtattaaa | tattttactt | ctttccataa | agagtagctc | aaaatatgca | 180 |
| attaatttaa | taatttctga | tgatggtttt | atctgcagta | atatgtatat | catctattag | 240 |
| aatttactta | atgaaaaact | gaagagaaca | aaatttgtaa | ccactagcac | ttaagtactc | 300 |
| ctgattctta | acattgtctt | taatgaccac | aagacaacca | acag | | 344 |

<210> SEQ ID NO 342
<211> LENGTH: 592
<212> TYPE: DNA
<213> ORGANISM: Homo sapien

<400> SEQUENCE: 342

| | | | | | |
|---|---|---|---|---|---|
| acagcaaaaa | agaaactgag | aagcccaaty | tgctttcttg | ttaacatcca | cttatccaac | 60 |
| caatgtggaa | acttcttata | cttggttcca | ttatgaagtt | ggacaattgc | tgctatcaca | 120 |
| cctggcaggt | aaaccaatgc | aagagagtg | atggaaacca | ttggcaagac | tttgttgatg | 180 |
| accaggattg | gaattttata | aaaatattgt | tgatgggaag | ttgctaaagg | gtgaattact | 240 |
| tccctcagaa | gagtgtaaag | aaaagtcaga | gatgctataa | tagcagctat | tttaattggc | 300 |
| aagtgccact | gtggaaagag | ttcctgtgtg | tgctgaagtt | ctgaagggca | gtcaaattca | 360 |
| tcagcatggg | ctgtttggtg | caaatgcaaa | agcacaggtc | ttttttagcat | gctggtctct | 420 |
| cccgtgtcct | tatgcaaata | atcgtcttct | tctaaatttc | tcctaggctt | cattttccaa | 480 |
| agttcttctt | ggtttgtgat | gtcttttctg | ctttccatta | attctataaa | atagtatggc | 540 |
| ttcagccacc | cactcttcgc | cttagcttga | ccgtgagtct | cggctgccgc | tg | 592 |

<210> SEQ ID NO 343
<211> LENGTH: 382
<212> TYPE: DNA
<213> ORGANISM: Homo sapien

<400> SEQUENCE: 343

| | | | | | | |
|---|---|---|---|---|---|---|
| ttcttgacct | cctcctcctt | caagctcaaa | caccacctcc | cttattcagg | accggcactt | 60 |
| cttaatgttt | gtggctttct | ctccagcctc | tcttaggagg | ggtaatggtg | gagttggcat | 120 |
| cttgtaactc | tcctttctcc | tttcttcccc | tttctctgcc | cgccttttccc | atcctgctgt | 180 |
| agacttcttg | attgtcagtc | tgtgtcacat | ccagtgattg | ttttggtttc | tgttcccttt | 240 |
| ctgactgccc | aagggctca | gaaccccagc | aatcccttcc | tttcactacc | ttctttttttg | 300 |
| ggggtagttg | gaagggactg | aaattgtggg | gggaaggtag | gaggcacatc | aataaagagg | 360 |
| aaaccaccaa | gctgaaaaaa | aa | | | | 382 |

<210> SEQ ID NO 344
<211> LENGTH: 536
<212> TYPE: DNA
<213> ORGANISM: Homo sapien

<400> SEQUENCE: 344

| | | | | | | |
|---|---|---|---|---|---|---|
| ctgggcctga | agctgtaggg | taaatcagag | gcaggcttct | gagtgatgag | agtcctgaga | 60 |
| caataggcca | cataaacttg | gctggatgga | acctcacaat | aaggtggtca | cctcttgttt | 120 |
| gtttagggg | atgccaagga | taaggccagc | tcagttatat | gaagagaagc | agaacaaaca | 180 |
| agtctttcag | agaaatggat | gcaatcgag | tgggatcccg | gtcacatcaa | ggtcacactc | 240 |
| caccttcatg | tgcctgaatg | gttgccaggt | cagaaaaatc | caccccttac | gagtgcggct | 300 |
| tcgaccctat | atccccgcc | cgcgtccctt | tctccataaa | attcttctta | gtagctatta | 360 |
| ccttcttatt | atttgatcta | gaaattgccc | tccttttacc | cctaccatga | gccctacaaa | 420 |
| caactaacct | gccactaata | gttatgtcat | ccctcttatt | aatcatcatc | ctagccctaa | 480 |
| gtctggccta | tgagtgacta | caaaaaggat | tagactgagc | cgaataacaa | aaaaaa | 536 |

<210> SEQ ID NO 345
<211> LENGTH: 251
<212> TYPE: DNA
<213> ORGANISM: Homo sapien

<400> SEQUENCE: 345

| | | | | | | |
|---|---|---|---|---|---|---|
| acctttttgag | gtctctctca | ccacctccac | agccaccgtc | accgtgggat | gtgctggatg | 60 |
| tgaatgaagc | cccatctttt | gtgcctcctg | aaaagagagt | ggaagtgtcc | gaggactttg | 120 |
| gcgtgggcca | ggaaatcaca | tcctacactg | cccaggagcc | agacacattt | atggaacaga | 180 |
| aaataacata | tcggatttgg | agagacactg | ccaactggct | ggagattaat | ccggacactg | 240 |
| gtgccatttc | c | | | | | 251 |

<210> SEQ ID NO 346
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 346

```
cgcgtctctg acactgtgat catgacaggg gttcaaacag aaagtgcctg ggccctcctt      60
ctaagtcttg ttaccaaaaa aaggaaaaag aaaagatctt ctcagttaca aattctggga     120
agggagacta tacctggctc ttgccctaag tgagaggtct ccctcccgc accaaaaaat      180 agaaaggctt tctatttcac tggcccaggt aggggggaagg agagtaactt tgagtctgtg    240
ggtctcattt cccaaggtgc cttcaatgct catnaaaacc aa                        282
```

<210> SEQ ID NO 347
<211> LENGTH: 201
<212> TYPE: DNA
<213> ORGANISM: Homo sapien
<220> FEATURE:
<221> NAME/KEY: misc_feature
<222> LOCATION: (1)...(201)
<223> OTHER INFORMATION: n = A,T,C or G

<400> SEQUENCE: 347

```
acacacataa tattataaaa tgccatctaa ttggaaggag ctttctatca ttgcaagtca      60
taaatataac ttttaaaana ntactancag cttttaccta ngctcctaaa tgcttgtaaa    120
tctgagactg actggaccca cccagaccca gggcaaagat acatgttacc atatcatctt   180
tataaagaat ttttttttgt c                                               201
```

<210> SEQ ID NO 348
<211> LENGTH: 251
<212> TYPE: DNA
<213> ORGANISM: Homo sapien

<400> SEQUENCE: 348

```
ctgttaatca caacatttgt gcatcacttg tgccaagtga aaaatgttc taaaatcaca       60 agagagaaca gtgccagaat gaaactgacc ctaagtccca ggtgcccctg gcaggcaga    120 aggagacact cccagcatgg aggagggttt atctttcat cctaggtcag gtctacaatg    180
ggggaaggtt ttattataga actcccaaca gcccacctca ctcctgccac ccacccgatg    240
gccctgcctc c                                                          251
```

<210> SEQ ID NO 349
<211> LENGTH: 251
<212> TYPE: DNA
<213> ORGANISM: Homo sapien

<400> SEQUENCE: 349

```
taaaaatcaa gccatttaat tgtatctttg aaggtaaaca atatatggga gctggatcac       60 aaccctgag gatgccagag ctatgggtcc agaacatggt gtggtattat caacagagtt     120
cagaagggtc tgaactctac gtgttaccag agaacataat gcaattcatg cattccactt    180
agcaattttg taaaatacca gaaacagacc ccaagagtct ttcaagatga ggaaaattca   240
actcctggtt t                                                          251
```

<210> SEQ ID NO 350
<211> LENGTH: 908
<212> TYPE: DNA
<213> ORGANISM: Homo sapien

<400> SEQUENCE: 350

```
ctggacactt tgcgagggct tttgctggct gctgctgctg cccgtcatgc tactcatcgt       60
agcccgcccg gtgaagctcg ctgcttccc tacctcctta agtgactgcc aaacgcccac    120
cggctggaat tgctctggtt atgatgacag agaaaatgat ctcttcctct gtgacaccaa   180
```

```
cacctgtaaa tttgatgggg aatgtttaag aattggagac actgtgactt gcgtctgtca    240
gttcaagtgc aacaatgact atgtgcctgt gtgtggctcc aatggggaga gctaccagaa    300
tgagtgttac ctgcgacagg ctgcatgcaa acagcagagt gagatacttg tggtgtcaga    360
aggatcatgt gccacagtcc atgaaggctc tggagaaact agtcaaaagg agacatccac    420
ctgtgatatt tgccagtttg gtgcagaatg tgacgaagat gccgaggatg tctggtgtgt    480
gtgtaatatt gactgttctc aaaccaactt caatcccctc tgcgcttctg atgggaaatc    540
ttatgataat gcatgccaaa tcaaagaagc atcgtgtcag aaacaggaga aaattgaagt    600
catgtctttg ggtcgatgtc aagataacac aactacaact actaagtctg aagatgggca    660
ttatgcaaga acagattatg cagagaatgc taacaaatta gaagaaagtg ccagagaaca    720
ccacatacct tgtccggaac attacaatgg cttctgcatg catgggaagt gtgagcattc    780
tatcaatatg caggagccat cttgcaggtg tgatgctggt tatactggac aacactgtga    840 aaaaaggac tacagtgttc tatacgttgt tcccggtcct gtacgatttc agtatgtctt    900
aatcgcag                                                             908

<210> SEQ ID NO 351
<211> LENGTH: 472
<212> TYPE: DNA
<213> ORGANISM: Homo sapien

<400> SEQUENCE: 351
ccagttattt gcaagtggta agagcctatt taccataaat aatactaaga accaactcaa     60
gtcaaacctt aatgccattg ttattgtgaa ttaggattaa gtagtaattt tcaaaattca    120
cattaacttg atttttaaaat cagwtttgyg agtcatttac cacaagctaa atgtgtacac    180
tatgataaaa acaaccattg tattcctgtt tttctaaaca gtcctaattt ctaacactgt    240
atatatcctt cgacatcaat gaactttgtt ttcttttact ccagtaataa agtaggcaca    300
gatctgtcca caacaaactt gccctctcat gccttgcctc tcaccatgct ctgctccagg    360 tcagcccct tttggcctgt ttgttttgtc aaaaacctaa tctgcttctt gcttttcttg    420
gtaatatata tttagggaag atgttgcttt gcccacacac gaagcaaagt aa            472

<210> SEQ ID NO 352
<211> LENGTH: 251
<212> TYPE: DNA
<213> ORGANISM: Homo sapien

<400> SEQUENCE: 352
ctcaaagcta atctctcggg aatcaaacca gaaaagggca aggatcttag gcatggtgga     60
tgtggataag gccaggtcaa tggctgcaag catgcagaga aagaggtaca tcggagcgtg    120
caggctgcgt tccgtcctta cgatgaagac cacgatgcag tttccaaaca ttgccactac    180
atacatggaa aggaggggga agccaaccca gaaatgggct ttctctaatc ctgggatacc    240
aataagcaca a                                                         251

<210> SEQ ID NO 353
<211> LENGTH: 436
<212> TYPE: DNA
<213> ORGANISM: Homo sapien

<400> SEQUENCE: 353
tttttttttt tttttttttt tttttacaa caatgcagtc atttatttat tgagtatgtg      60
```

```
cacattatgg tattattact atactgatta tatttatcat gtgacttcta attaraaaat    120
gtatccaaaa gcaaaacagc agatatacaa aattaaagag acagaagata gacattaaca    180
gataaggcaa cttatacatt gacaatccaa atccaataca tttaaacatt tgggaaatga    240
gggggacaaa tggaagccar atcaaatttg tgtaaaacta ttcagtatgt ttcccttgct    300
tcatgtctga raaggctctc ccttcaatgg ggatgacaaa ctccaaatgc cacacaaatg    360
ttaacagaat actagattca cactggaacg ggggtaaaga agaaattatt ttctataaaa    420
gggctcctaa tgtagt                                                   436

<210> SEQ ID NO 354
<211> LENGTH: 854
<212> TYPE: DNA
<213> ORGANISM: Homo sapien

<400> SEQUENCE: 354 cctttttctag ttcaccagtt ttctgcaagg atgctggtta gggagtgtct gcaggaggag    60
caagtctgaa accaaatcta ggaaacatag gaaacgagcc aggcacaggg ctggtgggcc   120
atcagggacc acctttggg ttgatatttt gcttaatctg catcttttga gtaagatcat    180
ctggcagtag aagctgttct ccaggtacat ttctctagct catgtacaaa acatcctga    240 aggactttgt caggtgcctt gctaaaagcc agatgcgttc ggcacttcct tggtctgagg    300
ttaattgcac acctcaggc actgggctca tgctttcaag tattttgtcc tcactttagg    360
gtgagtgaaa gatccccatt ataggagcac ttgggagaga tcatataaaa gctgactctt    420
gagtacatgc agtaatgggg tagatgtgtg tggtgtgtct tcattcctgc aagggtgctt    480
gttagggagt gtttccagga ggaacaagtc tgaaaccaat catgaaataa atggtaggtg    540
tgaactggaa aactaattca aagagagat cgtgatatca gtgtggttga tacaccttgg    600
caatatggaa ggctctaatt tgcccatatt tgaaataata attcagcttt ttgtaataca    660
aaataacaaa ggattgagaa tcatggtgtc taatgtataa aagacccagg aaacataaat    720
atatcaactg cataaatgta aaatgcatgt gacccaagaa ggcccaaag tggcagacaa     780 cattgtaccc attttcccctt ccaaaatgtg agcggcgggc ctgctgcttt caaggctgtc    840
acacgggatg tcag                                                   854

<210> SEQ ID NO 355
<211> LENGTH: 676
<212> TYPE: DNA
<213> ORGANISM: Homo sapien

<400> SEQUENCE: 355
gaaattaagt atgagctaaa ttccctgtta aaacctctag gggtgacaga tctcttcaac     60
caggtcaaag ctgatctttc tggaatgtca ccaaccaagg gcctatattt atcaaaagcc   120
atccacaagt catacctgga tgtcagcgaa gagggcacgg aggcagcagc agccactggg   180
gacagcatcg ctgtaaaaag cctaccaatg agagctcagt tcaaggcgaa ccacccctc     240 ctgttcttta taaggcacac tcataccaac acgatcctat tctgtggcaa gcttgcctct   300
ccctaatcag atggggttga gtaaggctca gagttgcaga tgaggtgcag agacaatcct   360
gtgactttcc cacggccaaa aagctgttca cacctcacgc acctctgtgc ctcagtttgc   420
tcatctgcaa aataggtcta ggatttcttc caaccatttc atgagttgtg aagctaaggc   480
tttgttaatc atgaaaaag gtagacttat gcagaaagcc tttctggctt tcttatctgt    540
ggtgtctcat ttgagtgctg tccagtgaca tgatcaagtc aatgagtaaa attttaaggg    600
```
attagatttt cttgacttgt atgtatctgt gagatcttga ataagtgacc tgacatctct    660
gcttaaagaa aaccag    676

<210> SEQ ID NO 356
<211> LENGTH: 574
<212> TYPE: DNA
<213> ORGANISM: Homo sapien

<400> SEQUENCE: 356
tttttttttt tttttcagga aaacattctc ttactttatt tgcatctcag caaaggttct     60
catgtggcac ctgactggca tcaaaccaaa gttcgtaggc caacaaagat gggccactca    120
caagcttccc atttgtagat ctcagtgcct atgagtatct gacacctgtt cctctcttca    180
gtctcttagg gaggcttaaa tctgtctcag gtgtgctaag agtgccagcc caaggkggtc    240
aaaagtccac aaaactgcag tctttgctgg gatagtaagc caagcagtgc ctggacagca    300
gagttctttt cttgggcaac agataaccag acaggactct aatcgtgctc ttattcaaca    360
ttcttctgtc tctgcctaga ctggaataaa agccaatcct ctctcgtggc acagggaagg    420
agatacaagc tcgtttacat gtgatagatc taacaaaggc atctaccgaa gtctggtctg    480
gatagacggc acagggagct cttaggtcag cgctgctggt tggaggacat tcctgagtcc    540
agctttgcag cctttgtgca acagtacttt ccca    574

<210> SEQ ID NO 357
<211> LENGTH: 393
<212> TYPE: DNA
<213> ORGANISM: Homo sapien

<400> SEQUENCE: 357
tttttttttt tttttttttt tttttttttt tacagaatat aratgcttta tcactgkact     60
taatatggkg kcttgttcac tatacttaaa aatgcaccac tcataaatat ttaattcagc    120
aagccacaac caaracttga ttttatcaac aaaaacccct aaatataaac ggsaaaaaag    180
atagatataa ttattccagt tttttttaaaa cttaaaarat attccattgc cgaattaara    240
araarataag tgttatatgg aaagaagggc attcaagcac actaaaraaa cctgaggkaa    300
gcataatctg tacaaaatta aactgtcctt tttggcattt taacaaattt gcaacgktct    360 ttttttttctt tttctgttttt tttttttttt tac    393

<210> SEQ ID NO 358
<211> LENGTH: 630
<212> TYPE: DNA
<213> ORGANISM: Homo sapien

<400> SEQUENCE: 358
acagggtaaa caggaggatc cttgctctca cggagcttac attctagcag gaggacaata     60
ttaatgttta taggaaaatg atgagtttat gacaaaggaa gtagatagtg ttttacaaga    120
gcatagagta gggaagctaa tccagcacag ggaggtcaca gagacatccc taaggaagtg    180
gagtttaaac tgagagaagc aagtgcttaa actgaaggat gtgttgaaga agaagggaga    240
gtagaacaat ttgggcagag ggaaccttat agaccctaag gtgggaaggt tcaaagaact    300
gaaagagagc tagaacagct ggagccgttc tccggtgtaa agaggagtca agagataag    360 attaaagatg tgaagattaa gatcttggtg gcattcaggg attggcactt ctacaagaaa    420
tcactgaagg gagtaatgtg acattacttt tcacttcagg atggccattc taactccagg    480

```
gggtagactg gactaggtaa gactggaggc aggtagacct cttctaaggc ctgcgatagt      540
gaaagacaaa aataagtggg gaaattcagg ggatagtgaa aatcagtagg acttaatgag      600
caagccagag gttcctccac aacaaccagt                                      630
```

<210> SEQ ID NO 359
<211> LENGTH: 620
<212> TYPE: DNA
<213> ORGANISM: Homo sapien

<400> SEQUENCE: 359

```
acagcattcc aaaatataca tctagagact aarrgtaaat gctctatagt gaagaagtaa       60
taattaaaaa atgctactaa tatagaaaat ttataatcag aaaaataaat attcagggag      120
ctcaccagaa gaataaagtg ctctgccagt tattaaagga ttactgctgg tgaattaaat      180
atggcattcc ccaagggaaa tagagagatt cttctggatt atgttcaata tttatttcac      240
aggattaact gttttaggaa cagatataaa gcttcgccac ggaagagatg gacaaagcac      300
aaagacaaca tgataccttt ggaagcaaca ctacccttttc aggcataaaa tttggagaaa      360
tgcaacatta tgcttcatga ataatatgta gaaagaaggt ctgatgaaaa tgacatcctt      420
aatgtaagat aactttataa gaattctggg tcaaataaaa ttctttgaag aaaacatcca      480
aatgtcattg acttatcaaa tactatcttg gcatataacc tatgaaggca aaactaaaca      540
aacaaaaagc tcacaccaaa caaaaccatc aacttatttt gtattctata acatacgaga      600
ctgtaaagat gtgacagtgt                                                 620
```

<210> SEQ ID NO 360
<211> LENGTH: 431
<212> TYPE: DNA
<213> ORGANISM: Homo sapien

<400> SEQUENCE: 360

```
aaaaaaaaaa agccagaaca acatgtgata gataatatga ttggctgcac acttccagac       60
tgatgaatga tgaacgtgat ggactattgt atggagcaca tcttcagcaa gagggggaaa      120
tactcatcat ttttggccag cagttgtttg atcaccaaac atcatgccag aatactcagc      180
aaaccttctt agctcttgag aagtcaaagt ccgggggaat ttattcctgg caattttaat      240
tggactcctt atgtgagagc agcggctacc cagctggggt ggtggagcga acccgtcact      300
agtggacatg cagtggcaga gctcctggta accacctaga ggaatacaca ggcacatgtg      360
tgatgccaag cgtgacacct gtagcactca aatttgtctt gtttttgtct ttcggtgtgt      420
agattcttag t                                                         431
```

<210> SEQ ID NO 361
<211> LENGTH: 351
<212> TYPE: DNA
<213> ORGANISM: Homo sapien

<400> SEQUENCE: 361

```
acactgattt ccgatcaaaa gaatcatcat ctttaccttg acttttcagg gaattactga       60
actttcttct cagaagatag ggcacagcca ttgccttggc ctcacttgaa gggtctgcat      120
ttgggtcctc tggtctcttg ccaagtttcc cagccactcg agggagaaat atcgggaggt      180
ttgacttcct ccgggggcttt ccgagggct tcaccgtgag ccctgcggcc ctcagggctg      240
caatcctgga ttcaatgtct gaaacctcgc tctctgcctc ctggacttct gaggccgtca      300
ctgccactct gtcctccagc tctgacagct cctcatctgt ggtcctgttg t              351
```

<210> SEQ ID NO 362
<211> LENGTH: 463
<212> TYPE: DNA
<213> ORGANISM: Homo sapien

<400> SEQUENCE: 362

| | | | | | |
|---|---|---|---|---|---|
| acttcatcag | gccataatgg | gtgcctcccg | tgagaatcca | agcacctttg | gactgcgcga | 60 |
| tgtagatgag | ccggctgaag | atcttgcgca | tgcgcggctt | cagggcgaag | ttcttggcgc | 120 |
| ccccggtcac | agaaatgacc | aggttgggtg | ttttcaggtg | ccagtgctgg | gtcagcagct | 180 |
| cgtaaaggat | ttccgcgtcc | gtgtcgcagg | acagacgtat | atacttccct | ttcttcccca | 240 |
| gtgtctcaaa | ctgaatatcc | ccaaaggcgt | cggtaggaaa | ttccttggtg | tgtttcttgt | 300 |
| agttccattt | ctcactttgg | ttgatctggg | tgccttccat | gtgctggctc | tgggcatagc | 360 |
| cacacttgca | cacattctcc | ctgataagca | cgatggtgtg | gacaggaagg | aaggatttca | 420 |
| ttgagcctgc | ttatggaaac | tggtattgtt | agcttaaata | gac | | 463 |

<210> SEQ ID NO 363
<211> LENGTH: 653
<212> TYPE: DNA
<213> ORGANISM: Homo sapien
<220> FEATURE:
<221> NAME/KEY: misc_feature
<222> LOCATION: (1)...(653)
<223> OTHER INFORMATION: n = A,T,C or G

<400> SEQUENCE: 363

| | | | | | |
|---|---|---|---|---|---|
| accccccgagt | ncctgnctgg | catactgnga | acgaccaacg | acacacccaa | gctcggcctc | 60 |
| ctcttggnga | ttctgggtga | catcttcatg | aatggcaacc | gtgccagwga | ggctgtcctc | 120 |
| tgggaggcac | tacgcaagat | gggactgcgt | cctggggtga | acatcctct | ccttggagat | 180 |
| ctaacgaaac | ttctcaccta | tgagttgtaa | agcagaaata | cctgnactac | agacgagtgc | 240 |
| ccaacagcaa | ccccccggaa | gtatgagttc | ctctrgggcc | tccgttccta | ccatgagasc | 300 |
| tagcaagatg | naagtgttga | gantcattgc | agaggttcag | aaaagagacc | cntcgtgact | 360 |
| ggtctgcaca | gttcatggag | gctgcagatg | aggcttgga | tgctctggat | gctgctgcag | 420 |
| ctgaggccga | agcccgggct | gaagcaagaa | cccgcatggg | aattggagat | gaggctgtgt | 480 |
| ntgggccctg | gagctgggat | gacattgagt | ttgagctgct | gacctgggat | gaggaaggag | 540 |
| attttggaga | tccntggtcc | agaattccat | ttaccttctg | ggccagatac | caccagaatg | 600 |
| cccgctccag | attccctcag | acctttgccg | gtcccattat | tggtcstggt | ggt | 653 |

<210> SEQ ID NO 364
<211> LENGTH: 401
<212> TYPE: DNA
<213> ORGANISM: Homo sapien

<400> SEQUENCE: 364

| | | | | | |
|---|---|---|---|---|---|
| actagaggaa | agacgttaaa | ccactctact | accacttgtg | gaactctcaa | agggtaaatg | 60 |
| acaaagccaa | tgaatgactc | taaaaacaat | atttacattt | aatggtttgt | agacaataaa | 120 |
| aaaacaaggt | ggatagatct | agaattgtaa | cattttaaga | aaaccatagc | atttgacaga | 180 |
| tgagaaagct | caattataga | tgcaaagtta | taactaaact | actatagtag | taaagaaata | 240 |
| catttcacac | ccttcatata | aattcactat | cttggcttga | ggcactccat | aaaatgtatc | 300 |
| acgtgcatag | taaatctttta | tatttgctat | ggcgttgcac | tagaggactt | ggactgcaac | 360 |

```
aagtggatgc gcggaaaatg aaatcttctt caatagccca g                401
```

<210> SEQ ID NO 365
<211> LENGTH: 356
<212> TYPE: DNA
<213> ORGANISM: Homo sapien

<400> SEQUENCE: 365

```
ccagtgtcat atttgggctt aaaatttcaa gaagggcact tcaaatggct ttgcatttgc    60
atgtttcagt gctagagcgt aggaatagac cctggcgtcc actgtgagat gttcttcagc   120
taccagagca tcaagtctct gcagcaggtc attcttgggt aaagaaatga cttccacaaa   180
ctctccatcc cctggctttg gcttcggcct tgcgttttcg gcatcatctc cgttaatggt   240
gactgtcacg atgtgtatag tacagtttga caagcctggg tccatacaga ccgctggaga   300
acattcggca atgtccccct tgtagccagt ttcttcttcg agctcccgga gagcag       356
```

<210> SEQ ID NO 366
<211> LENGTH: 1851
<212> TYPE: DNA
<213> ORGANISM: Homo sapien

<400> SEQUENCE: 366

```
tcatcaccat tgccagcagc ggcaccgtta gtcaggtttt ctgggaatcc cacatgagta    60
cttccgtgtt cttcattctt cttcaatagc cataaatctt ctagctctgg ctggctgttt   120
tcacttcctt taagcctttg tgactcttcc tctgatgtca gctttaagtc ttgttctgga   180
ttgctgtttt cagaagagat ttttaacatc tgttttttctt tgtagtcaga aagtaactgg   240
caaattacat gatgatgact agaaacagca tactctctgg ccgtctttcc agatcttgag   300
aagatacatc aacattttgc tcaagtagag ggctgactat acttgctgat ccacaacata   360
cagcaagtat gagagcagtt cttccatatc tatccagcgc atttaaattc gcttttttct   420
tgattaaaaa tttcaccact tgctgttttt gctcatgtat accaagtagc agtggtgtga   480
ggccatgctt gttttttgat tcgatatcag caccgtataa gagcagtgct ttggccatta   540
atttatcttc attgtagaca gcatagtgta gagtggtatt tccatactca tctggaatat   600
ttggatcagt gccatgttcc agcaacatta acgcacattc atcttcctgg cattgtacgg   660
cctttgtcag agctgtcctc tttttgttgt caaggacatt aagttgacat cgtctgtcca   720
gcacgagttt tactacttct gaattcccat tggcagaggc cagatgtaga gcagtcctct   780
tttgcttgtc cctcttgttc acatccgtgt ccctgagcat gacgatgaga tcctttctgg   840
ggactttacc ccaccaggca gctctgtgga gcttgtccag atcttctcca tggacgtggt   900
acctgggatc catgaaggcg ctgtcatcgt agtctcccca agcgaccacg ttgctcttgc   960
cgctcccctg cagcagggga agcagtggca gcaccacttg cacctcttgc tcccaagcgt  1020
cttcacagag gagtcgttgt ggtctccaga agtgcccacg ttgctcttgc cgctcccct   1080
gtccatccag ggaggaagaa atgcaggaaa tgaaagatgc atgcacgatg gtatactcct  1140
cagccatcaa acttctggac agcaggtcac ttccagcaag gtggagaaag ctgtccaccc  1200
acagaggatg agatccagaa accacaatat ccattcacaa acaaacactt ttcagccaga  1260
cacaggtact gaaatcatgt catctgcggc aacatggtgg aacctaccca atcacacatc  1320
aagagatgaa gacactgcag tatatctgca caacgtaata ctcttcatcc ataacaaaat  1380
aatataattt tcctctggag ccatatggat gaactatgaa ggaagaactc cccgaagaag  1440
ccagtcgcag agaagccaca ctgaagctct gtcctcagcc atcagcgcca cggacaggar  1500
```

| | |
|---|---|
| tgtgtttctt ccccagtgat gcagcctcaa gttatcccga agctgccgca gcacacggtg | 1560 |
| gctcctgaga acaccccag ctcttccggt ctaacacagg caagtcaata aatgtgataa | 1620 |
| tcacataaac agaattaaaa gcaaagtcac ataagcatcc aacagacac agaaaaggca | 1680 |
| tttgacaaaa tccagcatcc ttgtatttat tgttgcagtt ctcagaggaa atgcttctaa | 1740 |
| cttttcccca tttagtatta tgttggctgt gggcttgtca taggtggttt ttattacttt | 1800 |
| aaggtatgtc ccttctatgc ctgttttgct gagggtttta attctcgtgc c | 1851 |

<210> SEQ ID NO 367
<211> LENGTH: 668
<212> TYPE: DNA
<213> ORGANISM: Homo sapien

<400> SEQUENCE: 367

| | |
|---|---|
| cttgagcttc caaataygga agactggccc ttacacasgt caatgttaaa atgaatgcat | 60 |
| ttcagtattt tgaagataaa attrgtagat ctataccttg tttttttgatt cgatatcagc | 120 |
| accrtataag agcagtgctt tggccattaa tttatctttc attrtagaca gcrtagtgya | 180 |
| gagtggtatt tccatactca tctggaatat ttggatcagt gccatgttcc agcaacatta | 240 |
| acgcacatta atcttcctgg cattgtacgg cctgtcagta ttagacccaa aaacaaatta | 300 |
| catatcttag gaattcaaaa taacattcca cagctttcac caactagtta tatttaaagg | 360 |
| agaaaactca tttttatgcc atgtattgaa atcaaaccca cctcatgctg atatagttgg | 420 |
| ctactgcata cctttatcag agctgtcctc tttttgttgt caaggacatt aagttgacat | 480 |
| cgtctgtcca gcaggagttt tactacttct gaattcccat tggcagaggc cagatgtaga | 540 |
| gcagtcctat gagagtgaga agacttttta ggaaattgta gtgcactagc tacagccata | 600 |
| gcaatgattc atgtaactgc aaacactgaa tagcctgcta ttactctgcc ttcaaaaaaa | 660 |
| aaaaaaaa | 668 |

<210> SEQ ID NO 368
<211> LENGTH: 1512
<212> TYPE: DNA
<213> ORGANISM: Homo sapien

<400> SEQUENCE: 368

| | |
|---|---|
| gggtcgccca gggggsgcgt gggctttcct cgggtgggtg tgggttttcc ctgggtgggg | 60 |
| tgggctgggc trgaatcccc tgctggggtt ggcaggtttt ggctgggatt gactttttytc | 120 |
| ttcaaacaga ttggaaaccc ggagttacct gctagttggt gaaactggtt ggtagacgcg | 180 |
| atctgttggc tactactggc ttctcctggc tgttaaaagc agatggtggt tgaggttgat | 240 |
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatgggca agtggtgctg ccactgcttc | 540 |
| ccctgctgca gggggagcrg caagagcaag gtgggcgctt ggggagacta cgatgacagt | 600 |
| gccttcatgg agcccaggta ccacgtccgt ggagaagatc tggacaagct ccacagagct | 660 |
| gcctggtggg gtaaagtccc cagaaaggat ctcatcgtca tgctcaggga cactgacgtg | 720 |
| aacaagaagg acaagcaaaa gaggactgct ctacatctgg cctctgccaa tgggaattca | 780 |

-continued

```
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tatayggtgc tgatatcgaa   1020
tcaaaaaaca aggtatagat ctactaattt tatcttcaaa atactgaaat gcattcattt   1080
taacattgac gtgtgtaagg gccagtcttc cgtatttgga agctcaagca taacttgaat   1140
gaaaatattt tgaaatgacc taattatctm agactttatt ttaaatattg ttattttcaa   1200
agaagcatta gagggtacag ttttttttt ttaaatgcac ttctggtaaa tacttttgtt   1260
gaaaacactg aatttgtaaa aggtaatact tactatttt caatttttcc ctcctaggat   1320
ttttttcccc taatgaatgt aagatggcaa aatttgccct gaaataggtt ttacatgaaa   1380
actccaagaa aagttaaaca tgtttcagtg aatagagatc ctgctccttt ggcaagttcc   1440
taaaaaacag taatagatac gaggtgatgc gcctgtcagt ggcaaggttt aagatatttc   1500
tgatctcgtg cc                                                       1512
```

<210> SEQ ID NO 369
<211> LENGTH: 1853
<212> TYPE: DNA
<213> ORGANISM: Homo sapien

<400> SEQUENCE: 369

```
gggtcgccca gggggsgcgt gggctttcct cgggtgggtg tgggttttcc ctgggtgggg     60
tgggctgggc trgaatcccc tgctggggtt ggcaggtttt ggctgggatt gactttttyc    120
ttcaaacaga ttggaaaccc ggagttacct gctagttggt gaaactggtt ggtagacgcg    180
atctgttggc tactactggc ttctcctggc tgttaaaagc agatggtggt tgaggttgat    240
tccatgccgg ctgcttcttc tgtgaagaag ccatttggtc tcaggagcaa gatgggcaag    300
tggtgctgcc gttgcttccc ctgctgcagg gagagcggca agagcaacgt gggcacttct    360
ggagaccacg acgactctgc tatgaagaca ctcaggagca agatgggcaa gtggtgccgc    420
cactgcttcc cctgctgcag ggggagtggc aagagcaacg tgggcgcttc tggagaccac    480
gacgaytctg ctatgaagac actcaggaac aagatgggca gtggtgctg ccactgcttc    540
ccctgctgca gggggagcrg caagagcaag gtgggcgctt ggggagacta cgatgacagy    600
gccttcatgg akcccaggta ccacgtccrt ggagaagatc tggacaagct ccacagagct    660
gcctggtggg gtaaagtccc cagaaaggat ctcatcgtca tgctcaggga cackgaygtg    720
aacaagargg acaagcaaaa gaggactgct ctacatctgg cctctgccaa tgggaattca    780
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tatayggtgc tgatatcgaa   1020
tcaaaaaaca agcatggcct cacaccactg ytacttggtr tacatgagca aaaacagcaa   1080
gtsgtgaaat ttttaatyaa gaaaaaagcg aatttaaaat gcrctggata gatatggaag   1140
ractgctctc atacttgctg tatgttgtgg atcagcaagt atagtcagcc ytctacttga   1200
gcaaaatrtt gatgtatctt ctcaagatct ggaaagacgg ccagagagta tgctgtttct   1260
agtcatcatc atgtaatttg ccagttactt tctgactaca aagaaaaaca gatgttaaaa   1320
atctcttctg aaaacagcaa tccagaacaa gacttaaagc tgacatcaga ggaagagtca   1380
```

| | |
|---|---|
| caaaggctta aaggaagtga aaacagccag ccagaggcat ggaaactttt aaatttaaac | 1440 |
| ttttggttta atgttttttt tttttgcctt aataatatta gatagtccca aatgaaatwa | 1500 |
| cctatgagac taggctttga gaatcaatag attcttttt taagaatctt ttggctagga | 1560 |
| gcggtgtctc acgcctgtaa ttccagcacc ttgagaggct gaggtgggca gatcacgaga | 1620 |
| tcaggagatc gagaccatcc tggctaacac ggtgaaaccc catctctact aaaaatacaa | 1680 |
| aaacttagct gggtgtggtg gcgggtgcct gtagtcccag ctactcagga rgctgaggca | 1740 |
| ggagaatggc atgaacccgg gaggtggagg ttgcagtgag ccgagatccg ccactacact | 1800 |
| ccagcctggg tgacagagca agactctgtc tcaaaaaaaa aaaaaaaaaa aaa | 1853 |

<210> SEQ ID NO 370
<211> LENGTH: 2184
<212> TYPE: DNA
<213> ORGANISM: Homo sapien

<400> SEQUENCE: 370

| | |
|---|---|
| ggcacgagaa ttaaaaccct cagcaaaaca ggcatagaag ggacatacct taaagtaata | 60 |
| aaaaccacct atgacaagcc cacagccaac ataatactaa atggggaaaa gttagaagca | 120 |
| tttcctctga gaactgcaac aataaataca aggatgctgg attttgtcaa atgccttttc | 180 |
| tgtgtctgtt gagatgctta tgtgactttg cttttaattc tgtttatgtg attatcacat | 240 |
| ttattgactt gcctgtgtta gaccggaaga gctggggtgt ttctcaggag ccaccgtgtg | 300 |
| ctgcggcagc ttcgggataa cttgaggctg catcactggg gaagaaacac aytcctgtcc | 360 |
| gtggcgctga tggctgagga cagagcttca gtgtggcttc tctgcgactg gcttcttcgg | 420 |
| ggagttcttc cttcatagtt catccatatg gctccagagg aaaattatat tattttgtta | 480 |
| tggatgaaga gtattacgtt gtgcagatat actgcagtgt cttcatctct tgatgtgtga | 540 |
| ttgggtaggt tccaccatgt tgccgcagat gacatgattt cagtacctgt gtctggctga | 600 |
| aaagtgtttg tttgtgaatg gatattgtgg tttctggatc tcatcctctg tgggtggaca | 660 |
| gctttctcca ccttgctgga agtgacctgc tgtccagaag tttgatggct gaggagtata | 720 |
| ccatcgtgca tgcatctttc atttcctgca tttcttcctc cctggatgga caggggagc | 780 |
| ggcaagagca acgtgggcac ttctggagac cacaacgact cctctgtgaa gacgcttggg | 840 |
| agcaagaggt gcaagtggtg ctgccactgc ttcccctgct gcaggggagc ggcaagagca | 900 |
| acgtggtcgc ttggggagac tacgatgaca gcgccttcat ggatcccagg taccacgtcc | 960 |
| atggagaaga tctggacaag ctccacagag ctgcctggtg gggtaaagtc cccagaaagg | 1020 |
| atctcatcgt catgctcagg gacacggatg tgaacaagag ggacaagcaa agaggactg | 1080 |
| ctctacatct ggcctctgcc aatgggaatt cagaagtagt aaaactcgtg ctggacagac | 1140 |
| gatgtcaact taatgtcctt gacaacaaaa agaggacagc tctgacaaag gccgtacaat | 1200 |
| gccaggaaga tgaatgtgcg ttaatgttgc tggaacatgg cactgatcca aatattccag | 1260 |
| atgagtatgg aaataccact ctacactatg ctgtctacaa tgaagataaa ttaatggcca | 1320 |
| aagcactgct cttatacggt gctgatatcg aatcaaaaaa caagcatggc ctcacaccac | 1380 |
| tgctacttgg tatacatgag caaaacagc aagtggtgaa attttaatc aagaaaaaag | 1440 |
| cgaatttaaa tgcgctggat agatatggaa gaactgctct catacttgct gtatgttgtg | 1500 |
| gatcagcaag tatagtcagc cctctacttg agcaaaatgt tgatgtatct tctcaagatc | 1560 |
| tggaaagacg gccagagagt atgctgtttc tagtcatcat catgtaattt gccagttact | 1620 |

-continued

| | |
|---|---|
| ttctgactac aaagaaaaac agatgttaaa aatctcttct gaaaacagca atccagaaca | 1680 |
| agacttaaag ctgacatcag aggaagagtc acaaaggctt aaaggaagtg aaaacagcca | 1740 |
| gccagaggca tggaaacttt taaatttaaa cttttggttt aatgttttt tttttttgcct | 1800 |
| taataatatt agatagtccc aaatgaaatw acctatgaga ctaggctttg agaatcaata | 1860 |
| gattctttt ttaagaatct tttggctagg acggtgtct cacgcctgta attccagcac | 1920 |
| cttgagaggc tgaggtgggc agatcacgag atcaggagat cgagaccatc ctggctaaca | 1980 |
| cggtgaaacc ccatctctac taaaaataca aaaacttagc tgggtgtggt ggcgggtgcc | 2040 |
| tgtagtccca gctactcagg argctgaggc aggagaatgg catgaacccg ggaggtggag | 2100 |
| gttgcagtga gccgagatcc gccactacac tccagcctgg gtgacagagc aagactctgt | 2160 |
| ctcaaaaaaa aaaaaaaaaa aaaa | 2184 |

<210> SEQ ID NO 371
<211> LENGTH: 1855
<212> TYPE: DNA
<213> ORGANISM: Homo sapien
<220> FEATURE:
<221> NAME/KEY: misc_feature
<222> LOCATION: (1)...(1855)
<223> OTHER INFORMATION: n = A,T,C or G

<400> SEQUENCE: 371

| | |
|---|---|
| tgcacgcatc ggccagtgtc tgtgccacgt acactgacgc cccctgagat gtgcacgccg | 60 |
| cacgcgcacg ttgcacgcgc ggcagcggct tggctggctt gtaacggctt gcacgcgcac | 120 |
| gccgccccg cataaccgtc agactggcct gtaacggctt gcaggcgcac gccgcacgcg | 180 |
| cgtaacggct tggctgccct gtaacggctt gcacgtgcat gctgcacgcg cgttaacggc | 240 |
| ttggctggca tgtagccgct tggcttggct ttgcattytt tgctkggctk ggcgttgkty | 300 |
| tcttggattg acgcttcctc cttggatkga cgtttcctcc ttggatkgac gtttcytyty | 360 |
| tcgcgttcct tgctggact tgaccttty tctgctgggt ttggcattcc tttggggtgg | 420 |
| gctgggtgtt ttctccgggg gggktkgccc ttcctgggt gggcgtgggk cgcccccagg | 480 |
| gggcgtgggc tttccccggg tgggtgtggg ttttcctggg gtggggtggg ctgtgctggg | 540 |
| atccccctgc tggggttggc agggattgac tttttcttc aaacagattg gaaacccgga | 600 |
| gtaacntgct agttggtgaa actggttggt agacgcgatc tgctggtact actgtttctc | 660 |
| ctggctgtta aaagcagatg gtggctgagg ttgattcaat gccggctgct tcttctgtga | 720 |
| agaagccatt tggtctcagg agcaagatgg gcaagtggtg cgccactgct tcccctgctg | 780 |
| caggggagc ggcaagagca acgtgggcac ttctggagac cacaacgact cctctgtgaa | 840 |
| gacgcttggg agcaagaggt gcaagtggtg ctgcccactg cttcccctgc tgcaggggag | 900 |
| cggcaagagc aacgtggkcg cttggggaga ctacgatgac agcgccttca tggakcccag | 960 |
| gtaccacgtc crtggagaag atctggacaa gctccacaga gctgcctggt ggggtaaagt | 1020 |
| ccccagaaag gatctcatcg tcatgctcag ggacactgay gtgaacaaga rggacaagca | 1080 |
| aaagaggact gctctacatc tggcctctgc caatgggaat tcagaagtag taaaactcgt | 1140 |
| gctggacaga cgatgtcaac ttaatgtcct tgacaacaaa aagaggacag ctctgacaaa | 1200 |
| ggccgtacaa tgccaggaag atgaatgtgc gttaatgttg ctggaacatg gcactgatcc | 1260 |
| aaatattcca gatgagtatg gaaataccac tctacactat gctgtctaca atgaagataa | 1320 |
| attaatggcc aaagcactgc tcttatacgg tgctgatatc gaatcaaaaa acaaggtata | 1380 |
| gatctactaa ttttatcttc aaaatactga aatgcattca ttttaacatt gacgtgtgta | 1440 |

```
agggccagtc ttccgtattt ggaagctcaa gcataacttg aatgaaaata ttttgaaatg      1500
acctaattat ctaagacttt attttaaata ttgttatttt caaagaagca ttagagggta      1560
cagttttttt tttttaaatg cacttctggt aaatactttt gttgaaaaca ctgaatttgt      1620
aaaaggtaat acttactatt tttcaattt tccctcctag gattttttt ccctaatgaa      1680 tgtaagatgg caaaatttgc cctgaaatag gttttacatg aaaactccaa gaaaagttaa      1740
acatgtttca gtgaatagag atcctgctcc tttggcaagt cctaaaaaa cagtaataga      1800 tacgaggtga tgcgcctgtc agtggcaagg tttaagatat ttctgatctc gtgcc           1855
```

<210> SEQ ID NO 372
<211> LENGTH: 1059
<212> TYPE: DNA
<213> ORGANISM: Homo sapien

<400> SEQUENCE: 372

```
gcaacgtggg cacttctgga gaccacaacg actcctctgt gaagacgctt gggagcaaga        60
ggtgcaagtg gtgctgccca ctgcttcccc tgctgcaggg gagcggcaag agcaacgtgg       120
gcgcttgrgg agactmcgat gacagygcct tcatggagcc caggtaccac gtccgtggag       180
aagatctgga caagctccac agagctgccc tggtggggta aagtccccag aaaggatctc       240
atcgtcatgc tcagggacac tgaygtgaac aagargggaca agcaaaagag gactgctcta       300
catctggcct ctgccaatgg gaattcagaa gtagtaaaac tcstgctgga cagacgatgt       360
caacttaatg tccttgacaa caaaaagagg acagctctga yaaaggccgt acaatgccag       420
gaagatgaat gtgcgttaat gttgctggaa catggcactg atccaaatat tccagatgag       480
tatggaaata ccactctrca ctaygctrtc tayaatgaag ataaattaat ggccaaagca       540
ctgctcttat ayggtgctga tatcgaatca aaaaacaagg tatagatcta ctaattttat       600
cttcaaaata ctgaaatgca ttcattttaa cattgacgtg tgtaagggcc agtcttccgt       660
atttggaagc tcaagcataa cttgaatgaa aatattttga aatgacctaa ttatctaaga       720 cttttatttta aatattgtta ttttcaaaga agcattagag ggtacagttt ttttttttta       780
aatgcacttc tggtaaatac ttttgttgaa aacactgaat ttgtaaaagg taatacttac       840
tatttttcaa ttttccctc ctaggatttt tttcccctaa tgaatgtaag atggcaaaat       900
ttgccctgaa ataggtttta catgaaaact ccaagaaaag ttaaacatgt ttcagtgaat       960
agagatcctg ctcctttggc aagttcctaa aaaacagtaa tagatacgag gtgatgcgcc      1020
tgtcagtggc aaggtttaag atatttctga tctcgtgcc                             1059
```

<210> SEQ ID NO 373
<211> LENGTH: 1155
<212> TYPE: DNA
<213> ORGANISM: Homo sapien

<400> SEQUENCE: 373

```
atggtggttg aggttgattc catgccggct gcctcttctg tgaagaagcc atttggtctc        60
aggagcaaga tgggcaagtg gtgctgccgt tgcttcccct gctgcaggga gagcggcaag       120
agcaacgtgg gcacttctgg agaccacgac gactctgcta tgaagacact caggagcaag       180
atgggcaagt ggtgccgcca ctgcttcccc tgctgcaggg ggagtggcaa gagcaacgtg       240
ggcgcttctg gagaccacga cgactctgct atgaagacac tcaggaacaa gatgggcaag       300
tggtgctgcc actgcttccc ctgctgcagg ggagcggca agagcaaggt gggcgcttgg       360
```

-continued

```
ggagactacg atgacagtgc cttcatggag cccaggtacc acgtccgtgg agaagatctg    420
gacaagctcc acagagctgc ctggtggggt aaagtcccca gaaaggatct catcgtcatg    480
ctcagggaca ctgacgtgaa caagaaggac aagcaaaaga ggactgctct acatctggcc    540
tctgccaatg ggaattcaga agtagtaaaa ctcctgctgg acagacgatg tcaacttaat    600
gtccttgaca caaaaagag acagctctg ataaaggccg tacaatgcca ggaagatgaa    660
tgtgcgttaa tgttgctgga acatggcact gatccaaata ttccagatga gtatggaaat    720
accactctgc actacgctat ctataatgaa gataaattaa tggccaaagc actgctctta    780
tatggtgctg atatcgaatc aaaaaacaag catggcctca caccactgtt acttggtgta    840
catgagcaaa acagcaagt cgtgaaattt ttaatcaaga aaaaagcgaa tttaaatgca    900
ctggatagat atggaaggac tgctctcata cttgctgtat gttgtggatc agcaagtata    960
gtcagccttc tacttgagca aaatattgat gtatcttctc aagatctatc tggacagacg   1020
gccagagagt atgctgtttc tagtcatcat catgtaattt gccagttact ttctgactac   1080
aaagaaaaac agatgctaaa aatctcttct gaaaacagca atccagaaaa tgtctcaaga   1140
accagaaata aataa                                                    1155
```

<210> SEQ ID NO 374
<211> LENGTH: 2000
<212> TYPE: DNA
<213> ORGANISM: Homo sapien

<400> SEQUENCE: 374

```
atggtggttg aggttgattc catgccggct gcctcttctg tgaagaagcc atttggtctc     60
aggagcaaga tgggcaagtg gtgctgccgt tgcttcccct gctgcaggga gagcggcaag    120
agcaacgtgg gcacttctgg agaccacgac gactctgcta tgaagacact caggagcaag    180
atgggcaagt ggtgccgcca ctgcttcccc tgctgcaggg ggagtggcaa gagcaacgtg    240
ggcgcttctg agaccacga cgactctgct atgaagacac tcaggaacaa gatgggcaag    300
tggtgctgcc actgcttccc ctgctgcagg gggagcggca agagcaaggt gggcgcttgg    360
ggagactacg atgacagtgc cttcatggag cccaggtacc acgtccgtgg agaagatctg    420
gacaagctcc acagagctgc ctggtggggt aaagtcccca gaaaggatct catcgtcatg    480
ctcagggaca ctgacgtgaa caagaaggac aagcaaaaga ggactgctct acatctggcc    540
tctgccaatg ggaattcaga agtagtaaaa ctcctgctgg acagacgatg tcaacttaat    600
gtccttgaca caaaaagag acagctctg ataaaggccg tacaatgcca ggaagatgaa    660
tgtgcgttaa tgttgctgga acatggcact gatccaaata ttccagatga gtatggaaat    720
accactctgc actacgctat ctataatgaa gataaattaa tggccaaagc actgctctta    780
tatggtgctg atatcgaatc aaaaaacaag catggcctca caccactgtt acttggtgta    840
catgagcaaa acagcaagt cgtgaaattt ttaatcaaga aaaaagcgaa tttaaatgca    900
ctggatagat atggaaggac tgctctcata cttgctgtat gttgtggatc agcaagtata    960
gtcagccttc tacttgagca aaatattgat gtatcttctc aagatctatc tggacagacg   1020
gccagagagt atgctgtttc tagtcatcat catgtaattt gccagttact ttctgactac   1080
aaagaaaaac agatgctaaa aatctcttct gaaaacagca atccagaaca agacttaaag   1140
ctgacatcag aggaagagtc acaaaggttc aaggcagtg aaaatagcca gccagagaaa   1200
atgtctcaag aaccagaaat aaataaggat ggtgatagag aggttgaaga agaaatgaag   1260
aagcatgaaa gtaataatgt gggattacta gaaaacctga ctaatggtgt cactgctggc   1320
```

| | |
|---|---|
| aatggtgata atggattaat tcctcaaagg aagagcagaa cacctgaaaa tcagcaatttt | 1380 |
| cctgacaacg aaagtgaaga gtatcacaga atttgcgaat tagtttctga ctacaaagaa | 1440 |
| aaacagatgc caaaatactc ttctgaaaac agcaacccag aacaagactt aaagctgaca | 1500 |
| tcagaggaag agtcacaaag gcttgagggc agtgaaaatg ccagccaga gctagaaaat | 1560 |
| tttatggcta tcgaagaaat gaagaagcac ggaagtactc atgtcggatt cccagaaaac | 1620 |
| ctgactaatg gtgccactgc tggcaatggt gatgatggat taattcctcc aaggaagagc | 1680 |
| agaacacctg aaagccagca atttcctgac actgagaatg aagagtatca cagtgacgaa | 1740 |
| caaaatgata ctcagaagca attttgtgaa gaacagaaca ctggaatatt acacgatgag | 1800 |
| attctgattc atgaagaaaa gcagatagaa gtggttgaaa aaatgaattc tgagctttct | 1860 |
| cttagttgta agaaagaaaa agacatcttg catgaaaata gtacgttgcg ggaagaaatt | 1920 |
| gccatgctaa gactggagct agacacaatg aaacatcaga gccagctaaa aaaaaaaaa | 1980 |
| aaaaaaaaaa aaaaaaaaa | 2000 |

<210> SEQ ID NO 375
<211> LENGTH: 2040
<212> TYPE: DNA
<213> ORGANISM: Homo sapien

<400> SEQUENCE: 375

| | |
|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |
| ggcgcttctg gagaccacga cgactctgct atgaagacac tcaggaacaa gatgggcaag | 300 |
| tggtgctgcc actgcttccc ctgctgcagg gggagcggca agagcaaggt gggcgcttgg | 360 |
| ggagactacg atgacagtgc cttcatggag cccaggtacc acgtccgtgg agaagatctg | 420 |
| gacaagctcc acagagctgc ctggtggggt aaagtcccca gaaggatctc atcgtcatg | 480 |
| ctcagggaca ctgacgtgaa caagaaggac aagcaaaaga ggactgctct acatctggcc | 540 |
| tctgccaatg ggaattcaga agtagtaaaa ctcctgctgg acagacgatg tcaacttaat | 600 |
| gtccttgaca caaaaagag gacagctctg ataaaggccg tacaatgcca ggaagatgaa | 660 |
| tgtgcgttaa tgttgctgga acatggcact gatccaaata ttccagatga gtatggaaat | 720 |
| accactctgc actacgctat ctataatgaa gataaattaa tggccaaagc actgctctta | 780 |
| tatggtgctg atatcgaatc aaaaaacaag catggcctca caccactgtt acttggtgta | 840 |
| catgagcaaa acagcaagt cgtgaaattt taatcaaga aaaagcgaa tttaaatgca | 900 |
| ctggatagat atgaaggac tgctctcata cttgctgtat gttgtggatc agcaagtata | 960 |
| gtcagccttc tacttgagca aaatattgat gtatcttctc aagatctatc tggacagacg | 1020 |
| gccagagagt atgctgtttc tagtcatcat catgtaattt gccagttact ttctgactac | 1080 |
| aaagaaaaac agatgctaaa aatctcttct gaaaacagca atccagaaca agacttaaag | 1140 |
| ctgacatcag aggaagagtc acaaggtc aaggcagtg aaaatagcca gccagagaaa | 1200 |
| atgtctcaag aaccagaaat aaataaggat ggtgatagag aggttgaaga gaaatgaag | 1260 |
| aagcatgaaa gtaataatgt gggattacta gaaaacctga ctaatggtgt cactgctggc | 1320 |
| aatggtgata atggattaat tcctcaaagg aagagcagaa cacctgaaaa tcagcaatttt | 1380 |

-continued

```
cctgacaacg aaagtgaaga gtatcacaga atttgcgaat tagtttctga ctacaaagaa    1440
aaacagatgc caaaatactc ttctgaaaac agcaacccag aacaagactt aaagctgaca    1500
tcagaggaag agtcacaaag gcttgagggc agtgaaaatg ccagccagag aaaagatct     1560 caagaaccag aaataaataa ggatggtgat agagagctag aaaattttat ggctatcgaa    1620
gaaatgaaga agcacggaag tactcatgtc ggattcccag aaaacctgac taatggtgcc    1680
actgctggca atggtgatga tggattaatt cctccaagga agagcagaac acctgaaagc    1740
cagcaatttc ctgacactga gaatgaagag tatcacagtg acgaacaaaa tgatactcag    1800
aagcaatttt gtgaagaaca gaacactgga atattacacg atgagattct gattcatgaa    1860
gaaaagcaga tagaagtggt tgaaaaaatg aattctgagc tttctcttag ttgtaagaaa    1920
gaaaaagaca tcttgcatga aaatagtacg ttgcgggaag aaattgccat gctaagactg    1980
gagctagaca caatgaaaca tcagagccag ctaaaaaaaa aaaaaaaaaa aaaaaaaaa     2040
```

<210> SEQ ID NO 376
<211> LENGTH: 329
<212> TYPE: PRT
<213> ORGANISM: Homo sapien

<400> SEQUENCE: 376

```
Met Asp Ile Val Val Ser Gly Ser His Pro Leu Trp Val Asp Ser Phe
  1               5                  10                  15

Leu His Leu Ala Gly Ser Asp Leu Leu Ser Arg Ser Leu Met Ala Glu
             20                  25                  30

Glu Tyr Thr Ile Val His Ala Ser Phe Ile Ser Cys Ile Ser Ser Ser
         35                  40                  45

Leu Asp Gly Gln Gly Glu Arg Gln Glu Gln Arg Gly His Phe Trp Arg
 50                  55                  60

Pro Gln Arg Leu Leu Cys Glu Asp Ala Trp Glu Gln Glu Val Gln Val
 65                  70                  75                  80

Val Leu Pro Leu Leu Pro Leu Leu Gln Gly Ser Gly Lys Ser Asn Val
             85                  90                  95

Val Ala Trp Gly Asp Tyr Asp Asp Ser Ala Phe Met Asp Pro Arg Tyr
            100                 105                 110

His Val His Gly Glu Asp Leu Asp Lys Leu His Arg Ala Ala Trp Trp
        115                 120                 125

Gly Lys Val Pro Arg Lys Asp Leu Ile Val Met Leu Arg Asp Thr Asp
130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
                165                 170                 175

Gln Leu Asn Val Leu Asp Asn Lys Lys Arg Thr Ala Leu Thr Lys Ala
            180                 185                 190

Val Gln Cys Gln Glu Asp Glu Cys Ala Leu Met Leu Glu His Gly
        195                 200                 205

Thr Asp Pro Asn Ile Pro Asp Glu Tyr Gly Asn Thr Thr Leu His Tyr
    210                 215                 220

Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
                245                 250                 255

Leu Gly Ile His Glu Gln Lys Gln Gln Val Val Lys Phe Leu Ile Lys
```

-continued

```
                    260                 265                 270
Lys Lys Ala Asn Leu Asn Ala Leu Asp Arg Tyr Gly Arg Thr Ala Leu
            275                 280                 285
Ile Leu Ala Val Cys Cys Gly Ser Ala Ser Ile Val Ser Pro Leu Leu
        290                 295                 300
Glu Gln Asn Val Asp Val Ser Ser Gln Asp Leu Glu Arg Arg Pro Glu
305                 310                 315                 320
Ser Met Leu Phe Leu Val Ile Ile Met
                325

<210> SEQ ID NO 377
<211> LENGTH: 148
<212> TYPE: PRT
<213> ORGANISM: Homo sapien
<220> FEATURE:
<221> NAME/KEY: VARIANT
<222> LOCATION: (1)...(148)
<223> OTHER INFORMATION: Xaa = Any Amino Acid

<400> SEQUENCE: 377

Met Thr Xaa Pro Ser Trp Ser Pro Gly Thr Thr Ser Val Glu Lys Ile
 1               5                  10                  15
Trp Thr Ser Ser Thr Glu Leu Pro Trp Trp Gly Lys Val Pro Arg Lys
            20                  25                  30
Asp Leu Ile Val Met Leu Arg Asp Thr Asp Val Asn Lys Xaa Asp Lys
        35                  40                  45
Gln Lys Arg Thr Ala Leu His Leu Ala Ser Ala Asn Gly Asn Ser Glu
    50                  55                  60
Val Val Lys Leu Xaa Leu Asp Arg Arg Cys Gln Leu Asn Val Leu Asp
65                  70                  75                  80
Asn Lys Lys Arg Thr Ala Leu Xaa Lys Ala Val Gln Cys Gln Glu Asp
                85                  90                  95
Glu Cys Ala Leu Met Leu Leu Glu His Gly Thr Asp Pro Asn Ile Pro
            100                 105                 110
Asp Glu Tyr Gly Asn Thr Thr Leu His Tyr Ala Xaa Tyr Asn Glu Asp
        115                 120                 125
Lys Leu Met Ala Lys Ala Leu Leu Leu Tyr Gly Ala Asp Ile Glu Ser
    130                 135                 140
Lys Asn Lys Val
145

<210> SEQ ID NO 378
<211> LENGTH: 1719
<212> TYPE: PRT
<213> ORGANISM: Homo sapien

<400> SEQUENCE: 378

Met Val Val Glu Val Asp Ser Met Pro Ala Ala Ser Ser Val Lys Lys
 1               5                  10                  15
Pro Phe Gly Leu Arg Ser Lys Met Gly Lys Trp Cys Cys Arg Cys Phe
            20                  25                  30
Pro Cys Cys Arg Glu Ser Gly Lys Ser Asn Val Gly Thr Ser Gly Asp
        35                  40                  45
His Asp Asp Ser Ala Met Lys Thr Leu Arg Ser Lys Met Gly Lys Trp
    50                  55                  60
Cys Arg His Cys Phe Pro Cys Cys Arg Gly Ser Gly Lys Ser Asn Val
65                  70                  75                  80
```

```
Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Ser Ala Phe
        115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

Pro Arg Thr His Met Val Val Glu Val Asp Ser Met Pro Ala Ala Ser
385                 390                 395                 400

Ser Val Lys Lys Pro Phe Gly Leu Arg Ser Lys Met Gly Lys Trp Cys
                405                 410                 415

Cys Arg Cys Phe Pro Cys Arg Glu Ser Gly Lys Ser Asn Val Gly
            420                 425                 430

Thr Ser Gly Asp His Asp Asp Ser Ala Met Lys Thr Leu Arg Ser Lys
        435                 440                 445

Met Gly Lys Trp Cys Arg His Cys Phe Pro Cys Cys Arg Gly Ser Gly
    450                 455                 460

Lys Ser Asn Val Gly Ala Ser Gly Asp His Asp Asp Ser Ala Met Lys
465                 470                 475                 480

Thr Leu Arg Asn Lys Met Gly Leu Trp Cys Cys His Cys Phe Pro Cys
                485                 490                 495

Cys Arg Gly Ser Gly Lys Ser Lys Val Gly Ala Trp Gly Asp Tyr Asp
```

-continued

```
                 500                 505                 510
Asp Ser Ala Phe Met Glu Pro Arg Tyr His Val Arg Gly Glu Asp Leu
            515                 520                 525

Asp Lys Leu His Arg Ala Ala Trp Trp Gly Lys Val Pro Arg Lys Asp
530                 535                 540

Leu Ile Val Met Leu Arg Asp Thr Asp Val Asn Lys Lys Asp Lys Gln
545                 550                 555                 560

Lys Arg Thr Ala Leu His Leu Ala Ser Ala Asn Gly Asn Ser Glu Val
            565                 570                 575

Val Lys Leu Leu Leu Asp Arg Arg Cys Gln Leu Asn Val Leu Asp Asn
            580                 585                 590

Lys Lys Arg Thr Ala Leu Ile Lys Ala Val Gln Cys Gln Glu Asp Glu
            595                 600                 605

Cys Ala Leu Met Leu Leu Glu His Gly Thr Asp Pro Asn Ile Pro Asp
            610                 615                 620

Glu Tyr Gly Asn Thr Thr Leu His Tyr Ala Ile Tyr Asn Glu Asp Lys
625                 630                 635                 640

Leu Met Ala Lys Ala Leu Leu Leu Tyr Gly Ala Asp Ile Glu Ser Lys
            645                 650                 655

Asn Lys His Gly Leu Thr Pro Leu Leu Leu Gly Val His Glu Gln Lys
            660                 665                 670

Gln Gln Val Val Lys Phe Leu Ile Lys Lys Lys Ala Asn Leu Asn Ala
            675                 680                 685

Leu Asp Arg Tyr Gly Arg Thr Ala Leu Ile Leu Ala Val Cys Cys Gly
            690                 695                 700

Ser Ala Ser Ile Val Ser Leu Leu Leu Glu Gln Asn Ile Asp Val Ser
705                 710                 715                 720

Ser Gln Asp Leu Ser Gly Gln Thr Ala Arg Glu Tyr Ala Val Ser Ser
            725                 730                 735

His His His Val Ile Cys Gln Leu Leu Ser Asp Tyr Lys Glu Lys Gln
            740                 745                 750

Met Leu Lys Ile Ser Ser Glu Asn Ser Asn Pro Glu Gln Asp Leu Lys
            755                 760                 765

Leu Thr Ser Glu Glu Glu Ser Gln Arg Phe Lys Gly Ser Glu Asn Ser
            770                 775                 780

Gln Pro Glu Lys Met Ser Gln Glu Pro Glu Ile Asn Lys Asp Gly Asp
785                 790                 795                 800

Arg Glu Val Glu Glu Met Lys Lys His Glu Ser Asn Asn Val Gly
            805                 810                 815

Leu Leu Glu Asn Leu Thr Asn Gly Val Thr Ala Gly Asn Gly Asp Asn
            820                 825                 830

Gly Leu Ile Pro Gln Arg Lys Ser Arg Thr Pro Glu Asn Gln Gln Phe
            835                 840                 845

Pro Asp Asn Glu Ser Glu Glu Tyr His Arg Ile Cys Glu Leu Val Ser
850                 855                 860

Asp Tyr Lys Glu Lys Gln Met Pro Lys Tyr Ser Glu Asn Ser Asn
865                 870                 875                 880

Pro Glu Gln Asp Leu Lys Leu Thr Ser Glu Glu Ser Gln Arg Leu
            885                 890                 895

Glu Gly Ser Glu Asn Gly Gln Pro Glu Leu Glu Asn Phe Met Ala Ile
            900                 905                 910

Glu Glu Met Lys Lys His Gly Ser Thr His Val Gly Phe Pro Glu Asn
            915                 920                 925
```

```
Leu Thr Asn Gly Ala Thr Ala Gly Asn Gly Asp Asp Gly Leu Ile Pro
    930                 935                 940
Pro Arg Lys Ser Arg Thr Pro Glu Ser Gln Gln Phe Pro Asp Thr Glu
945                 950                 955                 960
Asn Glu Glu Tyr His Ser Asp Glu Gln Asn Asp Thr Gln Lys Gln Phe
                965                 970                 975
Cys Glu Glu Gln Asn Thr Gly Ile Leu His Asp Glu Ile Leu Ile His
            980                 985                 990
Glu Glu Lys Gln Ile Glu Val Val Glu Lys Met Asn Ser Glu Leu Ser
        995                 1000                1005
Leu Ser Cys Lys Lys Glu Lys Asp Ile Leu His Glu Asn Ser Thr Leu
    1010                1015                1020
Arg Glu Glu Ile Ala Met Leu Arg Leu Glu Leu Asp Thr Met Lys His
1025                1030                1035                1040
Gln Ser Gln Leu Pro Arg Thr His Met Val Val Glu Val Asp Ser Met
                1045                1050                1055
Pro Ala Ala Ser Ser Val Lys Lys Pro Phe Gly Leu Arg Ser Lys Met
            1060                1065                1070
Gly Lys Trp Cys Cys Arg Cys Phe Pro Cys Cys Arg Glu Ser Gly Lys
        1075                1080                1085
Ser Asn Val Gly Thr Ser Gly Asp His Asp Asp Ser Ala Met Lys Thr
    1090                1095                1100
Leu Arg Ser Lys Met Gly Lys Trp Cys Arg His Cys Phe Pro Cys Cys
1105                1110                1115                1120
Arg Gly Ser Gly Lys Ser Asn Val Gly Ala Ser Gly Asp His Asp Asp
                1125                1130                1135
Ser Ala Met Lys Thr Leu Arg Asn Lys Met Gly Lys Trp Cys Cys His
            1140                1145                1150
Cys Phe Pro Cys Cys Arg Gly Ser Gly Lys Ser Lys Val Gly Ala Trp
        1155                1160                1165
Gly Asp Tyr Asp Asp Ser Ala Phe Met Glu Pro Arg Tyr His Val Arg
    1170                1175                1180
Gly Glu Asp Leu Asp Lys Leu His Arg Ala Ala Trp Trp Gly Lys Val
1185                1190                1195                1200
Pro Arg Lys Asp Leu Ile Val Met Leu Arg Asp Thr Asp Val Asn Lys
                1205                1210                1215
Lys Asp Lys Gln Lys Arg Thr Ala Leu His Leu Ala Ser Ala Asn Gly
            1220                1225                1230
Asn Ser Glu Val Val Lys Leu Leu Leu Asp Arg Arg Cys Gln Leu Asn
    1235                1240                1245
Val Leu Asp Asn Lys Lys Arg Thr Ala Leu Ile Lys Ala Val Gln Cys
1250                1255                1260
Gln Glu Asp Glu Cys Ala Leu Met Leu Leu Glu His Gly Thr Asp Pro
1265                1270                1275                1280
Asn Ile Pro Asp Glu Tyr Gly Asn Thr Thr Leu His Tyr Ala Ile Tyr
                1285                1290                1295
Asn Glu Asp Lys Leu Met Ala Lys Ala Leu Leu Leu Tyr Gly Ala Asp
            1300                1305                1310
Ile Glu Ser Lys Asn Lys His Gly Leu Thr Pro Leu Leu Leu Gly Val
        1315                1320                1325
His Glu Gln Lys Gln Gln Val Val Lys Phe Leu Ile Lys Lys Lys Ala
    1330                1335                1340
```

-continued

```
Asn Leu Asn Ala Leu Asp Arg Tyr Gly Arg Thr Ala Leu Ile Leu Ala
1345                1350                1355                1360
Val Cys Cys Gly Ser Ala Ser Ile Val Ser Leu Leu Glu Gln Asn
            1365                1370                1375
Ile Asp Val Ser Ser Gln Asp Leu Ser Gly Gln Thr Ala Arg Glu Tyr
                1380                1385                1390
Ala Val Ser Ser His His His Val Ile Cys Gln Leu Leu Ser Asp Tyr
            1395                1400                1405
Lys Glu Lys Gln Met Leu Lys Ile Ser Ser Glu Asn Ser Asn Pro Glu
        1410                1415                1420
Gln Asp Leu Lys Leu Thr Ser Glu Glu Glu Ser Gln Arg Phe Lys Gly
1425                1430                1435                1440
Ser Glu Asn Ser Gln Pro Glu Lys Met Ser Gln Glu Pro Glu Ile Asn
            1445                1450                1455
Lys Asp Gly Asp Arg Glu Val Glu Glu Glu Met Lys Lys His Glu Ser
                1460                1465                1470
Asn Asn Val Gly Leu Leu Glu Asn Leu Thr Asn Gly Val Thr Ala Gly
            1475                1480                1485
Asn Gly Asp Asn Gly Leu Ile Pro Gln Arg Lys Ser Arg Thr Pro Glu
        1490                1495                1500
Asn Gln Gln Phe Pro Asp Asn Glu Ser Glu Glu Tyr His Arg Ile Cys
1505                1510                1515                1520
Glu Leu Val Ser Asp Tyr Lys Glu Lys Gln Met Pro Lys Tyr Ser Ser
            1525                1530                1535
Glu Asn Ser Asn Pro Glu Gln Asp Leu Lys Leu Thr Ser Glu Glu Glu
                1540                1545                1550
Ser Gln Arg Leu Glu Gly Ser Glu Asn Gly Gln Pro Glu Lys Arg Ser
            1555                1560                1565
Gln Glu Pro Glu Ile Asn Lys Asp Gly Asp Arg Glu Leu Glu Asn Phe
        1570                1575                1580
Met Ala Ile Glu Glu Met Lys Lys His Gly Ser Thr His Val Gly Phe
1585                1590                1595                1600
Pro Glu Asn Leu Thr Asn Gly Ala Thr Ala Gly Asn Gly Asp Asp Gly
            1605                1610                1615
Leu Ile Pro Pro Arg Lys Ser Arg Thr Pro Glu Ser Gln Gln Phe Pro
        1620                1625                1630
Asp Thr Glu Asn Glu Glu Tyr His Ser Asp Glu Gln Asn Asp Thr Gln
        1635                1640                1645
Lys Gln Phe Cys Glu Glu Gln Asn Thr Gly Ile Leu His Asp Glu Ile
        1650                1655                1660
Leu Ile His Glu Glu Lys Gln Ile Glu Val Val Lys Met Asn Ser
1665                1670                1675                1680
Glu Leu Ser Leu Ser Cys Lys Lys Glu Lys Asp Ile Leu His Glu Asn
            1685                1690                1695
Ser Thr Leu Arg Glu Glu Ile Ala Met Leu Arg Leu Glu Leu Asp Thr
        1700                1705                1710
Met Lys His Gln Ser Gln Leu
        1715
```

<210> SEQ ID NO 379
<211> LENGTH: 656
<212> TYPE: PRT
<213> ORGANISM: Homo sapien

<400> SEQUENCE: 379

-continued

```
Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
            35                  40                  45

His Asp Asp Ser Ala Met Lys Thr Leu Arg Ser Lys Met Gly Lys Trp
     50                  55                  60

Cys Arg His Cys Phe Pro Cys Cys Arg Gly Ser Gly Lys Ser Asn Val
 65                  70                  75                  80

Gly Ala Ser Gly Asp His Asp Ser Ala Met Lys Thr Leu Arg Asn
                 85                  90                  95

Lys Met Gly Lys Trp Cys Cys His Cys Phe Pro Cys Cys Arg Gly Ser
                100                 105                 110

Gly Lys Ser Lys Val Gly Ala Trp Gly Asp Tyr Asp Ser Ala Phe
            115                 120                 125

Met Glu Pro Arg Tyr His Val Arg Gly Glu Asp Leu Asp Lys Leu His
        130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Ala Asn Leu Asn Ala Leu Asp Arg Tyr
        290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415
```

-continued

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
            435                 440                 445

Gln Arg Lys Ser Arg Thr Pro Glu Asn Gln Gln Phe Pro Asp Asn Glu
450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
            485                 490                 495

Leu Lys Leu Thr Ser Glu Glu Ser Gln Arg Leu Glu Gly Ser Glu
            500                 505                 510

Asn Gly Gln Pro Glu Leu Glu Asn Phe Met Ala Ile Glu Glu Met Lys
            515                 520                 525

Lys His Gly Ser Thr His Val Gly Phe Pro Glu Asn Leu Thr Asn Gly
            530                 535                 540

Ala Thr Ala Gly Asn Gly Asp Asp Gly Leu Ile Pro Pro Arg Lys Ser
545                 550                 555                 560

Arg Thr Pro Glu Ser Gln Gln Phe Pro Asp Thr Glu Asn Glu Glu Tyr
            565                 570                 575

His Ser Asp Glu Gln Asn Asp Thr Gln Lys Gln Phe Cys Glu Glu Gln
            580                 585                 590

Asn Thr Gly Ile Leu His Asp Glu Ile Leu Ile His Glu Glu Lys Gln
            595                 600                 605

Ile Glu Val Val Glu Lys Met Asn Ser Glu Leu Ser Leu Ser Cys Lys
610                 615                 620

Lys Glu Lys Asp Ile Leu His Glu Asn Ser Thr Leu Arg Glu Glu Ile
625                 630                 635                 640

Ala Met Leu Arg Leu Glu Leu Asp Thr Met Lys His Gln Ser Gln Leu
            645                 650                 655

<210> SEQ ID NO 380
<211> LENGTH: 671
<212> TYPE: PRT
<213> ORGANISM: Homo sapien

<400> SEQUENCE: 380

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
            35                  40                  45

His Asp Asp Ser Ala Met Lys Thr Leu Arg Ser Lys Met Gly Lys Trp
50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
            85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
            115                 120                 125

Met Glu Pro Arg Tyr His Val Arg Gly Glu Asp Leu Asp Lys Leu His
            130                 135                 140

-continued

```
Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
            165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
            195                 200                 205

Ala Leu Ile Lys Ala Val Gln Cys Gln Glu Asp Glu Cys Ala Leu Met
210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
            245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
            275                 280                 285

Lys Phe Leu Ile Lys Lys Lys Ala Asn Leu Asn Ala Leu Asp Arg Tyr
290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
            325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
            355                 360                 365

Ser Ser Glu Asn Ser Asn Pro Glu Gln Asp Leu Lys Leu Thr Ser Glu
            370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
            405                 410                 415

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
            435                 440                 445

Gln Arg Lys Ser Arg Thr Pro Glu Asn Gln Gln Phe Pro Asp Asn Glu
450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
            485                 490                 495

Leu Lys Leu Thr Ser Glu Glu Ser Gln Arg Leu Glu Gly Ser Glu
            500                 505                 510

Asn Gly Gln Pro Glu Lys Arg Ser Gln Glu Pro Glu Ile Asn Lys Asp
            515                 520                 525

Gly Asp Arg Glu Leu Glu Asn Phe Met Ala Ile Glu Glu Met Lys Lys
            530                 535                 540

His Gly Ser Thr His Val Gly Phe Pro Glu Asn Leu Thr Asn Gly Ala
545                 550                 555                 560
```

| | | | | | | | | | | |
|---|---|---|---|---|---|---|---|---|---|---|
| Thr | Ala | Gly | Asn | Gly | Asp | Asp | Gly | Leu | Ile | Pro | Pro | Arg | Lys | Ser | Arg |
| | | | 565 | | | | | 570 | | | | 575 | | | |

Thr Ala Gly Asn Gly Asp Asp Gly Leu Ile Pro Pro Arg Lys Ser Arg
            565                 570                 575

Thr Pro Glu Ser Gln Gln Phe Pro Asp Thr Glu Asn Glu Glu Tyr His
        580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Glu Lys Gln Ile
    610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
                645                 650                 655

Met Leu Arg Leu Glu Leu Asp Thr Met Lys His Gln Ser Gln Leu
        660                 665                 670

<210> SEQ ID NO 381
<211> LENGTH: 251
<212> TYPE: DNA
<213> ORGANISM: Homo sapien

<400> SEQUENCE: 381

```
ggagaagcgt ctgctggggc aggaagggt tccctgccc tctcacctgt ccctcaccaa      60
ggtaacatgc ttccctaag ggtatcccaa cccaggggcc tcaccatgac ctctgagggg    120
ccaatatccc aggagaagca ttggggagtt gggggcaggt gaaggaccca ggactcacac   180
atcctgggcc tccaaggcag aggagagggt cctcaagaag gtcaggagga aaatccgtaa   240
caagcagtca g                                                        251
```

<210> SEQ ID NO 382
<211> LENGTH: 3279
<212> TYPE: DNA
<213> ORGANISM: Homo sapiens

<400> SEQUENCE: 382

```
cttcctgcag cccccatgct ggtgaggggc acgggcagga acagtggacc caacatggaa      60
atgctggagg gtgtcaggaa gtgatcgggc tctgggcag ggaggagggg tggggagtgt     120
cactgggagg ggacatcctg cagaaggtag gagtgagcaa cacccgctg caggggaggg    180
gagagccctg cggcacctgg gggagcgagg ggagcagcac ctgcccaggc ctggggaggag  240
gggcctggag ggcgtgagga ggagcgaggg ggctgcatgg ctggagtgag ggatcagggg   300
cagggcgcga gatggcctca cacagggaag agagggcccc tcctgcaggg cctcacctgg   360
gccacaggag gacactgctt ttcctctgag gagtcaggag ctgtggatgg tgctggacag   420
aagaaggaca gggcctggct caggtgtcca gaggctgtcg ctggcttccc tttgggatca   480
gactgcaggg agggagggcg gcagggttgt gggggagtg acgatgagga tgacctgggg   540
gtggctccag gccttgcccc tgcctgggcc ctcacccagc ctccctcaca gtctcctggc   600
cctcagtctc tcccctccac tccatcctcc atctggcctc agtgggtcat tctgatcact   660
gaactgacca tacccagccc tgcccacggc cctccatggc tccccaatgc cctggagagg   720
ggacatctag tcagagagta gtcctgaaga ggtggcctct gcgatgtgcc tgtggggca   780
gcatcctgca gatggtcccg gccctcatcc tgctgacctg tctgcaggga ctgtcctcct   840
ggaccttgcc cctttgtgcag gagctggacc ctgaagtccc ctccccatag gccaagactg   900
gagccttgtt ccctctgttg gactccctgc ccatattctt gtgggagtgg gttctggaga   960
```

```
catttctgtc tgttcctgag agctgggaat tgctctcagt catctgcctg cgcggttctg    1020
agagatggag ttgcctaggc agttattggg gccaatcttt ctcactgtgt ctctcctcct    1080
ttacccttag ggtgattctg ggggtccact tgtctgtaat ggtgtgcttc aaggtatcac    1140
atcatgggc cctgagccat gtgccctgcc tgaaaagcct gctgtgtaca ccaaggtggt    1200
gcattaccgg aagtggatca aggacaccat cgcagccaac ccctgagtgc ccctgtccca    1260
cccctacctc tagtaaattt aagtccacct cacgttctgg catcacttgg cctttctgga    1320
tgctggacac ctgaagcttg gaactcacct ggccgaagct cgagcctcct gagtcctact    1380
gacctgtgct ttctggtgtg gagtccaggg ctgctaggaa aaggaatggg cagacacagg    1440
tgtatgccaa tgtttctgaa atgggtataa tttcgtcctc tccttcggaa cactggctgt    1500
ctctgaagac ttctcgctca gtttcagtga ggacacacac aaagacgtgg gtgaccatgt    1560
tgtttgtggg gtgcagagat gggaggggtg gggcccaccc tggaagagtg gacagtgaca    1620
caaggtggac actctctaca gatcactgag gataagctgg agccacaatg catgaggcac    1680
acacacagca aggttgacgc tgtaaacata gcccacgctg tcctggggc actgggaagc    1740
ctagataagg ccgtgagcag aaagaagggg aggatcctcc tatgttgttg aaggagggac    1800
taggggagaga aactgaaagc tgattaatta caggaggttt gttcaggtcc cccaaaccac    1860
cgtcagattt gatgatttcc tagcaggact tacagaaata aagagctatc atgctgtggt    1920
ttattatggt ttgttacatt gataggatac atactgaaat cagcaaacaa aacagatgta    1980
tagattagag tgtggagaaa acagaggaaa acttgcagtt acgaagactg gcaacttggc    2040
tttactaagt tttcagactg gcaggaagtc aaacctatta ggctgaggac cttgtggagt    2100
gtagctgatc cagctgatag aggaactagc caggtggggg cctttccctt tggatggggg    2160
gcatatccga cagttattct ctccaagtgg agacttacgg acagcatata attctccctg    2220
caaggatgta tgataatatg tacaaagtaa ttccaactga ggaagctcac ctgatcctta    2280
gtgtccaggg tttttactgg gggtctgtag gacgagtatg gagtacttga ataattgacc    2340
tgaagtcctc agacctgagg ttccctagag ttcaaacaga tacagcatgg tccagagtcc    2400
cagatgtaca aaaacaggga ttcatcacaa atcccatctt tagcatgaag ggtctggcat    2460
ggcccaaggc cccaagtata tcaaggcact tgggcagaac atgccaagga atcaaatgtc    2520
atctcccagg agttattcaa gggtgagccc tttacttggg atgtacaggc tttgagcagt    2580
gcagggctgc tgagtcaacc ttttattgta caggggatga gggaaaggga gaggatgagg    2640
aagccccct ggggatttgg tttggtcttg tgatcaggtg gtctatgggg ctatccctac    2700
aaagaagaat ccagaaatag gggcacattg aggaatgata ctgagcccaa agagcattca    2760
atcattgttt tatttgcctt cttttcacac cattggtgag ggagggatta ccaccctggg    2820
gttatgaaga tggttgaaca ccccacacat agcaccggag atatgagatc aacagtttct    2880
tagccataga gattcacagc ccagagcagg aggacgctgc acaccatgca ggatgacatg    2940
ggggatgcgc tcgggattgg tgtgaagaag caaggactgt tagaggcagg ctttatagta    3000
acaagacggt ggggcaaact ctgatttccg tgggggaatg tcatggtctt gctttactaa    3060
gttttgagac tggcaggtag tgaaactcat taggctgaga accttgtgga atgcagctga    3120
cccagctgat agaggaagta gccaggtggg agcctttccc agtgggtgtg ggacatatct    3180
ggcaagattt tgtggcactc ctggttacag atactgggc agcaaataaa actgaatctt    3240
gttttcagac cttaaaaaaa aaaaaaaaaa aaaagtttt                           3279
```

<210> SEQ ID NO 383
<211> LENGTH: 154
<212> TYPE: PRT
<213> ORGANISM: Homo sapiens

<400> SEQUENCE: 383

Met Ala Gly Val Arg Asp Gln Gly Gln Gly Ala Arg Trp Pro His Thr
                 5                  10                  15
Gly Lys Arg Gly Pro Leu Leu Gln Gly Leu Thr Trp Ala Thr Gly Gly
            20                  25                  30
His Cys Phe Ser Ser Glu Glu Ser Gly Ala Val Asp Gly Ala Gly Gln
        35                  40                  45
Lys Lys Asp Arg Ala Trp Leu Arg Cys Pro Glu Ala Val Ala Gly Phe
    50                  55                  60
Pro Leu Gly Ser Asp Cys Arg Glu Gly Arg Gln Gly Cys Gly Gly
65                  70                  75                  80
Ser Asp Asp Glu Asp Asp Leu Gly Val Ala Pro Gly Leu Ala Pro Ala
                85                  90                  95
Trp Ala Leu Thr Gln Pro Pro Ser Gln Ser Pro Gly Pro Gln Ser Leu
            100                 105                 110
Pro Ser Thr Pro Ser Ser Ile Trp Pro Gln Trp Val Ile Leu Ile Thr
        115                 120                 125
Glu Leu Thr Ile Pro Ser Pro Ala His Gly Pro Pro Trp Leu Pro Asn
    130                 135                 140
Ala Leu Glu Arg Gly His Leu Val Arg Glu
145                 150

<210> SEQ ID NO 384
<211> LENGTH: 557
<212> TYPE: DNA
<213> ORGANISM: Homo sapiens

<400> SEQUENCE: 384
ggatcctcta gagcggccgc ctactactac taaattcgcg gccgcgtcga cgaagaagag     60
aaagatgtgt tttgttttgg actctctgtg gtcccttcca atgctgtggg tttccaacca    120
ggggaagggt ccctttttgca ttgccaagtg ccataaccat gagcactact ctaccatggt   180
tctgcctcct ggccaagcag gctggtttgc aagaatgaaa tgaatgattc tacagctagg    240
acttaacctt gaaatggaaa gtcttgcaat cccatttgca ggatccgtct gtgcacatgc    300
ctctgtagag agcagcattc ccagggacct tggaaacagt tggcactgta aggtgcttgc    360
tccccaagac acatcctaaa aggtgttgta atggtgaaaa cgtcttcctt ctttattgcc    420
ccttcttatt tatgtgaaca actgtttgtc ttttttttgta tctttttttaa actgtaaagt   480 tcaattgtga aaatgaatat catgcaaata aattatgcga ttttttttttc aaagtaaaaa   540 aaaaaaaaaa aaaaaaa                                                  557

<210> SEQ ID NO 385
<211> LENGTH: 337
<212> TYPE: DNA
<213> ORGANISM: Homo sapiens

<400> SEQUENCE: 385
ttcccaggtg atgtgcgagg gaagacacat ttactatcct tgatggggct gattcctta     60 gtttctctag cagcagatgg gttaggagga agtgacccaa gtggttgact ccatatgtgca   120 tctcaaagcc atctgctgtc ttcgagtacg gacacatcat cactcctgca ttgttgatca   180

```
aaacgtggag gtgcttttcc tcagctaaga agcccttagc aaaagctcga atagacttag     240
tatcagacag gtccagtttc cgcaccaaca cctgctggtt ccctgtcgtg gtctggatct     300
ctttggccac caattccccc ttttccacat cccggca                              337
```

<210> SEQ ID NO 386
<211> LENGTH: 300
<212> TYPE: DNA
<213> ORGANISM: Homo sapiens

<400> SEQUENCE: 386

```
gggcccgcta ccggcccagg ccccgcctcg cgagtcctcc tccccgggtg cctgcccgca      60
gcccgctcgg cccagagggt gggcgcgggg ctgcctctac cggctggcgg ctgtaactca     120
gcgaccttgg cccgaaggct ctagcaagga cccaccgacc cagccgcgg cggcggcggc     180 gcggactttg cccggtgtgt ggggcggagc ggactgcgtg tccgcggacg ggcagcgaag     240
atgttagcct tcgctgccag gaccgtggac cgatcccagg gctgtggtgt aacctcagcc     300
```

<210> SEQ ID NO 387
<211> LENGTH: 537
<212> TYPE: DNA
<213> ORGANISM: Homo sapiens

<400> SEQUENCE: 387

```
gggccgagtc gggcaccaag ggactctttg caggcttcct tcctcggatc atcaaggctg      60 cccctcctg tgccatcatg atcagcacct atgagttcgg caaaagcttc ttccagaggc     120
tgaaccagga ccggcttctg gcggctgaa aggggcaagg aggcaaggac cccgtctctc     180
ccacggatgg ggagagggca ggaggagacc cagccaagtg cctttcctc agcactgagg     240 gagggggctt gtttcccttc cctcccggcg acaagctcca gggcagggct gtccctctgg     300
gcggcccagc acttcctcag acacaacttc ttcctgctgc tccagtcgtg gggatcatca     360
cttacccacc ccccaagttc aagaccaaat cttccagctg ccccttcgt gtttccctgt     420 gtttgctgta gctgggcatg tctccaggaa ccaagaagcc ctcagcctgg tgtagtctcc     480
ctgacccttg ttaattcctt aagtctaaag atgatgaact caaaaaaaa aaaaaaa       537
```

<210> SEQ ID NO 388
<211> LENGTH: 520
<212> TYPE: DNA
<213> ORGANISM: Homo sapiens

<400> SEQUENCE: 388

```
aggataattt ttaaaccaat caaatgaaaa aaacaaacaa acaaaaaagg aaatgtcatg      60
tgaggttaaa ccagtttgca ttcccctaat gtggaaaaag taagaggact actcagcact     120
gtttgaagat tgcctcttct acagcttctg agaattgtgt tatttcactt gccaagtgaa     180 ggacccccctc cccaacatgc cccagcccac ccctaagcat ggtcccttgt caccaggcaa     240
ccaggaaact gctacttgtg gacctcacca gagaccagga gggtttggtt agctcacagg     300
acttccccca ccccagaaga ttagcatccc atactagact catactcaac tcaactaggc     360
tcatactcaa ttgatggtta ttagacaatt ccatttcttt ctggttatta taaacagaaa     420
atctttcctc ttctcattac cagtaaaggc tcttggtatc tttctgttgg aatgatttct     480
atgaacttgt cttatttta tggtgggttt ttttctggt                            520
```

<210> SEQ ID NO 389
<211> LENGTH: 365

```
<212> TYPE: DNA
<213> ORGANISM: Homo sapiens

<400> SEQUENCE: 389
cgttgcccca gtttgacaga aggaaaggcg gagcttattc aaagtctaga gggagtggag    60
gagttaaggc tggatttcag atctgcctgg ttccagccgc agtgtgccct ctgctccccc   120
aacgactttc caaataatct caccagcgcc ttccagctca ggcgtcctag aagcgtcttg   180
aagcctatgg ccagctgtct ttgtgttccc tctcacccgc ctgtcctcac agctgagact   240
cccaggaaac cttcagacta ccttcctctg ccttcagcaa ggggcgttgc ccacattctc   300
tgagggtcag tggaagaacc tagactccca ttgctagagg tagaaagggg aagggtgctg   360
gggag                                                               365

<210> SEQ ID NO 390
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 390
tgcctctcca tcctggcccc gacttctctg tcaggaaagt ggggatggac cccatctgca    60
tacacggntt ctcatgggtg tggaacatct ctgcttgcgg tttcaggaag gcctctggct   120
gctctangag tctgancnga ntcgttgccc cantntgaca naaggaaagg cggagcttat   180
tcaaagtcta gagggagtgg aggagttaag gctggatttc a                       221

<210> SEQ ID NO 391
<211> LENGTH: 325
<212> TYPE: DNA
<213> ORGANISM: Homo sapiens
<220> FEATURE:
<221> NAME/KEY: misc_feature
<222> LOCATION: (1)...(325)
<223> OTHER INFORMATION: n = A,T,C or G

<400> SEQUENCE: 391
tggagcaggt cccgaggcct ccctagagcc tggggccgac tctgtgncga tgcangcttt    60
ctctcgcgcc cagcctggag ctgctcctgg catctaccaa caatcagncg aggcgagcag   120
tagccagggc actgctgcca acagccagtc cnnataccat catgtnaccc ggtgngctct   180
naanttngat ntccanagcc ctacccatcn tagttctgct ctcccaccgg ntaccagccc   240
cactgcccag gaatcctaca gccagtaccc tgtcccgacg tctctaccta ccagtacgat   300
gagacctccg gctactacta tgacc                                         325

<210> SEQ ID NO 392
<211> LENGTH: 277
<212> TYPE: DNA
<213> ORGANISM: Homo sapiens
<220> FEATURE:
<221> NAME/KEY: misc_feature
<222> LOCATION: (1)...(277)
<223> OTHER INFORMATION: n = A,T,C or G

<400> SEQUENCE: 392
atattgttta actccttcct ttatatcttt taacattttc atggngaaag gttcacatct    60
agtctcactt nggcnagngn ctcctacttg agtctcttcc ccggcctgnn ccagtngnaa   120
```

```
antaccanga accgncatgn cttaanaacn ncctggtttn tgggttnntc aatgactgca      180
tgcagtgcac caccctgtcc actacgtgat gctgtaggat taaagtctca cagtgggcgg      240
ctgaggatac agcgccgcgt cctgtgttgc tggggaa                              277
```

<210> SEQ ID NO 393
<211> LENGTH: 566
<212> TYPE: DNA
<213> ORGANISM: Homo sapiens

<400> SEQUENCE: 393

```
actagtccag tgtggtggaa ttcgcggccg cgtcgacgga caggtcagct gtctggctca       60
gtgatctaca ttctgaagtt gtctgaaaat gtcttcatga ttaaattcag cctaaacgtt      120
ttgccgggaa cactgcagag acaatgctgt gagtttccaa ccttagccca tctgcgggca      180
gagaaggtct agtttgtcca tcagcattat catgatatca ggactggtta cttggttaag      240 gagggtcta ggagatctgt cccttttaga dacaccttac ttataatgaa gtatttggga       300
gggtggtttt caaaagtaga aatgtcctgt attccgatga tcatcctgta aacattttat      360
catttattaa tcatccctgc ctgtgtctat tattatattc atatctctac gctggaaact      420
ttctgcctca atgtttactg tgcctttgtt tttgctagtt tgtgttgttg aaaaaaaaaa      480
cattctctgc ctgagtttta attttttgtcc aaagttattt taatctatac aattaaaagc    540
ttttgcctat caaaaaaaaa aaaaaa                                          566
```

<210> SEQ ID NO 394
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 394

```
gaacatacat gtcccggcac ctgagctgca gtctgacatc atcgccatca cgggcctcgc       60
tgcaaattng gaccgggcca aggctggact gctggagcgt gtgaaggagc tacaggccna      120
gcaggaggac cgggctttaa ggagtttttaa gctgagtgtc actgtagacc ccaaatacca    180
tcccaagatt atcgggagaa aggggggcagt aattacccaa atccggttgg agcatgacgt     240
gaacatccag tttcctgata aggacgatgg gaaccagccc caggaccaaa ttaccatcac     300
agggtacgaa aagaacacag aagctgccag ggatgctata ctgagaattg tgggtgaact    360
tgagcagatg gtttctgagg acgt                                           384
```

<210> SEQ ID NO 395
<211> LENGTH: 399
<212> TYPE: DNA
<213> ORGANISM: Homo sapiens

<400> SEQUENCE: 395

```
ggcaaaactg tgtgacctca ataagacctc gcagatccaa ggtcaagtat cagaagtgac       60
tctgaccttg gactccaaga cctacatcaa cagcctggct atattagatg atgagccagt      120
tatcagaggt ttcatcattg cggaaattgt ggagtctaag gaaatcatgg cctctgaagt     180
attcacgtct ttccagtacc ctgagttctc tatagagttg cctaacacag gcagaattgg    240
ccagctactt gtctgcaatt gtatcttcaa gaatacccctg gccatccctt tgactgacgt    300
caagttctct ttggaaagcc tgggcatctc ctcactacag acctctgacc atgggacggt    360
```
gcagcctggt gagaccatcc aatcccaaat aaaatgcac                                399

<210> SEQ ID NO 396
<211> LENGTH: 403
<212> TYPE: DNA
<213> ORGANISM: Homo sapiens
<220> FEATURE:
<221> NAME/KEY: misc_feature
<222> LOCATION: (1)...(403)
<223> OTHER INFORMATION: n = A,T,C or G

<400> SEQUENCE: 396
tggagttntc agtgcaaaca agccataaag cttcagtagc aaattactgt ctcacagaaa     60
gacattttca acttctgctc cagctgctga taaaacaaat catgtgttta gcttgactcc    120
agacaaggac aacctgttcc ttcataactc tctagagaaa aaaggagtt gttagtagat     180
actaaaaaaa gtgatgaat aatctggata tttttcctaa aaagattcct tgaaacacat    240
taggaaaatg gagggcctta tgatcagaat gctagaatta gtccattgtg ctgaagcagg    300
gtttagggga gggagtgagg gataaaagaa ggaaaaaaag aagagtgaga aaacctattt    360
atcaaagcag gtgctatcac tcaatgttag gccctgctct ttt                      403

<210> SEQ ID NO 397
<211> LENGTH: 100
<212> TYPE: DNA
<213> ORGANISM: Homo sapiens
<220> FEATURE:
<221> NAME/KEY: misc_feature
<222> LOCATION: (1)...(100)
<223> OTHER INFORMATION: n = A,T,C or G

<400> SEQUENCE: 397
actagtncag tgtggtggaa ttcgcggccg cgtcgaccta naanccatct ctatagcaaa     60
tccatccccg ctcctggttg gtnacagaat gactgacaaa                          100

<210> SEQ ID NO 398
<211> LENGTH: 278
<212> TYPE: DNA
<213> ORGANISM: Homo sapiens
<220> FEATURE:
<221> NAME/KEY: misc_feature
<222> LOCATION: (1)...(278)
<223> OTHER INFORMATION: n = A,T,C or G

<400> SEQUENCE: 398
gcggccgcgt cgacagcagt tccgccagcg ctcgcccctg ggtggggatg tgctgcacgc     60
ccacctggac atctggaagt cagcggcctg gatgaaagag cggacttcac ctggggcgat    120
tcactactgt gcctcgacca gtgaggagag ctggaccgac agcgaggtgg actcatcatg    180
ctccgggcag cccatccacc tgtggcagtt cctcaaggag ttgctactca agccccacag    240
ctatggccgc ttcattangt ggctcaacaa ggagaagg                            278

<210> SEQ ID NO 399
<211> LENGTH: 298
<212> TYPE: DNA
<213> ORGANISM: Homo sapiens
<220> FEATURE:
<221> NAME/KEY: misc_feature
<222> LOCATION: (1)...(298)
<223> OTHER INFORMATION: n = A,T,C or G

<400> SEQUENCE: 399

```
acggaggtgg aggaagcgnc cctgggatcg anaggatggg tcctgncatt gaccnectcn    60 ggggtgccng catggagcgc atgggcgcgg gcctgggcca cggcatggat cgcgtgggct   120
ccgagatcga gcgcatgggc ctggtcatgg accgcatggg ctccgtggag cgcatgggct   180
ccggcattga gcgcatgggc ccgctgggcc tcgaccacat ggcctccanc attgancgca   240
tgggccagac catggagcgc attggctctg gcgtggagcn catgggtgcc ggcatggg    298
```

<210> SEQ ID NO 400
<211> LENGTH: 548
<212> TYPE: DNA
<213> ORGANISM: Homo sapiens

<400> SEQUENCE: 400

```
acatcaacta cttcctcatt ttaaggtatg gcagttccct tcatcccctt ttcctgcctt    60
gtacatgtac atgtatgaaa tttccttctc ttaccgaact ctctccacac atcacaaggt   120
caaagaacca cacgcttaga agggtaagag ggcaccctat gaaatgaaat ggtgatttct   180
tgagtctctt ttttccacgt ttaagggggcc atggcaggac ttagagttgc gagttaagac   240
tgcagagggc tagagaatta tttcatacag gctttgaggc cacccatgtc acttatcccg   300
tataccctct caccatcccc ttgtctactc tgatgccccc aagatgcaac tgggcagcta   360
gttggcccca taattctggg cctttgttgt ttgtttaat tacttgggca tcccaggaag   420
cttcccagtg atctcctacc atgggccccc ctcctgggat caagcccctc ccaggccctg   480
tccccagccc ctcctgcccc agcccacccg cttgccttgg tgctcagccc tcccattggg   540
agcaggtt    548
```

<210> SEQ ID NO 401
<211> LENGTH: 355
<212> TYPE: DNA
<213> ORGANISM: Homo sapiens
<220> FEATURE:
<221> NAME/KEY: misc_feature
<222> LOCATION: (1)...(355)
<223> OTHER INFORMATION: n = A,T,C or G

<400> SEQUENCE: 401

```
actgtttcca tgttatgttt ctacacattg ctacctcagt gctcctggaa acttagcttt    60
tgatgtctcc aagtagtcca ccttcattta actctttgaa actgtatcat ctttgccaag   120
taagagtggt ggcctatttc agctgctttg acaaaatgac tggctcctga cttaacgttc   180
tataaatgaa tgtgctgaag caaagtgccc atggtggcgg cgaagaagan aaagatgtgt   240
tttgttttgg actctctgtg gtcccttcca atgctgnggg tttccaacca ggggaagggt   300
cccttttgca ttgccaagtg ccataaccat gagcactact ctaccatggn tctgc       355
```

<210> SEQ ID NO 402
<211> LENGTH: 407
<212> TYPE: DNA
<213> ORGANISM: Homo sapiens
<220> FEATURE:
<221> NAME/KEY: misc_feature
<222> LOCATION: (1)...(407)
<223> OTHER INFORMATION: n = A,T,C or G

<400> SEQUENCE: 402

```
atggggcaag ctggataaag aaccaagacc cactggagta tgctgtcttc aagaaaccca    60
tctcacatgc ggtggcatac ataggctcaa aataaaggaa tggagaaaaa tatttcaagc   120
aaatggaaaa cagaaaaaag caggtgttgc actcctactt tctgacaaaa cagactatgc   180
```

```
gaataaagat aaaaaagaga aggacattac aaaggtggtc ctgacctttg ataaatctca      240
ttgcttgata ccaacctggg ctgttttaat tgcccaaacc aaaaggataa tttgctgagg      300
ttgtggagct tctcccctgc agagagtccc tgatctccca aaatttggtt gagatgtaag      360
gntgattttg ctgacaactc cttttctgaa gttttactca tttccaa                   407
```

<210> SEQ ID NO 403  
<211> LENGTH: 303  
<212> TYPE: DNA  
<213> ORGANISM: Homo sapiens  
<220> FEATURE:  
<221> NAME/KEY: misc_feature  
<222> LOCATION: (1)...(303)  
<223> OTHER INFORMATION: n = A,T,C or G

<400> SEQUENCE: 403

```
cagtatttat agccnaactg aaaagctagt agcaggcaag tctcaaatcc aggcaccaaa       60
tcctaagcaa gagccatggc atggtgaaaa tgcaaaagga gagtctggcc aatctacaaa      120
tagagaacaa gacctactca gtcatgaaca aaaaggcaga caccaacatg gatctcatgg      180
gggattggat attgtaatta tagagcagga agatgacagt gatcgtcatt tggcacaaca      240
tcttaacaac gaccgaaacc cattatttac ataaacctcc attcggtaac catgttgaaa      300
gga                                                                    303
```

<210> SEQ ID NO 404  
<211> LENGTH: 225  
<212> TYPE: DNA  
<213> ORGANISM: Homo sapiens

<400> SEQUENCE: 404

```
aagtgtaact tttaaaaatt tagtggattt tgaaaattct tagaggaaag taaaggaaaa       60
attgttaatg cactcattta cctttacatg gtgaaagttc tctcttgatc ctacaaacag      120
acattttcca ctcgtgtttc catagttgtt aagtgtatca gatgtgttgg gcatgtgaat      180
ctccaagtgc ctgtgtaata aataaagtat ctttatttca ttcat                      225
```

<210> SEQ ID NO 405  
<211> LENGTH: 334  
<212> TYPE: DNA  
<213> ORGANISM: Homo sapiens  
<220> FEATURE:  
<221> NAME/KEY: misc_feature  
<222> LOCATION: (1)...(334)  
<223> OTHER INFORMATION: n = A,T,C or G

<400> SEQUENCE: 405

```
gagctgttat actgtgagtt ctactaggaa atcatcaaat ctgagggttg tctggaggac       60
ttcaatacac ctccccccat agtgaatcag cttccagggg gtccagtccc tctccttact      120
tcatccccat cccatgccaa aggaagaccc tccctccttg gctcacagcc ttctctaggc      180
ttcccagtgc ctccaggaca gagtgggtta tgttttcagc tccatccttg ctgtgagtgt      240
ctggtgcggt tgtgcctcca gcttctgctc agtgcttcat ggacagtgtc cagcccatgt      300
cactctccac tctctcanng tggatcccac ccct                                  334
```

<210> SEQ ID NO 406  
<211> LENGTH: 216  
<212> TYPE: DNA  
<213> ORGANISM: Homo sapiens  
<220> FEATURE:

<221> NAME/KEY: misc_feature
<222> LOCATION: (1)...(216)
<223> OTHER INFORMATION: n = A,T,C or G

<400> SEQUENCE: 406

```
tttcatacct aatgagggag ttganatnac atnnaaccag gaaatgcatg gatctcaang    60
gaaacaaaca cccaataaac tcggagtggc agactgacaa ctgtgagaca tgcacttgct   120
acnaaacaca aatttnatgt tgcacccttg tttctacacc tgtgggttat gacaaagaca   180
actgccaaag aatnttcaag aaggaggact gccant                             216
```

<210> SEQ ID NO 407
<211> LENGTH: 413
<212> TYPE: DNA
<213> ORGANISM: Homo sapiens

<400> SEQUENCE: 407

```
gctgacttgc tagtatcatc tgcattcatt gaagcacaag aacttcatgc cttgactcat    60
gtaaatgcaa taggattaaa aaataaattt gatatcacat ggaaacagac aaaaaatatt   120
gtacaacatt gcacccagtg tcagattcta cacctggcca ctcaggaagc aagagttaat   180
cccagaggtc tatgtcctaa tgtgttatgg caaatggatg tcatgcacgt accttcattt   240
ggaaaattgt catttgtcca tgtgacagtt gatacttatt cacatttcat atgggcaacc   300
tgccagacag gagaaagtct tcccatgtta aaagacattt attatcttgt tttcctgtca   360
tgggagttcc agaaaaagtt aaaacagaca atgggccagg ttctgtagta aag          413
```

<210> SEQ ID NO 408
<211> LENGTH: 183
<212> TYPE: DNA
<213> ORGANISM: Homo sapiens
<220> FEATURE:
<221> NAME/KEY: misc_feature
<222> LOCATION: (1)...(183)
<223> OTHER INFORMATION: n = A,T,C or G

<400> SEQUENCE: 408

```
ggagctngcc ctcaattcct ccatntctat gttancatat ttaatgtctt ttgnnattaa    60
tncttaacta gttaatcctt aaagggctan ntaatcctta actagtccct ccattgtgag   120
cattatcctt ccagtattcn ccttctnttt tatttactcc ttcctggcta cccatgtact   180
ntt                                                                 183
```

<210> SEQ ID NO 409
<211> LENGTH: 250
<212> TYPE: DNA
<213> ORGANISM: Homo sapiens
<220> FEATURE:
<221> NAME/KEY: misc_feature
<222> LOCATION: (1)...(250)
<223> OTHER INFORMATION: n = A,T,C or G

<400> SEQUENCE: 409

```
cccacgcatg ataagctctt tatttctgta agtcctgcta ggaaatcatc aaatctgacg    60
gtggtttggg ggacctgaac aaacctcctg taattaatca gctttcagtt tctcccccta   120
gtccctcctt caacaacata ggaggatcct cccttctttt ctgctcacgg ccttatctag   180
gcttcccagt gcccccagga cagcgtgggc tatgtttaca gcgcntcctt gctgggggg    240
ggccntatgc                                                          250
```

<210> SEQ ID NO 410
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 410

```
ggctggtttg caagaatgaa atgaatgatt ctacagctag gacttaacct tgaaatggaa      60
agtcttgcaa tcccatttgc aggatccgtc tgtgcacatg cctctgtaga gagcagcatt     120
cccagggacc ttggaaacag ttggcactgt aaggtgcttg ctccccaaga cacatcctaa     180
aaggtgttgt aatggtgaaa accgcttcct tctttattgc cccttcttat ttatgtgaac     240
nactggttgg ctttttttgn atctttttta aactggaaag ttcaattgng aaaatgaata     300
tcntgc                                                                306
```

<210> SEQ ID NO 411
<211> LENGTH: 261
<212> TYPE: DNA
<213> ORGANISM: Homo sapiens
<220> FEATURE:
<221> NAME/KEY: misc_feature
<222> LOCATION: (1)...(261)
<223> OTHER INFORMATION: n = A,T,C or G

<400> SEQUENCE: 411

```
agagatattn cttaggtnaa agttcataga gttcccatga actatatgac tggccacaca      60
ggatcttttg tatttaagga ttctgagatt ttgcttgagc aggattagat aaggctgttc     120
tttaaatgtc tgaaatggaa cagatttcaa aaaaaaaccc cacaatctag ggtgggaaca     180
aggaaggaaa gatgtgaata ggctgatggg caaaaaacca atttacccat cagttccagc     240
cttctctcaa ggngaggcaa a                                              261
```

<210> SEQ ID NO 412
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

```
gttcaatgtt acctgacatt tctacaacac cccactcacc gatgtattcg ttgcccagtg      60
ggaacatacc agcctgaatt tgaaaaaat aattgtgttt cttgcccagg aaatactacg     120
actgactttg atggctccac aaacataacc cagtgtaaaa acagaagatg tggaggggag     180
ctgggagatt tcactgggta cattgaattc ccaaactacc cangcaatta cccagccaac     240
a                                                                    241
```

<210> SEQ ID NO 413
<211> LENGTH: 231
<212> TYPE: DNA
<213> ORGANISM: Homo sapiens
<220> FEATURE:
<221> NAME/KEY: misc_feature
<222> LOCATION: (1)...(231)
<223> OTHER INFORMATION: n = A,T,C or G

<400> SEQUENCE: 413

```
aactcttaca atccaagtga ctcatctgtg tgcttgaatc ctttccactg tctcatctcc      60
ctcatccaag tttctagtac cttctctttg ttgtgaagga taatcaaact gaacaacaaa     120
aagtttactc tcctcatttg gaacctaaaa actctcttct tcctgggtct gagggctcca     180
agaatccttg aatcanttct cagatcattg gggacaccan atcaggaacc t              231
```

<210> SEQ ID NO 414
<211> LENGTH: 234
<212> TYPE: DNA
<213> ORGANISM: Homo sapiens

<400> SEQUENCE: 414

```
actgtccatg aagcactgag cagaagctgg aggcacaacg caccagacac tcacagcaag      60
gatggagctg aaaacataac ccactctgtc ctggaggcac tgggaagcct agagaaggct     120
gtgagccaag gagggagggt cttcctttgg catgggatgg ggatgaagta aggagaggga     180
ctggaccccc tggaagctga ttcactatgg ggggaggtgt attgaagtcc tcca            234
```

<210> SEQ ID NO 415
<211> LENGTH: 217
<212> TYPE: DNA
<213> ORGANISM: Homo sapiens
<220> FEATURE:
<221> NAME/KEY: misc_feature
<222> LOCATION: (1)...(217)
<223> OTHER INFORMATION: n = A,T,C or G

<400> SEQUENCE: 415

```
gcataggatt aagactgagt atcttttcta cattctttta actttctaag gggcacttct      60
caaaacacag accaggtagc aaatctccac tgctctaagn ntctcaccac cactttctca     120
cacctagcaa tagtagaatt cagtcctact tctgaggcca aagaatggt tcagaaaaat      180 antggattat aaaaaataac aattaagaaa aataatc                               217
```

<210> SEQ ID NO 416
<211> LENGTH: 213
<212> TYPE: DNA
<213> ORGANISM: Homo sapiens
<220> FEATURE:
<221> NAME/KEY: misc_feature
<222> LOCATION: (1)...(213)
<223> OTHER INFORMATION: n = A,T,C or G

<400> SEQUENCE: 416

```
atgcatatnt aaagganact gcctcgcttt tagaagacat ctggnctgct ctctgcatga      60
ggcacagcag taaagctctt tgattcccag aatcaagaac tctcccottc agactattac     120 cgaatgcaag gtggttaatt gaaggccact aattgatgct caaatagaag gatattgact     180
atattggaac agatggagtc tctactacaa aag                                   213
```

<210> SEQ ID NO 417
<211> LENGTH: 303
<212> TYPE: DNA
<213> ORGANISM: Homo sapiens
<220> FEATURE:
<221> NAME/KEY: misc_feature
<222> LOCATION: (1)...(303)
<223> OTHER INFORMATION: n = A,T,C or G

<400> SEQUENCE: 417

```
nagtcttcag gcccatcagg gaagttcaca ctggagagaa gtcatacata tgtactgtat      60
gtgggaaagg ctttactctg agttcaaatc ttcaagccca tcagagagtc cacactggag     120
```
agaagccata caaatgcaat gagtgtggga agagcttcag gagggattcc cattatcaag     180
ttcatctagt ggtccacaca ggagagaaac cctataaatg tgagatatgt gggaagggct     240
tcantcaaag ttcgtatctt caaatccatc ngaaggncca cagtatanan aaaccttta      300 agt                                                                   303

<210> SEQ ID NO 418
<211> LENGTH: 328
<212> TYPE: DNA
<213> ORGANISM: Homo sapiens
<220> FEATURE:
<221> NAME/KEY: misc_feature
<222> LOCATION: (1)...(328)
<223> OTHER INFORMATION: n = A,T,C or G

<400> SEQUENCE: 418
tttttggcgg tggtggggca gggacgggac angagtctca ctctgttgcc caggctggag      60
tgcacaggca tgatctcggc tcactacaac ccctgcctcc catgtccaag cgattcttgt     120
gcctcagcct tccctgtagc tagaattaca ggcacatgcc accacaccca gctagttttt     180 gtattttag tagagacagg gtttcaccat gttggccagg ctggtctcaa actcctnacc      240
tcagnggtca ggctggtctc aaactcctga cctcaagtga tctgcccacc tcagcctccc     300
aaagtgctan gattacaggc cgtgagcc                                         328

<210> SEQ ID NO 419
<211> LENGTH: 389
<212> TYPE: DNA
<213> ORGANISM: Homo sapiens
<220> FEATURE:
<221> NAME/KEY: misc_feature
<222> LOCATION: (1)...(389)
<223> OTHER INFORMATION: n = A,T,C or G

<400> SEQUENCE: 419
cctcctcaag acggcctgtg gtccgcctcc cggcaaccaa gaagcctgca gtgccatatg      60 accctgagc catggactgg agcctgaaag gcagcgtaca ccctgctcct gatcttgctg     120
cttgtttcct ctctgtggct ccattcatag cacagttgtt gcactgaggc ttgtgcaggc     180
cgagcaaggc caagctggct caaagagcaa ccagtcaact ctgccacggt gtgccaggca     240
ccggttctcc agccaccaac ctcactcgct cccgcaaatg gcacatcagt tcttctaccc     300
taaaggtagg accaaagggc atctgctttt ctgaagtcct ctgctctatc agccatcacg     360
tggcagccac tcnggctgtg tcgacgcgg                                        389

<210> SEQ ID NO 420
<211> LENGTH: 408
<212> TYPE: DNA
<213> ORGANISM: Homo sapiens

<400> SEQUENCE: 420
gttcctccta actcctgcca gaaacagctc tcctcaacat gagagctgca cccctcctcc      60
tggccagggc agcaagcctt agccttggct tcttgtttct gctttttttc tggctagacc     120
gaagtgtact agccaaggag ttgaagtttg tgactttggt gtttcggcat ggagaccgaa     180
gtcccattga cacctttccc actgaccca taaggaatc ctcatggcca caaggatttg     240
gccaactcac ccagctgggc atggagcagc attatgaact ggagagtat ataagaaaga     300 gatatagaaa attcttgaat gagtcctata aacatgaaca ggtttatatt cgaagcacag     360

```
acgttgaccg gactttgatg aagtgctatg acaaacctgg caagcccg        408
```

<210> SEQ ID NO 421
<211> LENGTH: 352
<212> TYPE: DNA
<213> ORGANISM: Homo sapiens
<220> FEATURE:
<221> NAME/KEY: misc_feature
<222> LOCATION: (1)...(352)
<223> OTHER INFORMATION: n = A,T,C or G

<400> SEQUENCE: 421

```
gctcaaaaat cttttactg atnggcatgg ctacacaatc attgactatt acggaggcca     60
gaggagaatg aggcctggcc tgggagccct gtgcctacta naagcacatt agattatcca   120
ttcactgaca gaacaggtct tttttgggtc cttcttctcc accacnatat acttgcagtc   180
ctccttcttg aagattcttt ggcagttgtc tttgtcataa cccacaggtg tagaaacaag   240
ggtgcaacat gaaatttctg tttcgtagca agtgcatgtc tcacaagttg gcangtctgc   300
cactccgagt ttattgggtg tttgtttcct ttgagatcca tgcatttcct gg           352
```

<210> SEQ ID NO 422
<211> LENGTH: 337
<212> TYPE: DNA
<213> ORGANISM: Homo sapiens

<400> SEQUENCE: 422

```
atgccaccat gctggcaatg cagcgggcgg tcgaaggcct gcatatccag cccaagctgg     60
cgatgatcga cggcaaccgt tgcccgaagt tgccgatgcc agccgaagcg gtggtcaagg   120
gcgatagcaa ggtgccggcg atcgcggcgg cgtcaatcct ggccaaggtc agccgtgatc   180
gtgaaatggc agctgtcgaa ttgatctacc cgggttatgg catcggcggg cataagggct   240
atccgacacc ggtgcacctg gaagccttgc agcggctggg gccgacgccg attcaccgac   300
gcttcttccg ccggtacggc tggcctatga aaattat                            337
```

<210> SEQ ID NO 423
<211> LENGTH: 310
<212> TYPE: DNA
<213> ORGANISM: Homo sapiens
<220> FEATURE:
<221> NAME/KEY: misc_feature
<222> LOCATION: (1)...(310)
<223> OTHER INFORMATION: n = A,T,C or G

<400> SEQUENCE: 423

```
gctcaaaaat cttttactg atatggcatg gctacacaat cattgactat tagaggccag     60
aggagaatga ggcctggcct gggagccctg tgcctactan aagcncatta gattatccat   120
tcactgacag aacaggtctt ttttgggtcc ttcttctcca ccacgatata cttgcagtcc   180
tccttcttga agattctttg gcagttgtct ttgtcataac ccacaggtgt anaaacaagg   240
gtgcaacatg aaatttctgt ttcgtagcaa gtgcatgtct cacagttgtc aagtctgccc   300
tccgagttta                                                          310
```

<210> SEQ ID NO 424
<211> LENGTH: 370
<212> TYPE: DNA
<213> ORGANISM: Homo sapiens
<220> FEATURE:
<221> NAME/KEY: misc_feature
<222> LOCATION: (1)...(370)
<223> OTHER INFORMATION: n = A,T,C or G

<400> SEQUENCE: 424

| | | | | |
|---|---|---|---|---|
| gctcaaaaat | cttttactg | ataggcatgg | ctacacaatc | attgactatt agaggccaga | 60 |
| ggagaatgag | gcctggcctg | ggagccctgt | gcctactaga | agcacattag attatccatt | 120 |
| cactgacaga | acaggtcttt | tttgggtcct | tcttctccac | cacgatatac ttgcagtcct | 180 |
| ccttcttgaa | gattctttgg | cagttgtctt | tgtcataacc | cacaggtgta gaaacatcct | 240 |
| ggttgaatct | cctggaactc | cctcattagg | tatgaaatag | catgatgcat tgcataaagt | 300 |
| cacgaaggtg | gcaaagatca | caacgctgcc | cagganaaca | ttcattgtga taagcaggac | 360 |
| tccgtcgacg | | | | | 370 |

<210> SEQ ID NO 425
<211> LENGTH: 216
<212> TYPE: DNA
<213> ORGANISM: Homo sapiens
<220> FEATURE:
<221> NAME/KEY: misc_feature
<222> LOCATION: (1)...(216)
<223> OTHER INFORMATION: n = A,T,C or G

<400> SEQUENCE: 425

| | | | | |
|---|---|---|---|---|
| aattgctatn | ntttattttg | ccactcaaaa | taattaccaa | aaaaaaaaaa tnttaaatga | 60 |
| taacaacnca | acatcaaggn | aaananaaca | ggaatggntg | actntgcata aatnggccga | 120 |
| anattatcca | ttatnttaag | ggttgacttc | aggntacagc | acacagacaa acatgcccag | 180 |
| gaggntntca | ggaccgctcg | atgtnttntg | aggagg | | 216 |

<210> SEQ ID NO 426
<211> LENGTH: 596
<212> TYPE: DNA
<213> ORGANISM: Homo sapiens

<400> SEQUENCE: 426

| | | | | |
|---|---|---|---|---|
| cttccagtga | ggataaccct | gttgccccgg | gccgaggttc | tccattaggc tctgattgat | 60 |
| tggcagtcag | tgatggaagg | gtgttctgat | cattccgact | gccccaaggg tcgctggcca | 120 |
| gctctctgtt | ttgctgagtt | ggcagtagga | cctaatttgt | taattaagag tagatggtga | 180 |
| gctgtccttg | tattttgatt | aacctaatgg | ccttcccagc | acgactcgga ttcagctgga | 240 |
| gacatcacgg | caacttttaa | tgaaatgatt | tgaagggcca | ttaagaggca cttcccgtta | 300 |
| ttaggcagtt | catctgcact | gataacttct | tggcagctga | gctggtcgga gctgtggccc | 360 |
| aaacgcacac | ttggcttttg | gttttgagat | acaactctta | atcttttagt catgcttgag | 420 |
| ggtggatggc | cttttcagct | ttaacccaat | ttgcactgcc | ttggaagtgt agccaggaga | 480 |
| atacactcat | atactcgtgg | gcttagaggc | cacagcagat | gtcattggtc tactgcctga | 540 |
| gtcccgctgg | tccatccca | ggaccttcca | tcggcgagta | cctgggagcc cgtgct | 596 |

<210> SEQ ID NO 427
<211> LENGTH: 107
<212> TYPE: DNA
<213> ORGANISM: Homo sapiens
<220> FEATURE:
<221> NAME/KEY: misc_feature
<222> LOCATION: (1)...(107)
<223> OTHER INFORMATION: n = A,T,C or G

<400> SEQUENCE: 427

| | | | | |
|---|---|---|---|---|
| gaagaattca | agttaggttt | attcaaaggg | cttacngaga | atcctanacc caggncccag | 60 | cccgggagca gccttanaga gctcctgttt gactgcccgg ctcagng         107

<210> SEQ ID NO 428
<211> LENGTH: 38
<212> TYPE: DNA
<213> ORGANISM: Homo sapiens
<220> FEATURE:
<221> NAME/KEY: misc_feature
<222> LOCATION: (1)...(38)
<223> OTHER INFORMATION: n = A,T,C or G

<400> SEQUENCE: 428
gaacttccna anaangactt tattcactat tttacatt         38

<210> SEQ ID NO 429
<211> LENGTH: 544
<212> TYPE: DNA
<213> ORGANISM: Homo sapiens

<400> SEQUENCE: 429
ctttgctgga cggaataaaa gtggacgcaa gcatgacctc ctgatgaggg cgctgcattt         60
attgaagagc ggctgcagcc ctgcggttca gattaaaatc cgagaattgt atagacgccg        120
atatccacga actcttgaag gactttctga tttatccaca atcaaatcat cggttttcag        180
tttggatggt ggctcatcac ctgtagaacc tgacttggcc gtggctggaa tccactcgtt        240
gccttccact tcagttacac ctcactcacc atcctctcct gttggttctg tgctgcttca        300
agatactaag cccacatttg agatgcagca gccatctccc ccaattcctc ctgtccatcc        360
tgatgtgcag ttaaaaaatc tgccctttta tgatgtcctt gatgttctca tcaagcccac        420
gagtttagtt caaagcagta ttcagcgatt tcaagagaag ttttttattt ttgctttgac        480
acctcaacaa gttagagaga tatgcatatc cagggatttt tgccaggtg gtaggagaga        540
ttat        544

<210> SEQ ID NO 430
<211> LENGTH: 507
<212> TYPE: DNA
<213> ORGANISM: Homo sapiens
<220> FEATURE:
<221> NAME/KEY: misc_feature
<222> LOCATION: (1)...(507)
<223> OTHER INFORMATION: n = A,T,C or G

<400> SEQUENCE: 430
cttatcncaa tggggctccc aaacttggct gtgcagtgga aactccgggg gaattttgaa         60
gaacactgac acccatcttc caccccgaca ctctgattta attgggctgc agtgagaaca        120
gagcatcaat ttaaaaagct gcccagaatg ttntcctggg cagcgttgtg atctttgccn        180
ccttcgtgac tttatgcaat gcatcatgct atttcatacc taatgaggga gttccaggag        240
attcaaccag gatgtttcta cncctgtggg ttatgacaaa gcaactgcc aaagaatntt        300
caagaaggag gactgcaagt atatcgtggt ggagaagaag gacccaaaaa agacctgttc        360
tgtcagtgaa tggataatct aatgtgcttc tagtaggcac agggctccca ggccaggcct        420
cattctcctc tggcctctaa tagtcaatga ttgtgtagcc atgcctatca gtaaaaagat        480
ttttgagcaa aaaaaaaaaa aaaaaaa        507

<210> SEQ ID NO 431
<211> LENGTH: 392
<212> TYPE: DNA
<213> ORGANISM: Homo sapiens

```
<220> FEATURE:
<221> NAME/KEY: misc_feature
<222> LOCATION: (1)...(392)
<223> OTHER INFORMATION: n = A,T,C or G

<400> SEQUENCE: 431
gaaaattcag aatggataaa aacaaatgaa gtacaaaata tttcagattt acatagcgat      60
aaacaagaaa gcacttatca ggaggactta caaatggaag tacactctan aaccatcatc     120
tatcatggct aaatgtgaga ttagcacagc tgtattattt gtacattgca aacacctaga    180
aagagatggg aaacaaaatc ccaggagttt tgtgtgtgga gtcctgggtt ttccaacaga    240
catcattcca gcattctgag attagggnga ttggggatca ttctggagtt ggaatgttca    300
acaaaagtga tgttgttagg taaaatgtac aacttctgga tctatgcaga cattgaaggt   360
gcaatgagtc tggcttttac tctgctgttt ct                                   392

<210> SEQ ID NO 432
<211> LENGTH: 387
<212> TYPE: DNA
<213> ORGANISM: Homo sapiens
<220> FEATURE:
<221> NAME/KEY: misc_feature
<222> LOCATION: (1)...(387)
<223> OTHER INFORMATION: n = A,T,C or G

<400> SEQUENCE: 432
ggtatccnta cataatcaaa tatagctgta gtacatgttt tcattggngt agattaccac     60
aaatgcaagg caacatgtgt agatctcttg tcttattctt ttgtctataa tactgtattg    120
ngtagtccaa gctctcggna gtccagccac tgngaaacat gctcccttta gattaacctc    180
gtggacnctn ttgttgnatt gtctgaactg tagngccctg tattttgctt ctgtctgnga    240
attctgttgc ttctggggca tttccttgng atgcagagga ccaccacaca gatgacagca    300
atctgaattg ntccaatcac agctgcgatt aagacatact gaaatcgtac aggaccggga   360
acaacgtata gaacactgga gtcccttt                                        387

<210> SEQ ID NO 433
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n = A,T,C or G

<400> SEQUENCE: 433
ttcaactagc anagaanact gcttcagggn gtgtaaaatg aaaggcttcc acgcagttat     60
ctgattaaag aacactaaga gagggacaag gctagaagcc gcaggatgtc tacactatag   120
caggcnctat ttgggttggc tggaggagct gtggaaaaca tggagagatt ggcgctggag   180
atcgccgtgg ctattcctcn ttgntattac accagngagg ntctctgtnt gcccactggt   240
tnnaaaaccg ntatacaata atgatagaat aggacacaca t                        281

<210> SEQ ID NO 434
<211> LENGTH: 484
<212> TYPE: DNA
<213> ORGANISM: Homo sapiens

<400> SEQUENCE: 434
ttttaaaata agcatttagt gctcagtccc tactgagtac tctttctctc ccctcctctg     60
```

```
aatttaattc tttcaacttg caatttgcaa ggattacaca tttcactgtg atgtatattg    120
tgttgcaaaa aaaaaaagt gtctttgttt aaaattactt ggtttgtgaa tccatcttgc    180
tttttcccca ttggaactag tcattaaccc atctctgaac tggtagaaaa acatctgaag    240
agctagtcta tcagcatctg acaggtgaat tggatggttc tcagaaccat ttcacccaga    300
cagcctgttt ctatcctgtt taataaatta gtttgggttc tctacatgca taacaaaccc    360
tgctccaatc tgtcacataa agtctgtga cttgaagttt agtcagcacc cccaccaaac     420
tttatttttc tatgtgtttt ttgcaacata tgagtgtttt gaaataaag tacccatgtc     480 ttta                                                                484

<210> SEQ ID NO 435
<211> LENGTH: 424
<212> TYPE: DNA
<213> ORGANISM: Homo sapiens

<400> SEQUENCE: 435
gcgccgctca gagcaggtca ctttctgcct tccacgtcct ccttcaagga agccccatgt     60
gggtagcttt caatatcgca ggttcttact cctctgcctc tataagctca aacccaccaa    120
cgatcgggca agtaaacccc ctccctcgcc gacttcggaa ctggcgagag ttcagcgcag    180
atgggcctgt ggggaggggg caagatagat gaggggagc ggcatggtgc gggtgaccc     240 cttggagaga ggaaaaaggc cacaagaggg gctgccaccg ccactaacgg agatggccct    300
ggtagagacc tttgggggtc tggaacctct ggactcccca tgctctaact cccacactct    360
gctatcagaa acttaaactt gaggattttc tctgtttttc actcgcaata aattcagagc    420
aaac                                                                424

<210> SEQ ID NO 436
<211> LENGTH: 667
<212> TYPE: DNA
<213> ORGANISM: Homo sapiens
<220> FEATURE:
<221> NAME/KEY: misc_feature
<222> LOCATION: (1)...(667)
<223> OTHER INFORMATION: n = A,T,C or G

<400> SEQUENCE: 436
accttgggaa nactctcaca atataaaggg tcgtagactt tactccaaat tccaaaaagg     60
tcctggccat gtaatcctga aagttttccc aaggtagcta taaaatcctt ataagggtgc    120
agcctcttct ggaattcctc tgatttcaaa gtctcactct caagttcttg aaaacgaggg    180
cagttcctga aagcaggta tagcaactga tcttcagaaa gaggaactgt gtgcaccggg     240
atgggctgcc agagtaggat aggattccag atgctgacac cttctggggg aaacagggct    300
gccaggtttg tcatagcact catcaaagtc cggtcaacgt ctgtgcttcg aatataaacc    360
tgttcatgtt tataggactc attcaagaat tttctatatc tctttcttat atactctcca    420
agttcataat gctgctccat gcccagctgg gtgagttggc caaatccttg tggccatgag    480
gattccttta tgggtcagt gggaaaggtg tcaatggac ttcggtctcc atgccgaaac      540
accaaagtca caacttcaa ctccttggct agtacacttc ggtctagcca gaaaaaaagc     600
agaaacaaga agccaaggct aaggcttgct gccctgccag gaggagggt gcagctctca     660 tgttgag                                                             667

<210> SEQ ID NO 437
<211> LENGTH: 693
```

<212> TYPE: DNA
<213> ORGANISM: Homo sapiens

<400> SEQUENCE: 437

```
ctacgtctca accctcattt ttaggtaagg aatcttaagt ccaaagatat taagtgactc    60
acacagccag gtaaggaaag ctggattggc acactaggac tctaccatac cgggttttgt   120
taaagctcag gttaggaggc tgataagctt ggaaggaact tcagacagct tttcagatc    180
ataaaagata attcttagcc catgttcttc tccagagcag acctgaaatg acagcacagc   240
aggtactcct ctatttcac ccctcttgct tctactctct ggcagtcaga cctgtgggag    300
gccatgggag aaagcagctc tctggatgtt tgtacagatc atggactatt ctctgtggac   360
catttctcca ggttacccta ggtgtcacta ttgggggac agccagcatc tttagctttc    420
atttgagttt ctgtctgtct tcagtagagg aaactttgc tcttcacact tcacatctga    480
acacctaact gctgttgctc ctgaggtggt gaaagacaga tatagagctt acagtattta   540
tcctatttct aggcactgag ggctgtgggg taccttgtgg tgccaaaaca gatcctgttt    600
taaggacatg ttgcttcaga gatgtctgta actatctggg ggctctgttg gctctttacc   660
ctgcatcatg tgctctcttg gctgaaaatg acc                                693
```

<210> SEQ ID NO 438
<211> LENGTH: 360
<212> TYPE: DNA
<213> ORGANISM: Homo sapiens

<400> SEQUENCE: 438

```
ctgcttatca caatgaatgt tctcctgggc agcgttgtga tctttgccac cttcgtgact    60
ttatgcaatg catcatgcta tttcatacct aatgagggag ttccaggaga ttcaaccagg   120
atgtttctac acctgtgggt tatgacaaag acaactgcca aagaatcttc aagaaggagg   180
actgcaagta tatctggtgg agaagaagga cccaaaaaag acctgttctg tcagtgaatg   240
gataatctaa tgtgcttcta gtaggcacag ggctcccagg ccaggcctca ttctcctctg   300
gcctctaata gtcaataatt gtgtagccat gcctatcagt aaaaagattt ttgagcaaac   360
```

<210> SEQ ID NO 439
<211> LENGTH: 431
<212> TYPE: DNA
<213> ORGANISM: Homo sapiens
<220> FEATURE:
<221> NAME/KEY: misc_feature
<222> LOCATION: (1)...(431)
<223> OTHER INFORMATION: n = A,T,C or G

<400> SEQUENCE: 439

```
gttcctnnta actcctgcca gaaacagctc tcctcaacat gagagctgca cccctcctcc    60
tggccagggc agcaagcctt agccttggct tcttgtttct gcttttttc tggctagacc   120
gaagtgtact agccaaggag ttgaagtttg tgactttggt gtttcggcat ggagaccgaa   180
gtcccattga caccttccc actgacccca taaggaatc ctcatggcca caaggatttg    240
gccaactcac ccagctgggc atggagcagc attatgaact tggagagtat ataagaaaga   300
gatatagaaa attcttgaat gagtcctata aacatgaaca ggtttatatt cgaagcacag   360
acgttgaccg gactttgatg agtgctatga caaacctggc agcccgtcga cgcggccgcg   420
aatttagtag t                                                        431
```

<210> SEQ ID NO 440

<211> LENGTH: 523
<212> TYPE: DNA
<213> ORGANISM: Homo sapiens

<400> SEQUENCE: 440

| agagataaag cttaggtcaa agttcataga gttcccatga actatatgac tggccacaca | 60 |
| ggatctttg tatttaagga ttctgagatt ttgcttgagc aggattagat aaggctgttc | 120 |
| tttaaatgtc tgaaatggaa cagatttcaa aaaaaaccc cacaatctag ggtgggaaca | 180 |
| aggaaggaaa gatgtgaata ggctgatggg caaaaaacca atttacccat cagttccagc | 240 |
| cttctctcaa ggagaggcaa agaaaggaga tacagtggag acatctggaa agttttctcc | 300 |
| actggaaaac tgctactatc tgtttttata tttctgttaa aatatatgag gctacagaac | 360 |
| taaaaattaa aacctctttg tgtcccttgg tcctggaaca tttatgttcc ttttaaagaa | 420 |
| acaaaaatca aactttacag aaagatttga tgtatgtaat acatatagca gctcttgaag | 480 |
| tatatatatc atagcaaata agtcatctga tgagaacaag cta | 523 |

<210> SEQ ID NO 441
<211> LENGTH: 430
<212> TYPE: DNA
<213> ORGANISM: Homo sapiens

<400> SEQUENCE: 441

| gttcctccta actcctgcca gaaacagctc tcctcaacat gagagctgca cccctcctcc | 60 |
| tggccagggc agcaagcctt agccttggct tcttgtttct gctttttttc tggctagacc | 120 |
| gaagtgtact agccaaggag ttgaagtttg tgactttggt gtttcggcat ggagaccgaa | 180 |
| gtcccattga cacctttccc actgacccca taaaggaatc ctcatggcca caaggatttg | 240 |
| gccaactcac ccagctgggc atggagcagc attatgaact tggagagtat ataagaaaga | 300 |
| gatatagaaa attcttgaat gagtcctata acatgaaca ggtttatatt cgaagcacag | 360 |
| acgttgaccg gactttgatg agtgctatga caaacctggc agcccgtcga cgcggccgcg | 420 |
| aatttagtag | 430 |

<210> SEQ ID NO 442
<211> LENGTH: 362
<212> TYPE: DNA
<213> ORGANISM: Homo sapiens

<400> SEQUENCE: 442

| ctaaggaatt agtagtgttc ccatcacttg tttggagtgt gctattctaa aagattttga | 60 |
| tttcctggaa tgacaattat attttaactt tggtggggga aagagttata ggaccacagt | 120 |
| cttcacttct gatacttgta aattaatctt ttattgcact tgttttgacc attaagctat | 180 |
| atgtttagaa atggtcattt tacggaaaaa ttagaaaaat tctgataata gtgcagaata | 240 |
| aatgaattaa tgttttactt aatttatatt gaactgtcaa tgacaaataa aaattctttt | 300 |
| tgattatttt ttgttttcat ttaccagaat aaaaactaag aattaaaagt ttgattacag | 360 |
| tc | 362 |

<210> SEQ ID NO 443
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

```
<400> SEQUENCE: 443
tttttttttt gcaacacaat atacatcaca gtgaaatgtg taatccttgc aaattgcaag      60
ttgaaagaat taaattcaga ggaggggaga gaaagagtac tcagtaggga ctgagcacta     120
aatgcttatt ttaaaagaaa tgtaaagagc agaaagcaat tcaggctacc ctgccttttg     180
tgctggctag tactccggtc ggtgtcagca gcacgtggca ttgaacattg caatgtggag     240
cccaaaccac agaaatggg gtgaaattgg ccaactttct attaacttgg cttcctgttt     300
tataaaatat tgtgaataat atcacctact tcaaagggca gttatgaggc ttaaatgaac     360
taacgcctac aaaacactta aacatagata acataggtgc aagtactatg tatctggtac     420
atggtaaaca tccttattat taaagtcaac gctaaaatga atgtgtgtgc atatgctaat     480
agtacagaga gagggcactt aaaccaacta agggcctgga gggaaggttt cctggaaaga     540
ngatgcttgt gctgggtcca aatcttggtc tactatgacc ttggccaaat tatttaaact     600
ttgtccctat ctgctaaaca gatc                                           624

<210> SEQ ID NO 444
<211> LENGTH: 425
<212> TYPE: DNA
<213> ORGANISM: Homo sapiens
<220> FEATURE:
<221> NAME/KEY: misc_feature
<222> LOCATION: (1)...(425)
<223> OTHER INFORMATION: n = A,T,C or G

<400> SEQUENCE: 444
gcacatcatt nntcttgcat tctttgagaa taagaagatc agtaaatagt tcagaagtgg      60
gaagctttgt ccaggcctgt gtgtgaaccc aatgttttgc ttagaaatag aacaagtaag     120
ttcattgcta tagcataaca caaaatttgc ataagtggtg gtcagcaaat ccttgaatgc     180
tgcttaatgt gagaggttgg taaaatcctt tgtgcaacac tctaactccc tgaatgtttt     240
gctgtgctgg gacctgtgca tgccagacaa ggccaagctg gctgaaagag caaccagcca     300
cctctgcaat ctgccacctc ctgctggcag gatttgtttt tgcatcctgt gaagagccaa     360
ggaggcacca gggcataagt gagtagactt atggtcgacg cggccgcgaa tttagtagta     420
gtaga                                                                425

<210> SEQ ID NO 445
<211> LENGTH: 414
<212> TYPE: DNA
<213> ORGANISM: Homo sapiens
<220> FEATURE:
<221> NAME/KEY: misc_feature
<222> LOCATION: (1)...(414)
<223> OTHER INFORMATION: n = A,T,C or G

<400> SEQUENCE: 445
catgtttatg nttttggatt actttgggca cctagtgttt ctaaatcgtc tatcattctt      60
ttctgttttt caaaagcaga gatggccaga gtctcaacaa actgtatctt caagtctttg     120
tgaaattctt tgcatgtggc agattattgg atgtagtttc ctttaactag catataaatc     180
tggtgtgttt cagataaatg aacagcaaaa tgtggtggaa ttaccatttg gaacattgtg     240
aatgaaaaat tgtgtctcta gattatgtaa caaataacta tttcctaacc attgatcttt     300 ggattttat aatcctactc acaaatgact aggcttctcc tcttgtattt tgaagcagtg     360
tgggtgctgg attgataaaa aaaaaaaaag tcgacgcggc cgcgaattta gtag           414
```

<210> SEQ ID NO 446
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 446

| | | | | | |
|---|---|---|---|---|---|
| acaaattaga | anaaagtgcc | agagaacacc | acataccttg | tccggaacat | tacaatggct | 60 |
| tctgcatgca | tgggaagtgt | gagcattcta | tcaatatgca | ggagccatct | tgcaggtgtg | 120 |
| atgctggtta | tactggacaa | cactgtgaaa | aaaaggacta | cagtgttcta | tacgttgttc | 180 |
| ccggtcctgt | acgatttcag | tatgtcttaa | tcgcagctgt | gattggaaca | attcagattg | 240 |
| ctgtcatctg | tgtggtggtc | ctctgcatca | caagggccaa | actttaggta | atagcattgg | 300 |
| actgagattt | gtaaactttc | caaccttcca | ggaaatgccc | cagaagcaac | agaattcaca | 360 |
| gacagaagca | aaatacaggg | cactacagtt | cagacaatac | aacaagagcg | tccacgaggt | 420 |
| taatctaaag | ggagcatgtt | tcacagtggc | tggactaccg | agagcttgga | ctacacaata | 480 |
| cagtattata | gacaaaagaa | taagacaaga | gatctacaca | tgttgccttg | catttgtggt | 540 |
| aatctacacc | aatgaaaaca | tgtactacag | ctatatttga | ttatgtatgg | atatatttga | 600 |
| aatagtatac | attgtcttga | tgttttttct | g | | | 631 |

<210> SEQ ID NO 447
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n = A,T,C or G

<400> SEQUENCE: 447

| | | | | | |
|---|---|---|---|---|---|
| ccttgggaaa | antntcacaa | tataaagggt | cgtagacttt | actccaaatt | ccaaaaaggt | 60 |
| cctggccatg | taatcctgaa | agttttccca | aggtagctat | aaaatcctta | taagggtgca | 120 |
| gcctcttctg | gaattcctct | gatttcaaag | tctcactctc | aagttcttga | aaacgagggc | 180 |
| agttcctgaa | aggcaggtat | agcaactgat | cttcagaaag | aggaactgtg | tgcaccggga | 240 |
| tgggctgcca | gagtaggata | ggattccaga | tgctgacacc | ttctggggga | aacagggctg | 300 |
| ccaggtttgt | catagcactc | atcaaagtcc | ggtcaacgtc | tgtgcttcga | atataaacct | 360 |
| gttcatgttt | ataggactca | ttcaagaatt | ttctatatct | ctttcttata | tactctccaa | 420 |
| gttcataatg | ctgctccatg | cccagctggg | tgagttggcc | aaatccttgt | ggccatgagg | 480 |
| attcctttat | ggggtcagtg | ggaaaggtgt | caatgggact | tcggtctcca | tgccgaaaca | 540 |
| ccaaagtcac | aaacttcaac | tccttggcta | gtacacttcg | gtcta | | 585 |

<210> SEQ ID NO 448
<211> LENGTH: 93
<212> TYPE: DNA
<213> ORGANISM: Homo sapiens
<220> FEATURE:
<221> NAME/KEY: misc_feature
<222> LOCATION: (1)...(93)
<223> OTHER INFORMATION: n = A,T,C or G

<400> SEQUENCE: 448

| | | | | | |
|---|---|---|---|---|---|
| tgctcgtggg | tcattctgan | nnccgaactg | accntgccag | ccctgccgan | gggccnccat | 60 | ggctccctag tgccctggag aggangggc tag                    93

<210> SEQ ID NO 449
<211> LENGTH: 706
<212> TYPE: DNA
<213> ORGANISM: Homo sapiens
<220> FEATURE:
<221> NAME/KEY: misc_feature
<222> LOCATION: (1)...(706)
<223> OTHER INFORMATION: n = A,T,C or G

<400> SEQUENCE: 449
ccaagttcat gctntgtgct ggacgctgga caggggggcaa agcnnttgc tcgtgggtca    60
ttctgancac cgaactgacc atgccagccc tgccgatggt cctccatggc tccctagtgc   120
cctggagagg aggtgtctag tcagagagta gtcctggaag gtggcctctg ngaggagcca   180
cggggacagc atcctgcaga tggtcgggcg cgtcccattc gccattcagg ctgcgcaact   240
gttgggaagg gcgatcggtg cgggcctctt cgctattacg ccagctggcg aaaggggat    300
gtgctgcaaa gcgattaagt tgggtaacgc cagggttttc ccagtcncga cgttgtaaaa   360
cgacggccag tgaattgaat ttaggtgacn ctatagaaga gctatgacgt cgcatgcacg   420
cgtacgtaag cttggatcct ctagagcggc cgcctactac tactaaattc gcggccgcgt   480
cgacgtggga tccncactga gagtggag agtgacatgt gctggacnct gtccatgaag    540
cactgagcag aagctggagg cacaacgcnc cagacactca cagctactca ggaggctgag   600
aacaggttga acctgggagg tggaggttgc aatgagctga gatcaggccn ctgcnccca    660
gcatggatga cagagtgaaa ctccatctta aaaaaaaaaa aaaaaa                  706

<210> SEQ ID NO 450
<211> LENGTH: 493
<212> TYPE: DNA
<213> ORGANISM: Homo sapiens

<400> SEQUENCE: 450
gagacggagt gtcactctgt tgcccaggct ggagtgcagc aagacactgt ctaagaaaaa    60
acagttttaa aaggtaaaac aacataaaaa gaaatatcct atagtggaaa taagagagtc   120
aaatgaggct gagaacttta caaagggatc ttacagacat gtcgccaata tcactgcatg   180
agcctaagta taagaacaac ctttggggag aaaccatcat ttgacagtga ggtacaattc   240
caagtcaggt agtgaaatgg gtggaattaa actcaaatta atcctgccag ctgaaacgca   300
agagacactg tcagagagtt aaaaagtgag ttctatccat gaggtgattc cacagtcttc   360
tcaagtcaac acatctgtga actcacagac caagttctta aaccactgtt caaactctgc   420
tacacatcag aatcacctgg agagctttac aaactcccat tgccgagggt cgacgcggcc   480
gcgaatttag tag                                                      493

<210> SEQ ID NO 451
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n = A,T,C or G

<400> SEQUENCE: 451
gggcgcgtcc cattcgccat tcaggctgcg caactgttgg gaagggcgat cggtgcgggc    60

```
ctcttcgcta ttacgccagc tggcgaaagg gggatgtgct gcaaggcgat taagttgggt        120
aacgccaggg ttttcccagt cncgacgttg taaaacgacg gccagtgaat tgaatttagg        180
tgacnctata gaagagctat gacgtcgcat gcacgcgtac gtaagcttgg atcctctaga        240
gcggccgcct actactacta aattcgcggc cgcgtcgacg tgggatccnc actgagagag        300
tggagagtga catgtgctgg acnctgtcca tgaagcactg agcagaagct ggaggcacaa        360
cgcnccagac actcacagct actcaggagg ctgagaacag gttgaacctg ggaggtggag        420
gttgcaatga gctgagatca ggccnctgcn ccccagcatg gatgacagag tgaaactcca        480
tcttaaaaaa aaaaaaaaaa a                                                  501

<210> SEQ ID NO 452
<211> LENGTH: 51
<212> TYPE: DNA
<213> ORGANISM: Homo sapiens
<220> FEATURE:
<221> NAME/KEY: misc_feature
<222> LOCATION: (1)...(51)
<223> OTHER INFORMATION: n = A,T,C or G

<400> SEQUENCE: 452
agacggtttc accnttacaa cnccttttag gatgggnntt ggggagcaag c                 51

<210> SEQ ID NO 453
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 453
tacatcttgc ttttcccca ttggaactag tcattaaccc atctctgaac tggtagaaaa         60
acatctgaag agctagtcta tcagcatctg gcaagtgaat tggatggttc tcagaaccat       120
ttcacccana cagcctgttt ctatcctgtt taataaatta gtttgggttc tctacatgca       180
taacaaaccc tgctccaatc tgtcacataa aagtctgtga cttgaagttt antcagcacc       240
cccaccaaac tttatttttc tatgtgtttt ttgcaacata tgagtgtttt gaaataagg        300 tacccatgtc tttatta                                                      317

<210> SEQ ID NO 454
<211> LENGTH: 231
<212> TYPE: DNA
<213> ORGANISM: Homo sapiens

<400> SEQUENCE: 454
ttcgaggtac aatcaactct cagagtgtag tttccttcta tagatgagtc agcattaata        60
taagccacgc cacgctcttg aaggagtctt gaattctcct ctgctcactc agtagaacca       120
agaagaccaa attcttctgc atcccagctt gcaaacaaaa ttgttcttct aggtctccac       180
ccttcctttt tcagtgttcc aaagctcctc acaatttcat gaacaacagc t                231

<210> SEQ ID NO 455
<211> LENGTH: 231
<212> TYPE: DNA
<213> ORGANISM: Homo sapiens

<400> SEQUENCE: 455
taccaaagag ggcataataa tcagtctcac agtagggttc accatcctcc aagtgaaaaa        60
```

-continued

```
cattgttccg aatgggcttt ccacaggcta cacacacaaa acaggaaaca tgccaagttt      120
gtttcaacgc attgatgact tctccaagga tcttcctttg gcatcgacca cattcagggg     180
caaagaattt ctcatagcac agctcacaat acagggctcc tttctcctct a              231

<210> SEQ ID NO 456
<211> LENGTH: 231
<212> TYPE: DNA
<213> ORGANISM: Homo sapiens

<400> SEQUENCE: 456
ttggcaggta cccttacaaa gaagacacca taccttatgc gttattaggt ggaataatca      60
ttccattcag tattatcgtt attattcttg gagaaaccct gtctgtttac tgtaacctttt    120 tgcactcaaa ttcctttatc aggaataact acatagccac tatttacaaa gccattggaa    180
cctttttatt tggtgcagct gctagtcagt ccctgactga cattgccaag t              231

<210> SEQ ID NO 457
<211> LENGTH: 231
<212> TYPE: DNA
<213> ORGANISM: Homo sapiens
<220> FEATURE:
<221> NAME/KEY: misc_feature
<222> LOCATION: (1)...(231)
<223> OTHER INFORMATION: n = A,T,C or G

<400> SEQUENCE: 457
cgaggtaccc aggggtctga aaatctctnn tttantagtc gatagcaaaa ttgttcatca      60
gcattcctta atatgatctt gctataatta gatttttctc cattagagtt catacagtttt   120 tatttgattt tattagcaat ctctttcaga agacccttga gatcattaag ctttgtatcc    180
agttgtctaa atcgatgcct catttcctct gaggtgtcgc tggcttttgt g              231

<210> SEQ ID NO 458
<211> LENGTH: 231
<212> TYPE: DNA
<213> ORGANISM: Homo sapiens

<400> SEQUENCE: 458
aggtctggtt ccccccactt ccactcccct ctactctctc taggactggg ctgggccaag      60
agaagagggg tggttaggga agccgttgag acctgaagcc ccaccctcta ccttccttca    120
acaccctaac cttgggtaac agcatttgga attatcattt gggatgagta aatttccaa     180 ggtcctgggt taggcatttt ggggggccag accccaggag aagaagattc t              231

<210> SEQ ID NO 459
<211> LENGTH: 231
<212> TYPE: DNA
<213> ORGANISM: Homo sapiens

<400> SEQUENCE: 459
ggtaccgagg ctcgctgaca cagagaaacc ccaacgcgag gaaaggaatg gccagccaca      60
ccttcgcgaa acctgtggtg gcccaccagt cctaacggga caggacagag agacagagca    120
gccctgcact gttttccctc caccacagcc atcctgtccc tcattggctc tgtgcttttcc    180 actatacaca gtcaccgtcc caatgagaaa caagaaggag caccctccac a              231

<210> SEQ ID NO 460
<211> LENGTH: 231
<212> TYPE: DNA
```

<213> ORGANISM: Homo sapiens

<400> SEQUENCE: 460

| | | | | | |
|---|---|---|---|---|---|
| gcaggtataa | catgctgcaa | caacagatgt | gactaggaac | ggccggtgac | atggggaggg | 60 |
| cctatcaccc | tattcttggg | ggctgcttct | tcacagtgat | catgaagcct | agcagcaaat | 120 |
| cccacctccc | cacacgcaca | cggccagcct | ggagcccaca | gaagggtcct | cctgcagcca | 180 |
| gtggagcttg | gtccagcctc | cagtccaccc | ctaccaggct | taaggataga | a | 231 |

<210> SEQ ID NO 461
<211> LENGTH: 231
<212> TYPE: DNA
<213> ORGANISM: Homo sapiens

<400> SEQUENCE: 461

| | | | | | |
|---|---|---|---|---|---|
| cgaggtttga | gaagctctaa | tgtgcagggg | agccgagaag | caggcggcct | agggagggtc | 60 |
| gcgtgtgctc | cagaagagtg | tgtgcatgcc | agaggggaaa | caggcgcctg | tgtgtcctgg | 120 |
| gtggggttca | gtgaggagtg | ggaaattggt | tcagcagaac | caagccgttg | ggtgaataag | 180 |
| aggggggattc | catggcactg | atagagccct | atagtttcag | agctgggaat | t | 231 |

<210> SEQ ID NO 462
<211> LENGTH: 231
<212> TYPE: DNA
<213> ORGANISM: Homo sapiens

<400> SEQUENCE: 462

| | | | | | |
|---|---|---|---|---|---|
| aggtaccctc | attgtagcca | tgggaaaatt | gatgttcagt | ggggatcagt | gaattaaatg | 60 |
| gggtcatgca | agtataaaaa | ttaaaaaaaa | aagacttcat | gcccaatctc | atatgatgtg | 120 |
| gaagaactgt | tagagagacc | aacagggtag | tgggttagag | atttccagag | tcttacattt | 180 |
| tctagaggag | gtatttaatt | tcttctcact | catccagtgt | tgtatttagg | a | 231 |

<210> SEQ ID NO 463
<211> LENGTH: 231
<212> TYPE: DNA
<213> ORGANISM: Homo sapiens

<400> SEQUENCE: 463

| | | | | | |
|---|---|---|---|---|---|
| tactccagcc | tggtgacaga | gcgagaccct | atcaccgccc | cccaccccac | caaaaaaaaa | 60 |
| actgagtaga | caggtgtcct | cttggcatgg | taagtcttaa | gtcccctccc | agatctgtga | 120 |
| catttgacag | gtgtcttttc | ctctggacct | cggtgtcccc | atctgagtga | gaaaaggcag | 180 |
| tggggaggtg | gatcttccag | tcgaagcggt | atagaagccc | gtgtgaaaag | c | 231 |

<210> SEQ ID NO 464
<211> LENGTH: 231
<212> TYPE: DNA
<213> ORGANISM: Homo sapiens

<400> SEQUENCE: 464

| | | | | | |
|---|---|---|---|---|---|
| gtactctaag | attttatcta | agttgccttt | tctgggtggg | aaagtttaac | cttagtgact | 60 |
| aaggacatca | catatgaaga | atgtttaagt | tggaggtggc | aacgtgaatt | gcaaacaggg | 120 |
| cctgcttcag | tgactgtgtg | cctgtagtcc | cagctactcg | ggagtctgtg | tgaggccagg | 180 |
| ggtgccagcg | caccagctag | atgctctgta | acttctaggc | cccatttttcc | c | 231 |

<210> SEQ ID NO 465
<211> LENGTH: 231

```
<212> TYPE: DNA
<213> ORGANISM: Homo sapiens

<400> SEQUENCE: 465
catgttgttg tagctgtggt aatgctggct gcatctcaga cagggttaac ttcagctcct      60
gtggcaaatt agcaacaaat tctgacatca tatttatggt ttctgtatct ttgttgatga     120
aggatggcac aattttttgct tgtgttcata atatactcag attagttcag ctccatcaga    180
taaactggag acatgcagga cattagggta gtgttgtagc tctggtaatg a              231

<210> SEQ ID NO 466
<211> LENGTH: 231
<212> TYPE: DNA
<213> ORGANISM: Homo sapiens

<400> SEQUENCE: 466
caggtacctc tttccattgg atactgtgct agcaagcatg ctctccgggg tttttttaat     60
ggccttcgaa cagaacttgc cacatacccca gtataatag tttctaacat tgcccagga     120 cctgtgcaat caaatattgt ggagaattcc ctagctggag aagtcacaaa gactataggc    180
aataatggag accagtccca caagatgaca accagtcgtt gtgtgcggct g              231

<210> SEQ ID NO 467
<211> LENGTH: 311
<212> TYPE: DNA
<213> ORGANISM: Homo sapiens

<400> SEQUENCE: 467
gtacaccctg gcacagtcca atctgaactg gttcggcact catctttcat gagatggatg     60
tggtggcttt tctccttttt catcaagact cctcagcagg gagcccagac cagcctgcac    120
tgtgccttaa cagaaggtct tgagattcta agtgggaatc atttcagtga ctgtcatgtg    180
gcatgggtct ctgcccaagc tcgtaatgag actatagcaa ggcggctgtg ggacgtcagt    240
tgtgacctgc tgggcctccc aatagactaa caggcagtgc cagttggacc caagagaaga    300
ctgcagcaga c                                                          311

<210> SEQ ID NO 468
<211> LENGTH: 3112
<212> TYPE: DNA
<213> ORGANISM: Homo sapiens

<400> SEQUENCE: 468
cattgtgttg ggagaaaaac agagggggaga tttgtgtggc tgcagccgag ggagaccagg    60
aagatctgca tggtgggaag gacctgatga tacagagttt gataggagac aattaaaggc    120
tggaaggcac tggatgcctg atgatgaagt ggactttcaa actggggcac tactgaaacg    180
atgggatggc cagagacaca ggagatgagt tggagcaagc tcaataacaa agtggttcaa    240
cgaggacttg gaattgcatg gagctggagc tgaagtttag cccaattgtt tactagttga    300
gtgaatgtgg atgattggat gatcatttct catctctgag cctcaggttc cccatccata    360
aaatgggata cacagtatga tctataaagt gggatatagt atgatctact tcactgggtt    420
atttgaagga tgaattgaga taatttattt caggtgccta gaacaatgcc cagattagta    480
catttggtgg aactgagaaa tggcataaca ccaaatttaa tatatgtcag atgttactat    540
gattatcatt caatctcata gttttgtcat ggcccaattt atcctcactt gtgcctcaac    600
aaattgaact gttaacaaag gaatctctgg tcctgggtaa tggctgagca ccactgagca    660
```

-continued

```
tttccattcc agttggcttc ttgggtttgc tagctgcatc actagtcatc ttaaataaat    720
gaagttttaa catttctcca gtgattttt tatctcacct ttgaagatac tatgttatgt    780
gattaaataa agaacttgag aagaacaggt ttcattaaac ataaaatcaa tgtagacgca    840
aattttctgg atgggcaata cttatgttca caggaaatgc tttaaaatat gcagaagata    900
attaaatggc aatggacaaa gtgaaaaact tagactttt tttttttttt ggaagtatct    960
ggatgttcct tagtcactta aaggagaact gaaaatagc agtgagttcc acataatcca   1020
acctgtgaga ttaaggctct ttgtggggaa ggacaaagat ctgtaaattt acagtttcct   1080
tccaaagcca acgtcgaatt ttgaaacata tcaaagctct tcttcaagac aaataatcta   1140
tagtacatct ttcttatggg atgcacttat gaaaatggt ggctgtcaac atctagtcac   1200
tttagctctc aaaatggttc attttaagag aaagttttag aatctcatat ttattcctgt   1260
ggaaggacag cattgtggct tggactttat aaggtcttta ttcaactaaa taggtgagaa   1320
ataagaaagg ctgctgactt taccatctga ggccacacat ctgctgaaat ggagataatt   1380
aacatcacta gaaacagcaa gatgacaata taatgtctaa gtagtgacat gtttttgcac   1440
atttccagcc cctttaaata tccacacaca caggaagcac aaaaggaagc acagagatcc   1500
ctgggagaaa tgcccggccg ccatcttggg tcatcgatga gcctcgccct gtgcctggtc   1560
ccgcttgtga gggaaggaca ttagaaaatg aattgatgtg ttccttaaag gatgggcagg   1620
aaaacagatc ctgttgtgga tatttatttg aacgggatta cagatttgaa atgaagtcac   1680
aaagtgagca ttaccaatga gaggaaaaca gacgagaaaa tcttgatggc ttcacaagac   1740
atgcaacaaa caaatggaa tactgtgatg acatgaggca gccaagctgg ggaggagata   1800
accacggggc agagggtcag gattctggcc ctgctgccta actgtgcgt tcataaccaa   1860
atcatttcat atttctaacc ctcaaaacaa agctgttgta atatctgatc tctacggttc   1920
cttctgggcc caacattctc catatatcca gccacactca ttttaatat ttagttccca   1980
gatctgtact gtgacctttc tacactgtag aataacatta ctcatttgt tcaaagaccc   2040
ttcgtgttgc tgcctaatat gtagctgact gttttttccta aggagtgttc tggcccaggg   2100
gatctgtgaa caggctggga agcatctcaa gatctttcca gggttatact tactagcaca   2160
cagcatgatc attacggagt gaattatcta atcaacatca tcctcagtgt ctttgcccat   2220
actgaaattc atttcccact tttgtgccca ttctcaagac ctcaaaatgt cattccatta   2280
atatcacagg attaactttt ttttttaacc tggaagaatt caatgttaca tgcagctatg   2340
ggaatttaat tacatatttt gttttccagt gcaaagatga ctaagtcctt tatccctccc   2400
ctttgtttga tttttttttcc agtataaagt taaaatgctt agccttgtac tgaggctgta   2460
tacagccaca gcctctcccc atccctccag ccttatctgt catcaccatc aacccctccc   2520
atgcacctaa acaaaatcta acttgtaatt ccttgaacat gtcaggcata cattattcct   2580
tctgcctgag aagctcttcc ttgtctctta aatctagaat gatgtaaagt tttgaataag   2640
ttgactatct tacttcatgc aaagaaggga cacatatgag attcatcatc acatgagaca   2700
gcaaatacta aaagtgtaat ttgattataa gagtttagat aaatatatga aatgcaagag   2760
ccacagaggg aatgtttatg gggcacgttt gtaagcctgg gatgtgaagc aaaggcaggg   2820
aacctcatag tatcttatat aatatacttc atttctctat ctctatcaca atatccaaca   2880
agcttttcac agaattcatg cagtgcaaat ccccaaaggt aacctttatc catttcatgg   2940
tgagtgcgct ttagaatttt ggcaaatcat actggtcact tatctcaact ttgagatgtg   3000
tttgtccttg tagttaattg aaagaaatag ggcactcttg tgagccactt tagggttcac   3060
```

-continued

```
tcctggcaat aaagaattta caaagagcaa aaaaaaaaaa aaaaaaaaaa aa         3112
```

<210> SEQ ID NO 469
<211> LENGTH: 2229
<212> TYPE: DNA
<213> ORGANISM: Homo sapiens

<400> SEQUENCE: 469

```
agctctttgt aaattcttta ttgccaggag tgaaccctaa agtggctcac aagagtgccc    60
tatttctttc aattaactac aaggacaaac acatctcaaa gttgagataa gtgaccagta   120
tgatttgcca aaattctaaa gcgcactcac catgaaatgg ataaaggtta cctttgggga   180
tttgcactgc atgaattctg tgaaaagctt gttggatatt gtgatagaga tagagaaatg   240
aagtatatta tataagatac tatgaggttc cctgcctttg cttcacatcc caggcttaca   300
aacgtgcccc ataaacattc cctctgtggc tcttgcattt catatattta tctaaactct   360
tataatcaaa tacactttta gtatttgctg tctcatgtga tgatgaatct catatgtgtc   420
ccttctttgc atgaagtaag atagtcaact tattcaaaac tttacatcat tctagattta   480
agagacaagg aagagcttct caggcagaag gaataatgta tgcctgacat gttcaaggaa   540
ttacaagtta gattttgttt aggtgcatgg gaggggttga tggtgatgac agataaggct   600
ggagggatgg ggagaggctg tggctgtata cagcctcagt acaaggctaa gcattttaac   660
tttatactga aaaaaaatc aaacaaaggg gagggataaa ggacttagtc atctttgcac   720
tggaaaacaa aatatgtaat taaattccca tagctgcatg taacattgaa ttcttccagg   780
ttaaaaaaaa agttaatcct gtgatattaa tggaatgaca ttttgaggtc ttgagaatgg   840
gcacaaaagt gggaaatgaa tttcagtatg ggcaaagaca ctgaggatga tgttgattag   900
ataattcact ccgtaatgat catgctgtgt gctagtaagt ataaccctgg aaagatcttg   960
agatgcttcc cagcctgttc acagatcccc tgggccagaa cactccttag gaaaaacagt  1020
cagctacata ttaggcagca acacgaaggg tctttgaaca aaatgagtaa tgttattcta  1080
cagtgtagaa aggtcacagt acagatctgg gaactaaata ttaaaaatga gtgtggctgg  1140
atatatggag aatgttgggc ccagaaggaa ccgtagagat cagatattac aacagctttg  1200
ttttgagggt tagaaatatg aaatgatttg gttatgaacg cacagtttag gcagcagggc  1260
cagaatcctg accctctgcc ccgtggttat ctcctcccca gcttggctgc ctcatgtcat  1320
cacagtattc cattttgttt gttgcatgtc ttgtgaagcc atcaagattt tctcgtctgt  1380
tttcctctca ttggtaatgc tcactttgtg acttcatttc aaatctgtaa tcccgttcaa  1440
ataaatatcc acaacaggat ctgttttcct gcccatcctt taaggaacac atcaattcat  1500
tttctaatgt ccttccctca caagcgggac caggcacagg gcgaggctca tcgatgaccc  1560
aagatggcgg ccgggcattt ctcccaggga tctctgtgct tccttttgtg cttcctgtgt  1620
gtgtggatat ttaaaggggc tggaaatgtg caaaaacatg tcactactta gacattatat  1680
tgtcatcttg ctgtttctag tgatgttaat tatctccatt tcagcagatg tgtggcctca  1740
gatggtaaag tcagcagcct ttcttatttc tcacctggaa atacatacga ccatttgagg  1800
agacaaatgg caaggtgtca gcatacgctg aacttgagtt gagagctaca cacaatatta  1860
ttggtttccg agcatcacaa acaccctctc tgtttcttca ctgggcacag aattttaata  1920
cttatttcag tgggctgttg gcaggaacaa atgaagcaat ctacataaag tcactagtgc  1980
agtgcctgac acacaccatt ctcttgaggt cccctctaga gatcccacag gtcatatgac  2040
```

```
ttcttgggga gcagtggctc acacctgtaa tcccagcact tgggaggct gaggcaggtg      2100 ggtcacctga ggtcaggagt tcaagaccag cctggccaat atggtgaaac cccatctcta      2160
ctaaaaatac aaaaattagc tgggcgtgct ggtgcatgcc tgtaatccca gccccaacac      2220
aatggaatt                                                              2229

<210> SEQ ID NO 470
<211> LENGTH: 2426
<212> TYPE: DNA
<213> ORGANISM: Homo sapiens

<400> SEQUENCE: 470
gtaaattctt tattgccagg agtgaaccct aaagtggctc acaagagtgc cctatttctt        60
tcaattaact acaaggacaa acacatctca aagttgagat aagtgaccag tatgatttgc       120
caaaattcta aagcgcactc accatgaaat ggataaaggt tacctttggg gatttgcact       180
gcatgaattc tgtgaaaagc ttgttggata ttgtgataga gatagagaaa tgaagtatat       240
tatataagat actatgaggt tccctgcctt tgcttcacat cccaggctta caaacgtgcc       300
ccataaacat tccctctgtg gctcttgcat ttcatatatt tatctaaact cttataatca       360
aattacactt ttagtatttg ctgtctcatg tgatgatgaa tctcatatgt gtcccttctt       420
tgcatgaagt aagatagtca acttattcaa aactttacat cattctagat ttaagagaca       480
aggaagagct tctcaggcag aaggaataat gtatgcctga catgttcaag gaattacaag       540
ttagattttg tttaggtgca tgggagggt tgatggtgat gacagataag gctggaggga       600
tggggagagg ctgtggctgt atacagcctc agtacaaggc taagcatttt aactttatac       660
tggaaaaaaa atcaaacaaa ggggagggat aaaggactta gtcatctttg cactggaaaa       720
caaaatatgt aattaaattc ccatagctgc atgtaacatt gaattcttcc aggttaaaaa       780 aaaagttaa tcctgtgata ttaatggaat gacattttga ggtcttgaga atgggcacaa       840
aagtgggaaa tgaatttcag tatgggcaaa gacactgagg atgatgttga ttagataatt       900
cactccgtaa tgatcatgct gtgtgctagt aagtataacc ctggaaagat cttgagatgc       960
ttcccagcct gttcacagat cccctgggcc agaacactcc ttaggaaaaa cagtcagcta      1020
catattaggc agcaacacga aggtctttg aacaaaatga gtaatgttat tctacagtgt      1080
agaaaggtca cagtacagat ctgggaacta atattaaaa atgagtgtgg ctggatatat      1140
ggagaatgtt gggcccagaa ggaaccgtag agatcagata ttacaacagc tttgttttga      1200
gggttagaaa tatgaaatga tttggttatg aacgcacagt ttaggcagca gggccagaat      1260 cctgacccctc tgccccgtgg ttatctcctc cccagcttgg ctgcctcatg tcatcacagt      1320
attccatttt gtttgttgca tgtcttgtga agccatcaag attttctcgt ctgttttcct      1380
ctcattggta atgctcactt tgtgacttca tttcaaatct gtaatcccgt tcaaataaat      1440
atccacaaca ggatctgttt tcctgcccat cctttaagga acacatcaat tcattttcta      1500
atgtccttcc ctcacaagcg ggaccaggca cagggcgagg ctcatcgatg acccaagatg      1560
gcggccgggc atttctccca gggatctctg tgcttccttt tgtgcttcct gtgtgtgtgg      1620
atatttaaag gggctggaaa tgtgcaaaaa catgtcacta cttagacatt atattgtcat      1680
cttgctgttt ctagtgatgt taattatctc catttcagca gatgtgtggc ctcagatggt      1740
aaagtcagca gcctttctta tttctcacct ggaaatacat acgaccattt gaggagacaa      1800
atggcaaggt gtcagcatac cctgaacttg agttgagagc tacacacaat attattggtt      1860
tccgagcatc acaaacaccc tctctgtttc ttcactgggc acagaatttt aatacttatt      1920
```

```
tcagtgggct gttggcagga acaaatgaag caatctacat aaagtcacta gtgcagtgcc    1980
tgacacacac cattctcttg aggtcccctc tagagatccc acaggtcata tgacttcttg    2040
gggagcagtg gctcacacct gtaatcccag cactttggga ggctgaggca ggtgggtcac    2100
ctgaggtcag gagttcaaga ccagcctggc caatatggtg aaacccatc tctactaaaa    2160 atacaaaaat tagctgggcg tgctggtgca tgcctgtaat cccagctact tgggaggctg    2220
aggcaggaga attgctggaa catgggaggc ggaggttgca gtgagctgta attgtgccat    2280
tgcactcgaa cctgggcgac agagtggaac tctgtttcca aaaacaaac aaacaaaaaa    2340 ggcatagtca gatacaacgt gggtgggatg tgtaaataga agcaggatat aaagggcatg    2400
gggtgacggt tttgcccaac acaatg                                        2426

<210> SEQ ID NO 471
<211> LENGTH: 812
<212> TYPE: DNA
<213> ORGANISM: Homo sapiens

<400> SEQUENCE: 471
gaacaaaatg agtaatgtta ttctacagtg tagaaaggtc acagtacaga tctgggaact     60
aaatattaaa aatgagtgtg gctggatata tggagaatgt tgggcccaga aggaaccgta    120
gagatcagat attacaacag ctttgttttg agggttagaa atatgaaatg atttggttat    180
gaacgcacac tttaggcagc agggccagaa tcctgaccct ctgccccgtg ttatctcct     240 ccccagcttg gctgcctcat gtcatcacag tattccattt tgtttgttgc atgtcttgtg    300
aagccatcaa gattttctcg tctgttttcc tctcattggt aatgctcact ttgtgacttc    360
atttcaaatc tgtaatcccg ttcaaataaa tatccacaac aggatctgtt ttcctgccca    420
tcctttaagg aacacatcaa ttcattttct aatgtccttc cctcacaagc gggaccaggc    480
acagggcgag gctcatcgat gacccaagat ggcggccggg catttctccc agggatctct    540
gtgcttcctt ttgtgcttcc tgtgtgtgtg gatatttaaa ggggctggaa atgtgcaaaa    600
acatgtcact acttagacat tatattgtca tcttgctgtt tctagtgatg ttaattatct    660
ccatttcagc agatgtgtgg cctcagatgg taaagtcagc agccttttctt attctctcacc    720 tctgtatcat caggtccttc ccaccatgca gatcttcctg gtctccctcg gctgcagcca    780
cacaaatctc ccctctgttt ttctgatgcc ag                                 812

<210> SEQ ID NO 472
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 472
acggagactt attttctgat attgtctgca tatgtatgtt tttaagagtc tggaaatagt     60
cttatgactt tcctatcatg cttattaata aataatacag cccagagaag atgaaaatgg    120
gttccagaat tattggtcct tgcagccggg tgaatctcag caagaggaac caccaactga    180
caatcaggat attgaacctg acaagagag agaaggaaca cctccgatcg aagaacgtaa    240
agtagaaggt gattgccagg aaatggatct ggaaaagact cggagtgagc gtggagatgg    300
ctctgatgta aagagaagaa ctccacctaa tcctaagcat gctaagacta aagaagcagg    360
```

-continued

```
agatgggcag ccataagtta aaaagaagac aagctgaagc tacacacatg gctgatgtca      420
cattgaaaat gtgactgaaa atttgaaaat tctctcaata aagtttgagt tttctctgaa      480
gaaaaaaaaa naaaaaaaaa aaanaaaaan aaaaa                                 515
```